US012528767B2

(12) United States Patent
Wagner et al.

(10) Patent No.: US 12,528,767 B2
(45) Date of Patent: Jan. 20, 2026

(54) HDAC6 INHIBITORS AND USES THEREOF

(71) Applicant: Eikonizo Therapeutics, Inc., Beverly, MA (US)

(72) Inventors: Florence Fevrier Wagner, Cambridge, MA (US); Jacob Matthew Hooker, Winchester, MA (US); Stéphane Ouellet, Sudbury, MA (US)

(73) Assignee: Eikonizo Therapeutics, Inc., Cambridge, MA (US)

( * ) Notice: Subject to any disclaimer, the term of this patent is extended or adjusted under 35 U.S.C. 154(b) by 1005 days.

(21) Appl. No.: 17/631,422

(22) PCT Filed: Jul. 30, 2020

(86) PCT No.: PCT/US2020/044148

§ 371 (c)(1),
(2) Date: Jan. 28, 2022

(87) PCT Pub. No.: WO2021/021979

PCT Pub. Date: Feb. 4, 2021

(65) Prior Publication Data

US 2022/0281814 A1 Sep. 8, 2022

Related U.S. Application Data

(60) Provisional application No. 62/880,284, filed on Jul. 30, 2019.

(51) Int. Cl.

| | |
|---|---|
| ***C07D 205/12*** | (2006.01) |
| ***A61P 25/00*** | (2006.01) |
| ***A61P 25/28*** | (2006.01) |
| ***A61P 29/00*** | (2006.01) |
| ***A61P 31/00*** | (2006.01) |
| ***A61P 35/00*** | (2006.01) |
| ***A61P 37/00*** | (2006.01) |
| ***C07D 207/06*** | (2006.01) |
| ***C07D 209/08*** | (2006.01) |
| ***C07D 209/54*** | (2006.01) |
| ***C07D 209/96*** | (2006.01) |
| ***C07D 217/04*** | (2006.01) |
| ***C07D 221/20*** | (2006.01) |
| ***C07D 221/22*** | (2006.01) |
| ***C07D 237/30*** | (2006.01) |
| ***C07D 267/10*** | (2006.01) |
| ***C07D 295/15*** | (2006.01) |
| ***C07D 405/04*** | (2006.01) |
| ***C07D 405/06*** | (2006.01) |
| ***C07D 451/02*** | (2006.01) |
| ***C07D 451/06*** | (2006.01) |
| ***C07D 471/04*** | (2006.01) |
| ***C07D 471/08*** | (2006.01) |
| ***C07D 471/10*** | (2006.01) |
| ***C07D 487/04*** | (2006.01) |
| ***C07D 491/08*** | (2006.01) |
| ***C07D 491/107*** | (2006.01) |
| ***C07D 493/04*** | (2006.01) |

(Continued)

(52) U.S. Cl.

CPC ......... *C07D 205/12* (2013.01); *C07D 209/08* (2013.01); *C07D 217/04* (2013.01); *C07D 237/30* (2013.01); *C07D 405/04* (2013.01); *C07D 451/06* (2013.01); *C07D 471/04* (2013.01); *C07D 487/04* (2013.01); *C07D 491/08* (2013.01); *C07D 491/107* (2013.01); *C07D 493/08* (2013.01); *C07D 498/04* (2013.01)

(58) Field of Classification Search

CPC ................ C07D 205/12; C07D 209/08; C07D 209/54; C07D 209/96; C07D 217/04; C07D 237/30; C07D 405/04; C07D 405/06; C07D 451/06; C07D 451/02; C07D 471/04; C07D 487/04; C07D 491/08; C07D 491/107; C07D 493/08; C07D 493/04; C07D 207/06; C07D 221/20; C07D 221/22; C07D 267/10; C07D 295/15; C07D 471/08; A61P 25/00; A61P 25/28; A61P 29/00; A61P 31/00; A61P 35/00; A61P 37/00

See application file for complete search history.

(56) References Cited

U.S. PATENT DOCUMENTS 4,205,085 A 5/1980 Shepherd
5,231,097 A 7/1993 Klausener et al.

(Continued)

FOREIGN PATENT DOCUMENTS

CN 105884767 A 8/2016
CN 108884054 A 11/2018

(Continued)

OTHER PUBLICATIONS

SID_227322283, 2015, pubchem compound.*
Partial Supplementary European Search Report mailed Jul. 6, 2023 for European Application No. 20847655.6.
Yu et al., Quinazolin-2,4-dione-Based Hydroxamic Acids as Selective Histone Deacetylase-6 Inhibitors for Treatment of Non-Small Cell Lung Cancer. J Med Chem. Jan. 2, 20194;62(2):857-874. doi: 10.1021/acs.jmedchem.8b01590. Epub Dec. 20, 2018.
Extended European Search Report mailed Oct. 10, 2023 for European Application No. 20847655.6.

(Continued)

*Primary Examiner* — Sun Jae Yoo

(74) *Attorney, Agent, or Firm* — Wolf, Greenfield & Sacks, P.C.

(57) ABSTRACT

Provided herein are compounds that inhibit HDAC6, a protein whose activity is associated with a variety of diseases (e.g., cancer, neurological disorders). Also provided are pharmaceutical compositions and kits comprising the compounds, and methods of treating HDAC6-related diseases and disorders (e.g., Alzheimer's disease, cancer) with the compounds in a subject, by administering the compounds and/or compositions described herein.

19 Claims, 7 Drawing Sheets

(51) Int. Cl.

| | |
|---|---|
| ***C07D 493/08*** | (2006.01) |
| ***C07D 498/04*** | (2006.01) |
| ***C07D 498/08*** | (2006.01) |
| ***C07D 498/18*** | (2006.01) |

(56) References Cited

U.S. PATENT DOCUMENTS

| | | | |
|---|---|---|---|
| 5,272,158 | A | 12/1993 | Hartman et al. |
| 5,686,018 | A | 11/1997 | Demus et al. |
| 5,728,844 | A | 3/1998 | Muller et al. |
| 5,728,845 | A | 3/1998 | Muller et al. |
| 8,778,931 | B2 | 7/2014 | Gould |
| 9,096,518 | B2 | 8/2015 | Blackburn et al. |
| 9,145,405 | B2 | 9/2015 | Luo et al. |
| 9,650,379 | B2 | 5/2017 | Lee et al. |
| 10,357,493 | B2 | 7/2019 | Yates |
| 10,774,179 | B2 | 9/2020 | Kember et al. |
| 11,938,134 | B2 | 3/2024 | Yates |
| 2005/0165015 | A1 | 7/2005 | Ncube et al. |
| 2006/0052599 | A1 | 3/2006 | Ishibashi et al. |
| 2006/0142321 | A1 | 6/2006 | Jover et al. |
| 2006/0142332 | A1 | 6/2006 | Jover et al. |
| 2008/0214603 | A1 | 9/2008 | Jover et al. |
| 2009/0036480 | A1 | 2/2009 | Jover et al. |
| 2009/0074717 | A1 | 3/2009 | Leivers et al. |
| 2009/0197880 | A1 | 8/2009 | Leivers et al. |
| 2009/0247757 | A1 | 10/2009 | Li et al. |
| 2010/0130499 | A1 | 5/2010 | Tafesse |
| 2011/0039827 | A1 | 2/2011 | Blackburn et al. |
| 2011/0212969 | A1 | 9/2011 | Blackburn et al. |
| 2011/0251184 | A1 | 10/2011 | Blackburn et al. |
| 2011/0288117 | A1 | 11/2011 | Gould et al. |
| 2012/0040953 | A1 | 2/2012 | Barba et al. |
| 2012/0053201 | A1 | 3/2012 | Blackburn et al. |
| 2012/0094997 | A1 | 4/2012 | England et al. |
| 2012/0121502 | A1 | 5/2012 | van Duzer et al. |
| 2012/0165316 | A1 | 6/2012 | Gould |
| 2012/0202834 | A1 | 8/2012 | Aspnes et al. |
| 2014/0275093 | A1 | 9/2014 | Blackburn et al. |
| 2014/0329825 | A1 | 11/2014 | Hebach et al. |
| 2015/0197497 | A1 | 7/2015 | Abeywickrama et al. |
| 2015/0359794 | A1 | 12/2015 | Benz et al. |
| 2016/0039789 | A1 | 2/2016 | England et al. |
| 2017/0096405 | A1 | 4/2017 | Song et al. |
| 2017/0183325 | A1 | 6/2017 | Chen et al. |
| 2017/0313698 | A1 | 11/2017 | Shuttleworth et al. |
| 2017/0349540 | A1 | 12/2017 | Hooker et al. |
| 2018/0215726 | A1 | 8/2018 | Holson et al. |
| 2018/0256572 | A1 | 9/2018 | Yates |
| 2019/0077786 | A1 | 3/2019 | Ueng et al. |
| 2020/0171028 | A1 | 6/2020 | Yates |
| 2021/0253555 | A1 | 8/2021 | Zheng et al. |
| 2022/0088018 | A1 | 3/2022 | Yates |
| 2022/0251043 | A1 | 8/2022 | Pan et al. |
| 2024/0174616 | A1 | 5/2024 | Wagner et al. |
| 2024/0307391 | A1 | 9/2024 | Yates |
| 2025/0179065 | A1 | 6/2025 | Wagner et al. |

FOREIGN PATENT DOCUMENTS

| | | | |
|---|---|---|---|
| CN | 108976223 | A | 12/2018 |
| CN | 109651357 | A | 4/2019 |
| CN | 110950860 | A | 4/2020 |
| CN | 112794860 | A | 5/2021 |
| DE | 3929233 | A1 | 3/1991 |
| DE | 4029466 | A1 | 3/1991 |
| DE | 4307243 | A1 | 10/1993 |
| DE | 10312963 | A1 | 10/2004 |
| EP | 0540334 | A1 | 5/1993 |
| EP | 0625513 | A1 | 11/1994 |
| EP | 2100879 | A1 | 9/2009 |
| EP | 2624832 | B1 | 9/2017 |
| JP | S58-170780 | A | 10/1983 |
| JP | H04-272989 | A | 9/1992 |
| JP | H07-206829 | A | 8/1995 |
| JP | H10-251255 | A | 9/1998 |
| JP | 2002-305083 | A | 10/2002 |
| JP | 2011-8205 | A | 1/2011 |
| JP | 2011-148714 | A | 8/2011 |
| JP | 2013-542994 | A | 11/2013 |
| JP | 2017-190296 | A | 10/2017 |
| WO | WO 1995/11228 | A1 | 4/1995 |
| WO | WO 1997/040017 | A2 | 10/1997 |
| WO | WO 1998/45268 | A1 | 10/1998 |
| WO | WO 1999/019419 | A1 | 4/1999 |
| WO | WO 2000/015637 | A1 | 3/2000 |
| WO | WO 2000/068230 | A1 | 11/2000 |
| WO | WO 2001/072712 | A1 | 10/2001 |
| WO | WO 2001/085695 | A1 | 11/2001 |
| WO | WO 2002/002530 | A1 | 1/2002 |
| WO | WO 2002/026696 | A1 | 4/2002 |
| WO | WO 2002/026703 | A1 | 4/2002 |
| WO | WO 2002/030879 | A2 | 4/2002 |
| WO | WO 2002/098426 | A1 | 12/2002 |
| WO | WO 2003/024448 | A2 | 3/2003 |
| WO | WO 2003/041641 | A2 | 5/2003 |
| WO | WO 2003/074038 | A1 | 9/2003 |
| WO | WO 2003/082288 | A1 | 10/2003 |
| WO | WO 2004/065354 | A1 | 8/2004 |
| WO | WO 2004/069823 | A1 | 8/2004 |
| WO | WO 2004/076386 | A2 | 9/2004 |
| WO | WO 2004/082638 | A2 | 9/2004 |
| WO | WO 2004/098609 | A1 | 11/2004 |
| WO | WO 2005/000300 | A1 | 1/2005 |
| WO | WO 2005/020921 | A2 | 3/2005 |
| WO | WO 2005/051300 | A2 | 6/2005 |
| WO | WO 2005/065681 | A1 | 7/2005 |
| WO | WO 2005/066151 | A2 | 7/2005 |
| WO | WO 2005/092899 | A1 | 10/2005 |
| WO | WO 2006/018308 | A1 | 2/2006 |
| WO | WO 2006/018309 | A1 | 2/2006 |
| WO | WO 2006/044958 | A1 | 4/2006 |
| WO | WO 2006/065842 | A2 | 6/2006 |
| WO | WO 2006/066133 | A2 | 6/2006 |
| WO | WO 2006/084186 | A2 | 8/2006 |
| WO | WO 2006/087309 | A1 | 8/2006 |
| WO | WO 2007/003604 | A2 | 1/2007 |
| WO | WO 2007/011626 | A2 | 1/2007 |
| WO | 2007/029035 WO | A2 | 3/2007 |
| WO | WO 2007/056593 | A2 | 5/2007 |
| WO | WO 2007/084390 | A2 | 7/2007 |
| WO | WO 2007/084455 | A1 | 7/2007 |
| WO | WO 2007/093827 | A1 | 8/2007 |
| WO | WO 2007/098608 | A1 | 9/2007 |
| WO | WO 2007/115408 | A1 | 10/2007 |
| WO | WO 2008/016123 | A1 | 2/2008 |
| WO | WO 2008/060721 | A1 | 5/2008 |
| WO | WO 2008/064265 | A2 | 5/2008 |
| WO | WO 2008/074132 | A1 | 6/2008 |
| WO | WO 2008/097428 | A2 | 8/2008 |
| WO | WO 2008/128335 | A1 | 10/2008 |
| WO | WO 2009/011787 | A1 | 1/2009 |
| WO | WO 2009/011876 | A1 | 1/2009 |
| WO | WO 2009/027349 | A2 | 3/2009 |
| WO | WO 2009/079011 | A1 | 6/2009 |
| WO | WO 2009/112550 | A1 | 9/2009 |
| WO | WO 2009/129036 | A1 | 10/2009 |
| WO | WO 2009/129335 | A2 | 10/2009 |
| WO | WO 2010/028192 | A1 | 3/2010 |
| WO | WO 2010/033906 | A2 | 3/2010 |
| WO | WO 2010/043953 | A2 | 4/2010 |
| WO | WO 2010/054278 | A2 | 5/2010 |
| WO | WO 2010/075551 | A1 | 7/2010 |
| WO | WO 2010/078449 | A2 | 7/2010 |
| WO | WO 2010/081145 | A1 | 7/2010 |
| WO | WO 2010/083141 | A1 | 7/2010 |
| WO | WO 2010/086311 | A1 | 8/2010 |
| WO | WO 2010/088414 | A2 | 8/2010 |
| WO | WO 2010/122151 | A1 | 10/2010 |
| WO | WO 2010/139966 | A1 | 12/2010 |
| WO | WO 2010/151318 | A1 | 12/2010 |
| WO | WO 2011/002520 | A2 | 1/2011 |
| WO | WO 2011/038185 | A2 | 3/2011 |
| WO | WO 2011/058582 | A1 | 5/2011 |

(56) References Cited

FOREIGN PATENT DOCUMENTS

| | | | |
|---|---|---|---|
| WO | WO 2011/088181 | A1 | 7/2011 |
| WO | WO 2011/088187 | A1 | 7/2011 |
| WO | WO 2011/088192 | A1 | 7/2011 |
| WO | WO 2011/106632 | A1 | 9/2011 |
| WO | WO 2011/133888 | A1 | 10/2011 |
| WO | WO 2011/133920 | A1 | 10/2011 |
| WO | WO 2011/137320 | A2 | 11/2011 |
| WO | WO 2011/154374 | A1 | 12/2011 |
| WO | WO 2011/154431 | A1 | 12/2011 |
| WO | WO 2012/012320 | A1 | 1/2012 |
| WO | WO 2012/027564 | A1 | 3/2012 |
| WO | WO 2012/038438 | A1 | 3/2012 |
| WO | WO 2012/045804 | A1 | 4/2012 |
| WO | WO 2012/047852 | A2 | 4/2012 |
| WO | WO 2012/068109 | A2 | 5/2012 |
| WO | WO 2012/076898 | A1 | 6/2012 |
| WO | WO 2012/085038 | A1 | 6/2012 |
| WO | WO 2012/088015 | A2 | 6/2012 |
| WO | WO 2012/103008 | A1 | 8/2012 |
| WO | WO 2012/117027 | A1 | 9/2012 |
| WO | WO 2012/120023 | A1 | 9/2012 |
| WO | WO 2012/123916 | A2 | 9/2012 |
| WO | WO 2012/136111 | A1 | 10/2012 |
| WO | WO 2012/157984 | A2 | 11/2012 |
| WO | WO 2012/158957 | A2 | 11/2012 |
| WO | WO 2012/170867 | A1 | 12/2012 |
| WO | WO 2013/006408 | A1 | 1/2013 |
| WO | WO 2013/008162 | A1 | 1/2013 |
| WO | WO 2013/009810 | A1 | 1/2013 |
| WO | WO 2013/009812 | A1 | 1/2013 |
| WO | WO 2013/009827 | A1 | 1/2013 |
| WO | WO 2013/009830 | A1 | 1/2013 |
| WO | WO 2013/059582 | A2 | 4/2013 |
| WO | WO 2013/062344 | A1 | 5/2013 |
| WO | WO 2013/063549 | A1 | 5/2013 |
| WO | WO 2013/066831 | A1 | 5/2013 |
| WO | WO 2013/066832 | A1 | 5/2013 |
| WO | WO 2013/066833 | A1 | 5/2013 |
| WO | WO 2013/066834 | A1 | 5/2013 |
| WO | WO 2013/066835 | A2 | 5/2013 |
| WO | WO 2013/066836 | A1 | 5/2013 |
| WO | WO 2013/066838 | A1 | 5/2013 |
| WO | WO 2013/066839 | A2 | 5/2013 |
| WO | WO 2013/080120 | A1 | 6/2013 |
| WO | WO 2013/085890 | A1 | 6/2013 |
| WO | WO 2013/101600 | A1 | 7/2013 |
| WO | WO 2013/155262 | A2 | 10/2013 |
| WO | WO 2013/169574 | A2 | 11/2013 |
| WO | WO 2013/185353 | A1 | 12/2013 |
| WO | WO 2014/014900 | A1 | 1/2014 |
| WO | WO 2014/049107 | A1 | 4/2014 |
| WO | WO 2014/059306 | A1 | 4/2014 |
| WO | WO 2014/159210 | A1 | 10/2014 |
| WO | WO 2014/159214 | A1 | 10/2014 |
| WO | WO 2014/159218 | A1 | 10/2014 |
| WO | WO 2014/159224 | A1 | 10/2014 |
| WO | WO 2014/172191 | A1 | 10/2014 |
| WO | WO 2014/178606 | A1 | 11/2014 |
| WO | WO 2014/179528 | A2 | 11/2014 |
| WO | WO 2014/180984 | A1 | 11/2014 |
| WO | WO 2014/181137 | A1 | 11/2014 |
| WO | WO 2014/194280 | A2 | 12/2014 |
| WO | WO 2014/202827 | A1 | 12/2014 |
| WO | WO 2015/017546 | A1 | 2/2015 |
| WO | WO 2015/052160 | A1 | 4/2015 |
| WO | WO 2015/058106 | A1 | 4/2015 |
| WO | WO 2015/087151 | A1 | 6/2015 |
| WO | WO 2015/102426 | A1 | 7/2015 |
| WO | WO 2015/137750 | A1 | 9/2015 |
| WO | WO 2015/154064 | A2 | 10/2015 |
| WO | WO 2015/165960 | A1 | 11/2015 |
| WO | WO 2015/187542 | A1 | 12/2015 |
| WO | WO 2016/012485 | A1 | 1/2016 |
| WO | WO 2016/018795 | A1 | 2/2016 |
| WO | WO 2016/031815 | A1 | 3/2016 |
| WO | WO 2016/040223 | A1 | 3/2016 |
| WO | WO 2016/055786 | A1 | 4/2016 |
| WO | WO 2016/087257 | A1 | 6/2016 |
| WO | WO 2016/087265 | A1 | 6/2016 |
| WO | WO 2016/100619 | A2 | 6/2016 |
| WO | WO 2016/105518 | A1 | 6/2016 |
| WO | WO 2016/120182 | A1 | 8/2016 |
| WO | WO 2016/126721 | A1 | 8/2016 |
| WO | WO 2016/126722 | A1 | 8/2016 |
| WO | WO 2016/126724 | A1 | 8/2016 |
| WO | WO 2016/126725 | A1 | 8/2016 |
| WO | WO 2016/126726 | A1 | 8/2016 |
| WO | WO 2016/128541 | A1 | 8/2016 |
| WO | WO 2016/168598 | A1 | 10/2016 |
| WO | WO 2016/168660 | A1 | 10/2016 |
| WO | WO 2016/179550 | A1 | 11/2016 |
| WO | WO 2016/179554 | A1 | 11/2016 |
| WO | WO 2016/183331 | A1 | 11/2016 |
| WO | WO 2016/190630 | A1 | 12/2016 |
| WO | WO 2016/196771 | A1 | 12/2016 |
| WO | WO 2017/011323 | A1 | 1/2017 |
| WO | WO 2017/014321 | A1 | 1/2017 |
| WO | WO 2017/018803 | A1 | 2/2017 |
| WO | WO 2017/018804 | A1 | 2/2017 |
| WO | WO 2017/018805 | A1 | 2/2017 |
| WO | WO 2017/023133 | A2 | 2/2017 |
| WO | WO 2017/024009 | A1 | 2/2017 |
| WO | WO 2017/029514 | A1 | 2/2017 |
| WO | WO 2017/033946 | A1 | 3/2017 |
| WO | WO 2017/060854 | A1 | 4/2017 |
| WO | WO 2017/065473 | A1 | 4/2017 |
| WO | WO 2017/076757 | A1 | 5/2017 |
| WO | WO 2017/081310 | A1 | 5/2017 |
| WO | WO 2017/081311 | A1 | 5/2017 |
| WO | WO 2017/083368 | A1 | 5/2017 |
| WO | WO 2017/093019 | A1 | 6/2017 |
| WO | WO 2017/109044 | A1 | 6/2017 |
| WO | WO 2017/110861 | A1 | 6/2017 |
| WO | WO 2017/110862 | A1 | 6/2017 |
| WO | WO 2017/111152 | A1 | 6/2017 |
| WO | WO 2017/123568 | A2 | 7/2017 |
| WO | WO 2017/142883 | A1 | 8/2017 |
| WO | WO 2017/156350 | A1 | 9/2017 |
| WO | WO 2017/162834 | A1 | 9/2017 |
| WO | WO 2017/165256 | A1 | 9/2017 |
| WO | WO 2017/190109 | A1 | 11/2017 |
| WO | WO 2017/193030 | A1 | 11/2017 |
| WO | WO 2017/197046 | A1 | 11/2017 |
| WO | WO 2017/208032 | A1 | 12/2017 |
| WO | WO 2017/213252 | A1 | 12/2017 |
| WO | WO 2017/222950 | A1 | 12/2017 |
| WO | WO 2017/222951 | A1 | 12/2017 |
| WO | WO 2017/222952 | A1 | 12/2017 |
| WO | WO 2018/005192 | A1 | 1/2018 |
| WO | WO 2018/050656 | A2 | 3/2018 |
| WO | WO 2018/055135 | A1 | 3/2018 |
| WO | WO 2018/075959 | A1 | 4/2018 |
| WO | WO 2018/085170 | A1 | 5/2018 |
| WO | WO 2018/129533 | A1 | 7/2018 |
| WO | WO 2018/154466 | A1 | 8/2018 |
| WO | WO 2018/165520 | A1 | 9/2018 |
| WO | WO 2018/187553 | A1 | 10/2018 |
| WO | WO 2018/188962 | A1 | 10/2018 |
| WO | WO 2018/189340 | A1 | 10/2018 |
| WO | WO 2018/191360 | A1 | 10/2018 |
| WO | 2018/213364 | A1 | 11/2018 |
| WO | WO 2018/202491 | A1 | 11/2018 |
| WO | WO 2018/219356 | A1 | 12/2018 |
| WO | WO 2019/027054 | A1 | 2/2019 |
| WO | WO 2019/060210 | A1 | 3/2019 |
| WO | WO 2019/100735 | A1 | 5/2019 |
| WO | WO 2019/101709 | A1 | 5/2019 |
| WO | WO 2019/109046 | A1 | 6/2019 |
| WO | WO 2019/110663 | A1 | 6/2019 |
| WO | WO 2019/122323 | A1 | 6/2019 |
| WO | WO 2019/139921 | A1 | 7/2019 |
| WO | WO 2019/164222 | A1 | 8/2019 |
| WO | WO 2019/166824 | A1 | 9/2019 |
| WO | WO 2019/171234 | A1 | 9/2019 |

(56) References Cited

FOREIGN PATENT DOCUMENTS

| | | | |
|---|---|---|---|
| WO | 2019/204550 | A1 | 10/2019 |
| WO | WO 2019/200238 | A1 | 10/2019 |
| WO | WO 2019/212927 | A1 | 11/2019 |
| WO | WO 2019/228289 | A1 | 12/2019 |
| WO | WO 2020/011816 | A1 | 1/2020 |
| WO | WO 2020/022794 | A1 | 1/2020 |
| WO | WO 2020/028150 | A1 | 2/2020 |
| WO | WO 2020/029908 | A1 | 2/2020 |
| WO | WO 2020/039028 | A1 | 2/2020 |
| WO | WO 2020/061112 | A1 | 3/2020 |
| WO | WO 2020/061118 | A1 | 3/2020 |
| WO | WO 2020/061216 | A1 | 3/2020 |
| WO | WO 2020/070610 | A1 | 4/2020 |
| WO | WO 2020/096916 | A2 | 5/2020 |
| WO | WO 2020/106119 | A1 | 5/2020 |
| WO | WO 2020/127974 | A1 | 6/2020 |
| WO | WO 2020/132561 | A1 | 6/2020 |
| WO | WO 2020/158762 | A1 | 8/2020 |
| WO | WO 2020/194272 | A1 | 10/2020 |
| WO | WO 2020/201773 | A1 | 10/2020 |
| WO | WO 2020/207941 | A1 | 10/2020 |
| WO | WO 2020/212479 | A1 | 10/2020 |
| WO | WO 2020/219650 | A1 | 10/2020 |
| WO | WO 2020/223136 | A1 | 11/2020 |
| WO | WO 2020/240492 | A1 | 12/2020 |
| WO | WO 2020/240493 | A1 | 12/2020 |
| WO | WO 2020/245381 | A1 | 12/2020 |
| WO | WO 2020/254494 | A1 | 12/2020 |
| WO | WO 2020/264437 | A1 | 12/2020 |
| WO | WO 2021/021979 | A2 | 2/2021 |
| WO | WO 2021/022076 | A1 | 2/2021 |
| WO | WO 2021/046183 | A1 | 3/2021 |
| WO | WO 2021/048242 | A1 | 3/2021 |
| WO | WO 2021/057872 | A1 | 4/2021 |
| WO | WO 2021/060567 | A1 | 4/2021 |
| WO | WO 2021/067859 | A1 | 4/2021 |
| WO | WO 2021/092151 | A1 | 5/2021 |
| WO | WO 2021/092153 | A1 | 5/2021 |
| WO | WO 2021/092174 | A1 | 5/2021 |
| WO | WO 2021/127643 | A1 | 6/2021 |
| WO | WO 2021/133957 | A1 | 7/2021 |
| WO | WO 2021/172886 | A1 | 9/2021 |
| WO | WO 2021/172887 | A1 | 9/2021 |
| WO | WO 2021/208945 | A1 | 10/2021 |
| WO | WO 2021/210857 | A1 | 10/2021 |
| WO | WO 2021/236491 | A1 | 11/2021 |
| WO | WO 2021/263171 | A1 | 12/2021 |
| WO | WO 2022/013728 | A1 | 1/2022 |
| WO | WO 2022/029041 | A1 | 2/2022 |
| WO | WO 2022/049496 | A1 | 3/2022 |
| WO | WO 2022/081928 | A1 | 4/2022 |
| WO | WO 2022/133551 | A1 | 6/2022 |
| WO | WO 2022/169985 | A1 | 8/2022 |
| WO | WO 2022/174193 | A1 | 8/2022 |
| WO | WO 2022/187690 | A1 | 9/2022 |
| WO | WO 2022/197690 | A1 | 9/2022 |
| WO | WO 2022/215020 | A1 | 10/2022 |
| WO | WO 2022/216616 | A1 | 10/2022 |
| WO | WO 2023/118507 | A2 | 6/2023 |

OTHER PUBLICATIONS

PCT/US2022/015129, Jun. 24, 2022, International Search Report and Written Opinion.

U.S. Appl. No. 15/917,555, filed Mar. 9, 2018, Yates.

U.S. Appl. No. 16/518,279, filed Jul. 22, 2019, Yates.

U.S. Appl. No. 17/336,444, filed Jun. 2, 2021, Yates.

PCT/US2020/044148, Sep. 24, 2020, Invitation to Pay Additional Fees.

PCT/US2020/044148, Feb. 16, 2021, International Search Report and Written Opinion.

PCT/US2020/044148, Feb. 10, 2022, International Preliminary Report on Patentability.

PCT/US2018/021696, May 10, 2018, International Search Report and Written Opinion.

PCT/US2018/021696, Sep. 19, 2021, International Preliminary Report on Patentability.

PCT/US2022/015129, Apr. 29, 2022, Invitation to Pay Additional Fees.

Hubbert et al., HDAC6 is a microtubule-associated deacetylase. Nature. May 23, 2002;417(6887):455-8. doi: 10.1038/417455a.

Kozikowski et al., Brain Penetrable Histone Deacetylase 6 Inhibitor SW-100 Ameliorates Memory and Learning Impairments in a Mouse Model of Fragile X Syndrome. ACS Chem Neurosci. Mar. 20, 2019;10(3):1679-1695. doi: 10.1021/acschemneuro.8b00600. Epub Dec. 14, 2018.

Kozikowski, A.P., Application for Federal Assistance for Study of the New HDAC6i SW-100 as a Treatment for Alzheimer's Disease and Other Tauopathies; Title: Study of the New HDAC6i SW-100 as a Treatment for Alzheimer's Disease and Other Tauopathies for StarWise Therapeutics LLC and University of South Florida. FOA: PAS17-065. Received Mar. 31, 2017. 62 pages.

Krukowski et al., HDAC6 inhibition effectively reverses chemotherapy-induced peripheral neuropathy. Pain. Jun. 2017;158(6):1126-1137. doi: 10.1097/j.pain.0000000000000893.

Lechner et al., Target deconvolution of HDAC pharmacopoeia reveals MBLAC2 as common off-target. Nat Chem Biol. Aug. 2022;18(8):812-820. doi: 10.1038/s41589-022-01015-5. Epub Apr. 28, 2022. Erratum in: Nat Chem Biol. Jul. 15, 2022.

Rivieccio et al., HDAC6 is a target for protection and regeneration following injury in the nervous system. Proc Natl Acad Sci U S A. Nov. 17, 2009;106(46):19599-604. doi: 10.1073/pnas.0907935106. Epub Nov. 2, 2009.

Zhang et al., Design, synthesis, and biological evaluation of novel histone deacetylase 6 selective inhibitors. J Saudi Chem Soc. May 2022;26(3):101450. doi: 10.1016/j.jscs.2022.101450.

International Preliminary Report on Patentability mailed Aug. 17, 2023 for Application No. PCT/US2022/015129.

Invitation to Pay Additional Fees mailed Apr. 3, 2023 for Application No. PCT/US2023/012174.

International Search Report and Written Opinion mailed Jun. 29, 2023 for Application No. PCT/US2023/012174.

International Preliminary Report on Patentability mailed Aug. 15, 2024 for Application No. PCT/US2023/012174.

[No Author Listed], Augustine Therapeutics Showcase Presentation. Recorded at the 2022 Investival Showcase in London, England on Nov. 14, 2022. Accessed Feb. 7, 2023 from <https://www.youtube.com/watch?v=8wJXGd2CgQU>. Selected screenshots. 6 pages.

[No Author Listed], Bringing NHA HDAC6 inhibitors to the clinic for cardiovascular and neurodegenerative disorders. Chong Kun Dang Pharmaceutical Corp. Nature Research Custom Media. Jun. 2022;B41.

[No Author Listed], Cancer Innovates, accelerating early cancer drug discovery. Cancer Innova. Feb. 2022. Accessed from <https://www-cancerinnova-com.translate.goog/en/cancer-innova-acelerando-el-descubrimiento-temprano-de-farmacos-en-cancer/?_x_tr_sl=auto&_x_tr_tl=en&_x_tr_hl=en&_x_tr_pto=wapp>. 10 pages.

[No Author Listed], Highlights of Prescribing Information for ABRAXANE® for Injectable Suspension (paclitaxel protein-bound particles for injectable suspension). Abraxis BioScience, LLC. 2005. 24 pages.

[No Author Listed], Highlights of Prescribing Information for QALSODY® (tofersen) injection, for intrathecal use. Biogen Inc. 2023. 14 pages.

[No Author Listed], Jubilant Therapeutics Inc. receives Orphan Drug Designation for JBI-802 for Acute Myeloid Leukemia (AML) and Small Cell Lung Cancer (SCLC). Jubilant Therapeutics. Jan. 5, 2023. Accessed from <https://www.prnewswire.com/news-releases/jubilant-therapeutics-inc-receives-orphan-drug-designation-for-jbi-802-for-acute-myeloid-leukemia-aml-and-small-cell-lung-cancer-sclc-301714552.html>. 3 pages.

[No Author Listed], NCT03713892: CKD-504 in SAD and MAD in Healthy Korean and Caucasian Adult Male and Female Subjects. Last Update Posted Feb. 24, 2020. 6 pages. Accessed Feb. 7, 2023 from <https://clinicaltrials.gov/ct2/show/NCT03713892>.

(56) References Cited

OTHER PUBLICATIONS

[No Author Listed], NCT04746287: Evaluation of the Safety and Tolerability of CKD-510 in Healthy Subjects. Last Update Posted May 4, 2022. 8 pages. Accessed Feb. 7, 2023 from <https://clinicaltrials.gov/ct2/show/NCT04746287>.
[No Author Listed], NCT05526742: A Study to Evaluate the Relative Bioavailability of Formulations of CKD-510 and to Assess the Effect of Food on the CKD-510 Tablet Formulation in Healthy Subjects. Last Update Posted 2022 Sept 8. 7 pages. Accessed Feb. 7, 2023 from <https://clinicaltrials.gov/ct2/show/NCT05526742>.
[No Author Listed], OnKure Expands Executive Team with the Addition of Chief Scientific Officer and Chief Development Officer. OnKure Therapeutics. Aug. 3, 2021. Accessed from <https://onkuretherapeutics.com/press-release/onkure-expands-executive-team-and-appoints-head-of-discovery-chief-financial-officer-and-general-counsel-2/>. 4 pages.
[No Author Listed], OnKure Therapeutics Appoints Jennifer R. Diamond, M.D., as Chief Medical Officer. OnKure Therapeutics. Oct. 14, 2021. Accessed from <https://onkuretherapeutics.com/year/2021/onkure-therapeutics-appoints-jennifer-r-diamond-m-d-as-chief-medical-officer/>. 3 pages.
[No Author Listed], Oryzon collaborates with the CMT Research Foundation in the US. Oryzon Press Release. Jul. 26, 2022. 2 pages.
[No Author Listed], Pipeline Program and Development Status. OnKure Therapeutics. May 13, 2021. Accessed from <https://web.archive.org/web/20210513123624/https:/onkuretherapeutics.com/pipeline/>. 2 pages.
[No Author Listed], Pipeline Program and Development Status. OnKure Therapeutics. Oct. 8, 2021. Accessed from <https://web.archive.org/web/20210513123624/https:/onkuretherapeutics.com/pipeline/>. 2 pages.
[No Author Listed], Precision oral medicines with enhanced therapeutic index. Jubilant Therapeutics. Corporate Presentation. Jan. 2023. 38 pages.
[No Author Listed], Scaling New Heights in the Fight Against Heart Disease. Tenaya Therapeutics. Corporate Presentation. 2022 Sep. 38 pages.
[No Author Listed], Tenaya Therapeutics Announces TN-201 IND Clearance and Anticipated 2023 Milestones. GlobeNewswire. Jan. 9, 2023. Accessed from <https://www.globenewswire.com/news-release/2023/01/09/2585026/0/en/Tenaya-Therapeutics-Announces-TN-201-IND-Clearance-and-Anticipated-2023-Milestones.html>. 7 pages.
[No Author Listed], The basque-based company Quimatryx licenses a cancer drug for 92 million dollars. Basque Press. Jul. 29, 2022. Accessed from <https://basque.press/the-guipuzcoa-based-company-quimatryx-licenses-a-cancer-drug-for-92-million-dollars-la-empresa-guipuzcoana-quimatryx-licencia-un-farmaco-contra-el-cancer-por-92-millones-de-dolares/>. 5 pages.
Bae et al., CKD-506: A novel HDAC6-selective inhibitor that exerts therapeutic effects in a rodent model of multiple sclerosis. Sci Rep. Jul. 14, 2021;11(1):14466. doi: 10.1038/s41598-021-93232-6.
Bae et al., CKD-510, a novel non-hydroxamic acid histone deacetylase 6 (HDAC6) inhibitor for Charcot-Marie-Tooth disease type 1A. J Peripher Nerv Syst.2022;27(Suppl. 3):S4. Abstract Only.
Buommino et al., Synergism of a Novel 1,2,4-oxadiazole-containing Derivative with Oxacillin against Methicillin-Resistant Staphylococcus aureus. Antibiotics (Basel). Oct. 16, 2021;10(10):1258. doi: 10.3390/antibiotics10101258.
Choi et al., Acetylation changes tau interactome to degrade tau in Alzheimer's disease animal and organoid models. Aging Cell. Jan. 2020;19(1):e13081. doi: 10.1111/acel.13081. Epub Nov. 25, 2019.
Choi et al., CKD-506, a novel HDAC6-selective inhibitor, improves renal outcomes and survival in a mouse model of systemic lupus erythematosus. Sci Rep. Nov. 23, 2018;8(1):17297. doi: 10.1038/s41598-018-35602-1.
Faridoon et al., Medicinal chemistry insights into non-hydroxamate HDAC6 selective inhibitors. Med Chem Res. Oct. 31, 2022;32(1):1-14. doi: 10.1007/s00044-022-02987-8.
Gajendran et al., Novel dual LSD1/HDAC6 inhibitor for the treatment of cancer. PLoS One. Jan. 3, 2023;18(1):e0279063. doi: 10.1371/journal.pone.0279063.
Ha et al., A novel histone deacetylase 6 inhibitor improves myelination of Schwann cells in a model of Charcot-Marie-Tooth disease type 1A. Br J Pharmacol. Nov. 2020;177(22):5096-5113. doi: 10.1111/bph.15231. Epub Sep. 27, 2020.
Hong et al., CKD-510, a novel selective HDAC6 inhibitor, is well-tolerated and increased acetyl-tubulin in healthy volunteers. J Peripher Nerv Syst.2022;27(Suppl. 3):S76-7. Abstract Only.
James et al., Development of EKZ-102, a potent and selective CNS-penetrant HDAC6 inhibitor with the potential to benefit a broad population of people with ALS. Oct. 23, 2024. Poster. 3 pages.
Jeong et al., Therapeutic Potential of CKD-504, a Novel Selective Histone Deacetylase 6 Inhibitor, in a Zebrafish Model of Neuromuscular Junction Disorders. Mol Cells. Apr. 30, 2022;45(4):231-242. doi: 10.14348/molcells.2022.5005.
Kim et al., HDAC6 Inhibitors Rescued the Defective Axonal Mitochondrial Movement in Motor Neurons Derived from the Induced Pluripotent Stem Cells of Peripheral Neuropathy Patients with HSPB1 Mutation. Stem Cells Int. 2016;2016:9475981. doi: 10.1155/2016/9475981. Epub Dec. 26, 2016.
Lee et al., Novel Histone Deacetylase 6 Inhibitor CKD-506 Inhibits NF-κB Signaling in Intestinal Epithelial Cells and Macrophages and Ameliorates Acute and Chronic Murine Colitis. Inflamm Bowel Dis. May 12, 2020;26(6):852-862. doi: 10.1093/ibd/izz317.
Lee et al., Novel Histone Deacetylase 6 Inhibitor Confers Anti-inflammatory Effects and Enhances Gut Barrier Function. Gut Liver. Sep. 27, 2022. doi: 10.5009/gnl220159. Epub ahead of print.
Li et al., A Novel HDAC6 Inhibitor, CKD-504, is Effective in Treating Preclinical Models of Huntington's Disease. BMB Rep. Jan. 3, 2023:5747. Epub ahead of print.
Li et al., Abstract 4441: CS3003, an HDAC6-selective inhibitor, improves anti-PD-1 immune checkpoint blockade therapy efficacy. Proceedings of the Annual Meeting of the American Association for Cancer Research. Apr. 27-28, 2020 and Jun. 22-24. Philadelphia, PA. Cancer Res 2020;80(16 Suppl). Poster. 1 page.
Mejzini et al., ALS Genetics, Mechanisms, and Therapeutics: Where Are We Now? Front Neurosci. Dec. 6, 2019;13:1310. doi: 10.3389/fnins.2019.01310.
Park et al., Therapeutic potential of CKD-506, a novel selective histone deacetylase 6 inhibitor, in a murine model of rheumatoid arthritis. Arthritis Res Ther. Jul. 25, 2020;22(1):176. doi: 10.1186/s13075-020-02258-0.
Shen et al., Structural and in Vivo Characterization of Tubastatin A, a Widely Used Histone Deacetylase 6 Inhibitor. ACS Med Chem Lett. Jan. 15, 2020;11(5):706-712. doi: 10.1021/acsmedchemlett.9b00560.
Shukla et al., Histone Deacetylases Inhibitors in Neurodegenerative Diseases, Neuroprotection and Neuronal Differentiation. Front Pharmacol. Apr. 24, 2020;11:537. doi: 10.3389/fphar.2020.00537.
Staff et al., Chemotherapy-induced peripheral neuropathy: A current review. Ann Neurol. Jun. 2017;81(6):772-781. doi: 10.1002/ana.24951. Epub Jun. 5, 2017. Author Manuscript, 17 pages.
Tang et al., Identification of a novel aminotetralin class of HDAC6 and HDAC8 selective inhibitors. J Med Chem. Oct. 9, 2014;57(19):8026-34. doi: 10.1021/jm5008962. Epub Sep. 30, 2014.
Koole et al., Clinical validation of the novel HDAC6 radiotracer [18F]EKZ-001 in the human brain. Eur J Nucl Med Mol Imaging. Feb. 2021;48(2):596-611. doi: 10.1007/s00259-020-04891-y. Epub Jul. 8, 2020.
Invitation to Pay Additional Fees mailed Sep. 24, 2020 for Application No. PCT/US2020/044148.
International Search Report and Written Opinion mailed Feb. 16, 2021 for Application No. PCT/US2020/044148.
International Preliminary Report on Patentability mailed Feb. 10, 2022 for Application No. PCT/US2020/044148.
International Search Report and Written Opinion mailed May 10, 2018 for Application No. PCT/US2018/021696.
International Preliminary Report on Patentability mailed Sep. 19, 2021 for Application No. PCT/US2018/021696.

(56) References Cited

OTHER PUBLICATIONS

Invitation to Pay Additional Fees mailed Apr. 29, 2022 for Application No. PCT/US2022/015129.
[No Author Listed], CAS Registration No. 1332894-18-4. Registry (STN). Sep. 20, 2011. 1 page.
[No Author Listed], CAS Registration No. 1860746-44-6. Registry (STN). Feberuary 5, 2016. 1 page.
[No Author Listed], CAS Registration No. 1875612-53-5. Registry (STN). Feb. 28, 2016. 1 page.
[No Author Listed], CAS Registration No. 73779-41-6. Registry (STN). Nov. 16, 1984. 1 page.
[No Author Listed], HDAC: Inhibitory Selectivity. AdooQ Bioscience. 21 pages. Accessed May 1, 20228 from <https://www.adooq.com/epigenetics-histone-deacetylase-hdac.html?gclid=EAIaIQobChMI4K_CiJzk9AIVpQaICR2_rgPTEAMYASAAEgKHnvD_BwE>.
[No Author Listed], Pharmacology review for belinostat. Center for Drug Evaluation and Research. Application No. 206256Orig1s000. May 22, 2014. 98 pages.
[No Author Listed], Pharmacology review for panobinostat. Center for Drug Evaluation and Research. Application No. 205353Orig1s000. Sep. 2, 2014. 125 pages.
[No Author Listed], Pharmacology review for vorinostat. Center for Drug Evaluation and Research. Application No. 21-991. Oct. 5, 2006. 106 pages.
[No Author Listed], PubChem Substance Record for PubChem SID 227322283, SCHEMBL1075847. Accessed Sep. 21, 2020. 9 pages.
[No Author Listed], PubChem Substance Record for PubChem SID 274711921, 2-[5-(3-Nitrophenyl)furfuryl]-1,2,3,4-tetrahydroisoquinoline-7-carbohydroximic acid. Accessed Sep. 21, 2020. 8 pages.
[No Author Listed], The McQuade Center for Strategic Research and Development and Eikonizo Therapeutics Enter Agreement to Develop Treatments for Patients with Rare Diseases. Business Wire. Feb. 9, 2021.
Adalbert et al., Novel HDAC6 Inhibitors Increase Tubulin Acetylation and Rescue Axonal Transport of Mitochondria in a Model of Charcot-Marie-Tooth Type 2F. ACS Chem Neurosci. Feb. 5, 2020;11(3):258-267. doi: 10.1021/acschemneuro.9b00338. Epub Jan. 8, 2020.
Beshore et al., Redefining the Histone Deacetylase Inhibitor Pharmacophore: High Potency with No. Zinc Cofactor Interaction. ACS Med Chem Lett. Mar. 7, 2021;12(4):540-547. doi: 10.1021/acsmedchemlett.1c00074.
Blackburn et al., Histone deacetylase inhibitors derived from 1,2,3,4-tetrahydropyrrolo[1,2-alpyrazine and related heterocycles selective for the HDAC6 isoform. Bioorg Med Chem Lett. Dec. 1, 2014;24(23):5450-4. doi: 10.1016/j.bmcl.2014.10.022.
Blackburn et al., Potent histone deacetylase inhibitors derived from 4-(aminomethyl)-N-hydroxybenzamide with high selectivity for the HDAC6 isoform. J Med Chem. Sep. 26, 2013;56(18):7201-11. doi: 10.1021/jm400385r. Epub Sep. 4, 2013.
Bondarev et al., Recent developments of HDAC inhibitors: Emerging indications and novel molecules. Br J Clin Pharmacol. 2021; 87( 12): 4577- 4597. https://doi.org/10.1111/bcp.14889.
Chang et al., The Role of HDAC6 in Autophagy and NLRP3 Inflammasome. Front Immunol. Oct. 27, 2021;12:763831. doi: 10.3389/fimmu.2021.763831.
Cragin et al., A Novel Zinc Binding Group for HDAC6 Inhibition. FASEB J. May 2022;36 Suppl 1. doi: 10.1096/fasebj.2022.36.S1.R3604. Abstract Only.
Fazal et al., HDAC6 inhibition restores TDP-43 pathology and axonal transport defects in human motor neurons with TARDBP mutations. EMBO J. 2021;40:e106177.
Gaisina et al., Activation of Nrf2 and Hypoxic Adaptive Response Contribute to Neuroprotection Elicited by Phenylhydroxamic Acid Selective HDAC6 Inhibitors. ACS Chem Neurosci. May 16, 2018;9(5):894-900. doi: 10.1021/acschemneuro.7b00435. Epub Jan. 17, 2018.
Hendricks et al., In vivo PET imaging of histone deacetylases by 18F-suberoylanilide hydroxamic acid (18F-SAHA). J Med Chem. Aug. 11, 2011;54(15):5576-82. doi: 10.1021/jm200620f. Epub Jul. 18, 2011.
Hu et al., 3D-QSAR Studies of HDAC6 Inhibitors Using Docking-Based Alignment. Lett Drug Des Discov. Jul. 2017;14(7):798-810. doi: 10.2174/1570180813666161028165151.
Kattar, et al., Parallel medicinal chemistry approaches to selective HDAC1/HDAC2 inhibitor (SHI-1:2) optimization. Bioorg Med Chem Lett. Feb. 1, 20095;19(4):1168-72. doi: 10.1016/j.bmcl.2008.12.083. Epub Dec. 25, 2008.
Kim et al., HDAC6 inhibitor blocks amyloid beta-induced impairment of mitochondrial transport in hippocampal neurons. PLoS One. 2012;7(8):e42983. doi: 10.1371/journal.pone.0042983. Epub Aug. 22, 2012.
Kleinschek et al., Potent and Selective Non-hydroxamate Histone Deacetylase 8 Inhibitors. ChemMedChem. Dec. 6, 2016;11(23):2598-2606. doi: 10.1002/cmdc.201600528. Epub Nov. 9, 2016.
Lipczynska-Kochany et al., Mutagenicity of pyridine- and quinoline-carbohydroxamic acid derivatives. Mutat Res. Mar. 1984;135(3):139-48. doi: 10.1016/0165-1218(84)90114-9.
Liu et al., MiR-222-3p Inhibits Trophoblast Cell Migration and Alleviates Preeclampsia in Rats Through Inhibiting HDAC6 and Notch1 Signaling. Reprod Sci. Nov. 18, 2021. doi: 10.1007/s43032-021-00793-y. Epub ahead of print. PMID: 34796469.
Mahmoud et al., Nimbolide inhibits 2D and 3D prostate cancer cells migration, affects microtubules and angiogenesis and suppresses B-RAF/p.ERK-mediated in vivo tumor growth. Phytomedicine. Jan. 2022;94:153826. doi: 10.1016/j.phymed.2021.153826. Epub Nov. 1, 2021. PMID: 34775358.
Martin et al., Discovery of novel N-hydroxy-2-arylisoindoline-4-carboxamides as potent and selective inhibitors of HDAC11. Bioorg Med Chem Lett. Jul. 1, 2018;28(12):2143-2147. doi: 10.1016/j.bmcl.2018.05.021. Epub May 9, 2018.
Mcmahon, VEGF receptor signaling in tumor angiogenesis. The Oncologist. 2000;5(suppl 1):3-10.
Munakata et al., Mutagenicity of N-acylglycinohydroxamic acids and related compounds. J Pharmacobiodyn. Nov. 1980;3(11):557-61. doi: 10.1248/bpb1978.3.557.
Neidle, Cancer Drug Design and Discovery. Elsevier/Academic Press. 2008; 427-431.
Onishi et al., A novel orally active HDAC6 inhibitor T-518 shows a therapeutic potential for Alzheimer's disease and tauopathy in mice. Sci Rep. Jul. 29, 2021;11(1):15423. doi: 10.1038/s41598-021-94923-w.
Pinedo et al., Translational Research: The Role of VEGF in Tumor Angiogenesis. The Oncologist. 2000;5(Suppl 1):1-2.
Sandrone et al., Role of Fluorination in the Histone Deacetylase 6 (HDAC6) Selectivity of Benzohydroxamate-Based Inhibitors. ACS Med Chem Lett. Oct. 11, 2021;12(11):1810-1817. doi: 10.1021/acsmedchemlett.1c00425.
Selenica et al., Histone deacetylase 6 inhibition improves memory and reduces total tau levels in a mouse model of tau deposition. Alzheimers Res Ther. Feb. 27, 2014;6(1):12. doi: 10.1186/alzrt241.
Shen et al., A patent review of histone deacetylase 6 inhibitors in neurodegenerative diseases (2014-2019). Expert Opin Ther Pat. 2020;30(2):121-136. doi:10.1080/13543776.2019.1708901.
Shen et al., Bicyclic-Capped Histone Deacetylase 6 Inhibitors with Improved Activity in a Model of Axonal Charcot-Marie-Tooth Disease. ACS Chem Neurosci. Feb. 17, 2016;7(2):240-58. doi: 10.1021/acschemneuro.5b00286. Epub Dec. 7, 2015.
Shen et al., Why Hydroxamates May Not Be the Best Histone Deacetylase Inhibitors—What Some May Have Forgotten or Would Rather Forget? ChemMedChem. Jan. 5, 2016;11(1):15-21. doi: 10.1002/cmdc.201500486. Epub Nov. 25, 2015.
Simoes-Pires et al., HDAC6 as a target for neurodegenerative diseases: what makes it different from the other HDACs? Mol Neurodegener. Jan. 29, 2013;8:7. doi: 10.1186/1750-1326-8-7.
Sixto-Lopez et al., silico design of HDAC6 inhibitors with neuroprotective effects. J Biomol Struct Dyn. Nov. 16, 2021:1-19. doi: 10.1080/07391102.2021.2001378. Epub ahead of print.

(56) References Cited

OTHER PUBLICATIONS

Wang et al., Mutagenicity and antibacterial activity of hydroxamic acids. Antimicrob Agents Chemother. Apr. 1977;11(4):753-5. doi: 10.1128/AAC.11.4.753.
Wang, C.Y., Mutagenicity of hydroxamic acids for Salmonella typhimurium. Mutat Res. Sep. 1977;56(1):7-12. doi: 10.1016/0027-5107(77)90235-4.
Watson et al., Aromatic C-F Interactions Influence Binding Mode of Inhibitors in HDAC6. FASEB J. May 2022;36 Suppl 1. doi: 10.1096/fasebj.2022.36.S1.R2257. Abstract Only.
Wei et al., Mutagenicity of some monoaromatic hydroxamic acids. Toxicol Lett. Jan. 1985;24(1):111-6. doi: 10.1016/0378-4274(85)90148-1.
Zhang et al., Tubastatin A/ACY-1215 improves cognition in Alzheimer's disease transgenic mice. J Alzheimers Dis. 2014;41(4):1193-205. doi: 10.3233/JAD-140066.
International Search Report and Written Opinion mailed Jun. 24, 2022 for Application No. PCT/US2022/015129.
[No Author Listed], CAY10603: Catalog No. S7596; Synonyms: BML-281. Apr. 2015. 4 pages. Accessed Jul. 19, 2022 from <https://www.selleckchem.com/products/cay10603.html?gclid=CjwKCAjwoMSWBhAdEiwAVJ2ndvOI8KYzzn0XiWLIF5DRM50crFNHcVSDwVsA6XALwr0yzmIKn10muxoCgkcQAvD_BwE>.
Xu et al., Design, Synthesis, Bioactivity Evaluation, Crystal Structures, and In Silico Studies of New β-Amino Amide Derivatives as Potential Histone Deacetylase 6 Inhibitors. Molecules. May 22, 2022;27(10):3335. doi: 10.3390/molecules27103335.
Yang et al., Phenotypic screening with deep learning identifies HDAC6 inhibitors as cardioprotective in a BAG3 mouse model of dilated cardiomyopathy. Sci Transl Med. Jul. 6, 2022;14(652):1-15. doi: 10.1126/scitranslmed.ab15654.

* cited by examiner

HDAC6 INHIBITORS AND USES THEREOF

RELATED APPLICATIONS

This application is a national stage filing under 35 U.S.C. § 371 of International PCT Application PCT/US2020/044148, filed Jul. 30, 2020, which claims priority under 35 U.S.C. § 119(e) to U.S. Provisional Application, U.S. Ser. No. 62/880,284, filed on Jul. 30, 2019, each of which is incorporated herein by reference in its entirety.

BACKGROUND

Histone deacetylases (HDACs) are divided into four classes based on sequence homology. HDAC6, a class II HDAC, is a cytoplasmic, microtubule-associated enzyme. HDAC6 has unique features among the HDAC paralogs. Unlike other HDACs, HDAC6 contains two deacetylase domains and an ubiquitin binding domain allowing HDAC6 to function in distinct cell signaling systems involving protein acetylation and ubiquitination, respectively. Importantly, it does not deacetylate histones. HDAC6 deacetylates tubulin, tau, Hsp90, cortactin, and other emerging targets. HDAC6 deacetylase function is involved in microtubule-based cargo transport, protein degradation/recycling and stress-induced glucocorticoid receptor signaling. HDAC6 deacetylase function is also involved in cell morphology, motility and migration, as well as cell growth and survival. In addition to deacetylase functions, HDAC6 forms complexes with partner proteins linked to ubiquitin-dependent functions, and influences protein aggregation, trafficking and degradation via the aggresome pathway. HDAC6 expression was shown to be elevated in postmortem brain samples from Alzheimer's disease patients. Aberrant expression of HDAC6 also correlates with tumorigenesis and is linked to the metastasis of cancer cells.

SUMMARY

The cytosolic location, distinct substrates, and structure of HDAC6 is unique among the HDAC paralogs and HDAC6-selective treatment regimens show promise to avoid many of the side effects of first-generation pan-HDAC inhibitors. However, paralog selectivity is difficult to obtain. The present disclosure stems from the recognition that the unique structure and function of HDAC6, among the HDAC paralogs, provides an opportunity for the design of selective HDAC6 inhibitors. The present disclosure also recognizes that targeting HDAC6-mediated pathways may provide improved treatments for neurological disorders. In relation to neurodegeneration, HDAC6 (1) impairs microtubule function by deacetylating tubulin, which leads to defects in axonal and mitochondrial transport; (2) promotes tau aggregation by deacetylating tau, which leads to pathological tau phosphorylation and neurofibrillary tangle formation; and (3) prevents degradation of HSP90 client proteins, including misfolded tau, by deacetylating HSP90, which stabilizes the chaperone complex associated with protein refolding/recycling. Thus, the present disclosure provides brain-penetrant, selective HDAC6 inhibitors. These compounds provide new compositions and methods for the treatment of diseases associated with HDAC6 activity (e.g., neurological disorders, such as Alzheimer's disease and other tauopathies, amyotrophic lateral sclerosis, and cancer).

In one aspect, provided are compounds of Formula (I):

(I)

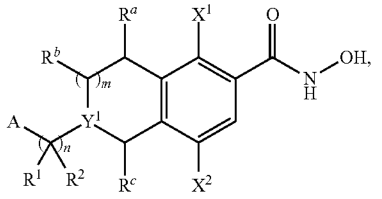

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro; provided that at least one of $X^1$ and $X^2$ is fluoro;

A is substituted or unsubstituted alkyl, substituted or unsubstituted carbocyclyl, substituted or unsubstituted heterocyclyl, substituted or unsubstituted heteroaryl, or substituted or unsubstituted aryl;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl;

$R^a$ is hydrogen or is joined with $R^c$ to form a substituted or unsubstituted bridged ring;

$R^b$ is hydrogen or is joined with $R^c$ to form a substituted or unsubstituted bridged ring;

$R^c$ is hydrogen or substituted or unsubstituted alkyl or is joined with at least one of $R^a$ and $R^b$ to form a substituted or unsubstituted bridged ring;

m is 0 or 1; and n is 0 or 1.

In certain embodiments, the compounds of Formula (I) are compounds of Formula (I-a), (I-b), (I-c), or (I-d):

(I-a)

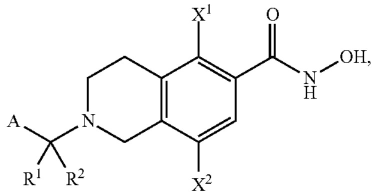

(I-b)

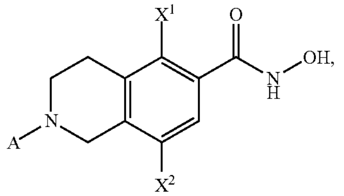

(I-c)

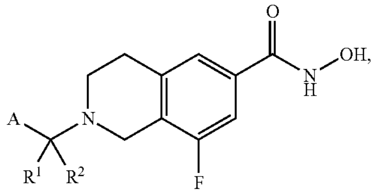

-continued
(I-d)
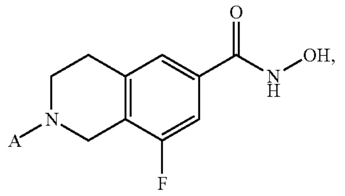
or pharmaceutically acceptable salts thereof.
Exemplary compounds of Formula (I) include, but are not limited to:
1
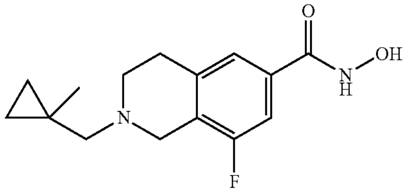
2
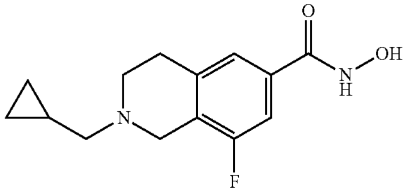
3
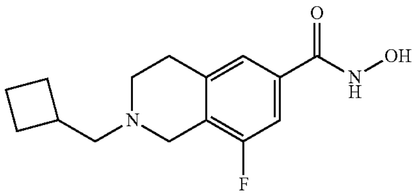
4
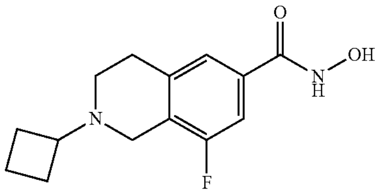
5
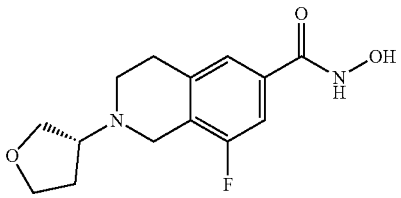
6
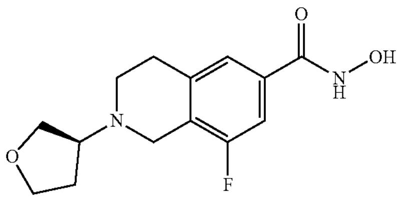
-continued
7
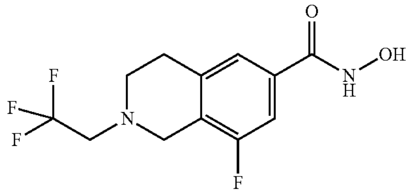
8
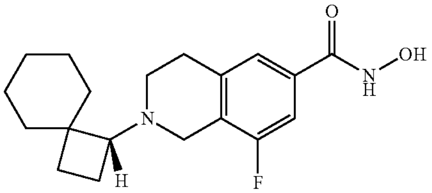
9
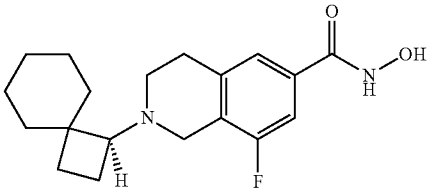
10
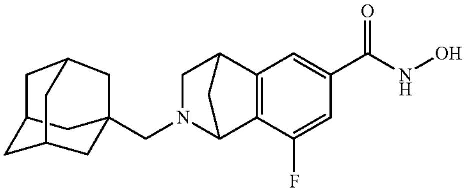
11
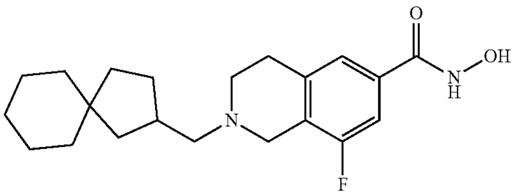
12
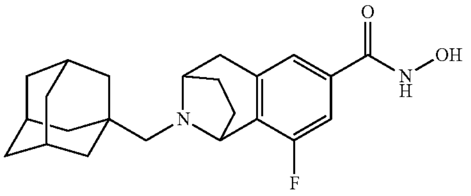
13
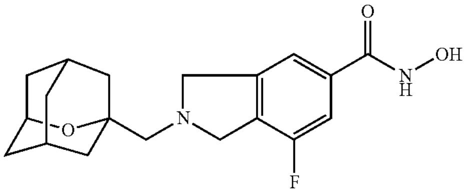
14
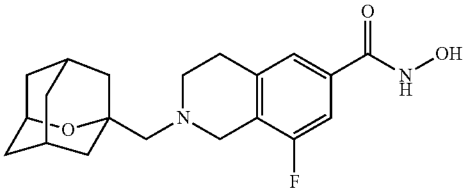

-continued
15
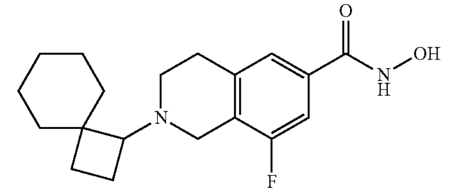
16
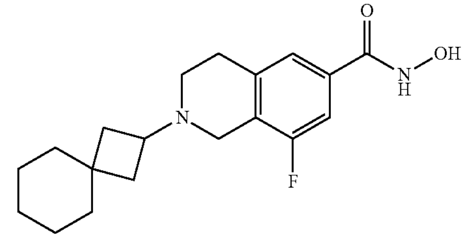
17
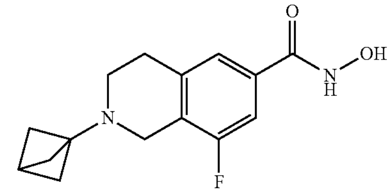
18
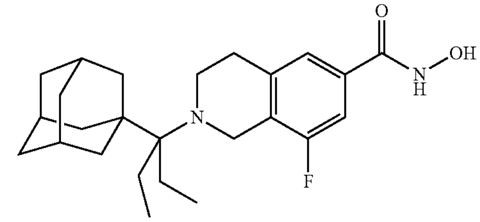
19
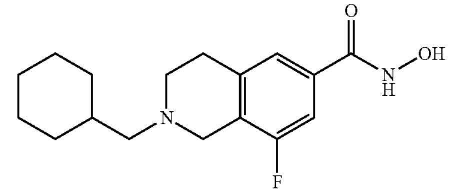
20
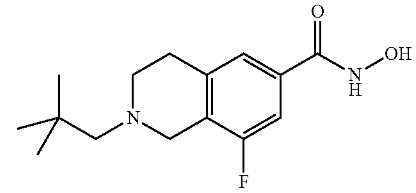
21
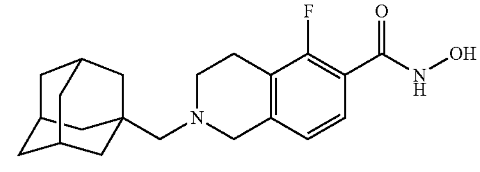
-continued
22
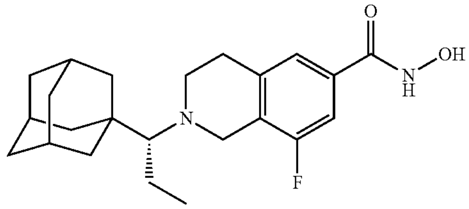
23
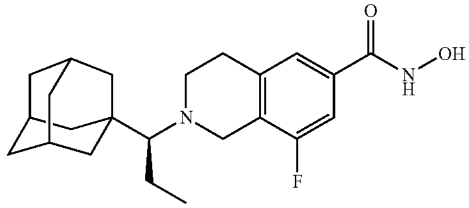
24
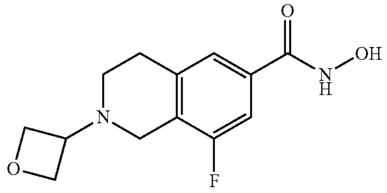
25
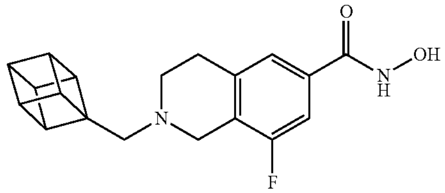
26
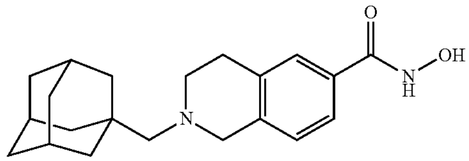
27
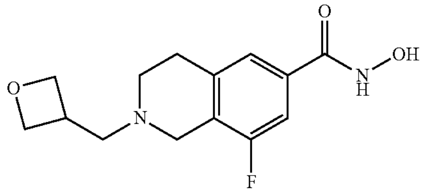
28
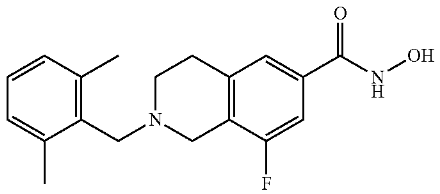
29
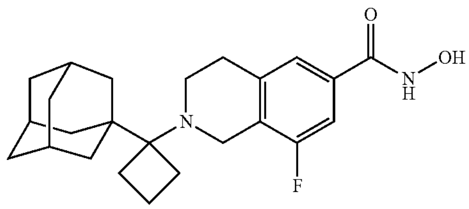

-continued

30

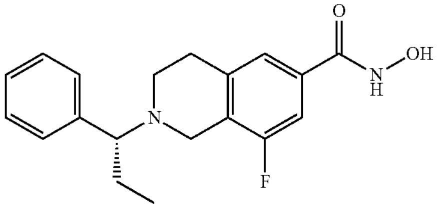

31

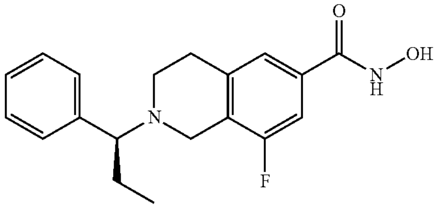

32

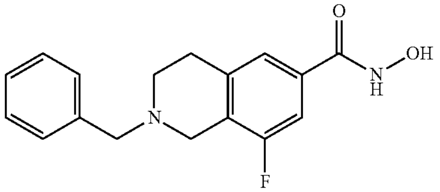

33

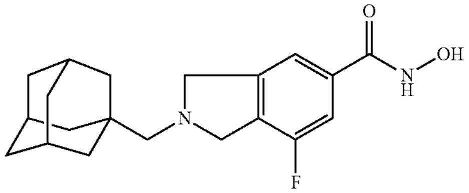

34

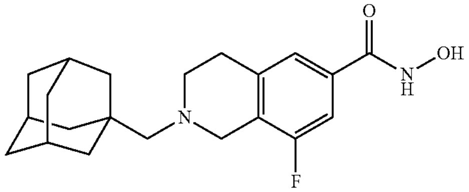

35

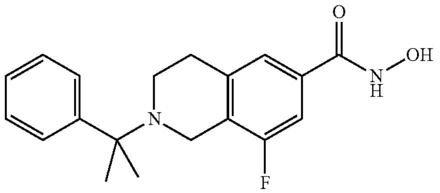

107

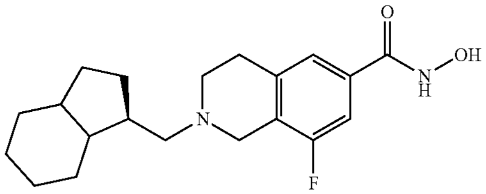

-continued

108

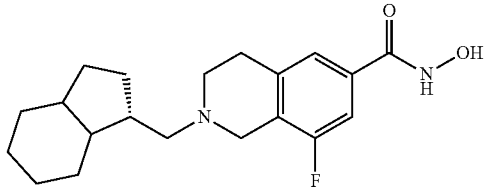

109

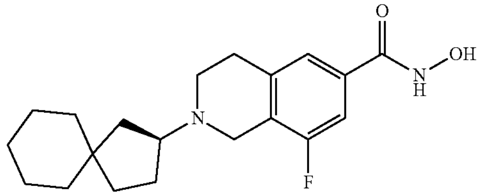

110

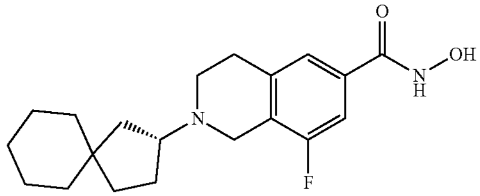

111

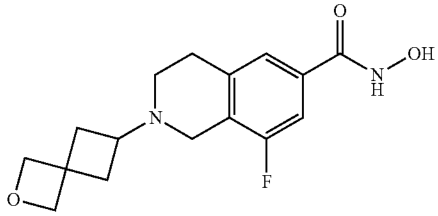

112

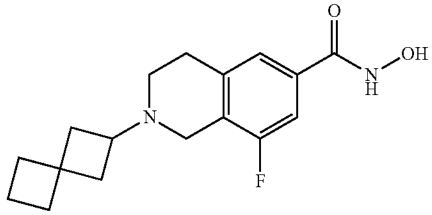

and pharmaceutically acceptable salts thereof.

In another aspect, provided are compounds of Formula (II):

(II)

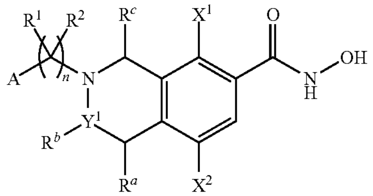

or a pharmaceutically acceptable salt thereof, wherein:

$X^1$ is hydrogen or fluoro;

$X^2$ is hydrogen or fluoro;

$Y^1$ is nitrogen or $CR^x$;

each A is independently hydrogen, substituted or unsubstituted alkyl, substituted or unsubstituted carbocyclyl, substituted or unsubstituted heterocyclyl, substituted or unsubstituted heteroaryl, or substituted or unsubstituted aryl;

each $R^1$ is independently hydrogen or substituted or unsubstituted alkyl;

each $R^2$ is independently hydrogen or substituted or unsubstituted alkyl; or $R^1$ and $R^2$ together form a substituted or unsubstituted heterocyclyl, or a substituted or unsubstituted cycloalkyl;

$R^x$ is hydrogen or substituted or unsubstituted alkyl;

$R^a$ is hydrogen or is joined with $R^c$ to form a substituted or unsubstituted bridged ring;

$R^b$ is hydrogen, substituted or unsubstituted alkyl, or $A(CR^1R^2)_n$—, or is joined with $R^c$ to form a substituted or unsubstituted bridged ring;

$R^c$ is hydrogen or substituted or unsubstituted alkyl or is joined with at least one of $R^a$ and $R^b$ to form a substituted or unsubstituted bridged ring; and each n is independently 0 or 1.

In certain embodiments, the compounds of Formula (II) are compounds of Formula (II-a), (II-b), (II-c), (II-d), (II-e), (II-f), (II-g), or (II-hl:

(II-a)

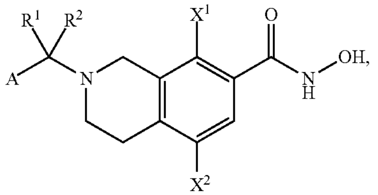

(II-b)

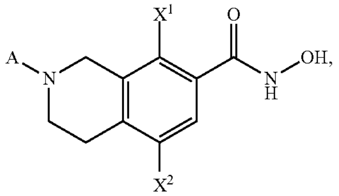

(II-c)

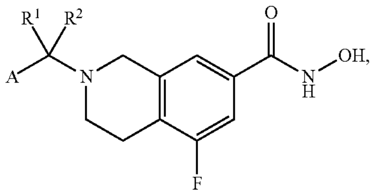

(II-d)

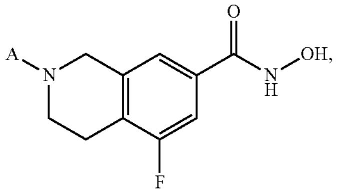

(II-e)

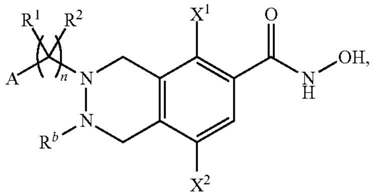

-continued (II-f)

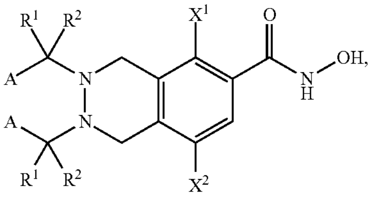

(II-g)

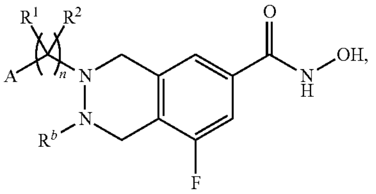

(II-h)

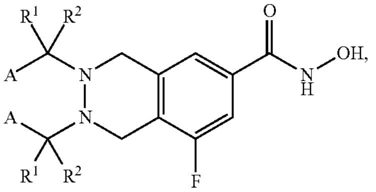

or pharmaceutically acceptable salts thereof.

Exemplary compounds of Formula (II) include, but are not limited to:

115

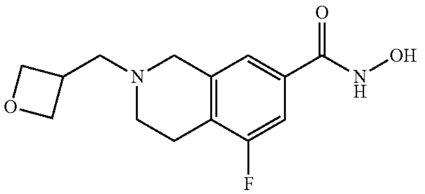

114

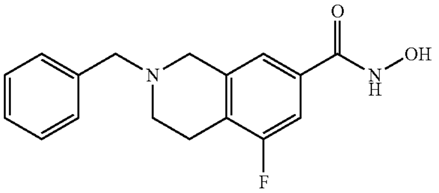

113

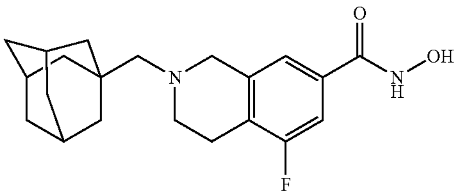

39

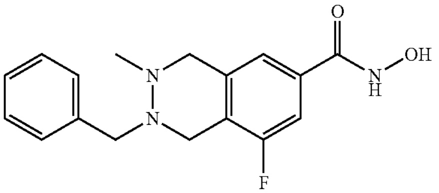

-continued

117

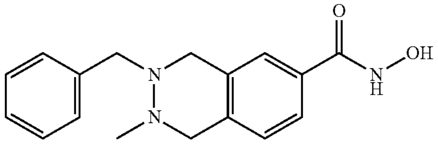

41

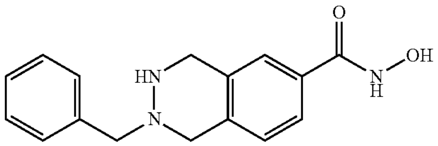

42

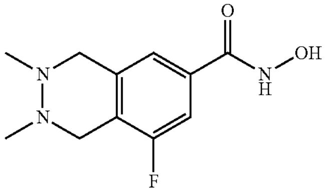

43

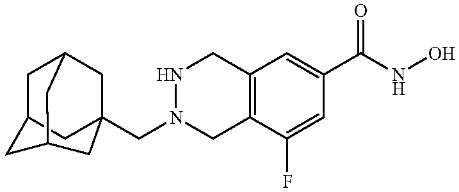

44

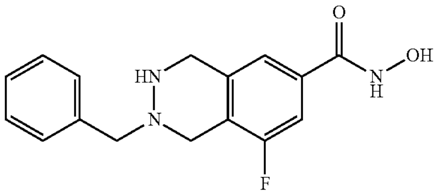

116

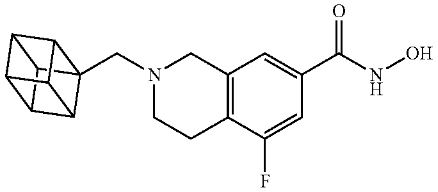

118

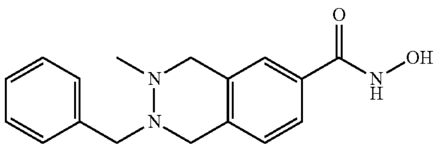

and pharmaceutically acceptable salts thereof.

In another aspect, provided are compounds of Formula (III):

(III)

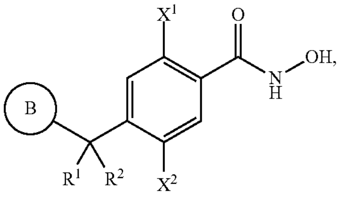

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl; and B is a substituted or unsubstituted polycyclic spiro ring system, a substituted or unsubstituted bridged ring system,

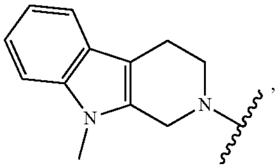
,
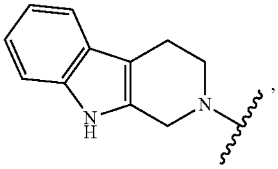
,
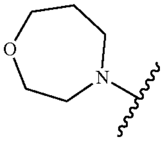
,
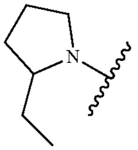
, or
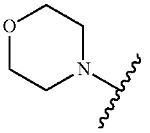
.

In certain embodiments, the compounds of Formula (III) are compounds of Formula (III-a), (III-b), or (III-c):

(III-a)

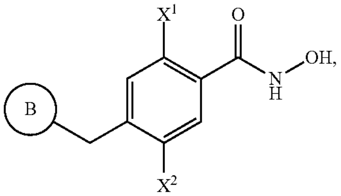

(III-b)

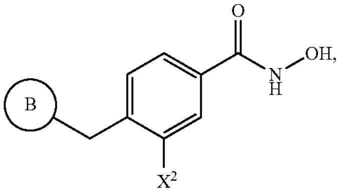

-continued
(III-c)
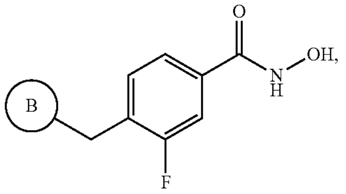
or pharmaceutically acceptable salts thereof.
Exemplary compounds of Formula (III) include, but are not limited to:
45
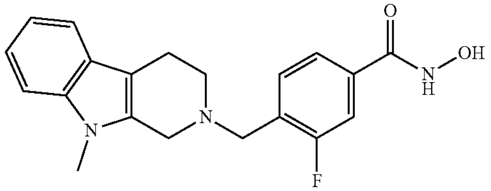
46
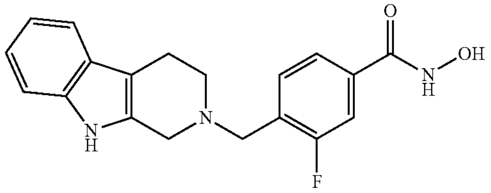
47
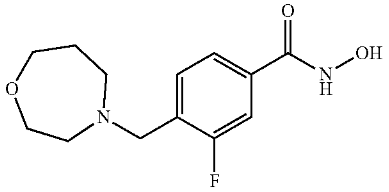
48
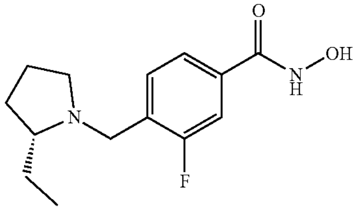
49
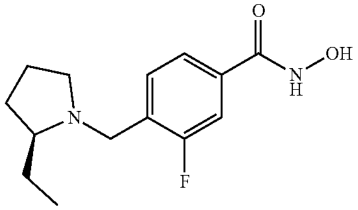
50
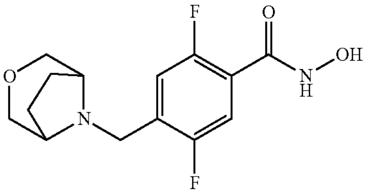
-continued
51
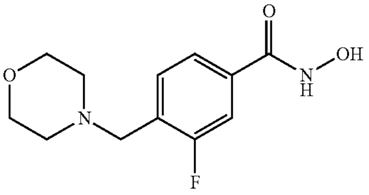
52
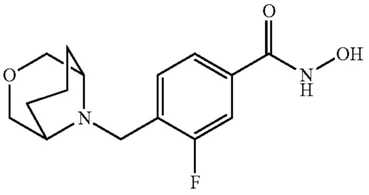
53
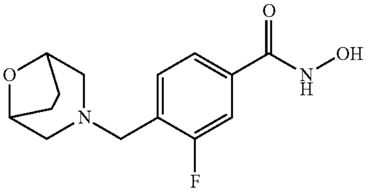
54
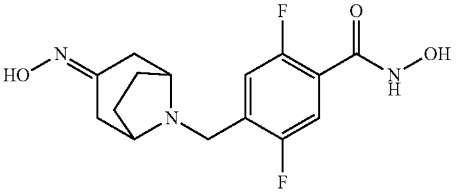
55
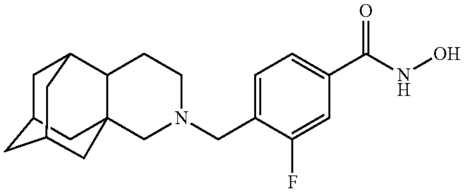
56
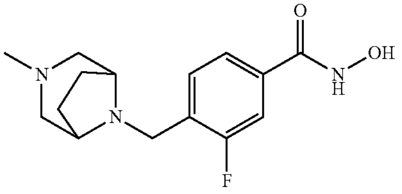
57
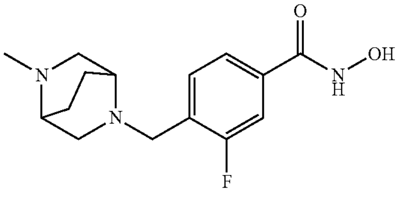
58
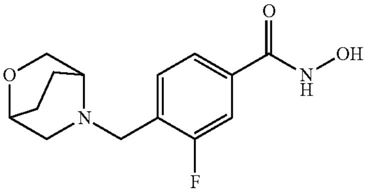

-continued

59

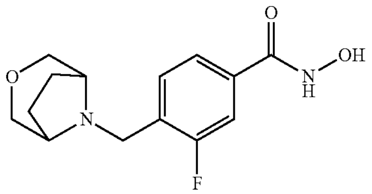

60

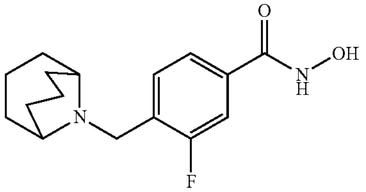

61

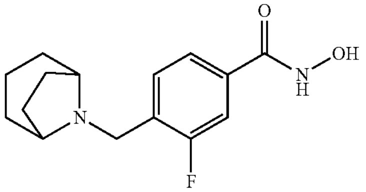

62

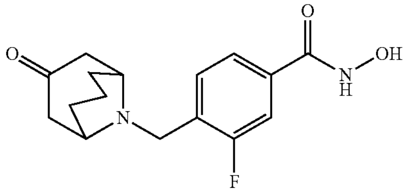

63

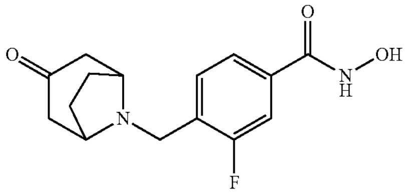

64

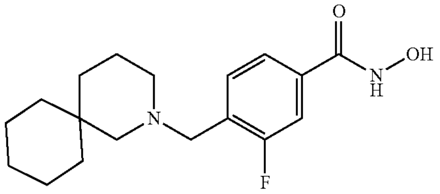

169

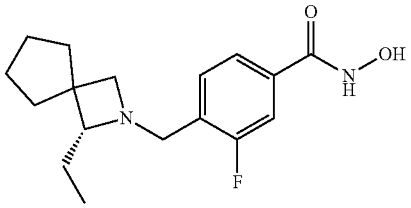

172

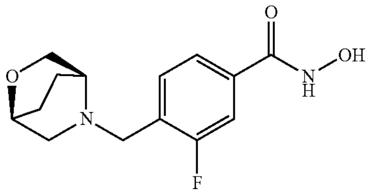

-continued

173

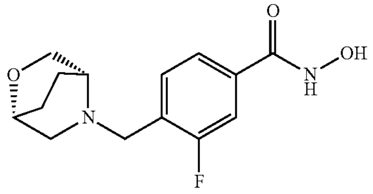

and pharmaceutically acceptable salts thereof.

In certain embodiments, the compounds of Formula (III) are compounds of Formula (IV):

(IV)

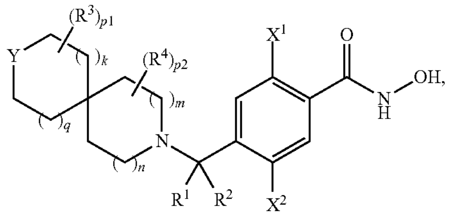

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl;

Y is —O—, —S—, —$NR^{a1}$—, or —($CR^3R^4$)—;

each occurrence of $R^3$ and $R^4$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroalkyl, —$N(R^{a1})_2$, —$OR^{b1}$, —$SR^{c1}$, or —CN; wherein two or three $R^3$ groups are optionally joined to form a substituted or unsubstituted bridged ring; wherein two or three $R^4$ groups are optionally joined to form a substituted or unsubstituted bridged ring;

each occurrence of Rai is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group, or two $R^{a1}$ groups are joined to form a substituted or unsubstituted heterocyclic ring;

each occurrence of $R^{b1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or an oxygen protecting group;

each occurrence of $R^{c1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or a sulfur protecting group;

m, n, k, and q are each independently 0, 1, or 2; and p1 and p2 are each independently 0, 1, 2, 3, or 4.

In certain embodiments, the compounds of Formula (IV) are compounds of Formula (IV-a), (IV-b), (IV-c), (IV-d), (IV-e), (IV-f), (IV-g), or (IV-h):

(IV-a)

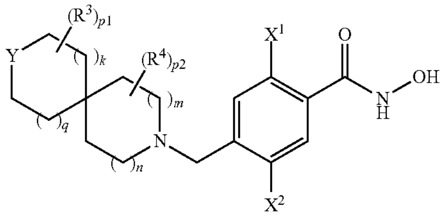

(IV-b)

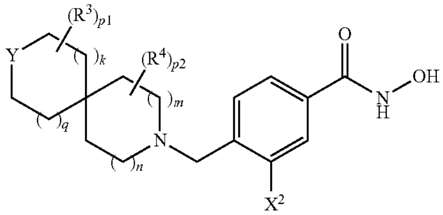

(IV-c)

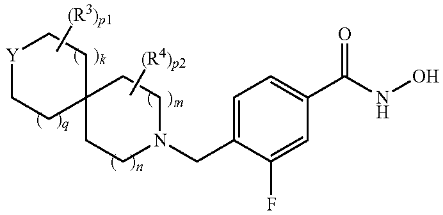

(IV-d)

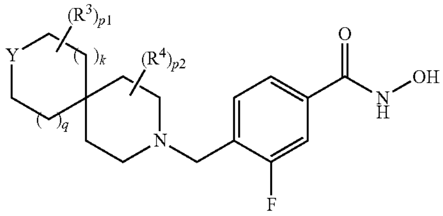

(IV-e)

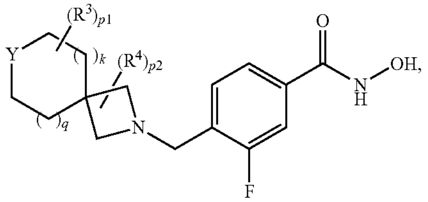

(IV-f)

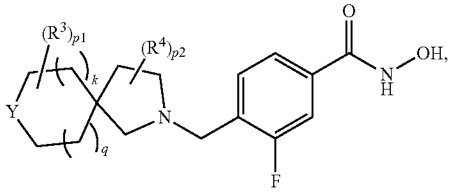

-continued (IV-g)

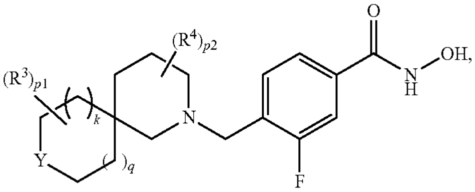

(IV-h)

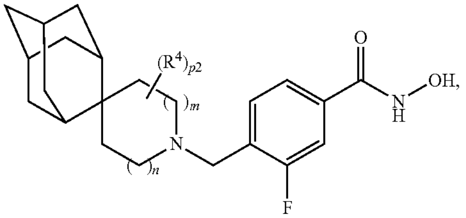

or pharmaceutically acceptable salts thereof.

Exemplary compounds of Formula (IV) include, but are not limited to:

64

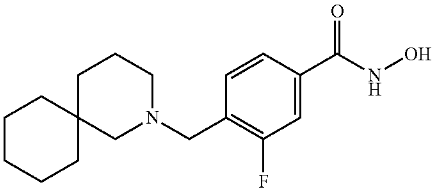

169

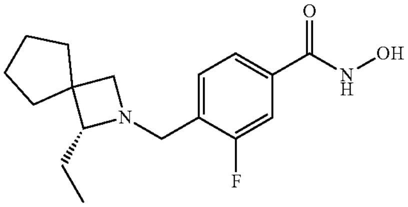

168

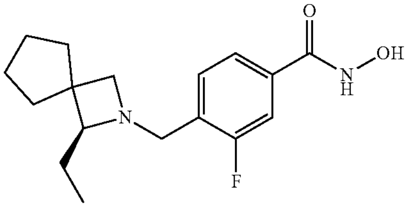

67

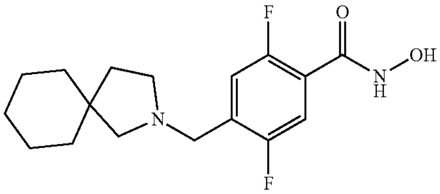

-continued

68

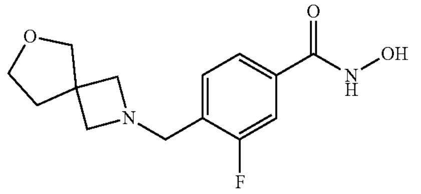

69

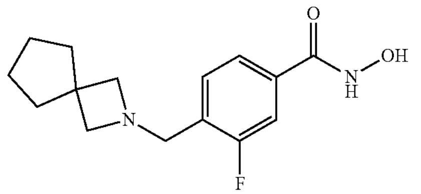

70

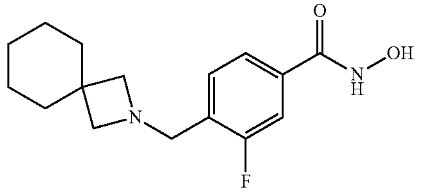

71

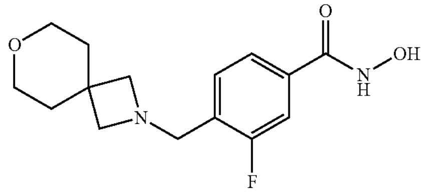

72

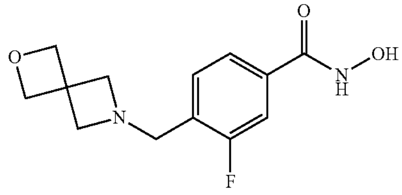

73

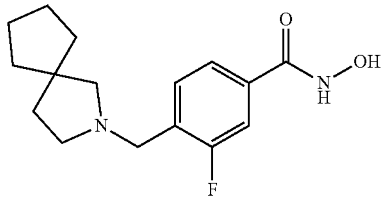

74

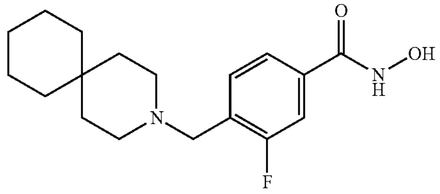

75

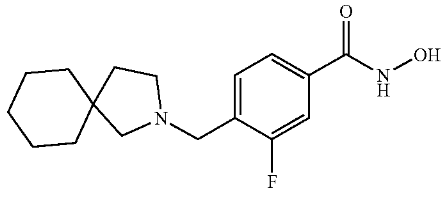

-continued

167

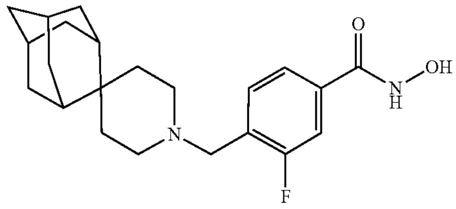

77

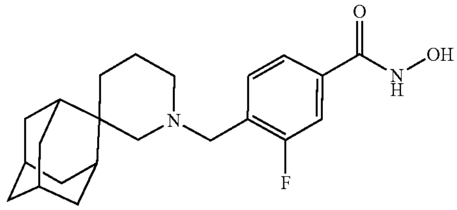

78

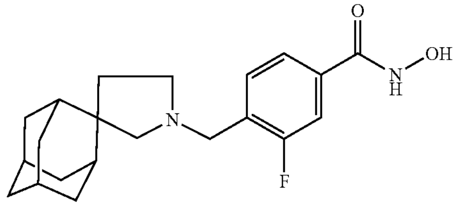

and pharmaceutically acceptable salts thereof.

In another aspect, provided are compounds of Formula (V):

(V)

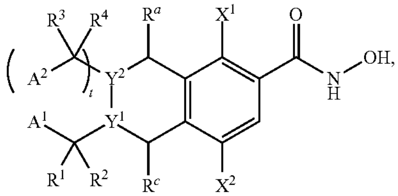

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro;

$Y^1$ is independently nitrogen or $CR^x$;

$Y^2$ is independently nitrogen, $CR^d$, a bond, —$CH_2$—, or —NH—;

$A^1$ is joined with one of $A^2$, $R^a$, or $R^c$ to form a substituted or unsubstituted ring;

$A^2$ is hydrogen or joined with $A^1$ to form a substituted or unsubstituted ring;

$R^1$ is hydrogen or substituted or unsubstituted alkyl, or $R^1$ is joined with $R^d$, $R^3$, or $R^4$ to form a substituted or unsubstituted ring;

$R^2$ is hydrogen or substituted or unsubstituted alkyl, or $R^2$ is joined with $R^d$, $R^3$, or $R^4$ to form a substituted or unsubstituted ring; or $R^1$ and $R^2$ together form a carbonyl;

$R^3$ is hydrogen or substituted or unsubstituted alkyl, or $R^3$ is joined with $R^1$ or $R^2$ to form a substituted or unsubstituted ring;

$R^4$ is hydrogen or substituted or unsubstituted alkyl, or $R^4$ is joined with $R^1$ or $R^2$ to form a substituted or unsubstituted ring; or $R^3$ and $R^4$ together form a carbonyl;

$R^x$ is hydrogen or substituted or unsubstituted alkyl;

$R^a$ is hydrogen or is joined with $A^1$ to form a substituted or unsubstituted ring;

$R^c$ is hydrogen or is joined with $A^1$ to form a substituted or unsubstituted ring;

$R^d$ is hydrogen or is joined with $R^3$ or $R^4$ to form a substituted or unsubstituted ring; and t is 0 or 1.

In certain embodiments, the compounds of Formula (V) are compounds of Formula (V-a), (V-b), (V-c), (V-d), (V-e), (V-f), (V-g), (V-h), (V-i), (V-j), (V-k), (V-l), (V-m), or (V-n):

(V-a)

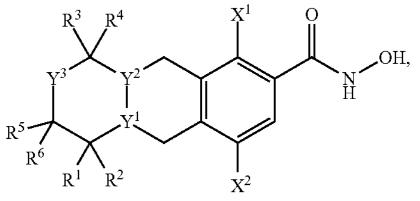

(V-b)

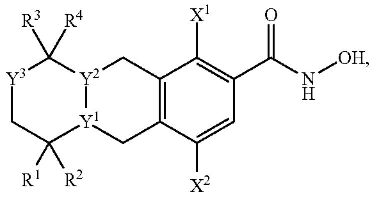

(V-c)

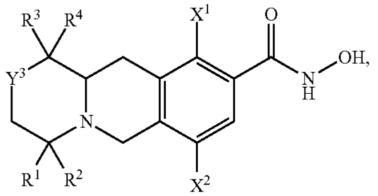

(V-d)

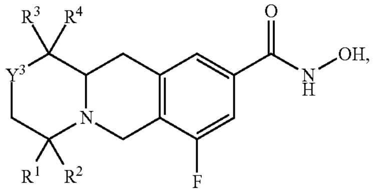

(V-e)

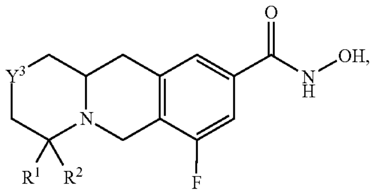

(V-f)

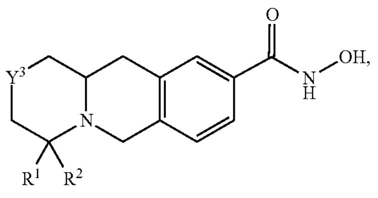

-continued (V-g)

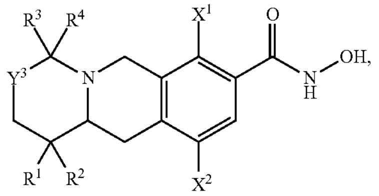

(V-h)

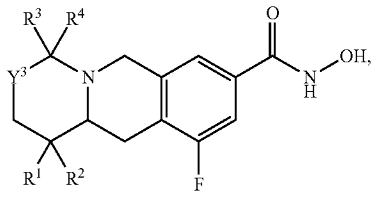

(V-i)

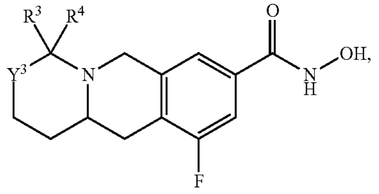

(V-j)

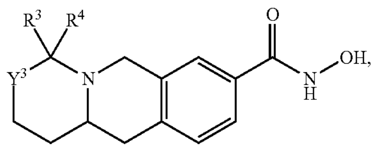

(V-k)

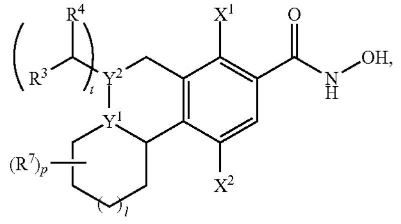

(V-l)

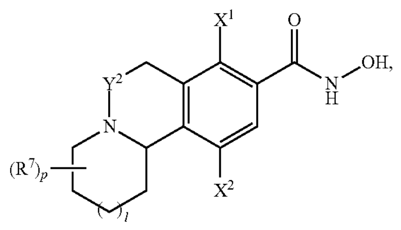

(V-m)

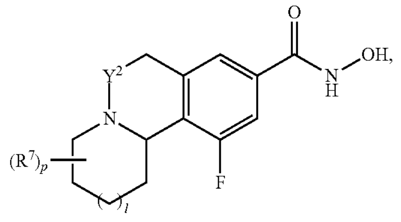

-continued
(V-n)
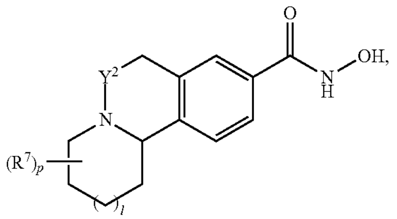
or pharmaceutically acceptable salts thereof.
Exemplary compounds of Formula (V) include, but are not limited to:
79
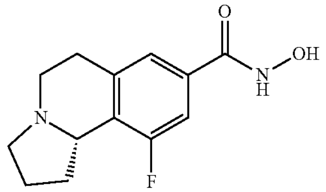
80
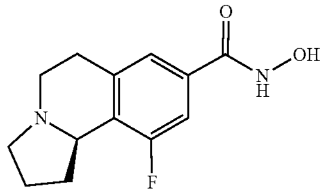
119
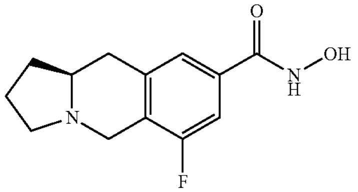
120
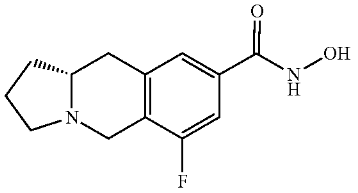
140
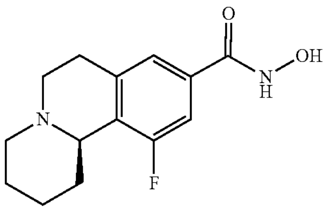
139
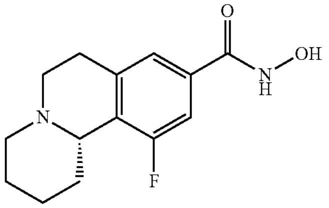
-continued
134
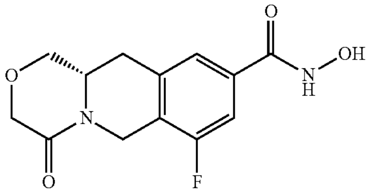
133
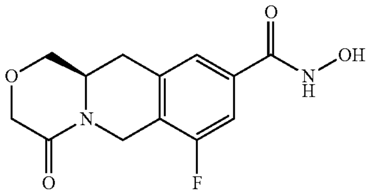
135
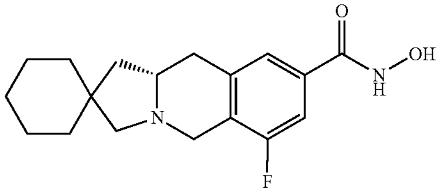
136
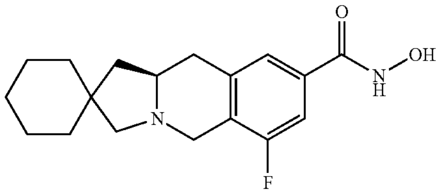
90
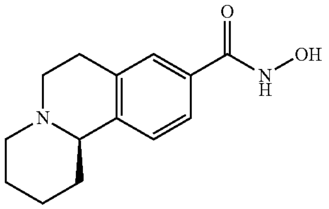
89
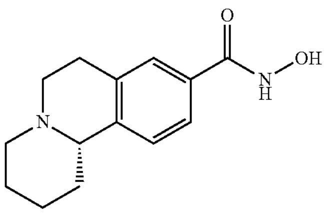
130
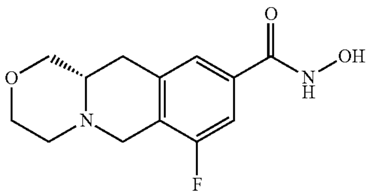

-continued
129
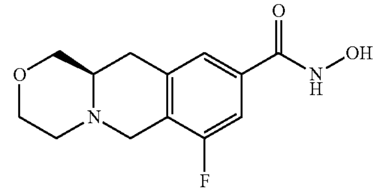
93
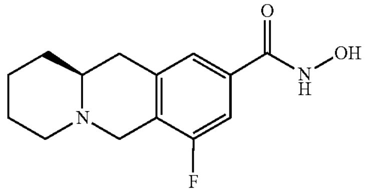
94
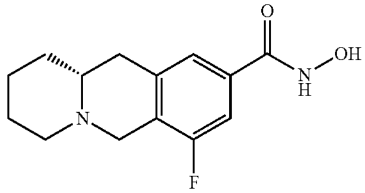
95
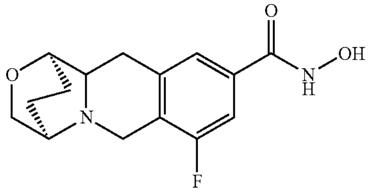
96
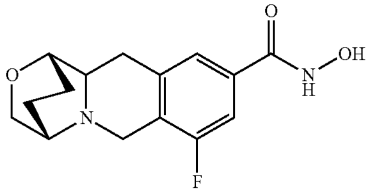
97
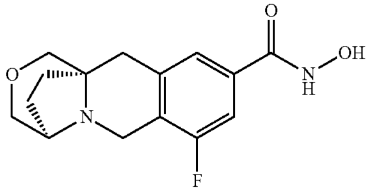
98
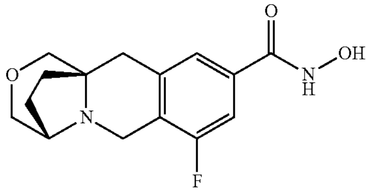
132
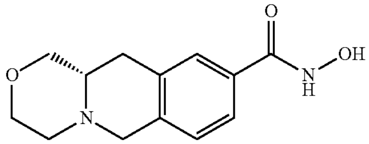
-continued
131
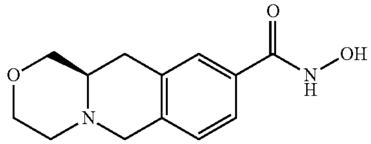
121
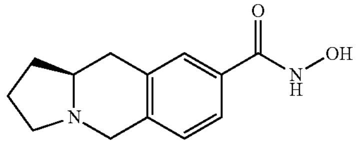
122
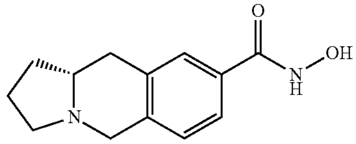
103
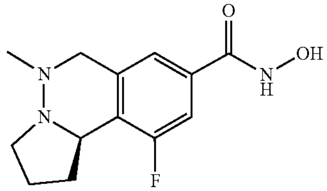
104
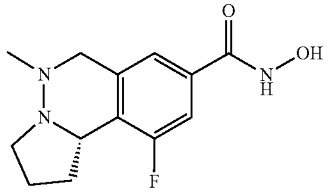
105
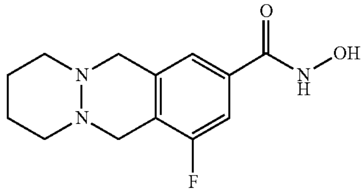
106
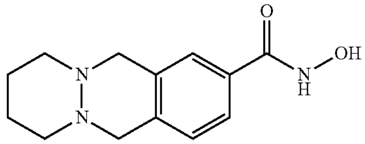
124
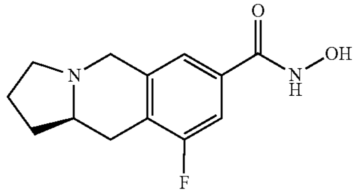
123
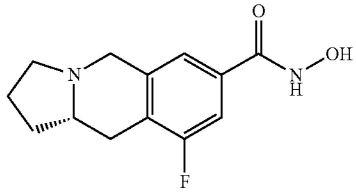

144
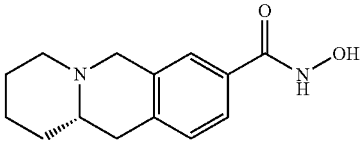
143
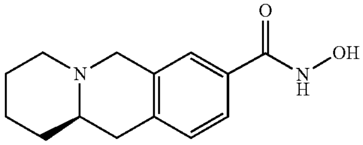
146
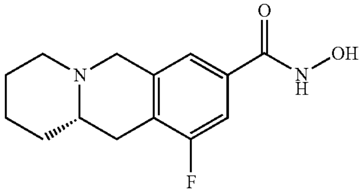
145
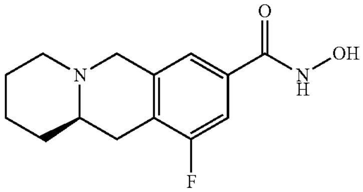
180
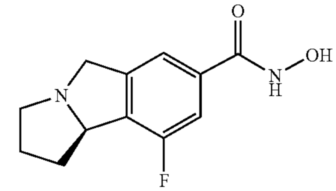
181
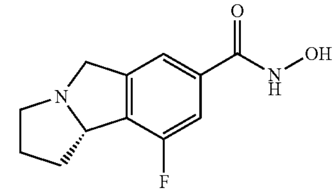
137
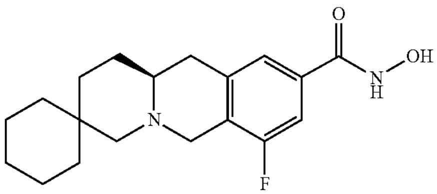
138
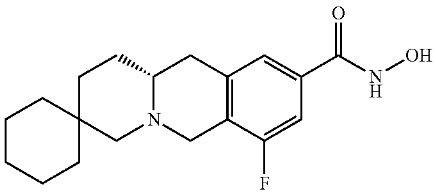
125
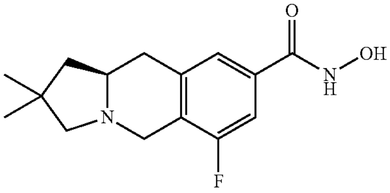
126
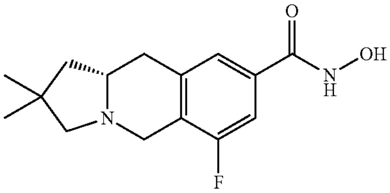
127
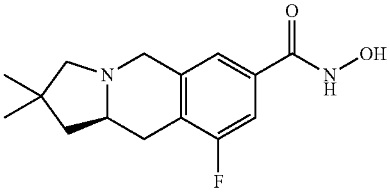
128
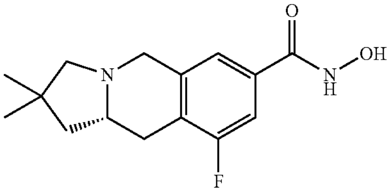
147
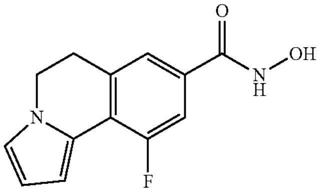
148
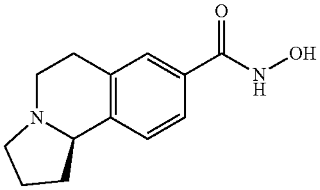
149
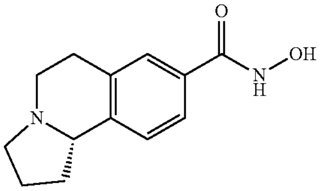

-continued
150
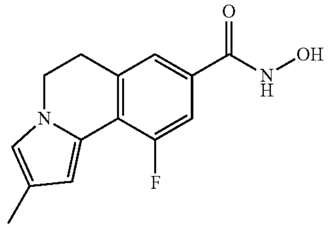
151
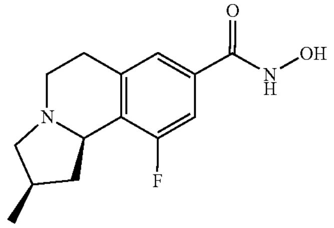
152
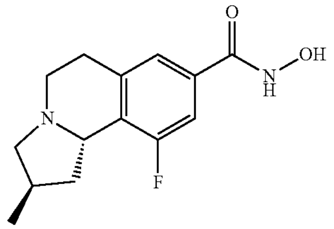
153
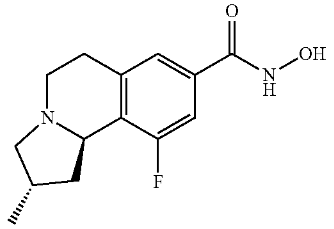
154
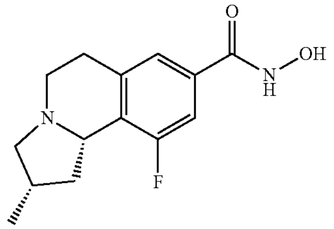
155
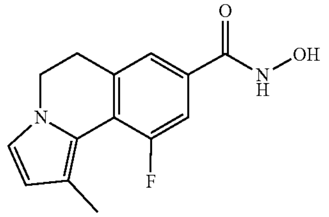
156
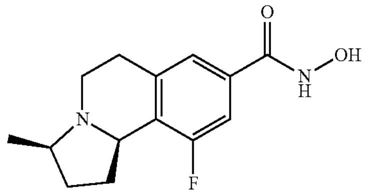
-continued
157
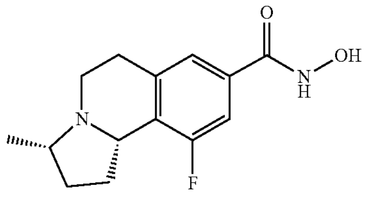
158
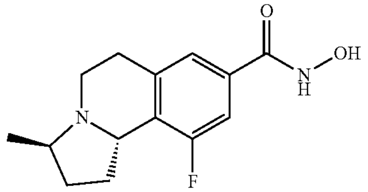
159
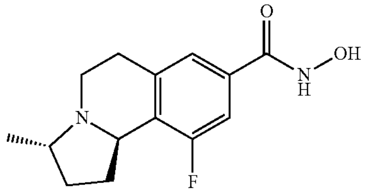
160
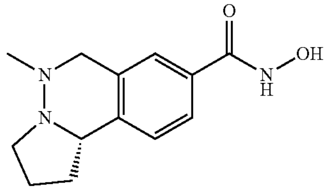
161
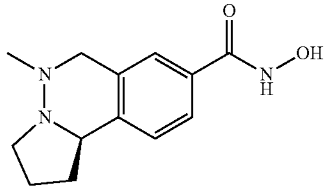
162
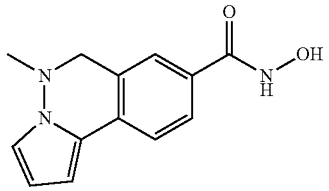
163
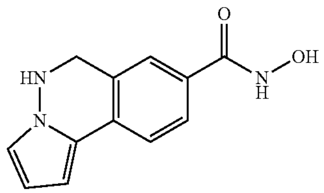
164
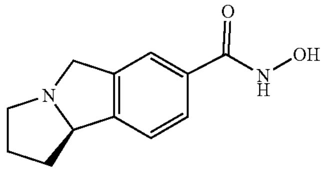

-continued

165

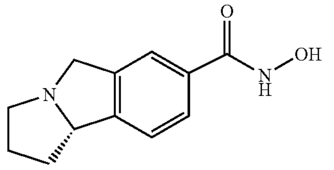

166

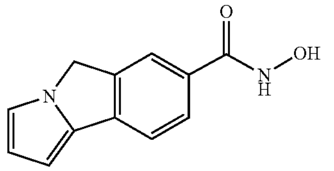

and pharmaceutically acceptable salts thereof.

In another aspect, provided are compounds of Formula (VI):

(VI)

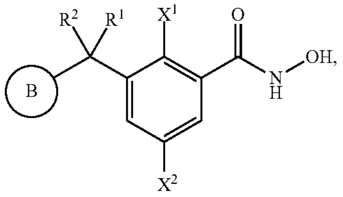

and pharmaceutically acceptable salts, co-crystals, tautomers, stereoisomers, solvates, hydrates, polymorphs, isotopically enriched derivatives, or prodrugs thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl; and B is a substituted or unsubstituted heterocyclyl, substituted or unsubstituted carbocyclyl, a substituted or unsubstituted polycyclic spiro ring system, or a substituted or unsubstituted bridged ring system.

In certain embodiments, the compounds of Formula (VI) are compounds of Formula (VI-a), (VI-b), or (VI-c):

(VI-a)

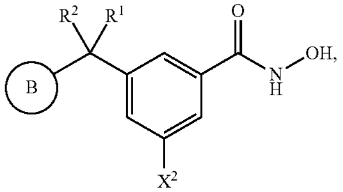

(VI-b)

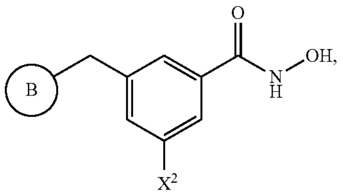

-continued (VI-c)

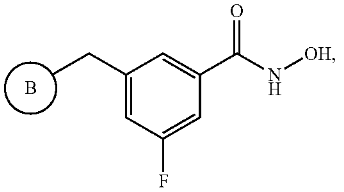

or pharmaceutically acceptable salts thereof.

Exemplary compounds of Formula (VI) include, but are not limited to:

170

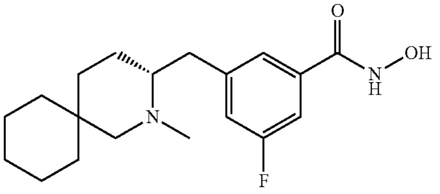

171

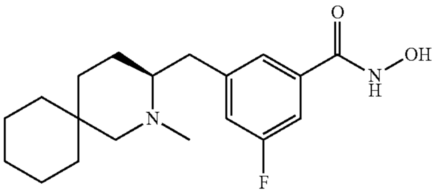

In another aspect, provided are pharmaceutical compositions comprising a compound of Formula (I), (II), (III), (IV), (V), or (VI), or a pharmaceutically acceptable salt thereof, and optionally a pharmaceutically acceptable excipient.

In another aspect, provided are methods of treating a disease or disorder in a subject in need thereof, wherein the disease or disorder is a proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation in a subject in need thereof, the method comprising administering a compound of Formula (I), (II), (III), (IV), (V), or (VI), or a pharmaceutically acceptable salt thereof, or a pharmaceutical composition comprising a compound of Formula (I), (II), (III), (IV), (V), or (VI), to the subject.

In certain embodiments, the disease or disorder being treated using a compound or composition described herein is a proliferative disease. In certain embodiments, the proliferative disease is cancer. In certain embodiments, the cancer is a hematological cancer. In certain embodiments, the cancer is a leukemia, T-cell lymphoma, Hodgkin's Disease, non-Hodgkin's lymphoma, or multiple myeloma. In certain embodiments, the cancer comprises a solid tumor. In certain embodiments, the cancer is mantle cell lymphoma. In certain embodiments, the cancer is cancer is glioma, glioblastoma, non-small cell lung cancer, brain tumor, neuroblastoma, bone tumor, soft-tissue sarcoma, head and neck cancer, genitourinary cancer, lung cancer, breast cancer, pancreatic cancer, melanoma, stomach cancer, brain cancer, liver cancer, thyroid cancer, clear cell carcinoma, uterine cancer, or ovarian cancer.

In certain embodiments, the disease or disorder being treated using a compound or composition described herein is a neurodegenerative, neurodevelopmental, neuropsychiatric, or neuropathy disease. In certain embodiments, the neurodegenerative, neurodevelopmental, neuropsychiatric, or neuropathy disease is Fragile-X syndrome, Charcot-Marie-Tooth disease, Alzheimer's disease, Parkinson's diseases, Huntington's disease, multiple sclerosis, amyotrophic lateral sclerosis, Creutzfeldt-Jakob disease, Lewy body dementia, vascular dementia, muscular atrophy, seizure induced memory loss, schizophrenia, Rubinstein Taybi syndrome, Rett Syndrome, attention deficit hyperactivity disorder, dyslexia, bipolar disorder, social, cognitive and learning disorders associated with autism, attention deficit disorder, schizophrenia, major depressive disorder, peripheral neuropathy, diabetic retinopathy, diabetic peripheral neuropathy, chemotherapy-induced peripheral neuropathy, traumatic brain injury (TBI), chronic traumatic encephalopathy (CTE), or a tauopathy. In certain embodiments, the tauopathy is primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, lipofuscinosis, Alzheimer's disease, or argyrophilic grain disease.

In another aspect, provided are methods of inhibiting the activity of HDAC6, the method comprising contacting HDAC6 with a compound of Formula (I), (II), (III), (IV), (V), or (VI), or a pharmaceutically acceptable salt thereof. In certain embodiments, the HDAC6 is in a cell (e.g., a human cell).

In another aspect, provided are compounds of Formula (I), (II), (III), (IV), (V), or (VI), and pharmaceutically acceptable salts thereof, and pharmaceutical compositions comprising a compound of Formula (I), (II), (III), (IV), (V), or (VI), or a pharmaceutically acceptable salt thereof, for use in treating a proliferative disease, inflammatory disease, infectious disease, autoimmune disease, heteroimmune disease, neurological disorder, metabolic disease, or disease or disorder mediated by or linked to T-cell dysregulation in a subject in need thereof.

In another aspect, provided are kits comprising a compound of Formula (I), (II), (III), (IV), (V), or (VI), or a pharmaceutically acceptable salt thereof, or a pharmaceutical composition comprising a compound of Formula (I), (II), (III), (IV), (V), or (VI), or a pharmaceutically acceptable salt thereof. In certain embodiments, the kits further comprise instructions for administration (e.g., human administration).

The details of certain embodiments of the invention are set forth in the Detailed Description of Certain Embodiments, as described below. Other features, objects, and advantages of the invention will be apparent from the Definitions, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry,* $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts;

or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula,  is a single bond where the stereochemistry of the moieties immediately attached thereto is not specified, - - - is absent or a single bond, and  or  is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "alkoxy" refers to an alkyl group, as defined herein, appended to the parent molecular moiety through an oxygen atom. In some embodiments, the alkoxy moiety has 1 to 8 carbon atoms ("$C_{1-8}$ alkoxy"). In some embodiments, the alkoxy moiety has 1 to 6 carbon atoms ("$C_{1-6}$ alkoxy"). In some embodiments, the alkoxy moiety has 1 to 4 carbon atoms ("$C_{1-4}$ alkoxy"). In some embodiments, the alkoxy moiety has 1 to 3 carbon atoms ("$C_{1-3}$ alkoxy"). In some embodiments, the alkoxy moiety has 1 to 2 carbon atoms ("$C_{1-2}$ alkoxy"). Representative examples of alkoxy include, but are not limited to, methoxy, ethoxy, propoxy, 2-propoxy, butoxy and tert-butoxy.

The term "alkoxyalkyl" is a substituted alkyl group, wherein one or more of the hydrogen atoms are independently replaced by an alkoxy group, as defined herein. In some embodiments, the alkoxyalkyl moiety has 1 to 8 carbon atoms ("$C_{1-8}$ alkoxyalkyl"). In some embodiments, the alkoxyalkyl moiety has 1 to 6 carbon atoms ("$C_{1-6}$ alkoxyalkyl"). In some embodiments, the alkoxyalkyl moiety has 1 to 4 carbon atoms ("$C_{1-4}$ alkoxyalkyl"). In some embodiments, the alkoxyalkyl moiety has 1 to 3 carbon atoms ("$C_{1-3}$ alkoxyalkyl"). In some embodiments, the alkoxyalkyl moiety has 1 to 2 carbon atoms ("$C_{1-2}$ alkoxyalkyl").

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl"). In some embodiments, a heteroalkyl group is a saturated group having 1 to 18 carbon atoms and 1 or more heteroatoms within the parent chain ("hetero$C_{1-18}$ alkyl"). In some embodiments, a heteroalkyl group is a saturated group having 1 to 16 carbon atoms and 1 or more heteroatoms within the parent chain ("hetero$C_{1-6}$ alkyl"). In some embodiments, a heteroalkyl group is a saturated group having 1 to 14 carbon atoms and 1 or more heteroatoms within the parent chain ("hetero$C_{1-4}$ alkyl"). In some embodiments, a heteroalkyl group is a saturated group having 1 to 12 carbon atoms and 1 or more heteroatoms within the parent chain ("hetero$C_{1-2}$ alkyl"). In some embodiments, a heteroalkyl group is a saturated group having 1 to 10 carbon atoms and 1 or more heteroatoms within the parent chain ("hetero$C_{1-10}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, the heteroalkyl group defined herein is a partially unsaturated group having 1 or more heteroatoms within the parent chain and at least one unsaturated carbon, such as a carbonyl group. For example, a heteroalkyl group may comprise an amide or ester functionality in its parent chain such that one or more carbon atoms are unsaturated carbonyl groups. Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-20}$ alkyl. In certain embodiments, the heteroalkyl group is an unsubstituted hetero$C_{1-10}$ alkyl. In certain embodiments, the heteroalkyl group is a substituted hetero$C_{1-20}$ alkyl. In certain embodiments, the heteroalkyl group is an unsubstituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., —CH═CHCH$_3$ or

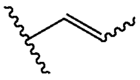

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_4$), cyclooctenyl ($C_4$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "polycyclic spiro ring system" refers to ring systems having two or more rings linked by one common atom. The common atom is known as a spiro atom. The ring systems may be fully carbocyclic (all carbon) or heterocyclic (having one or more non-carbon atom). A ring system is considered heterocyclic if the spiro atom or any atom in either ring are not carbon atoms.

The term "bridged ring system" refers to ring systems having two or more rings that contain a bridge—a single atom or an unbranched chain of atoms (or even just a valence bond) that connect two "bridgehead" atoms. The bridgehead atoms are defined as any atom that is not a hydrogen, and that is part of the skeletal framework of the molecule that is bonded to three or more other skeletal atoms. The ring systems may be fully carbocyclic (all carbon) or heterocyclic (having one or more non-carbon atoms). A ring system is considered heterocyclic if any atom is not a carbon atom.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, $—NO_2$, $—N_3$, $—SO_2H$, $—SO_3H$, —OH, $—OR^{aa}$, $—ON(R^{bb})_2$, $—N(R^{bb})_2$, $—N(R^{bb})_3^+X^-$, $—N(OR^{cc})R^{bb}$, —SH, $—SR^{aa}$, $—SSR^{cc}$, $—C({=}O)R^{aa}$, $—CO_2H$, —CHO, $—C(OR^{cc})_3$, $—CO_2R^{aa}$, $—OC({=}O)R^{aa}$, $—OCO_2R^{aa}$, $—C({=}O)N(R^{bb})_2$, $—OC({=}O)N(R^{bb})_2$, $—NR^{bb}C({=}O)R^{aa}$, $—NR^{bb}CO_2R^{aa}$, $—NR^{bb}C({=}O)N(R^{bb})_2$, $—C({=}NR^{bb})R^{aa}$, $—C({=}NR^{bb})OR^{aa}$, $—OC({=}NR^{bb})R^{aa}$, $—OC({=}NR^{bb})OR^{aa}$, $—C({=}NR^{bb})N(R^{bb})_2$, $—OC({=}NR^{bb})N(R^{bb})_2$, $—NR^{bb}C({=}NR^{bb})N(R^{bb})_2$, $—C({=}O)NR^{bb}SO_2R^{aa}$, $—NR^{bb}SO_2R^{aa}$, $—SO_2N(R^{bb})_2$, $—SO_2R^{cc}$, $—SO_2OR^{cc}$, $—OSO_2R^{aa}$, $—S({=}O)R^{aa}$, $—OS({=}O)R^{aa}$, $—Si(R^{aa})_3$, $—OSi(R^{aa})_3$ $—C({=}S)N(R^{bb})_2$, $—C({=}O)SR^{aa}$, $—C({=}S)SR^{aa}$, $—SC({=}S)SR^{aa}$, $—SC({=}O)SR^{aa}$, $—OC({=}O)SR^{aa}$, $—SC({=}O)OR^{aa}$, $—SC({=}O)R^{aa}$, $—P({=}O)(R^{aa})_2$, $—P({=}O)(OR^{cc})_2$, $—OP({=}O)(R^{aa})_2$, $—OP({=}O)(OR^{cc})_2$, $—P({=}O)(N(R^{bb})_2)_2$, $—OP({=}O)(N(R^{bb})_2)_2$, —NR bbP(=O)$(R^{aa})_2$, $—NR^{bb}P({=}O)(OR^{cc})_2$, $—NR^{bb}P({=}O)(N(R^{bb})_2)_2$, $—P(R^{cc})_2$, $—P(OR^{cc})_2$, $—P(R^{cc})_3^+X^-$, $—P(OR^{cc})_3^+X^-$, $—P(R^{cc})_4$, $—P(OR^{cc})_4$, $—OP(R^{cc})_2$, $—OP(R^{cc})_3^+X^-$, $—OP(OR^{cc})_2$, $—OP(OR^{cc})_3^+X^-$, $—OP(R^{cc})_4$, $—OP(OR^{cc})_4$, $—B(R^{aa})_2$, $—B(OR^{cc})_2$, $—BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, $=NN(R^{bb})_2$, $=NNR^{bb}C({=}O)R^{aa}$, $=NNR^{bb}C({=}O)OR^{aa}$, $=NNR^{bb}S({=}O)_2R^{aa}$, $=NR^{bb}$, or $=NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, $—OR^{aa}$, $—N(R^{cc})_2$, —CN, $—C({=}O)R^{aa}$, $—C({=}O)N(R^{cc})_2$, $—CO_2R^{cc}$, $—SO_2R^{cc}$, $—C({=}NR^{cc})OR^{aa}$, $—C({=}NR^{cc})N(R^{cc})_2$, $—SO_2N(R^{cc})_2$, $—SO_2R^{cc}$, $—SO_2OR^{cc}$, $—SOR^{aa}$, $—C({=}S)N(R^{cc})_2$, $—C({=}O)SR^{cc}$, $—C({=}S)SR^{cc}$, $—P({=}O)(R^{aa})_2$, $—P({=}O)(OR^{cc})_2$, $—P({=}O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-11}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{dd}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3^+X^-$, —$N(OR^{ee})R^{ff}$, —SH, —$SR^{ee}$, —$SSR^{ee}$, —$C({=}O)R^{ee}$, —$CO_2H$, —$CO_2R^{ee}$, —$OC({=}O)R^{ee}$, —$OCO_2R^{ee}$, —$C({=}O)N(R^{ff})_2$, —$OC({=}O)N(R^{ff})_2$, —$NR^{ff}C({=}O)R^{ee}$, —$NR^{ff}CO_2R^{ee}$, —$NR^{ff}C({=}O)N(R^{ff})_2$, —$C({=}NR^{ff})OR^{ee}$, —$OC({=}NR^{ff})R^{ee}$, —$OC({=}NR^{ff})OR^{ee}$, —$C({=}NR^{ff})N(R^{ff})_2$, —$OC({=}NR^{ff})N(R^{ff})_2$, —$NR^{ff}C({=}NR^{ff})N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —$S({=}O)R^{ee}$, —$Si(R^{ee})_3$, —$OSi(R^{ee})_3$, —$C({=}S)N(R^{ff})_2$, —$C({=}O)SR^{ee}$, —$C({=}S)SR^{ee}$, —$SC({=}S)SR^{ee}$, —$P({=}O)(OR^{ee})_2$, —$P({=}O)(R^{ee})_2$, —$OP({=}O)(R^{ee})_2$, —$OP({=}O)(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{99}$ groups, or two geminal $R^{dd}$ substituents can be joined to form ═O or ═S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{a}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl and 5-10 membered heteroaryl, or two $R^{a}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6}$ alkyl$)_2^+X^-$, —$NH_2(C_{1-6}$ alkyl$)^+X^-$, —$NH_3^+X^-$, —$N(OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(═O)($C_{1-6}$ alkyl), —$CO_2H$, —$CO_2(C_{1-6}$ alkyl), —OC(═O)($C_{1-6}$ alkyl), —$OCO_2(C_{1-6}$ alkyl), —C(═O)$NH_2$, —C(═O)N($C_{1-6}$ alkyl$)_2$, —OC(═O)NH($C_{1-6}$ alkyl), —NHC(═O)($C_{1-6}$ alkyl), —N($C_{1-6}$ alkyl)C(═O)($C_{1-6}$ alkyl), —$NHCO_2(C_{1-6}$ alkyl), —NHC(═O)N($C_{1-6}$ alkyl$)_2$, —NHC(═O)NH($C_{1-6}$ alkyl), —NHC(═O)$NH_2$, —C(═NH)O($C_{1-6}$ alkyl), —OC(═NH)($C_{1-6}$ alkyl), —OC(═NH)$OC_{1-6}$ alkyl, —C(═NH)N($C_{1-6}$ alkyl$)_2$, —C(═NH)NH($C_{1-6}$ alkyl), —C(═NH)$NH_2$, —OC(═NH)N($C_{1-6}$ alkyl$)_2$, —OC(═NH)NH($C_{1-6}$ alkyl), —OC(═NH)$NH_2$, —NHC(═NH)N($C_{1-6}$ alkyl$)_2$, —NHC(═NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2(C_{1-6}$ alkyl), —$SO_2O(C_{1-6}$ alkyl), —$OSO_2(C_{1-6}$ alkyl), —SO($C_{1-6}$ alkyl), —Si($C_{1-6}$ alkyl$)_3$, —OSi($C_{1-6}$ alkyl$)_3$ —C(═S)N($C_{1-6}$ alkyl$)_2$, C(═S)NH($C_{1-6}$ alkyl), C(═S)$NH_2$, —C(═O)S($C_{1-6}$ alkyl), —C(═S)$SC_{1-6}$ alkyl, —SC(═S)$SC_{1-6}$ alkyl, —P(═O)($OC_{1-6}$ alkyl$)_2$, —P(═O)($C_{1-6}$ alkyl$)_2$, —OP(═O)($C_{1-6}$ alkyl$)_2$, —OP(═O)($OC_{1-6}$ alkyl$)_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form ═O or ═S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —$ON(R^{bb})_2$, —$OC({=}O)SR^{aa}$, —$OC({=}O)R^{aa}$, —$OCO_2R^{aa}$, —$OC({=}O)N(R^{bb})_2$, —$OC({=}NR^{bb})R^{aa}$, —$OC({=}NR^{bb})OR^{aa}$, —$OC({=}NR^{bb})N(R^{bb})_2$, —$OS({=}O)R^{aa}$, —$OSO_2R^{aa}$, —$OSi(R^{cc})_3$, —$OP(R^{cc})_2$, —$OP(R^{cc})_3^+X^-$, —$OP(OR^{cc})_2$, —$OP(OR^{cc})_3^+X^-$, —$OP({=}O)(R^{cc})_2$, —$OP({=}O)(OR^{cc})_2$, and —$OP({=}O)(N(R^{bb})_2)_2$, wherein $X^-$, $R^{aa}$, $R^{bb}$, and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —$NH(R^{bb})$, —$NHC({=}O)R^{aa}$, —$NHCO_2R^{aa}$, —$NHC({=}O)N(R^{bb})_2$, —$NHC({=}NR^{bb})N(R^{bb})_2$, —$NHSO_2R^{aa}$, —$NHP({=}O)(OR^{cc})_2$, and —$NHP({=}O)(N(R^{bb})_2)_2$, wherein $R^{aa}$, $R^{bb}$ and $R^{cc}$ are as defined herein, and wherein $R^{bb}$ of the group —$NH(R^{bb})$ is not hydrogen.

The term "disubstituted amino" refers to an amino group wherein the nitrogen atom directly attached to the parent molecule is substituted with two groups other than hydrogen, and includes groups selected from —$N(R^{bb})_2$, —$NR^{bb}C({=}O)R^{aa}$, —$NR^{bb}CO_2R^{aa}$, —$NR^{bb}C({=}O)N(R^{bb})_2$, —$NR^{bb}C({=}NR^{bb})N(R^{bb})_2$, —$NR^{bb}SO_2R^{aa}$, —$NR^{bb}P({=}O)(OR^{cc})_2$, and —$NR^{bb}P({=}O)(N(R^{bb})_2)_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —$N(R^{bb})_3$ and —$N(R^{bb})_3^+X^-$, wherein $R^{bb}$ and $X^-$ are as defined herein.

The term "sulfonyl" refers to a group selected from —$SO_2N(R^{bb})_2$, —$SO_2R^{aa}$, and —$SO_2OR^{aa}$, wherein $R^{aa}$ and $R^{bb}$ are as defined herein.

The term "sulfinyl" refers to the group —S(═O)$R^{aa}$, wherein $R^{aa}$ is as defined herein.

The term "acyl" refers to a group having the general formula: —C(═O)$R^{X1}$, —C(═O)O$R^{X1}$, —C(═O)—O—C(═O)$R^{X1}$, —C(═O)S$R^{X1}$, —C(═O)N$(R^{X1})_2$, —C(═S)$R^{X1}$, —C(═S)N$(R^{X1})_2$, —C(═S)O($R^{X1}$), —C(═S)S($R^{X1}$), —C(═N$R^{X1}$)$R^{X1}$, —C(═N$R^{X1}$)O$R^{X1}$, —C(═N$R^{X1}$)S$R^{X1}$, or —C(═N$R^{X1}$)N$(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "oxo" refers to the group ═O, and the term "thiooxo" refers to the group ═S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{cc}$, —$N(R^{cc})_2$, —CN, —C(═O)$R^{aa}$, —C(═O)N$(R^{cc})_2$, —$CO_2R^{aa}$, —$SO_2R^{aa}$, —C(═N$R^{bb}$)$R^{aa}$, —C(═N$R^{cc}$)O$R^{aa}$, —C(═N$R^{cc}$)N$(R^{cc})_2$, —$SO_2N(R^{cc})_2$, —$SO_2R^{cc}$, —$SO_2OR^{cc}$, —$SOR^{aa}$, —C(═S)N$(R^{cc})_2$, —C(═O)S$R^{cc}$, —C(═S)S$R^{cc}$, —P(═O)$(OR^{cc})_2$, —P(═O)$(R^{aa})_2$, —P(═O)$(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein.

In certain embodiments, the substituent present on the nitrogen atom is an nitrogen protecting group (also referred to herein as an "amino protecting group"). Nitrogen protecting groups include, but are not limited to, —OH, —$OR^{aa}$, —$N(R^{cc})_2$, —C(═O)$R^{aa}$, —C(═O)N$(R^{cc})_2$, —$CO_2R^{aa}$, —$SO_2R^{aa}$, —C(═N$R^{cc}$)$R^{aa}$, —C(═N$R^{cc}$)O$R^{aa}$, —C(═N$R^{cc}$)N$(R^{cc})_2$, —$SO_2N(R^{cc})_2$, —$SO_2R^{cc}$, —$SO_2OR^{cc}$, —$SOR^{aa}$, —C(═S)N$(R^{cc})_2$, —C(═O)S$R^{cc}$, —C(═S)S$R^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(═O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $—S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{cc})_3$, $—P(R^{cc})_2$, $—P(R^{cc})_3^+X^-$, $—P(OR^{cc})_2$, $—P(OR^{cc})_3^+X^-$, $—P(=O)(R^{aa})_2$, $—P(=O)(OR^{cc})_2$, and $—P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR)_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

These and other exemplary substituents are described in more detail in the Detailed Description, Examples, and Claims. The invention is not intended to be limited in any manner by the above exemplary listing of substituents.

Other Definitions

The following definitions are more general terms used throughout the present application.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and/or animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences,* 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\text{ alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water molecules. Typically, the number of the water molecules contained in a hydrate of a compound is in a definite ratio to the number of the compound molecules in the hydrate. Therefore, a hydrate of a compound may be represented, for example, by the general formula $R\cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R\cdot 0.5H_2O$)), and polyhydrates (x is a number greater than 1, e.g., dihydrates ($R\cdot 2H_2O$) and hexahydrates ($R\cdot 6H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). Many compounds can adopt a variety of different crystal forms (i.e., different polymorphs). Typically, such different crystalline forms have different X-ray diffraction patterns, infrared spectra, and/or can vary in some or all properties such as melting points, density, hardness, crystal shape, optical and electrical properties, stability, solubility, and bioavailability. Recrystallization solvent, rate of crystallization, storage temperature, and other factors may cause one crystal form to dominate a given preparation. Various polymorphs of a compound can be prepared by crystallization under different conditions.

The term "co-crystal" refers to a crystalline structure composed of at least two components. In certain embodiments, a co-crystal contains a compound of the present disclosure and one or more other component(s), including, but not limited to, atoms, ions, molecules, or solvent molecules. In certain embodiments, a co-crystal contains a compound of the present disclosure and one or more solvent molecules. In certain embodiments, a co-crystal contains a compound of the present disclosure and one or more acid or base. In certain embodiments, a co-crystal contains a compound of the present disclosure and one or more components related to said compound, including, but not limited to, an isomer, tautomer, salt, solvate, hydrate, synthetic precursor, synthetic derivative, fragment, or impurity of said compound.

The term "prodrugs" refers to compounds that have cleavable groups that are removed, by solvolysis or under physiological conditions, to provide the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_{1-8}$ alkyl, $C_{2-8}$ alkenyl, $C_{2-8}$ alkynyl, aryl, $C_{7-12}$ substituted aryl, and $C_{7-12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. For example, in treating cancer, an effective amount of an inventive composition may prevent tumor regrowth, reduce the tumor burden, or stop the growth or spread of a tumor. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for HDAC6 inhibition (e.g., at least 5%, at least 10%, at least 20%, at least 30%, at least 40%, at least 50%, at least 60%, at least 70%, at least 80%, at least 90%, at least 95%, or at least 99% inhibition of the activity of HDAC6). In certain embodiments, a therapeutically effective amount is an amount sufficient for treating a disease or disorder (e.g., neurological disorder, cancer). In certain embodiments, a therapeutically effective amount is an amount sufficient for HDAC6 inhibition and treating a disease or disorder (e.g., neurological disorder, cancer).

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for HDAC6 inhibition. In certain embodiments, a prophylactically effective amount is an amount sufficient for treating a disease or disorder (e.g., neurological disorder, cancer). In certain embodiments, a prophylactically effective amount is an amount sufficient for HDAC6 inhibition and treating a disease or disorder (e.g., neurological disorder, cancer).

As used herein, the term "inhibit" or "inhibition" in the context of enzymes, for example, in the context of HDAC6, refers to a reduction in the activity of the enzyme. In some embodiments, the term refers to a reduction of the level of enzyme activity, e.g., HDAC6 activity, to a level that is statistically significantly lower than an initial level, which may, for example, be a baseline level of enzyme activity. In some embodiments, the term refers to a reduction of the level of enzyme activity, e.g., HDAC6 activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as matrix metalloproteinases (e.g., collagenases, gelatinases, and elastases); or 4) pathological angiogenesis as in proliferative retinopathy and tumor metastasis. Exemplary proliferative diseases include cancers (i.e., "malignant neoplasms"), benign neoplasms, angiogenesis or diseases associated with angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary,* 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematological cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "immunotherapy" refers to a therapeutic agent that promotes the treatment of disease by inducing, enhancing, or suppressing an immune response. Immunotherapies designed to elicit or amplify an immune response are classified as activation immunotherapies, while immunotherapies that reduce or suppress are classified as suppression immunotherapies. Immunotherapies are typically, but not always, biotherapeutic agents. Numerous immunotherapies are used to treat cancer. These include, but are not limited to, monoclonal antibodies, adoptive cell transfer, cytokines, chemokines, vaccines, and small molecule inhibitors.

The terms "biologic," "biologic drug," and "biological product" refer to a wide range of products such as vaccines, blood and blood components, allergenics, somatic cells, gene therapy, tissues, nucleic acids, and proteins. Biologics may include sugars, proteins, or nucleic acids, or complex combinations of these substances, or may be living entities, such as cells and tissues. Biologics may be isolated from a variety of natural sources (e.g., human, animal, microorganism) and may be produced by biotechnological methods and other technologies.

The term "small molecule" or "small molecule therapeutic" refers to molecules, whether naturally occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics, or combinations thereof.

The term "chemotherapeutic agent" refers to a therapeutic agent known to be of use in chemotherapy for cancer.

A "hematological cancer" includes a cancer which affects a hematopoietic cell or tissue. Hematological cancers include cancers associated with aberrant hematological content and/or function. Examples of hematological cancers include, but are nor limited to, leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), chronic lymphocytic leukemia (CLL) (e.g., B-cell CLL, T-cell CLL)), lymphoma such as Hodgkin's lymphoma (HL) (e.g., B-cell HL, T-cell HL), non-Hodgkin's lymphoma (NHL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma, primary central nervous system (CNS) lymphoma, T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma), a mixture of one or more leukemia/lymphoma as described above, multiple myeloma, heavy chain disease (e.g., alpha chain disease, gamma chain disease, mu chain disease) acute non-lymphocytic leukemia (ANLL), acute promyelocytic leukemia (APL), acute myelomonocytic leukemia (AMMoL), polycythemia vera, Wilm's tumor, and Ewing's sarcoma.

The term "heteroimmune disease" refers to a state in which an immune response to an exogenous antigen (e.g., drug, pathogen) results in immunopathological changes. The immune response is triggered by an antigen from a different species (heteroimmune), thus it differs from an infectious disease because the emphasis is on the immune response, not the foreign species (infectious pathogen) causing the disease.

BRIEF DESCRIPTION OF THE DRAWINGS

FIG. 3A shows that treatment with 16, 173 or ACY-1083 (but not blinded DMSO or 79) decreased blebs per area compared to vehicle in the presence of cisplatin. FIG. 3B shows that treatment with 16 and 79 (but not blinded DMSO, ACY-1083 or 173) increased axon area compared to vehicle in the presence of cisplatin. P values determined by ordinary one-way ANOVA with false discovery rate (FDR) multiple comparisons correction, compared to cisplatin+vehicle; mean with standard error of the mean (SEM) shown. * $P<0.05$,  $P<0.01$, * $P<0.001$, **** $P<0.0001$.

FIG. 4B is a Kaplan-Meier graph showing that treatment with 16 but not ACY-1083 rescued survival compared to vehicle in the presence of cisplatin. FIGS. 4C and 4D are graphs showing that treatment with 16 but not ACY-1083 increased body weight compared to vehicle in the presence of cisplatin.

FIG. 4E is a graph showing that treatment with 16 but not ACY-1083 improved mechanical allodynia at Day 16 compared to vehicle in the presence of cisplatin. FIG. 4F is a graph showing that treatment with 16 and ACY-1083 rescued IENF density compared to vehicle in the presence of cisplatin. P values determined by ordinary one-way ANOVA with FDR multiple comparisons correction (except Kaplan Meier), compared to cisplatin+vehicle; mean with SEM shown. * $P<0.05$,  $P<0.01$, * $P<0.001$, **** $P<0.0001$.

FIG. 5A is two graphs showing that treatment with 58 or ACY-775 restored mitochondrial movement (n=21 neurites per condition) to wild-type levels (left) and treatment with ACY-775 increased tubulin acetylation (n=3 lysates per condition) (right), with 58 showing a trend level increase.

FIG. 5B is two graphs showing that treatment with 173 and 79 (but not blinded DMSO) restored mitochondrial movement (n=28 neurites per condition) to wild-type levels (left) and increased tubulin acetylation (n=3 lysates per condition) (right). P values determined by ordinary one-way ANOVA with FDR multiple comparisons correction, compared to ALS (P525L); mean with SEM shown. * $P<0.05$,  $P<0.01$, * $P<0.001$, **** $P<0.0001$.

DETAILED DESCRIPTION OF CERTAIN EMBODIMENTS

Figure 1:
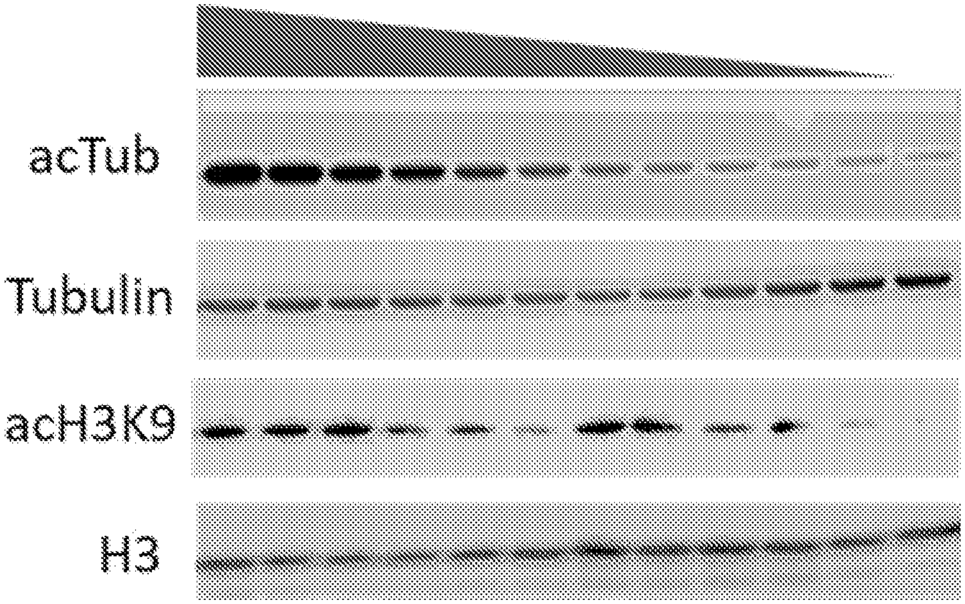
FIG. 1 is a western immunoblot showing the effect of compound 34 on acetyl tubulin, tubulin, acetyl histone H3K9, and histone H3 in undifferentiated SH-SY5Y cells.

Provided herein are compounds that are HDAC inhibitors (e.g., HDAC6 inhibitors). The compounds described herein possess advantageous properties, such as selective inhibition of HDAC6 and/or the ability to cross the blood-brain-barrier, that allow the compounds to be useful as therapeutic agents. In one aspect, the provided HDAC6 inhibitors are compounds of Formula (I), (II), (III), (IV), (V), and (VI), and pharmaceutically acceptable salts, solvates, hydrates, polymorphs, co-crystals, tautomers, stereoisomers, isotopically labeled derivatives, prodrugs, and pharmaceutical compositions thereof. Accordingly, the compounds are useful for the treatment and/or prevention of diseases and disorders associated with HDAC6 activity (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof.

The compounds described herein interact with HDAC6. As described herein, the therapeutic effect may be a result of inhibition, modulation, binding, and/or modification of HDAC6 by the compounds described herein. The compounds may be provided for use in any composition, kit, or method described herein as a pharmaceutically acceptable salt, co-crystal, tautomer, stereoisomer, solvate, hydrate, polymorph, isotopically enriched derivative, or prodrug thereof.

Compounds of Formula (I)

In one aspect, disclosed is a compound of Formula (I):

(I)

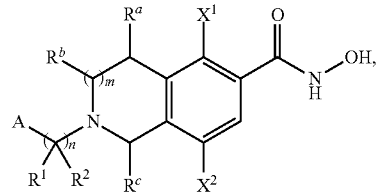

or a pharmaceutically acceptable salt, co-crystal, tautomer, stereoisomer, solvate, hydrate, polymorph, isotopically enriched derivative, or prodrug thereof, wherein:

$X^1$ is hydrogen or fluoro;

$X^2$ is hydrogen or fluoro; provided that at least one of $X^1$ and $X^2$ is fluorine;

A is substituted or unsubstituted alkyl, substituted or unsubstituted carbocyclyl, substituted or unsubstituted heterocyclyl, substituted or unsubstituted heteroaryl, or substituted or unsubstituted aryl;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl;

$R^a$ is hydrogen or is joined with $R^c$ to form a substituted or unsubstituted bridged ring;

$R^b$ is hydrogen or is joined with $R^c$ to form a substituted or unsubstituted bridged ring;

$R^c$ is hydrogen or substituted or unsubstituted alkyl or is joined with at least one of $R^a$ and $R^b$ to form a substituted or unsubstituted bridged ring;

m is 0 or 1; and n is 0 or 1.

$X^1$ and $X^2$

As described herein, $X^1$ is hydrogen or fluoro; and $X^2$ is hydrogen or fluoro; provided that at least one of $X^1$ and $X^2$ is fluorine In certain embodiments, $X^1$ is hydrogen; and $X^2$ is fluoro. In certain embodiments, $X^1$ is fluoro; and $X^2$ is hydrogen. In certain embodiments, $X^1$ is fluoro; and $X^2$ is fluoro.

A

As described herein, A is substituted or unsubstituted alkyl, substituted or unsubstituted carbocyclyl, substituted or unsubstituted heterocyclyl, substituted or unsubstituted heteroaryl, or substituted or unsubstituted aryl.

In certain embodiments, A is unsubstituted $C_{1-4}$ alkyl, $C_{1-4}$ haloalkyl, substituted or unsubstituted cycloalkyl, substituted or unsubstituted heterocyclyl, substituted or unsubstituted heteroaryl, or substituted or unsubstituted aryl.

In certain embodiments, A is substituted or unsubstituted cycloalkyl, substituted or unsubstituted heterocyclyl, or substituted or unsubstituted aryl.

In certain embodiments, A is substituted or unsubstituted cycloalkyl. In certain embodiments, A is substituted or unsubstituted $C_{3-10}$ cycloalkyl. In certain embodiments, A is a substituted or unsubstituted $C_{5-10}$ bridged cycloalkyl, substituted or unsubstituted $C_{5-10}$ spirocyclic cycloalkyl, or substituted or unsubstituted $C_{3-8}$ monocyclic cycloalkyl. In certain embodiments, A is a substituted or unsubstituted $C_{5-10}$ bridged cycloalkyl. In certain embodiments, A is a substituted or unsubstituted $C_{5-10}$ spirocyclic cycloalkyl. In certain embodiments, A is a substituted or unsubstituted $C_{8-10}$ spirocyclic cycloalkyl. In certain embodiments, A is substituted or unsubstituted $C_{3-8}$ monocyclic cycloalkyl. In certain embodiments, A is substituted or unsubstituted $C_{3-6}$ monocyclic cycloalkyl.

In certain embodiments, A is cyclopropyl, cyclobutyl, cyclopentyl, cyclohexyl, adamantyl,

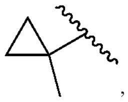
,
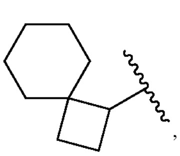
,
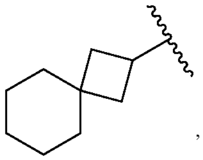
,

-continued

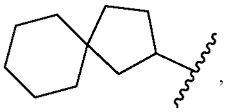
,
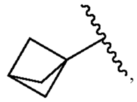
, or

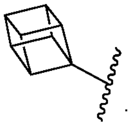
.

In certain embodiments, A is cyclopropyl, cyclobutyl, cyclopentyl, cyclohexyl, adamantyl,

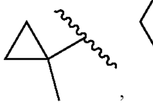
,
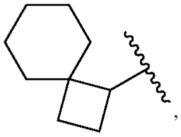
,
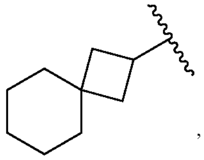
,

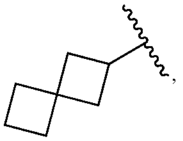
,
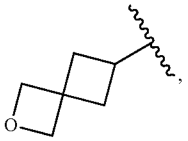
,

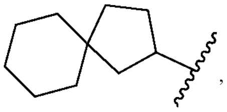
,
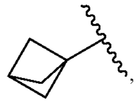
, or

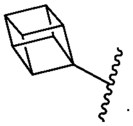
.

In certain embodiments, A is substituted or unsubstituted heterocyclyl. In certain embodiments, A is substituted or unsubstituted 4-10 membered heterocyclyl. In certain embodiments, A is substituted or unsubstituted monocyclic 4-7 membered heterocyclyl or substituted or unsubstituted 5-10 membered bridged heterocyclyl. In certain embodiments, A is substituted or unsubstituted monocyclic 4-7 membered heterocyclyl. In certain embodiments, A is substituted or unsubstituted monocyclic 4-6 membered heterocyclyl. In certain embodiments, A is substituted or unsubstituted monocyclic 4-5 membered heterocyclyl. In certain embodiments, A is substituted or unsubstituted monocyclic 5-6 membered heterocyclyl. In certain embodiments, A is substituted or unsubstituted 5-10 membered bridged heterocyclyl. In certain embodiments, A is substituted or unsubstituted 6-10 membered bridged heterocyclyl. In certain embodiments, A is substituted or unsubstituted 8-10 membered bridged heterocyclyl. In certain embodiments, A is substituted or unsubstituted 10-membered bridged heterocyclyl.

In certain embodiments, A is substituted or unsubstituted oxetanyl, substituted or unsubstituted tetrahydrofuranyl, substituted or unsubstituted pyranyl, substituted or unsubstituted dihydropyranyl, substituted or unsubstituted tetrahydropyranyl, substituted or unsubstituted dioxanyl, substituted or unsubstituted oxepanyl, substituted or unsubstituted azetidinyl, substituted or unsubstituted pyrrolidinyl, substituted or unsubstituted piperidinyl, substituted or unsubstituted piperazinyl, substituted or unsubstituted azepanyl, substituted or unsubstituted diazepanyl, substituted or unsubstituted morpholinyl, substituted or unsubstituted oxazepanyl, or oxaadamantanyl. In certain embodiments, A is tetrahydrofuranyl, oxetanyl, or

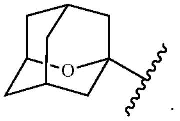 [SMILES: *C12CC3CC(CC(C3)O1)C2].

In certain embodiments, A is substituted or unsubstituted aryl. In certain embodiments, A is substituted or unsubstituted phenyl. In certain embodiments, A is unsubstituted phenyl. In certain embodiments, A is phenyl substituted with 1-5 substituents selected from halogen, cyano, alkyl, haloalkyl, alkenyl, alkynyl, alkoxy, haloalkoxy, or alkoxyalkyl. In certain embodiments, A is 2,6-dimethylphenyl.

In certain embodiments, A is unsubstituted $C_{1-4}$ alkyl or $C_{1-4}$ haloalkyl. In certain embodiments, A is unsubstituted $C_{1-4}$ alkyl. In certain embodiments, A is methyl, ethyl, n-propyl, isopropyl, n-butyl, sec-butyl, t-butyl, or isobutyl. In certain embodiments, A is t-butyl. In certain embodiments, A is $C_{1-4}$ haloalkyl. In certain embodiments, A is $—CF_3$, $—CHF_2$, or $—CH_2F$. In certain embodiments, A is $—CF_3$. In certain embodiments, A is $—CF_3$ or t-butyl.

In certain embodiments, A is unsubstituted $C_{1-4}$ alkyl, $C_{1-4}$ haloalkyl, substituted or unsubstituted $C_{8-10}$ spirocyclic cycloalkyl, substituted or unsubstituted $C_{3-6}$ monocyclic cycloalkyl, substituted or unsubstituted monocyclic 4-7 membered heterocyclyl, substituted or unsubstituted 8-10 membered bridged heterocyclyl, or substituted or unsubstituted phenyl.

In certain embodiments, A is $—CF_3$, $—C(CH_3)_3$, phenyl, 2,6-dimethylphenyl, tetrahydrofuranyl, oxetanyl, cyclopropyl, cyclobutyl, cyclopentyl, cyclohexyl, adamantyl, or.

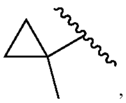, 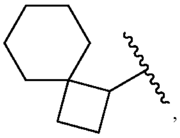, 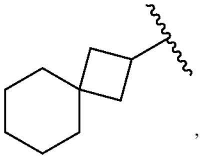, 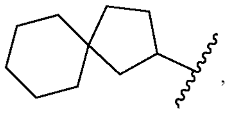, 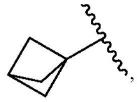, 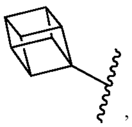, or 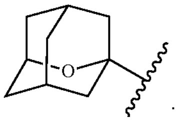.

In certain embodiments, A is $—CF_3$, $—C(CH_3)_3$, phenyl, 2,6-dimethylphenyl, tetrahydrofuranyl, oxetanyl, cyclopropyl, cyclobutyl, cyclopentyl, cyclohexyl, adamantyl,

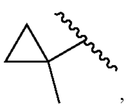, 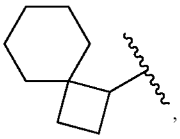, 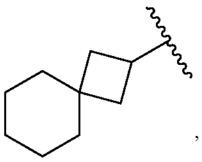,

-continued

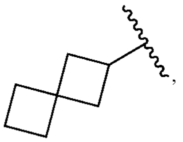, 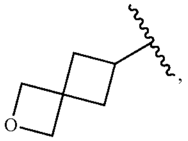, 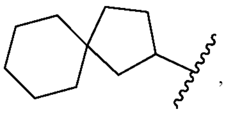, 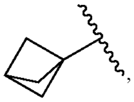, 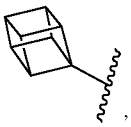, or 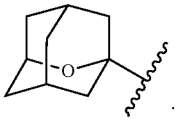.

$R^1$ and $R^2$

As described herein, $R^1$ is hydrogen or substituted or unsubstituted alkyl; and $R^2$ is hydrogen or substituted or unsubstituted alkyl; or $R^1$ and $R^2$ together form a substituted or unsubstituted heterocyclyl, or a substituted or unsubstituted cycloalkyl.

In certain embodiments, $R^1$ is hydrogen; and $R^2$ is unsubstituted $C_{1-4}$ alkyl; or $R^1$ and $R^2$ together form an unsubstituted cycloalkyl. In certain embodiments, $R^1$ is hydrogen; and $R^2$ is unsubstituted $C_{1-4}$ alkyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted cyclobutyl. In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ is unsubstituted $C_{1-4}$ alkyl; and $R^2$ is hydrogen; or $R^1$ and $R^2$ together form an unsubstituted cycloalkyl. In certain embodiments, $R^1$ is unsubstituted $C_{1-4}$ alkyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted cyclobutyl.

In certain embodiments, $R^1$ is unsubstituted $C_{1-4}$ alkyl; and $R^2$ is hydrogen. In certain embodiments, $R^1$ is methyl or ethyl; and $R^2$ is hydrogen. In certain embodiments, $R^1$ is methyl; and $R^2$ is hydrogen. In certain embodiments, $R^1$ is ethyl; and $R^2$ is hydrogen.

In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ and $R^2$ together form a substituted or unsubstituted cycloalkyl. In certain embodiments, $R^1$ and $R^2$ together form an unsubstituted cycloalkyl. In certain embodiments, $R^1$ and $R^2$ together form an unsubstituted $C_{3-6}$ cycloalkyl. In certain embodiments, $R^1$ and $R^2$ together form an unsubstituted cyclopropyl. In certain embodiments, $R^1$ and $R^2$ together form an unsubstituted cyclobutyl. In certain embodiments, $R^1$ and $R^2$ together form an unsubstituted cyclopentyl. In certain embodiments, $R^1$ and $R^2$ together form an unsubstituted cyclohexyl.

In certain embodiments, $R^1$ is hydrogen; and $R^2$ is hydrogen.

$R^a$, $R^b$, $R^c$, m, and n

As described herein, $R^a$ is hydrogen or is joined with $R^c$ to form a substituted or unsubstituted bridged ring; $R^b$ is hydrogen or is joined with $R^c$ to form a substituted or unsubstituted bridged ring; and $R^c$ is hydrogen or substituted or unsubstituted alkyl or is joined with at least one of $R^a$ and $R^b$ to form a substituted or unsubstituted bridged ring.

In certain embodiments, $R^a$ is joined with $R^c$ to form a substituted or unsubstituted bridged ring. In certain embodiments, $R^a$ is joined with $R^c$ to form a substituted or unsubstituted bridged ring; and $R^b$ is hydrogen. In certain embodiments, $R^a$ is joined with $R^c$ to form an unsubstituted bridged ring; and $R^b$ is hydrogen. In certain embodiments, $R^a$ is joined with $R^c$ to form an unsubstituted carbocyclic bridged ring; and $R^b$ is hydrogen. In certain embodiments, $R^a$ is joined with $R^c$ to form an unsubstituted heterocyclic bridged ring; and $R^b$ is hydrogen.

In certain embodiments, $R^b$ is joined with $R^c$ to form a substituted or unsubstituted bridged ring. In certain embodiments, $R^b$ is joined with $R^c$ to form a substituted or unsubstituted bridged ring; and $R^a$ is hydrogen. In certain embodiments, $R^b$ is joined with $R^c$ to form an unsubstituted bridged ring; and $R^a$ is hydrogen. In certain embodiments, $R^b$ is joined with $R^c$ to form an unsubstituted carbocyclic bridged ring; and $R^a$ is hydrogen. In certain embodiments, $R^b$ is joined with $R^c$ to form an unsubstituted heterocyclic bridged ring; and $R^a$ is hydrogen.

In certain embodiments, $R^a$ is hydrogen; $R^b$ is hydrogen; and $R^c$ is hydrogen or substituted or unsubstituted alkyl. In certain embodiments, $R^a$ is hydrogen; $R^b$ is hydrogen; and $R^c$ is hydrogen or unsubstituted alkyl. In certain embodiments, $R^a$ is hydrogen; $R^b$ is hydrogen; and $R^c$ is hydrogen or unsubstituted $C_{1-4}$ alkyl. In certain embodiments, $R^a$ is hydrogen; $R^b$ is hydrogen; and $R^c$ is hydrogen. In certain embodiments, $R^a$ is hydrogen; $R^b$ is hydrogen; and $R^c$ is unsubstituted $C_{1-4}$ alkyl.

As described herein, m is 0 or 1. In certain embodiments, m is 0. In certain embodiments, m is 1. As described herein, n is 0 or 1. In certain embodiments, n is 0. In certain embodiments, n is 1.

In certain embodiments, m is 0 or 1; and n is 0. In certain embodiments, m is 0 or 1; and n is 1. In certain embodiments, m is 0; and n is 0 or 1. In certain embodiments, m is 1; and n is 0 or 1. In certain embodiments, m is 0; and n is 1. In certain embodiments, m is 0; and n is 0. In certain embodiments, m is 1; and n is 0.

Certain Embodiments

In certain embodiments, the compound of Formula (I) is of Formula (I-a):

(I-a)

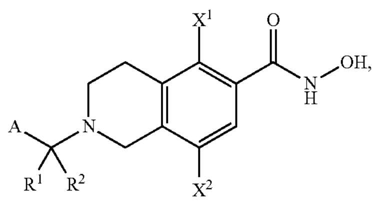

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, and $X^2$ are as defined herein.

In certain embodiments, the compound of Formula (I) is of Formula (I-b):

(I-b)

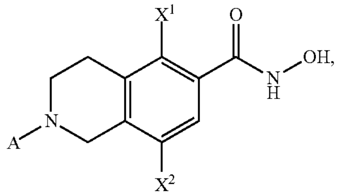

or a pharmaceutically acceptable salt, co-crystal, tautomer, stereoisomer, solvate, hydrate, polymorph, isotopically enriched derivative, or prodrug thereof; wherein A, $X^1$, and $X^2$ are as defined herein.

In certain embodiments, the compound of Formula (I) is of Formula (I-c):

(I-c)

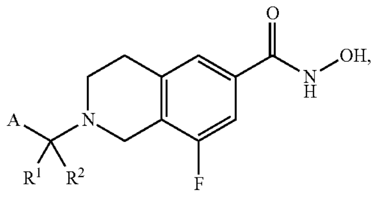

or a pharmaceutically acceptable salt, co-crystal, tautomer, stereoisomer, solvate, hydrate, polymorph, isotopically enriched derivative, or prodrug thereof; wherein A, $R^1$, and $R^2$ are as defined herein.

In certain embodiments, the compound of Formula (I) is of Formula (I-d):

(I-d)

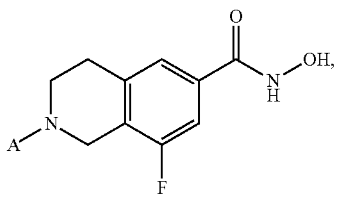

or a pharmaceutically acceptable salt, co-crystal, tautomer, stereoisomer, solvate, hydrate, polymorph, isotopically enriched derivative, or prodrug thereof; wherein A is as defined herein.

In certain embodiments, the compound of Formula (I) is of Formula (I-e):

(I-e)

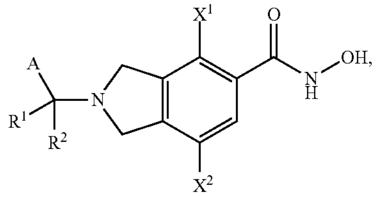

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, and $X^2$ are as defined herein.

In certain embodiments, the compound of Formula (I) is of Formula (I-f):

(I-f)

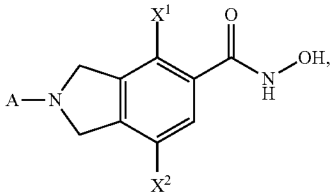

or a pharmaceutically acceptable salt, co-crystal, tautomer, stereoisomer, solvate, hydrate, polymorph, isotopically enriched derivative, or prodrug thereof; wherein A, $X^1$, and $X^2$ are as defined herein.

In certain embodiments, the compound of Formula (I) is of Formula (I-g):

(I-g)

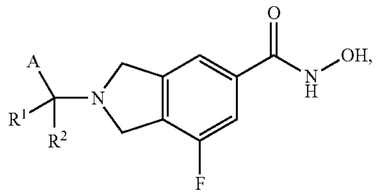

or a pharmaceutically acceptable salt, co-crystal, tautomer, stereoisomer, solvate, hydrate, polymorph, isotopically enriched derivative, or prodrug thereof; wherein A, $R^1$, and $R^2$ are as defined herein.

In certain embodiments, the compound of Formula (I) is of Formula (I-h):

(I-h)

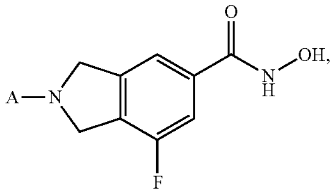

or a pharmaceutically acceptable salt, co-crystal, tautomer, stereoisomer, solvate, hydrate, polymorph, isotopically enriched derivative, or prodrug thereof; wherein A is as defined herein.

In certain embodiments, the compound of Formula (I) is one of the following compounds, or a pharmaceutically acceptable salt, co-crystal, tautomer, stereoisomer, solvate, hydrate, polymorph, isotopically enriched derivative, or prodrug thereof:

1

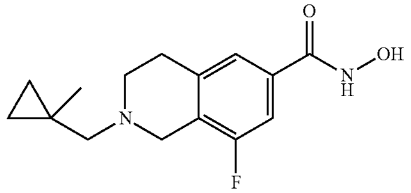

2

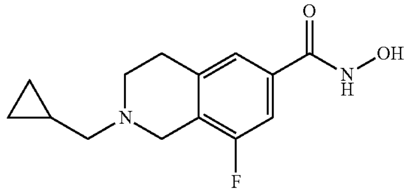

3

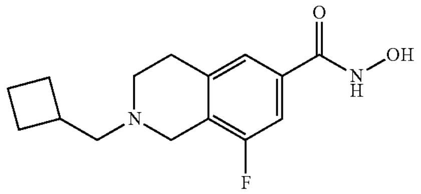

4

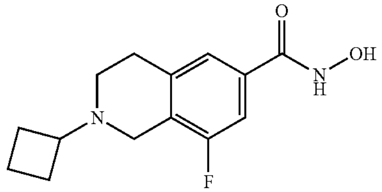

5

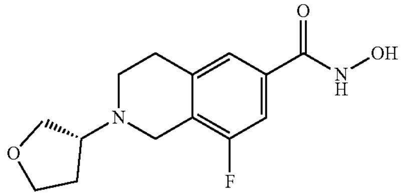

6

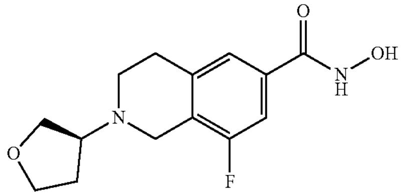

-continued
7
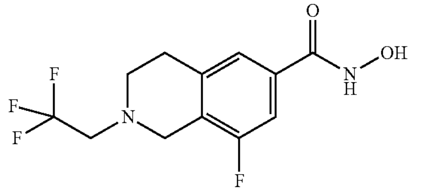
8
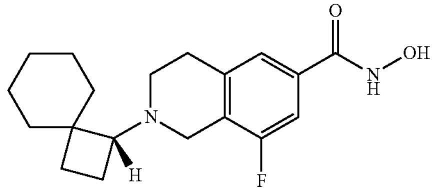
9
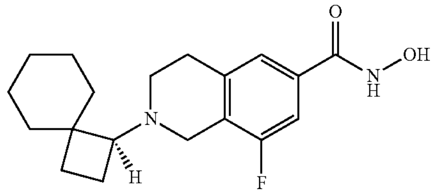
10
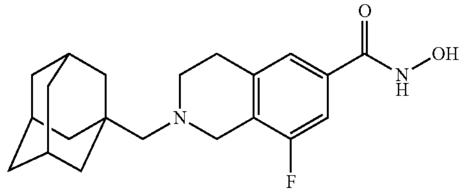
11
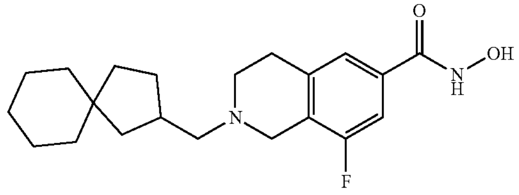
12
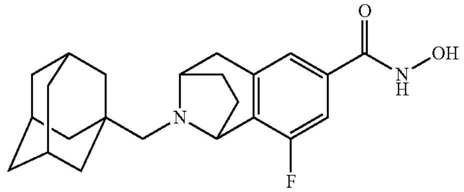
13
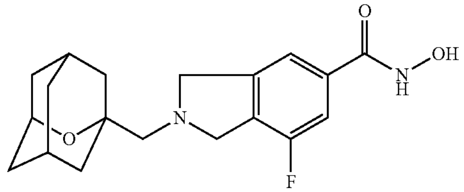
14
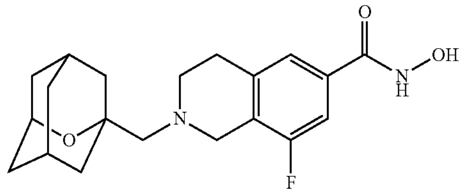
-continued
15
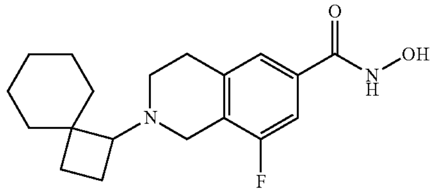
16
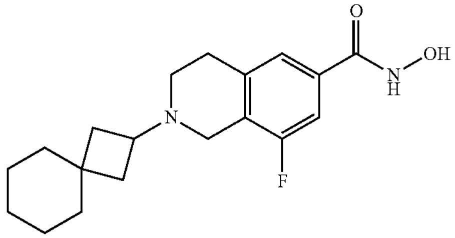
17
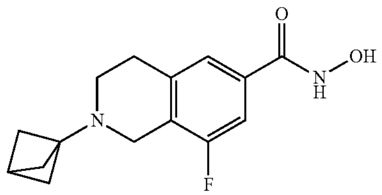
18
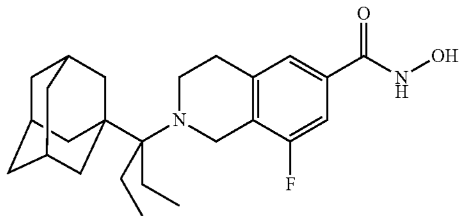
19
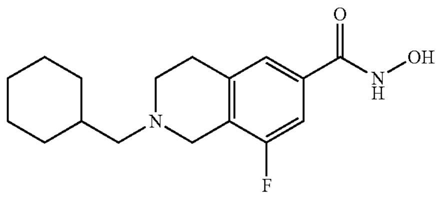
20
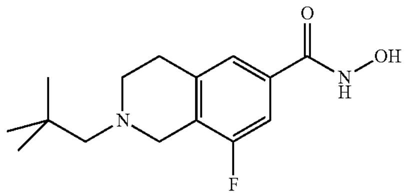
21
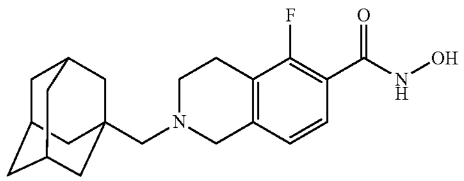

-continued
22
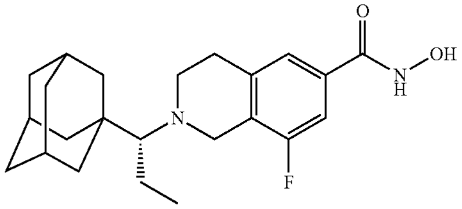
23
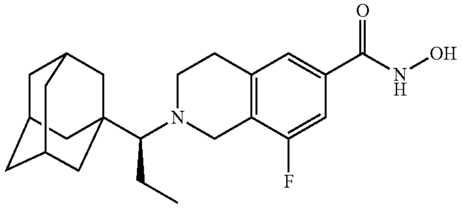
24
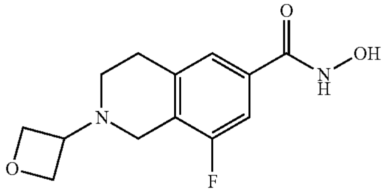
25
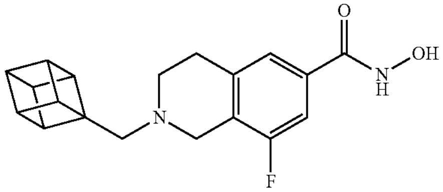
26
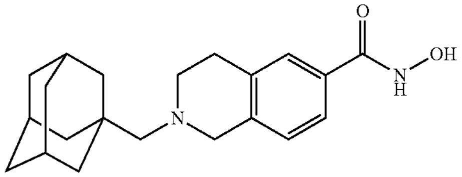
27
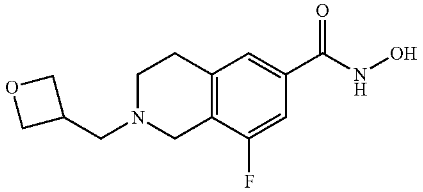
28
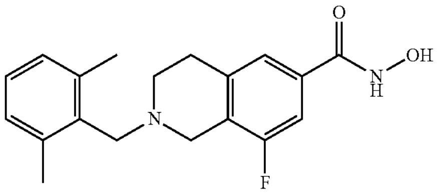
29
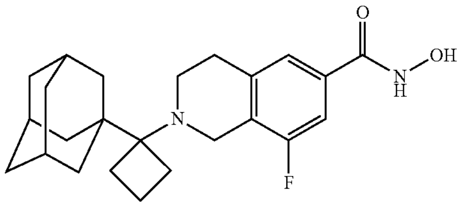
-continued
30
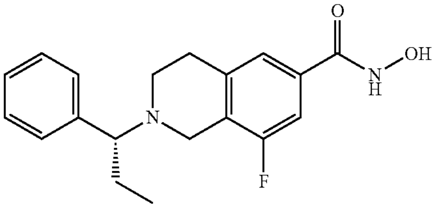
31
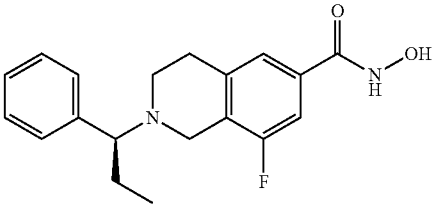
32
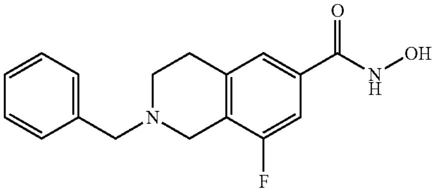
33
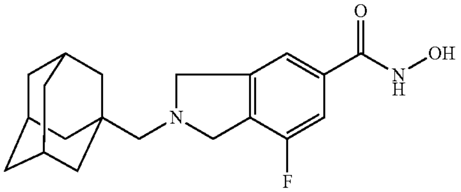
34
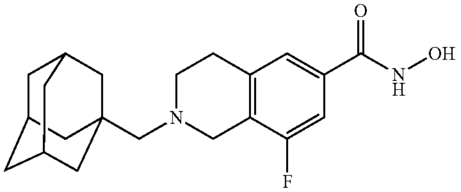
35
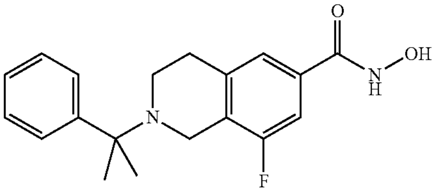
107
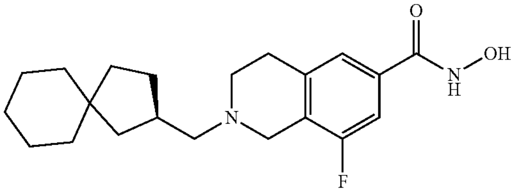

-continued
108
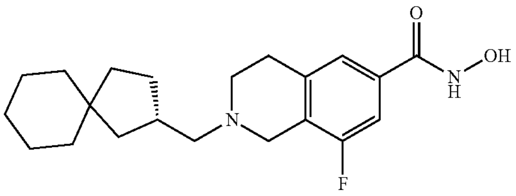
109
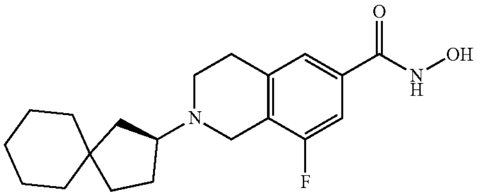
110
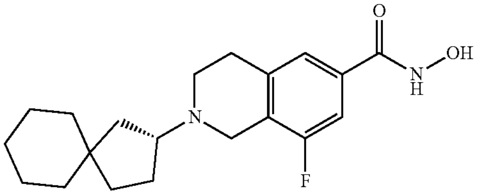
111
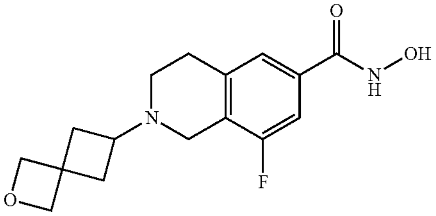
112
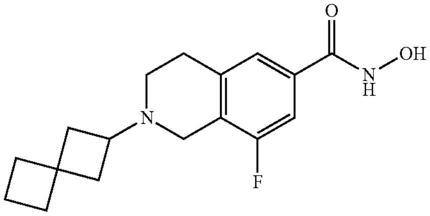
In certain embodiments, the compound of Formula (I) is one of the following compounds, or a pharmaceutically acceptable salt, co-crystal, tautomer, stereoisomer, solvate, hydrate, polymorph, isotopically enriched derivative, or prodrug thereof:
1
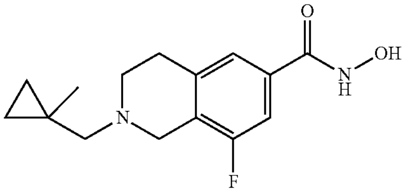
-continued
2
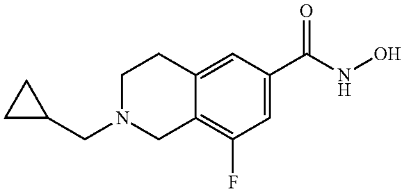
3
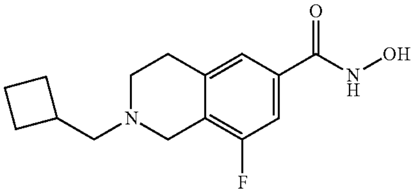
4
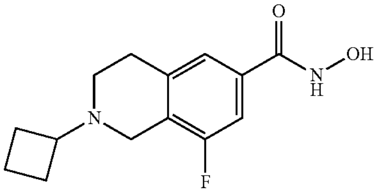
7
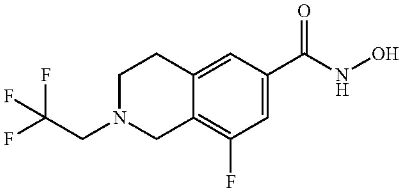
8
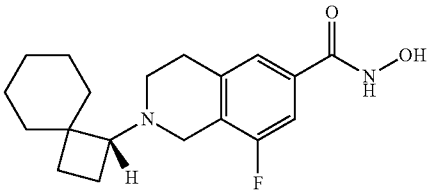
9
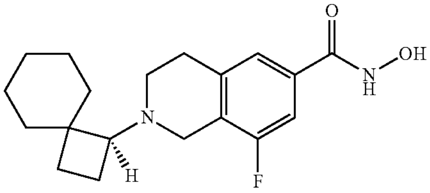
13
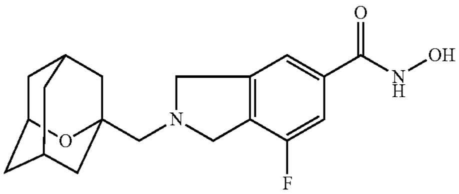
14
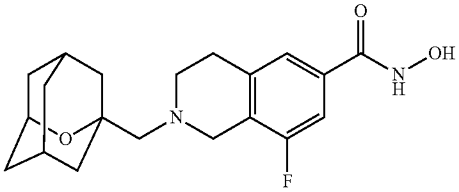

-continued
15
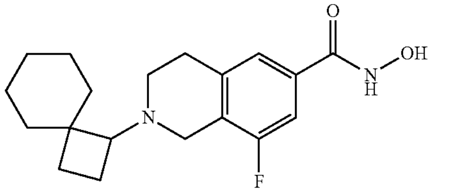
16
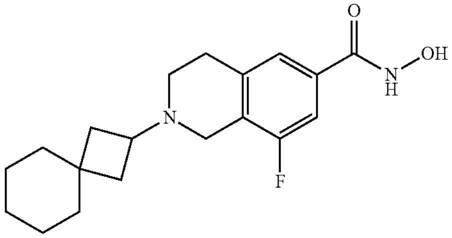
19
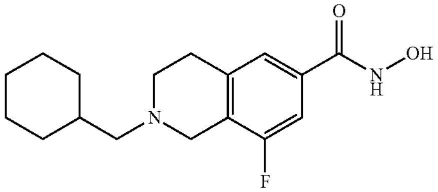
20
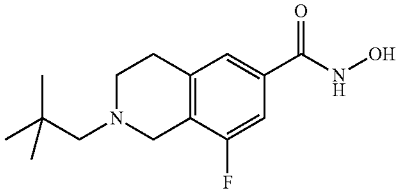
21
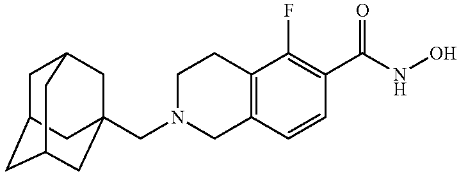
24
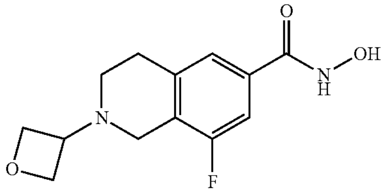
25
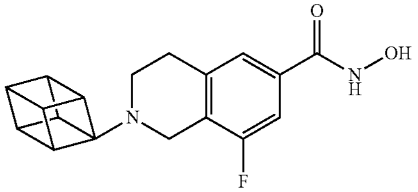
26
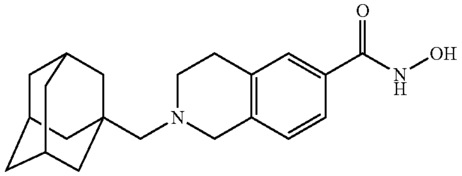
-continued
27
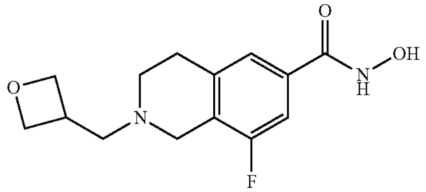
28
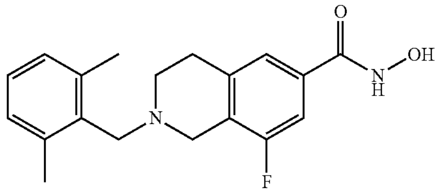
29
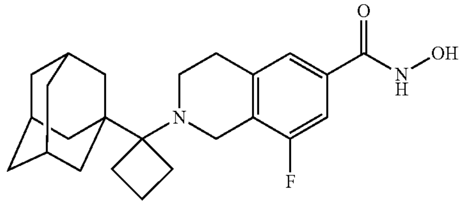
30
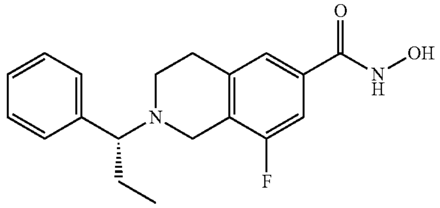
31
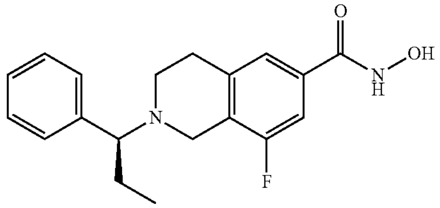
32
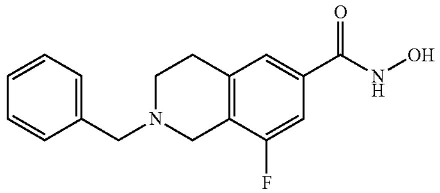
33
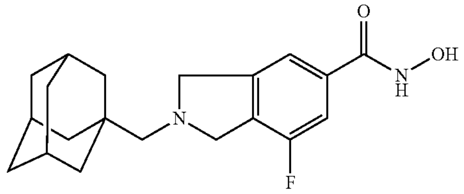

-continued

34

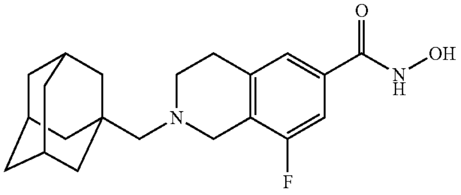

108

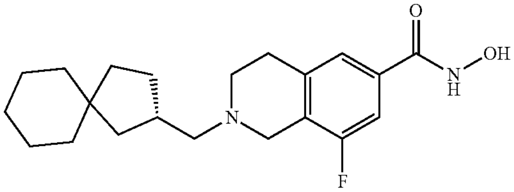

109

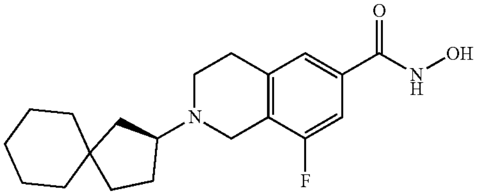

110

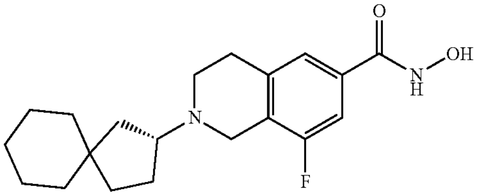

111

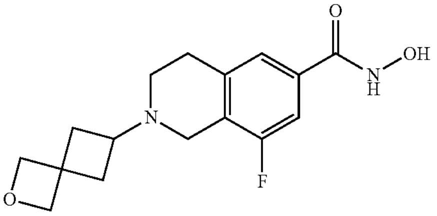

112

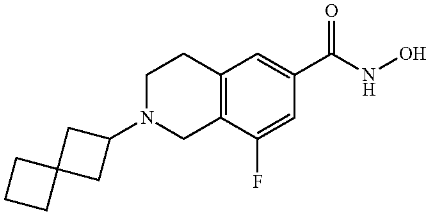

Compounds of Formula (II)

In another aspect, disclosed is a compound of Formula (II):

(II)

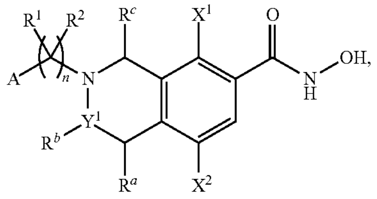

or a pharmaceutically acceptable salt, co-crystal, tautomer, stereoisomer, solvate, hydrate, polymorph, isotopically enriched derivative, or prodrug thereof, wherein:

$X^1$ is hydrogen or fluoro;

$X^2$ is hydrogen or fluoro;

$Y^1$ is nitrogen or $CR^x$;

each A is independently hydrogen, substituted or unsubstituted alkyl, substituted or unsubstituted carbocyclyl, substituted or unsubstituted heterocyclyl, substituted or unsubstituted heteroaryl, or substituted or unsubstituted aryl;

each $R^1$ is independently hydrogen or substituted or unsubstituted alkyl;

each $R^2$ is independently hydrogen or substituted or unsubstituted alkyl; or $R^1$ and $R^2$ together form a substituted or unsubstituted heterocyclyl, or a substituted or unsubstituted cycloalkyl;

$R^x$ is hydrogen or substituted or unsubstituted alkyl;

$R^a$ is hydrogen or is joined with $R^c$ to form a substituted or unsubstituted bridged ring;

$R^b$ is hydrogen, substituted or unsubstituted alkyl, or $A(CR^1R^2)_n$—, or is joined with $R^c$ to form a substituted or unsubstituted bridged ring;

$R^c$ is hydrogen or substituted or unsubstituted alkyl or is joined with at least one of $R^a$ and $R^b$ to form a substituted or unsubstituted bridged ring; and each n is independently 0 or 1.

$X^1$ and $X^2$

As described herein, $X^1$ is hydrogen or fluoro; and $X^2$ is hydrogen or fluoro. In certain embodiments, $X^1$ is hydrogen or fluoro; and $X^2$ is hydrogen or fluoro; provided that at least one of $X^1$ and $X^2$ is fluoro. In certain embodiments, $X^1$ is hydrogen; and $X^2$ is fluoro. In certain embodiments, $X^1$ is fluoro; and $X^2$ is hydrogen. In certain embodiments, $X^1$ is hydrogen; and $X^2$ is hydrogen. In certain embodiments, $X^1$ is fluoro; and $X^2$ is fluoro.

$Y^1$

As described herein, $Y^1$ is nitrogen or CH. In certain embodiments, $Y^1$ is nitrogen. In certain embodiments, $Y^1$ is CH.

A

As described herein, each A is independently hydrogen, substituted or unsubstituted alkyl, substituted or unsubstituted carbocyclyl, substituted or unsubstituted heterocyclyl, substituted or unsubstituted heteroaryl, or substituted or unsubstituted aryl. In certain embodiments, A is substituted or unsubstituted alkyl, substituted or unsubstituted carbocyclyl, substituted or unsubstituted heterocyclyl, substituted or unsubstituted heteroaryl, or substituted or unsubstituted aryl.

In certain embodiments, A is unsubstituted $C_{1-4}$ alkyl, $C_{1-4}$ haloalkyl, substituted or unsubstituted cycloalkyl, substituted or unsubstituted heterocyclyl, substituted or unsubstituted heteroaryl, or substituted or unsubstituted aryl.

In certain embodiments, A is substituted or unsubstituted cycloalkyl, substituted or unsubstituted heterocyclyl, or substituted or unsubstituted aryl.

In certain embodiments, A is substituted or unsubstituted cycloalkyl. In certain embodiments, A is substituted or unsubstituted $C_{3-10}$ cycloalkyl. In certain embodiments, A is a substituted or unsubstituted $C_{5-10}$ bridged cycloalkyl, substituted or unsubstituted $C_{5-10}$ spirocyclic cycloalkyl, or substituted or unsubstituted $C_{3-8}$ monocyclic cycloalkyl. In certain embodiments, A is a substituted or unsubstituted $C_{5-10}$ bridged cycloalkyl. In certain embodiments, A is a substituted or unsubstituted $C_{5-10}$ spirocyclic cycloalkyl. In certain embodiments, A is a substituted or unsubstituted $C_{8-10}$ spirocyclic cycloalkyl. In certain embodiments, A is substituted or unsubstituted $C_{3-8}$ monocyclic cycloalkyl. In certain embodiments, A is substituted or unsubstituted $C_{3-6}$ monocyclic cycloalkyl.

In certain embodiments, A is cyclopropyl, cyclobutyl, cyclopentyl, cyclohexyl, adamantyl,

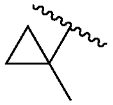, 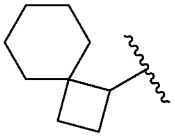,

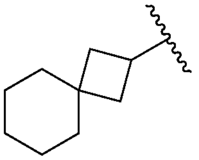, 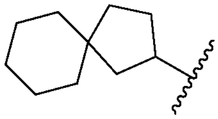,

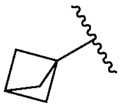, or 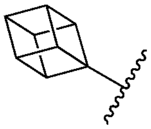.

In certain embodiments, A is adamantyl.

In certain embodiments, A is substituted or unsubstituted heterocyclyl. In certain embodiments, A is substituted or unsubstituted 4-10 membered heterocyclyl. In certain embodiments, A is substituted or unsubstituted monocyclic 4-7 membered heterocyclyl or substituted or unsubstituted 5-10 membered bridged heterocyclyl. In certain embodiments, A is substituted or unsubstituted monocyclic 4-7 membered heterocyclyl. In certain embodiments, A is substituted or unsubstituted monocyclic 4-6 membered heterocyclyl. In certain embodiments, A is substituted or unsubstituted monocyclic 4-5 membered heterocyclyl. In certain embodiments, A is substituted or unsubstituted monocyclic 5-6 membered heterocyclyl. In certain embodiments, A is substituted or unsubstituted 5-10 membered bridged heterocyclyl. In certain embodiments, A is substituted or unsubstituted 6-10 membered bridged heterocyclyl. In certain embodiments, A is substituted or unsubstituted 8-10 membered bridged heterocyclyl. In certain embodiments, A is substituted or unsubstituted 10-membered bridged heterocyclyl.

In certain embodiments, A is substituted or unsubstituted oxetanyl, substituted or unsubstituted tetrahydrofuranyl, substituted or unsubstituted pyranyl, substituted or unsubstituted dihydropyranyl, substituted or unsubstituted tetrahydropyranyl, substituted or unsubstituted dioxanyl, substituted or unsubstituted oxepanyl, substituted or unsubstituted azetidinyl, substituted or unsubstituted pyrrolidinyl, substituted or unsubstituted piperidinyl, substituted or unsubstituted piperazinyl, substituted or unsubstituted azepanyl, substituted or unsubstituted diazepanyl, substituted or unsubstituted morpholinyl, substituted or unsubstituted oxazepanyl, or oxaadamantanyl. In certain embodiments, A is tetrahydrofuranyl, oxetanyl, or

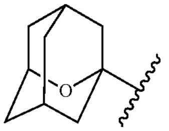.

In certain embodiments, A is oxetanyl.

In certain embodiments, A is substituted or unsubstituted aryl. In certain embodiments, A is substituted or unsubstituted phenyl. In certain embodiments, A is unsubstituted phenyl. In certain embodiments, A is phenyl substituted with 1-5 substituents selected from halogen, cyano, alkyl, haloalkyl, alkenyl, alkynyl, alkoxy, haloalkoxy, or alkoxyalkyl. In certain embodiments, A is 2,6-dimethylphenyl.

In certain embodiments, A is hydrogen, unsubstituted $C_{1-4}$ alkyl, or $C_{1-4}$ haloalkyl. In certain embodiments, A is hydrogen or unsubstituted $C_{1-4}$ alkyl. In certain embodiments, A is unsubstituted $C_{1-4}$ alkyl or $C_{1-4}$ haloalkyl. In certain embodiments, A is unsubstituted $C_{1-4}$ alkyl. In certain embodiments, A is methyl, ethyl, n-propyl, isopropyl, n-butyl, sec-butyl, t-butyl, or isobutyl. In certain embodiments, A is t-butyl. In certain embodiments, A is $C_{1-4}$ haloalkyl. In certain embodiments, A is $-CF_3$, $-CHF_2$, or $-CH_2F$. In certain embodiments, A is $-CF_3$. In certain embodiments, A is $-CF_3$ or t-butyl. In certain embodiments, A is methyl or hydrogen. In certain embodiments, A is methyl or hydrogen, and n is 0. In certain embodiments, A is methyl. In certain embodiments, A is methyl, and n is 0. In certain embodiments, A is hydrogen. In certain embodiments, A is hydrogen, and n is 0.

In certain embodiments, A is unsubstituted $C_{1-4}$ alkyl, $C_{1-4}$ haloalkyl, substituted or unsubstituted $C_{5-10}$ spirocyclic cycloalkyl, substituted or unsubstituted $C_{3-6}$ monocyclic cycloalkyl, substituted or unsubstituted monocyclic 4-7 membered heterocyclyl, substituted or unsubstituted 8-10 membered bridged heterocyclyl, or substituted or unsubstituted phenyl.

In certain embodiments, A is $-CF_3$, $-C(CH_3)_3$, phenyl, 2,6-dimethylphenyl, tetrahydrofuranyl, oxetanyl, cyclopropyl, cyclobutyl, cyclopentyl, cyclohexyl, adamantyl,

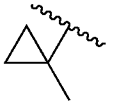, 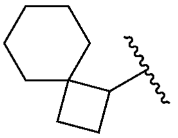,

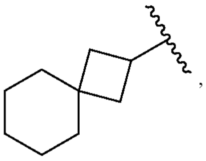, 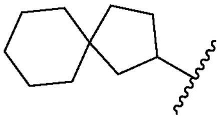,

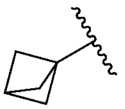, 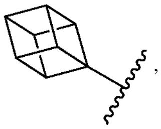, or

-continued

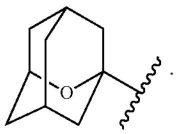.

In certain embodiments, A is —$CF_3$, —$C(CH_3)_3$, phenyl, 2,6-dimethylphenyl, tetrahydrofuranyl, oxetanyl, cyclopropyl, cyclobutyl, cyclopentyl, cyclohexyl, adamantyl,

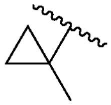, 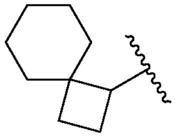, 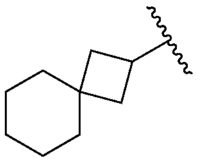, 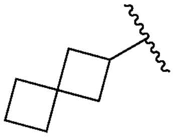, 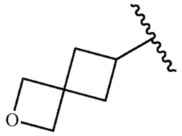, 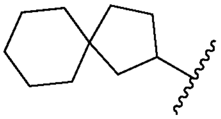, 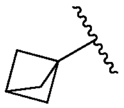, 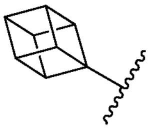, or 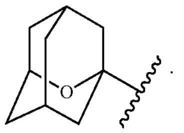 [SMILES: *C12CC3CC(CC(C3)O1)C2].

In certain embodiments, A is phenyl, oxetanyl, or adamantyl. In certain embodiments, A is

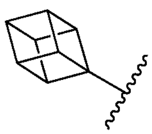, phenyl, oxetanyl, or adamantyl.

$R^1$ and $R^2$

As described herein, each $R^1$ is independently hydrogen or substituted or unsubstituted alkyl; and each $R^2$ is independently hydrogen or substituted or unsubstituted alkyl; or $R^1$ and $R^2$ together form a substituted or unsubstituted heterocyclyl, or a substituted or unsubstituted cycloalkyl.

In certain embodiments, $R^1$ is hydrogen; and $R^2$ is unsubstituted $C_{1-4}$ alkyl; or $R^1$ and $R^2$ together form an unsubstituted cycloalkyl. In certain embodiments, $R^1$ is hydrogen; and $R^2$ is unsubstituted $C_{1-4}$ alkyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted cyclobutyl. In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ is unsubstituted $C_{1-4}$ alkyl; and $R^2$ is hydrogen; or $R^1$ and $R^2$ together form an unsubstituted cycloalkyl. In certain embodiments, $R^1$ is unsubstituted $C_{1-4}$ alkyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted cyclobutyl.

In certain embodiments, $R^1$ is unsubstituted $C_{1-4}$ alkyl; and $R^2$ is hydrogen. In certain embodiments, $R^1$ is methyl or ethyl; and $R^2$ is hydrogen. In certain embodiments, $R^1$ is methyl; and $R^2$ is hydrogen. In certain embodiments, $R^1$ is ethyl; and $R^2$ is hydrogen.

In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ and $R^2$ together form a substituted or unsubstituted cycloalkyl. In certain embodiments, $R^1$ and $R^2$ together form an unsubstituted cycloalkyl. In certain embodiments, $R^1$ and $R^2$ together form an unsubstituted $C_{3-6}$ cycloalkyl. In certain embodiments, $R^1$ and $R^2$ together form an unsubstituted cyclopropyl. In certain embodiments, $R^1$ and $R^2$ together form an unsubstituted cyclobutyl. In certain embodiments, $R^1$ and $R^2$ together form an unsubstituted cyclopentyl. In certain embodiments, $R^1$ and $R^2$ together form an unsubstituted cyclohexyl.

In certain embodiments, $R^1$ is hydrogen; and $R^2$ is hydrogen.

$R^a$, $R^b$, $R^c$, $R^x$, and n

As described herein, $R^x$ is hydrogen or substituted or unsubstituted alkyl; $R^a$ is hydrogen or is joined with $R^c$ to form a substituted or unsubstituted bridged ring; $R^b$ is hydrogen, substituted or unsubstituted alkyl, or $A(CR^1R^2)_n$—, or is joined with $R^c$ to form a substituted or unsubstituted bridged ring; and $R^c$ is hydrogen or substituted or unsubstituted alkyl or is joined with at least one of $R^a$ and $R^b$ to form a substituted or unsubstituted bridged ring.

In certain embodiments, $R^x$ is hydrogen. In certain embodiments, $R^x$ is substituted or unsubstituted alkyl. In certain embodiments, $R^x$ is substituted or unsubstituted $C_{1-6}$ alkyl. In certain embodiments, $R^x$ is substituted or unsubstituted $C_{1-4}$ alkyl. In certain embodiments, $R^x$ is substituted or unsubstituted $C_{1-3}$ alkyl. In certain embodiments, $R^x$ is substituted alkyl. In certain embodiments, $R^x$ is substituted $C_{1-6}$ alkyl. In certain embodiments, $R^x$ is substituted $C_{1-4}$ alkyl. In certain embodiments, $R^x$ is substituted $C_{1-3}$ alkyl. In certain embodiments, $R^x$ is unsubstituted alkyl. In certain embodiments, $R^x$ is unsubstituted $C_{1-6}$ alkyl. In certain embodiments, $R^x$ is unsubstituted $C_{1-4}$ alkyl. In certain embodiments, $R^x$ is unsubstituted $C_{1-3}$ alkyl.

In certain embodiments, $R^a$ is joined with $R^c$ to form a substituted or unsubstituted bridged ring. In certain embodiments, $R^a$ is joined with $R^c$ to form a substituted or unsubstituted bridged ring; and $R^b$ is hydrogen. In certain embodiments, $R^a$ is joined with $R^c$ to form an unsubstituted bridged ring; and $R^b$ is hydrogen. In certain embodiments, $R^a$ is joined with $R^c$ to form an unsubstituted carbocyclic bridged ring; and $R^b$ is hydrogen. In certain embodiments, $R^a$ is joined with $R^c$ to form an unsubstituted heterocyclic bridged ring; and $R^b$ is hydrogen.

In certain embodiments, $R^b$ is hydrogen. In certain embodiments, $R^b$ is substituted or unsubstituted alkyl. In certain embodiments, $R^b$ is unsubstituted alkyl. In certain embodiments, $R^b$ is unsubstituted $C_{1-4}$ alkyl. In certain embodiments, $R^b$ is $A(CR^1R^2)_n$—, and n is 1. In certain embodiments, $R^b$ is $A(CR^1R^2)_n$—, and n is 0. In certain embodiments, $R^b$ is joined with $R^c$ to form a substituted or unsubstituted bridged ring. In certain embodiments, $R^b$ is joined with $R^c$ to form a substituted or unsubstituted bridged ring; and $R^a$ is hydrogen. In certain embodiments, $R^b$ is joined with $R^c$ to form an unsubstituted bridged ring; and $R^a$ is hydrogen. In certain embodiments, $R^b$ is joined with $R^c$ to form an unsubstituted carbocyclic bridged ring; and $R^a$ is hydrogen. In certain embodiments, $R^b$ is joined with $R^c$ to form an unsubstituted heterocyclic bridged ring; and $R^a$ is hydrogen.

In certain embodiments, $R^a$ is hydrogen; $R^b$ is hydrogen; and $R^c$ is hydrogen or substituted or unsubstituted alkyl. In certain embodiments, $R^a$ is hydrogen; $R^b$ is hydrogen; and $R^c$ is hydrogen or unsubstituted alkyl. In certain embodiments, $R^a$ is hydrogen; $R^b$ is hydrogen; and $R^c$ is hydrogen or unsubstituted $C_{1-4}$ alkyl. In certain embodiments, $R^a$ is hydrogen; $R^b$ is hydrogen; and $R^c$ is hydrogen. In certain embodiments, $R^a$ is hydrogen; $R^b$ is hydrogen; and $R^c$ is unsubstituted $C_{1-4}$ alkyl.

In certain embodiments, n is 0. In certain embodiments, n is 1.

Certain Embodiments

In certain embodiments, the compound of Formula (II) is of Formula (II-a):

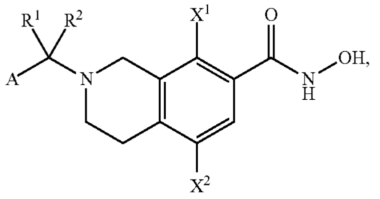

(II-a)

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, and $X^2$ are as defined herein.

In certain embodiments, the compound of Formula (II) is of Formula (II-b):

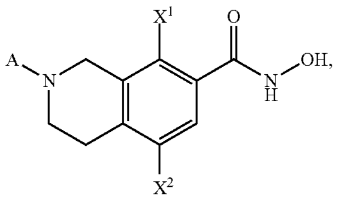

(II-b)

or a pharmaceutically acceptable salt, co-crystal, tautomer, stereoisomer, solvate, hydrate, polymorph, isotopically enriched derivative, or prodrug thereof; wherein A, $X^1$, and $X^2$ are as defined herein.

In certain embodiments, the compound of Formula (II) is of Formula (II-c):

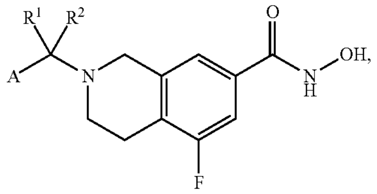

(II-c)

or a pharmaceutically acceptable salt, co-crystal, tautomer, stereoisomer, solvate, hydrate, polymorph, isotopically enriched derivative, or prodrug thereof; wherein A, $R^1$, and $R^2$ are as defined herein.

In certain embodiments, the compound of Formula (II) is of Formula (II-d):

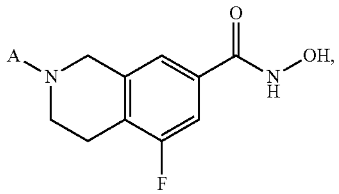

(II-d)

or a pharmaceutically acceptable salt, co-crystal, tautomer, stereoisomer, solvate, hydrate, polymorph, isotopically enriched derivative, or prodrug thereof; wherein A is as defined herein.

In certain embodiments, the compound of Formula (II) is of Formula (II-e):

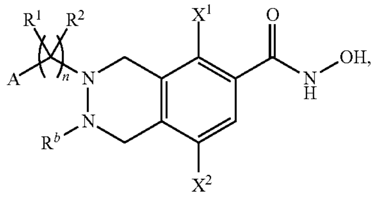

(II-e)

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, $X^2$, $R^b$, and n are as defined herein.

In certain embodiments of the compound of Formula (II-e), $R^b$ is hydrogen or unsubstituted alkyl. In certain embodiments of the compound of Formula (II-e), $R^b$ is hydrogen. In certain embodiments of the compound of Formula (II-e), $R^b$ is methyl.

In certain embodiments, the compound of Formula (II-e is of Formula (II-e-1):

(II-e-1)

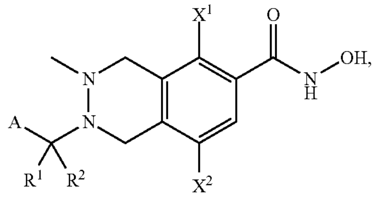

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, and $X^2$ are as defined herein.

In certain embodiments, the compound of Formula (II-e) is of Formula (II-e-2):

(II-e-2)

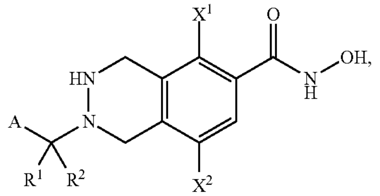

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, and $X^2$ are as defined herein.

In certain embodiments, the compound of Formula (II) is of Formula (II-f):

(II-f)

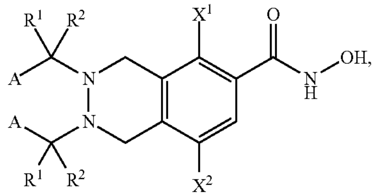

or a pharmaceutically acceptable salt, co-crystal, tautomer, stereoisomer, solvate, hydrate, polymorph, isotopically enriched derivative, or prodrug thereof; wherein A, $R^1$, $R^2$, $X^1$, and $X^2$ are as defined herein.

In certain embodiments, the compound of Formula (II) is of Formula (II-g):

(II-g)

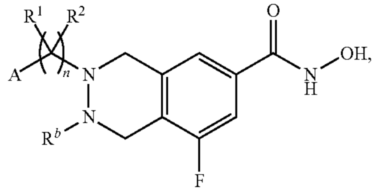

or a pharmaceutically acceptable salt, co-crystal, tautomer, stereoisomer, solvate, hydrate, polymorph, isotopically enriched derivative, or prodrug thereof; wherein A, $R^1$, $R^2$, $R^b$, and n are as defined herein.

In certain embodiments of the compound of Formula (II-g), $R^b$ is hydrogen or unsubstituted alkyl. In certain embodiments of the compound of Formula (II-g), $R^b$ is hydrogen. In certain embodiments of the compound of Formula (II-g), $R^b$ is methyl.

In certain embodiments, the compound of Formula (II-g) is of Formula (II-g-1):

(II-g-1)

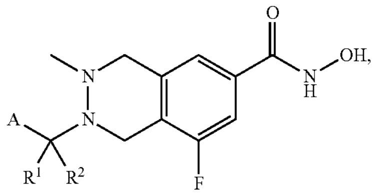

or a pharmaceutically acceptable salt, co-crystal, tautomer, stereoisomer, solvate, hydrate, polymorph, isotopically enriched derivative, or prodrug thereof; wherein A, $R^1$, and $R^2$ are as defined herein.

In certain embodiments, the compound of Formula (II-g) is of Formula (II-g-2):

(II-g-2)

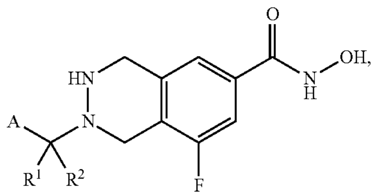

or a pharmaceutically acceptable salt, co-crystal, tautomer, stereoisomer, solvate, hydrate, polymorph, isotopically enriched derivative, or prodrug thereof; wherein A, $R^1$, and $R^2$ are as defined herein.

In certain embodiments, the compound of Formula (II) is of Formula (II-h):

(II-h)

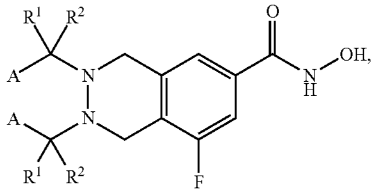

or a pharmaceutically acceptable salt, co-crystal, tautomer, stereoisomer, solvate, hydrate, polymorph, isotopically enriched derivative, or prodrug thereof; wherein A, $R^1$, and $R^2$ are as defined herein.

In certain embodiments, the compound of Formula (II) is one of the following compounds, or a pharmaceutically acceptable salt, co-crystal, tautomer, stereoisomer, solvate, hydrate, polymorph, isotopically enriched derivative, or prodrug thereof:

115
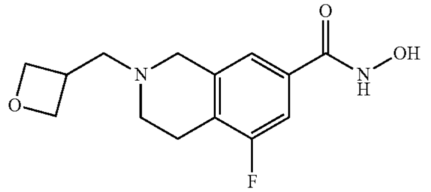
114
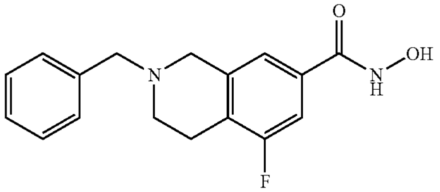
113
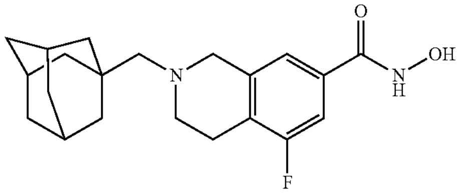
39
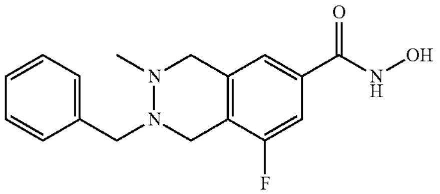
117
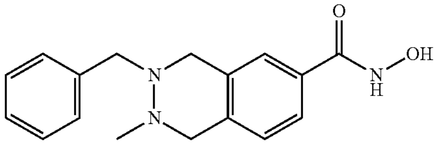
41
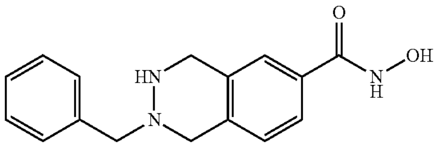
42
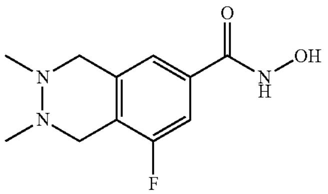
43
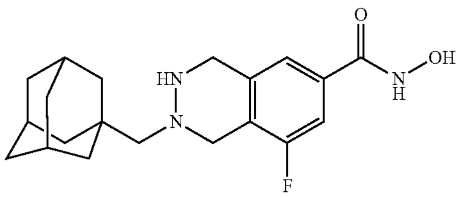
-continued
44
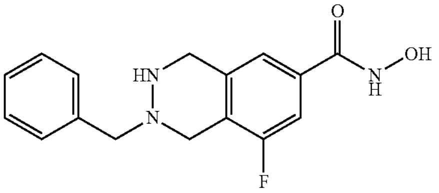
116
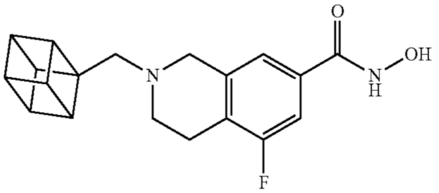
118
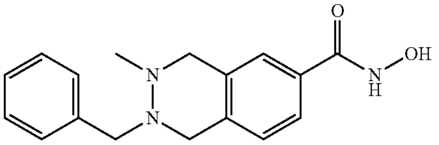
In certain embodiments, the compound of Formula (II) is one of the following compounds, or a pharmaceutically acceptable salt, co-crystal, tautomer, stereoisomer, solvate, hydrate, polymorph, isotopically enriched derivative, or prodrug thereof:
115
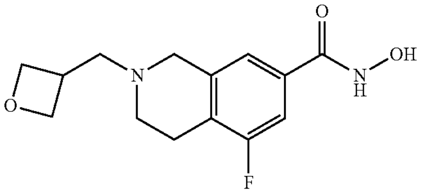
114
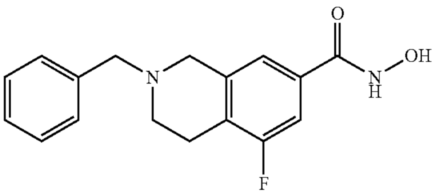
113
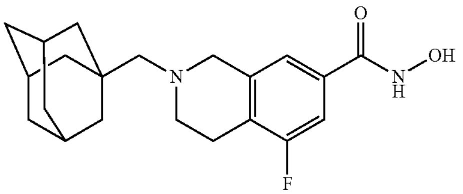
117
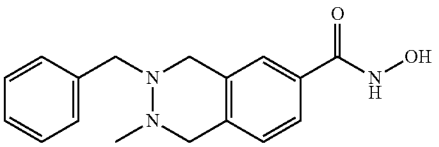

-continued

116

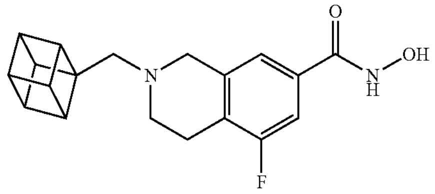

118

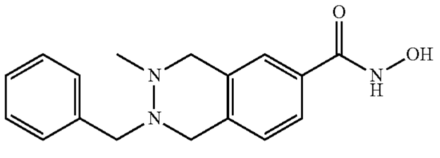

Compounds of Formula (III)

In another aspect, disclosed is a compound of Formula (III):

(III)

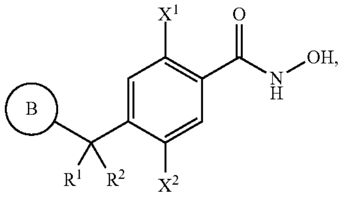

or a pharmaceutically acceptable salt, co-crystal, tautomer, stereoisomer, solvate, hydrate, polymorph, isotopically enriched derivative, or prodrug thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl; and B is a substituted or unsubstituted polycyclic spiro ring system, a bridged ring system,

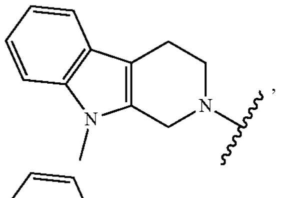,

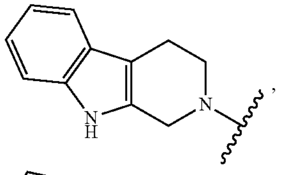, 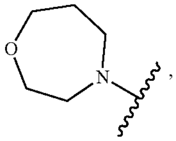,

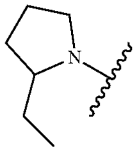, or 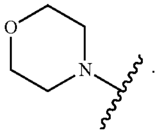.

$X^1$ and $X^2$

As described herein, $X^1$ is hydrogen or fluoro; and $X^2$ is hydrogen or fluoro. In certain embodiments, $X^1$ is hydrogen or fluoro; and $X^2$ is hydrogen or fluoro; provided that at least one of $X^1$ and $X^2$ is fluoro. In certain embodiments, $X^1$ is hydrogen; and $X^2$ is fluoro. In certain embodiments, $X^1$ is fluoro; and $X^2$ is hydrogen. In certain embodiments, $X^1$ is fluoro; and $X^2$ is fluoro. In certain embodiments, $X^1$ is hydrogen; and $X^2$ is hydrogen.

B

As described herein, B is a substituted or unsubstituted polycyclic spiro ring system, a substituted or unsubstituted bridged ring system,

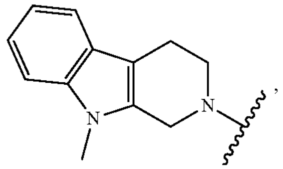,

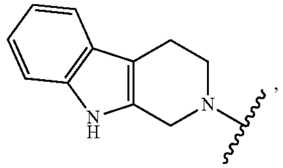, 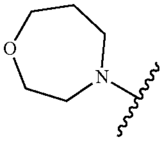,

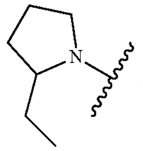, or 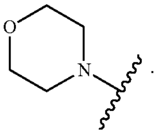.

In certain embodiments, B is a substituted or unsubstituted bridged ring system. In certain embodiments, B is a substituted or unsubstituted heterocyclic bridged ring system.

In certain embodiments, B is of formula:

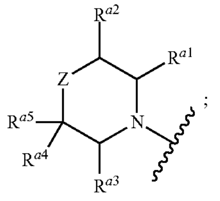;

wherein Z is —O—, —$NCH_3$—, —C(═O)—, —C(═NOH)—, or —$CHR^{a6}$—; $R^{a1}$ is hydrogen or is joined with $R^{a3}$ or $R^{a4}$ to form a 1-4 carbon bridge; $R^{a2}$ is hydrogen or is joined with $R^{a3}$ or $R^{a4}$ to form a 1-4 carbon bridge; $R^{a5}$ is hydrogen or is joined with $R^{a1}$ or $R^{a2}$ to form a 1-4 carbon bridge; $R^{a4}$ is hydrogen or is joined with $R^{a1}$ or $R^{a2}$ to form a 1-4 carbon bridge; $R^{a5}$ is hydrogen or is joined with $R^{a6}$ to form a substituted or unsubstituted cycloalkyl; and $R^{a6}$ is hydrogen or is joined with $R^{a5}$ to form a substituted or unsubstituted cycloalkyl.

In certain embodiments, B is of formula:

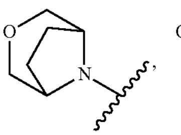, 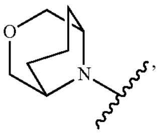, 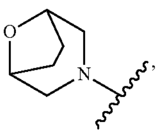,

-continued
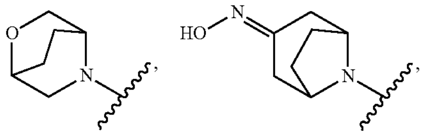
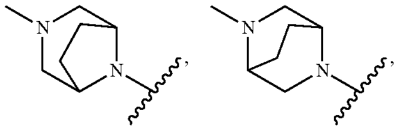
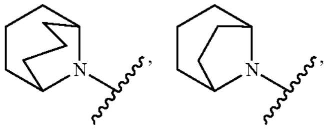
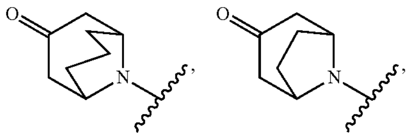 or
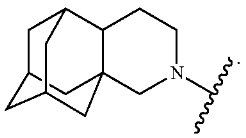
In certain embodiments, B is of formula:
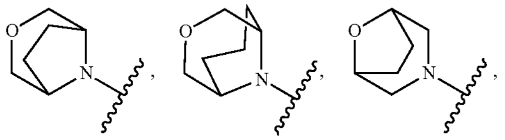
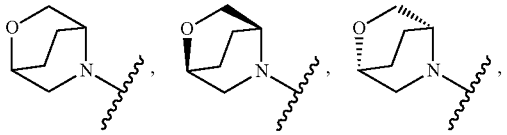
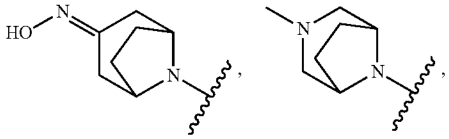
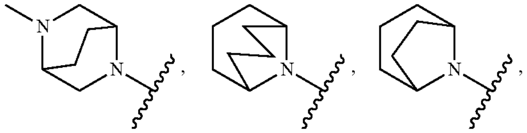
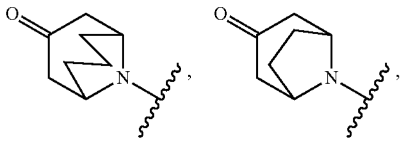
or
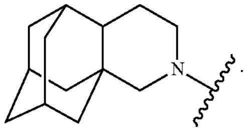
In certain embodiments, B is of formula:
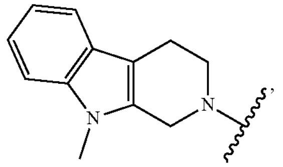
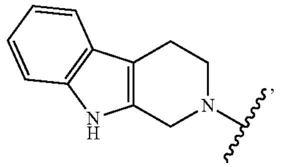
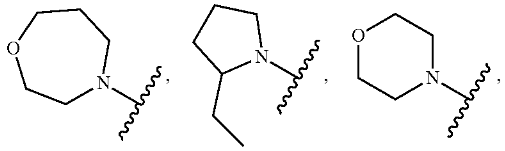
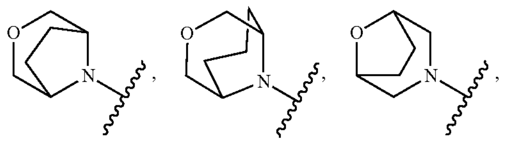
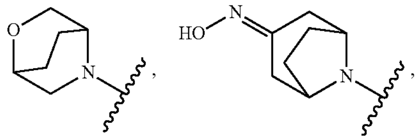
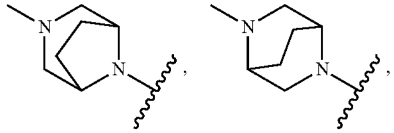
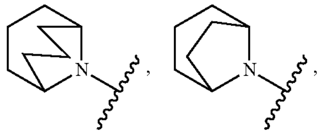
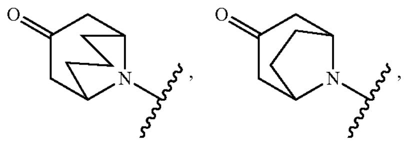
or
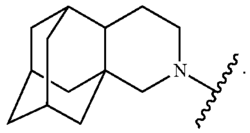
In certain embodiments, B is of formula:
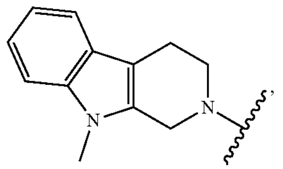

-continued
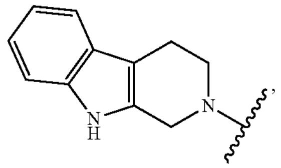,
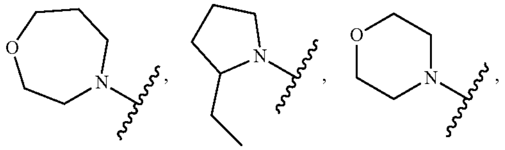,
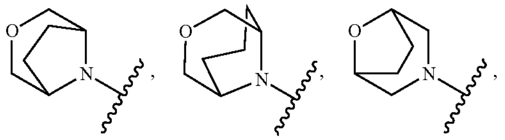,
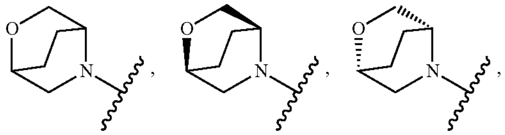,
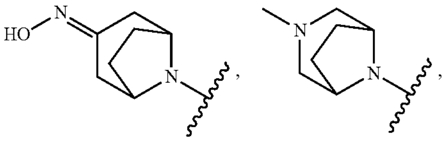,
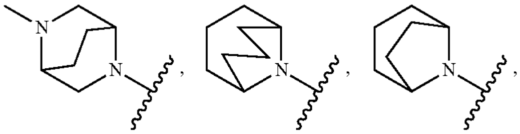,
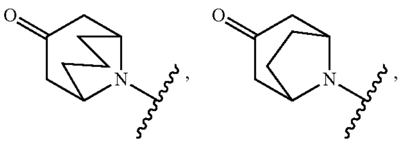,
or 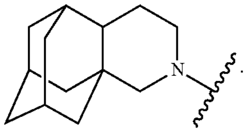.
In certain embodiments, B is of formula:
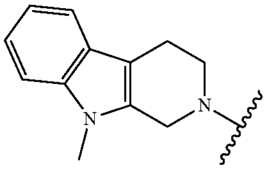 or
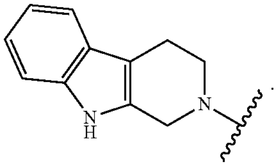.
In certain embodiments, B is of formula:
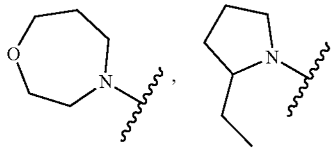, or
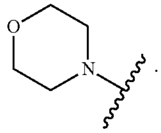.
In certain embodiments, B is of formula:
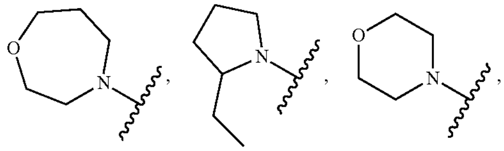,
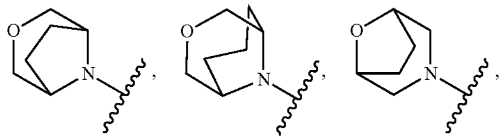,
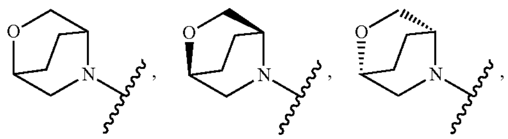,
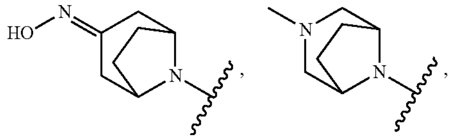,
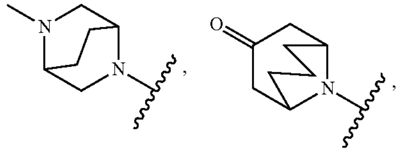,
or 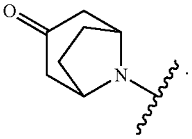.
In certain embodiments, B is of formula:
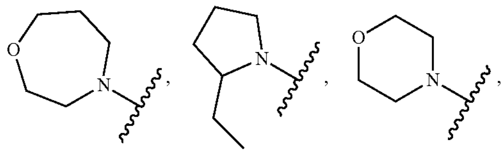,
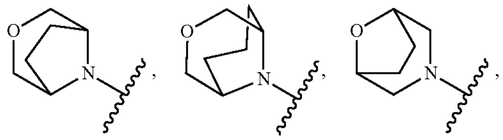, -continued

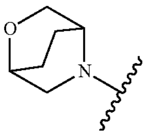, 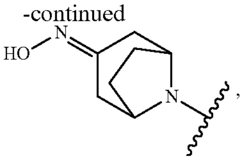,

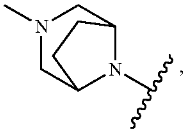, 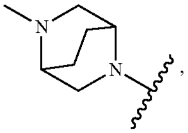,

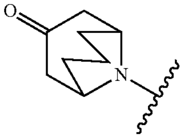, or 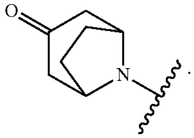.

$R^1$ and $R^2$

As described herein, $R^1$ is hydrogen or substituted or unsubstituted alkyl; and $R^2$ is hydrogen or substituted or unsubstituted alkyl; or $R^1$ and $R^2$ together form a substituted or unsubstituted heterocyclyl, or a substituted or unsubstituted cycloalkyl.

In certain embodiments, $R^1$ is hydrogen; and $R^2$ is unsubstituted $C_{1-4}$ alkyl; or $R^1$ and $R^2$ together form an unsubstituted cycloalkyl. In certain embodiments, $R^1$ is hydrogen; and $R^2$ is unsubstituted $C_{1-4}$ alkyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted cyclobutyl. In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ is unsubstituted $C_{1-4}$ alkyl; and $R^2$ is hydrogen; or $R^1$ and $R^2$ together form an unsubstituted cycloalkyl. In certain embodiments, $R^1$ is unsubstituted $C_{1-4}$ alkyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted cyclobutyl.

In certain embodiments, $R^1$ is unsubstituted $C_{1-4}$ alkyl; and $R^2$ is hydrogen. In certain embodiments, $R^1$ is methyl or ethyl; and $R^2$ is hydrogen. In certain embodiments, $R^1$ is methyl; and $R^2$ is hydrogen. In certain embodiments, $R^1$ is ethyl; and $R^2$ is hydrogen.

In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ and $R^2$ together form a substituted or unsubstituted cycloalkyl. In certain embodiments, $R^1$ and $R^2$ together form an unsubstituted cycloalkyl. In certain embodiments, $R^1$ and $R^2$ together form an unsubstituted $C_{3-6}$ cycloalkyl. In certain embodiments, $R^1$ and $R^2$ together form an unsubstituted cyclopropyl. In certain embodiments, $R^1$ and $R^2$ together form an unsubstituted cyclobutyl. In certain embodiments, $R^1$ and $R^2$ together form an unsubstituted cyclopentyl. In certain embodiments, $R^1$ and $R^2$ together form an unsubstituted cyclohexyl.

In certain embodiments, $R^1$ is hydrogen; and $R^2$ is hydrogen.

Certain Embodiments

In certain embodiments, the compound of Formula (III) is of Formula (III-a):

(III-a)

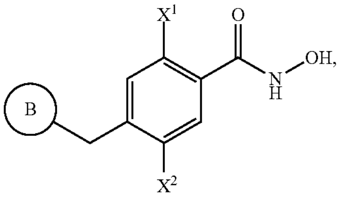

or a pharmaceutically acceptable salt, co-crystal, tautomer, stereoisomer, solvate, hydrate, polymorph, isotopically enriched derivative, or prodrug thereof; wherein B, $X^1$, and $X^2$ are as defined herein.

In certain embodiments, the compound of Formula (III) is of Formula (III-b):

(III-b)

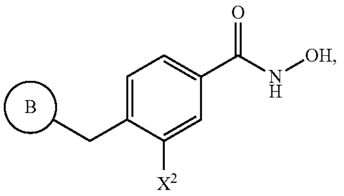

or a pharmaceutically acceptable salt, co-crystal, tautomer, stereoisomer, solvate, hydrate, polymorph, isotopically enriched derivative, or prodrug thereof; wherein B and $X^2$ are as defined herein.

In certain embodiments, the compound of Formula (III) is of Formula (III-c):

(III-c)

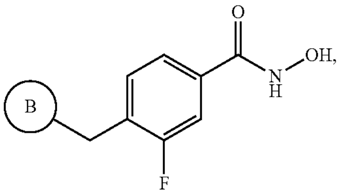

or a pharmaceutically acceptable salt, co-crystal, tautomer, stereoisomer, solvate, hydrate, polymorph, isotopically enriched derivative, or prodrug thereof; wherein B is as defined herein.

In certain embodiments, the compound of Formula (III) is one of the following compounds, or a pharmaceutically acceptable salt, co-crystal, tautomer, stereoisomer, solvate, hydrate, polymorph, isotopically enriched derivative, or prodrug thereof:

45
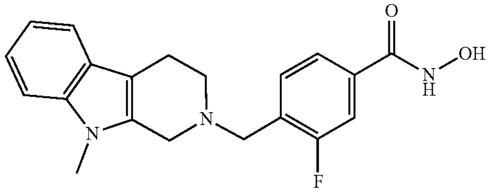
46
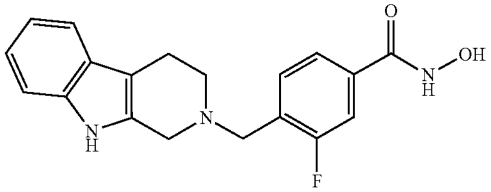
47
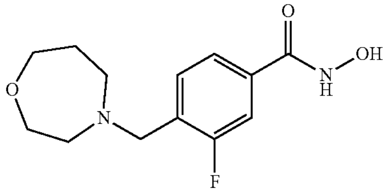
48
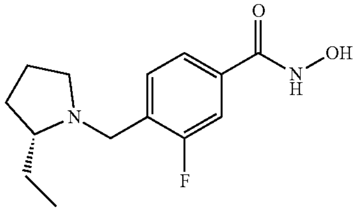
49
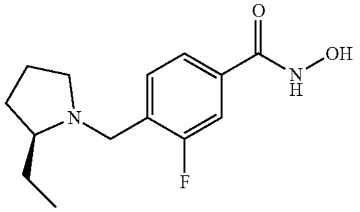
50
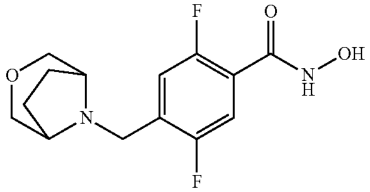
51
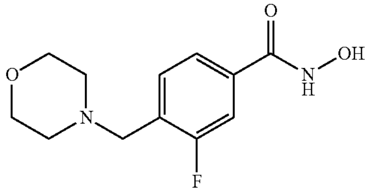
-continued
52
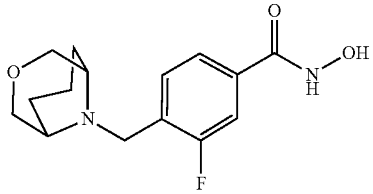
53
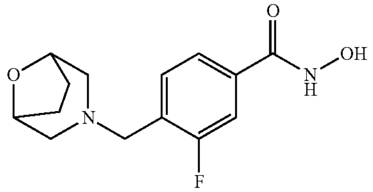
54
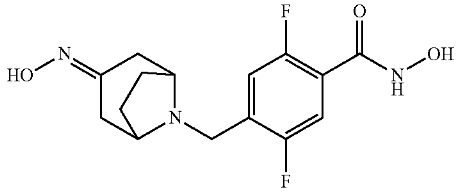
55
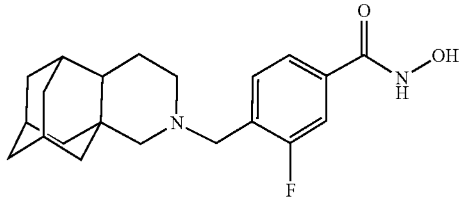
56
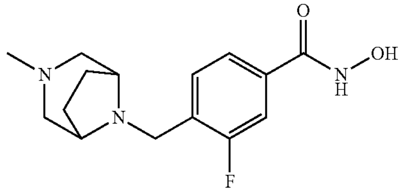
57
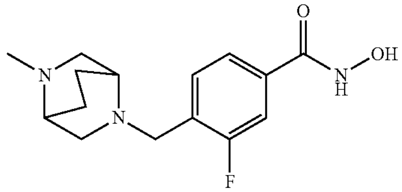
58
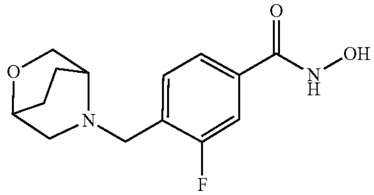
59
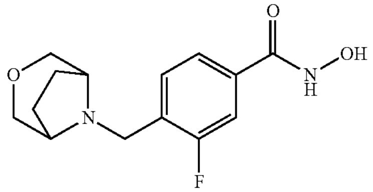

-continued
60
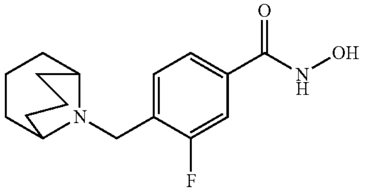
61
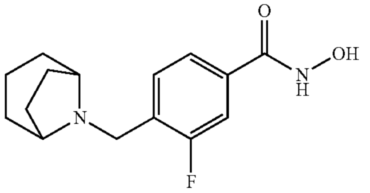
62
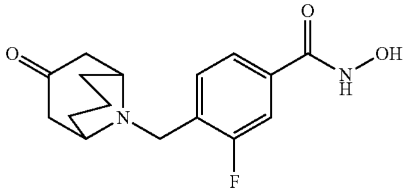
63
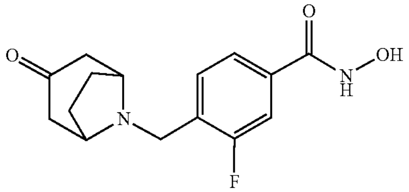
64
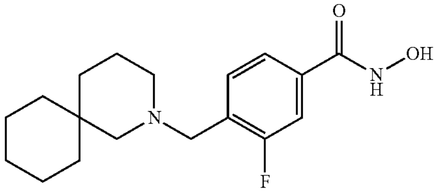
169
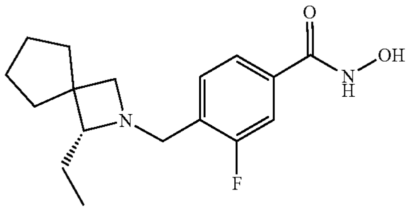
172
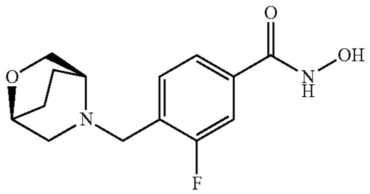
-continued
173
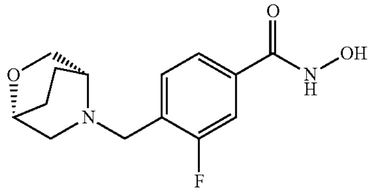
In certain embodiments, the compound of Formula (III) is one of the following compounds, or a pharmaceutically acceptable salt, co-crystal, tautomer, stereoisomer, solvate, hydrate, polymorph, isotopically enriched derivative, or prodrug thereof:
45
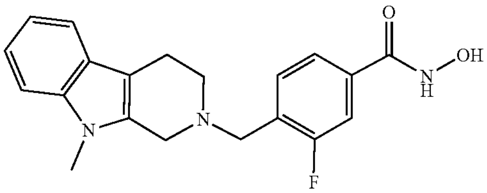
46
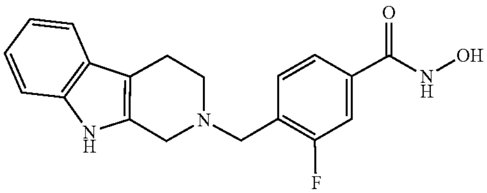
47
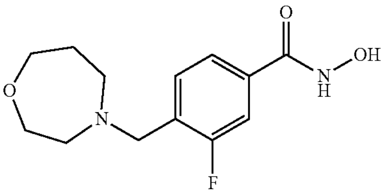
48
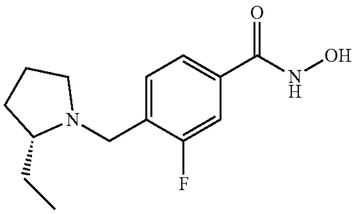
49
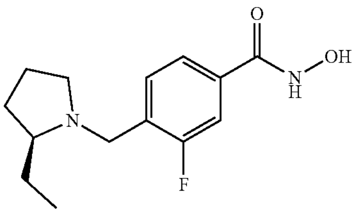

-continued
50
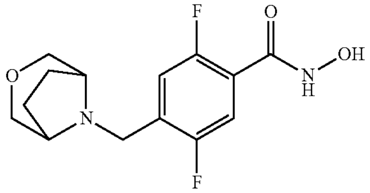
51
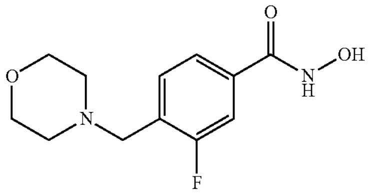
52
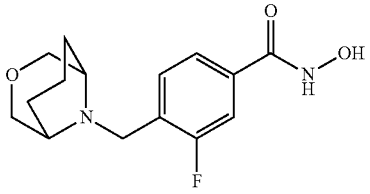
53
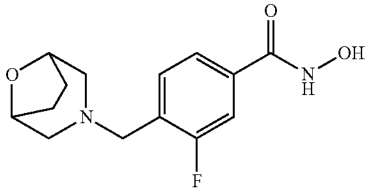
54
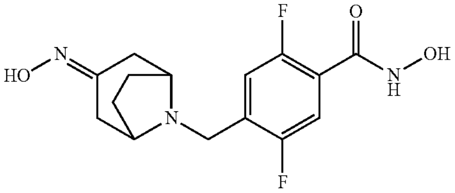
56
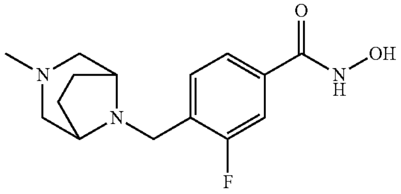
57
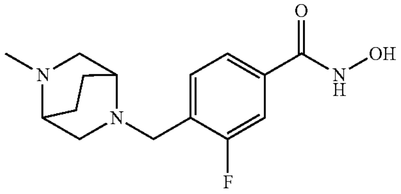
58
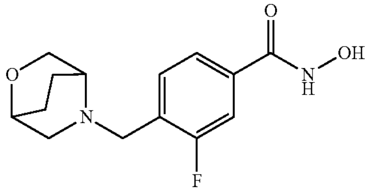
-continued
59
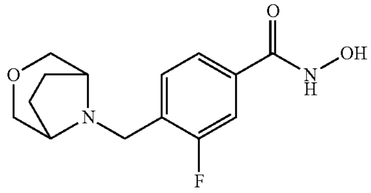
60
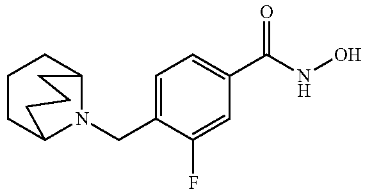
61
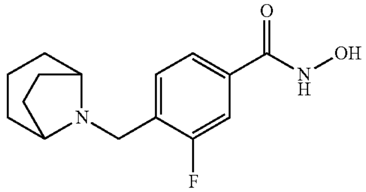
62
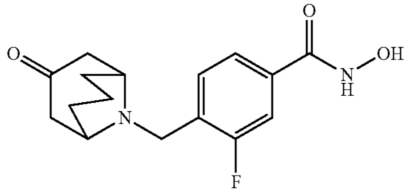
63
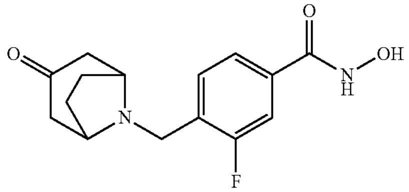
172
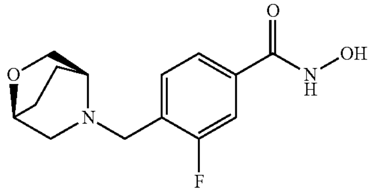
173
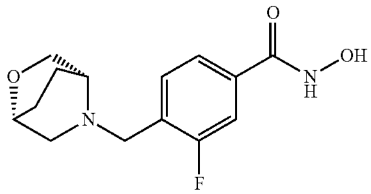
Compounds of Formula (IV)
In certain embodiments of the compound of Formula (III), B is a substituted or unsubstituted polycyclic spiro ring system. In certain embodiments, the compound of Formula (III) is of Formula (IV):

(IV)

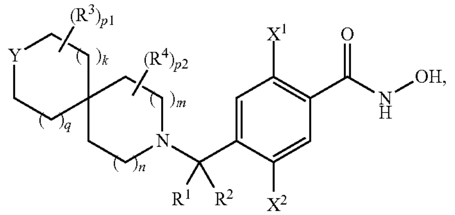

or a pharmaceutically acceptable salt, co-crystal, tautomer, stereoisomer, solvate, hydrate, polymorph, isotopically enriched derivative, or prodrug thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl;

Y is —O—, —S—, —$NR^{a1}$—, or —$(CR^3R^4)$—;

each occurrence of $R^3$ and $R^4$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroalkyl, —$N(R^{a1})_2$, —$OR^{b1}$, —$SR^{c1}$, or —CN; wherein two or three $R^3$ groups are optionally joined to form a substituted or unsubstituted bridged ring; wherein two or three $R^4$ groups are optionally joined to form a substituted or unsubstituted bridged ring;

each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group, or two $R^{a1}$ groups are joined to form a substituted or unsubstituted heterocyclic ring;

each occurrence of $R^{b1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or an oxygen protecting group;

each occurrence of $R^{c1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or a sulfur protecting group;

m, n, k, and q are each independently 0, 1, or 2; and p1 and p2 are each independently 0, 1, 2, 3, or 4.

$X^1$ and $X^2$

In certain embodiments, $X^1$ is hydrogen or fluoro; and $X^2$ is hydrogen or fluoro; provided that at least one of $X^1$ and $X^2$ is fluoro. In certain embodiments, $X^1$ is hydrogen; and $X^2$ is fluoro. In certain embodiments, $X^1$ is fluoro; and $X^2$ is hydrogen. In certain embodiments, $X^1$ is fluoro; and $X^2$ is fluoro. In certain embodiments, $X^1$ is hydrogen; and $X^2$ is hydrogen.

$R^1$ and $R^2$

In certain embodiments, $R^1$ is hydrogen; and $R^2$ is unsubstituted $C_{1-4}$ alkyl; or $R^1$ and $R^2$ together form an unsubstituted cycloalkyl. In certain embodiments, $R^1$ is hydrogen; and $R^2$ is unsubstituted $C_{1-4}$ alkyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted cyclobutyl. In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ is unsubstituted $C_{1-4}$ alkyl; and $R^2$ is hydrogen; or $R^1$ and $R^2$ together form an unsubstituted cycloalkyl. In certain embodiments, $R^1$ is unsubstituted $C_{1-4}$ alkyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted cyclobutyl.

In certain embodiments, $R^1$ is unsubstituted $C_{1-4}$ alkyl; and $R^2$ is hydrogen. In certain embodiments, $R^1$ is methyl or ethyl; and $R^2$ is hydrogen. In certain embodiments, $R^1$ is methyl; and $R^2$ is hydrogen. In certain embodiments, $R^1$ is ethyl; and $R^2$ is hydrogen.

In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ and $R^2$ together form a substituted or unsubstituted cycloalkyl. In certain embodiments, $R^1$ and $R^2$ together form an unsubstituted cycloalkyl. In certain embodiments, $R^1$ and $R^2$ together form an unsubstituted $C_{3-6}$ cycloalkyl. In certain embodiments, $R^1$ and $R^2$ together form an unsubstituted cyclobutyl.

In certain embodiments, $R^1$ is hydrogen; and $R^2$ is hydrogen.

B

As described herein, Y is —O—, —S—, —$NR^{a1}$—, or —$(CR^3R^4)$—;

each occurrence of $R^3$ and $R^4$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroalkyl, —$N(R^{a1})_2$, —$OR^{b1}$, —$SR^{c1}$, or —CN; wherein two or three $R^3$ groups are optionally joined to form a substituted or unsubstituted bridged ring; wherein two or three $R^4$ groups are optionally joined to form a substituted or unsubstituted bridged ring;

each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group, or two $R^{a1}$ groups are joined to form a substituted or unsubstituted heterocyclic ring;

each occurrence of $R^{b1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or an oxygen protecting group;

each occurrence of $R^{c1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or a sulfur protecting group;

m, n, k, and q are each independently 0, 1, or 2; and p1 and p2 are each independently 0, 1, 2, 3, or 4.

In certain embodiments, Y is —O—, —($CR^3R^4$)—, or —$NR^{a1}$—; and $R^3$, $R^4$, and $R^{a1}$ are as defined herein. In certain embodiments, Y is —O—. In certain embodiments, Y is —($CR^3R^4$)—; and $R^3$, $R^4$, and $R^{a1}$ are as defined herein. In certain embodiments, Y is —$NR^{a1}$—; and $R^{a1}$ is as defined herein.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; and each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group; the sum of m and n is 0, 1, or 2; and the sum of k and q is 0, 1, or 2.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; and each occurrence of $R^{a1}$ is, independently, hydrogen, substituted or unsubstituted acyl, substituted or unsubstituted alkyl, or a nitrogen protecting group.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; each occurrence of $R^{a1}$ is, independently, hydrogen, substituted or unsubstituted acyl, substituted or unsubstituted alkyl, or a nitrogen protecting group; the sum of m and n is 0, 1, or 2; and the sum of k and q is 0, 1, or 2.

In certain embodiments, Y is —O—, —($CR^3R^4$)—, or —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; and each occurrence of $R^{a1}$ is, independently, hydrogen, substituted or unsubstituted acyl, substituted or unsubstituted alkyl, or a nitrogen protecting group.

In certain embodiments, Y is —O—, —($CR^3R^4$)—, or —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; each occurrence of $R^{a1}$ is, independently, hydrogen, substituted or unsubstituted acyl, substituted or unsubstituted alkyl, or a nitrogen protecting group; the sum of m and n is 0, 1, or 2; and the sum of k and q is 0, 1, or 2.

In certain embodiments, Y is —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; and each occurrence of $R^{a1}$ is, independently, hydrogen, substituted or unsubstituted acyl, substituted or unsubstituted alkyl, or a nitrogen protecting group.

In certain embodiments, Y is —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; each occurrence of $R^{a1}$ is, independently, hydrogen, substituted or unsubstituted acyl, substituted or unsubstituted alkyl, or a nitrogen protecting group; the sum of m and n is 0, 1, or 2; and the sum of k and q is 0, 1, or 2.

In certain embodiments, Y is —O— or —($CR^3R^4$)—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —O— or —($CR^3R^4$)—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —O— or —($CR^3R^4$)—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —O— or —($CR^3R^4$)—; each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, Y is —O—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —O—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —O—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —O—; and each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, Y is —($CR^3R^4$)—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —($CR^3R^4$)—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —($CR^3R^4$)—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —($CR^3R^4$)—; each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, Y is —($CHR^3$)—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —($CHR^3$)—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —($CHR^3$)—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —($CHR^3$)—; and each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, the sum of m and n is 0, 1, or 2. In certain embodiments, m is 0; and n is 0. In certain embodiments, m is 1; and n is 0. In certain embodiments, m is 2; and n is 0. In certain embodiments, m is 0; and n is 1. In certain embodiments, m is 1; and n is 1. In certain embodiments, m is 0; and n is 2.

In certain embodiments, the sum of k and q is 0, 1, or 2. In certain embodiments, k is 0; and q is 0. In certain embodiments, k is 1; and q is 0. In certain embodiments, k is 2; and q is 0. In certain embodiments, k is 0; and q is 1. In certain embodiments, k is 1; and q is 1. In certain embodiments, k is 0; and q is 2.

In certain embodiments, B is of formula:

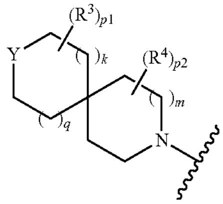 ;

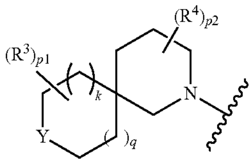 ;

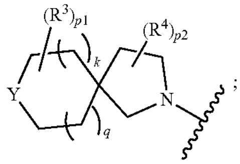 ;

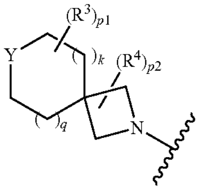 ; or

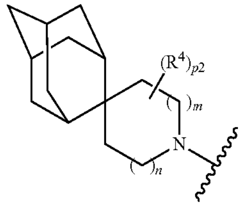 .

In certain embodiment, B is of formula:

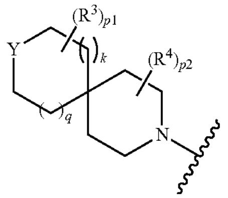 ;

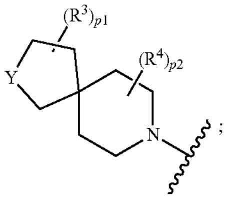 ;

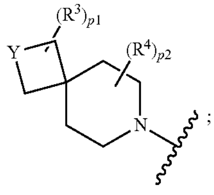 ;

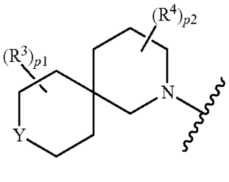 ;

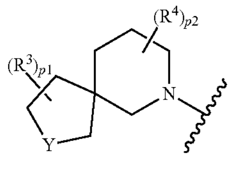 ;

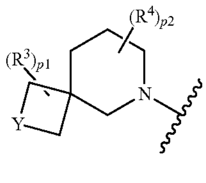 ;

-continued

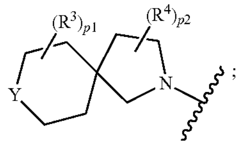 ;

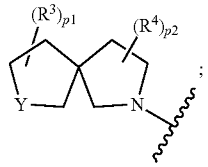 ;

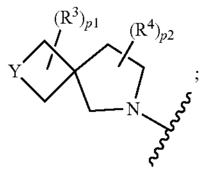 ;

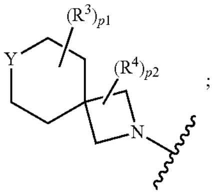 ;

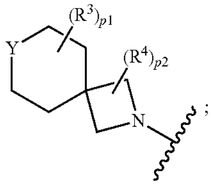 ;

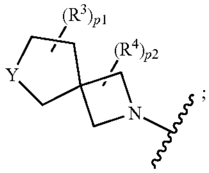 ;

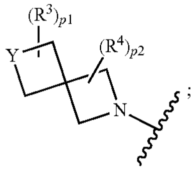 ;

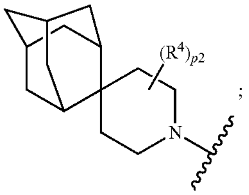 ;

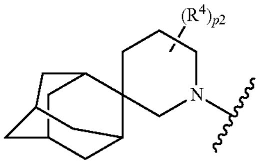 ;

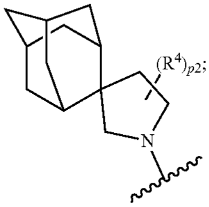 ; or

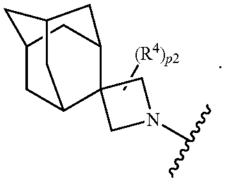 .

Certain Embodiments

In certain embodiments, the compound of Formula (IV) is of Formula (IV-a):

(IV-a)

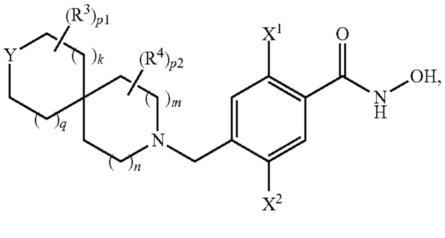

or a pharmaceutically acceptable salt, co-crystal, tautomer, stereoisomer, solvate, hydrate, polymorph, isotopically enriched derivative, or prodrug thereof; wherein $X^1$, $X^2$, $R^3$, $R^4$, Y, p1, p2, m, n, k, and q are as defined herein.

In certain embodiments, the compound of Formula (IV) is of Formula (IV-b):

(IV-b)

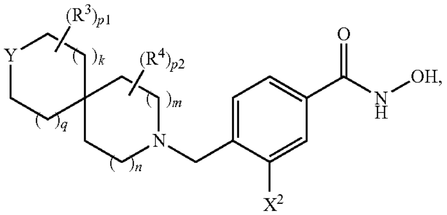

or a pharmaceutically acceptable salt, co-crystal, tautomer, stereoisomer, solvate, hydrate, polymorph, isotopically enriched derivative, or prodrug thereof; wherein $X^2$, $R^3$, $R^4$, Y, p1, p2, m, n, k, and q are as defined herein.

In certain embodiments, the compound of Formula (IV) is of Formula (IV-c):

(IV-c)

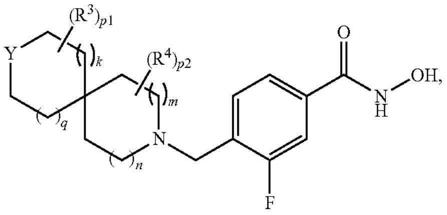

or a pharmaceutically acceptable salt, co-crystal, tautomer, stereoisomer, solvate, hydrate, polymorph, isotopically enriched derivative, or prodrug thereof; wherein $R^3$, $R^4$, Y, p1, p2, m, n, k, and q are as defined herein.

In certain embodiments, the compound of Formula (IV) is of Formula (IV-d):

(IV-d)

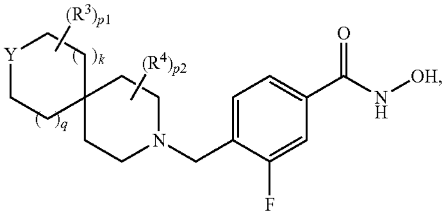

or a pharmaceutically acceptable salt, co-crystal, tautomer, stereoisomer, solvate, hydrate, polymorph, isotopically enriched derivative, or prodrug thereof; wherein $R^3$, $R^4$, Y, p1, p2, k, and q are as defined herein.

In certain embodiments, the compound of Formula (IV) is of Formula (IV-e):

(IV-e)

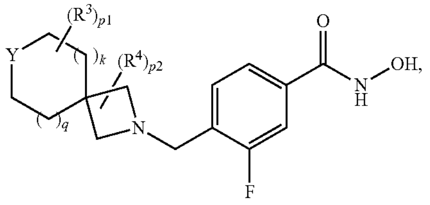

or a pharmaceutically acceptable salt, co-crystal, tautomer, stereoisomer, solvate, hydrate, polymorph, isotopically enriched derivative, or prodrug thereof; wherein $R^3$, $R^4$, Y, p1, p2, k, and q are as defined herein.

In certain embodiments, the compound of Formula (IV) is of Formula (IV-f):

(IV-f)

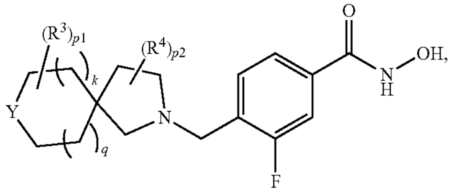

or a pharmaceutically acceptable salt, co-crystal, tautomer, stereoisomer, solvate, hydrate, polymorph, isotopically enriched derivative, or prodrug thereof; wherein $R^3$, $R^4$, Y, p1, p2, k, and q are as defined herein.

In certain embodiments, the compound of Formula (IV) is of Formula (IV-g):

(IV-g)

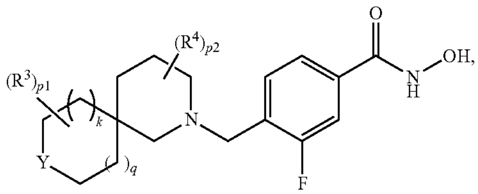

or a pharmaceutically acceptable salt, co-crystal, tautomer, stereoisomer, solvate, hydrate, polymorph, isotopically enriched derivative, or prodrug thereof; wherein $R^3$, $R^4$, Y, p1, p2, k, and q are as defined herein.

In certain embodiments, the compound of Formula (IV) is of Formula (IV-h):

(IV-h)

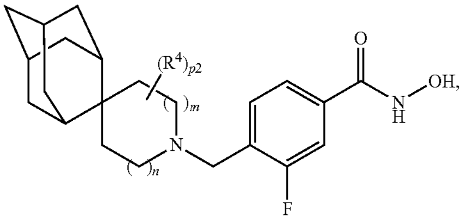

or a pharmaceutically acceptable salt, co-crystal, tautomer, stereoisomer, solvate, hydrate, polymorph, isotopically enriched derivative, or prodrug thereof; wherein $R^4$, p2, m, and n are as defined herein.

In certain embodiments, the compound of Formula (IV) is one of the following compounds, or a pharmaceutically acceptable salt, co-crystal, tautomer, stereoisomer, solvate, hydrate, polymorph, isotopically enriched derivative, or prodrug thereof:

64

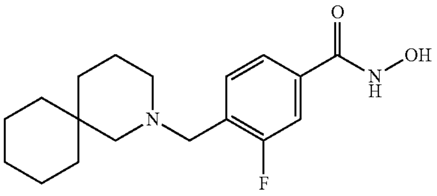

169

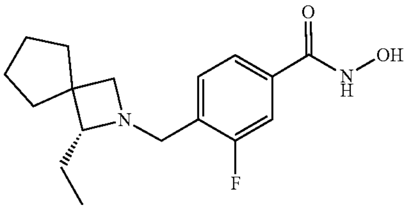

168

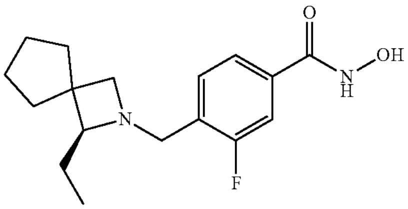

67

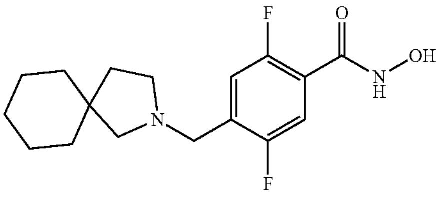

68

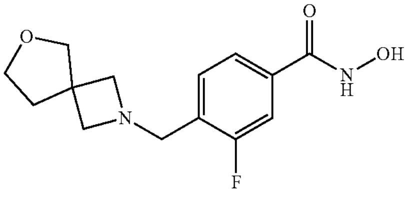

-continued

69

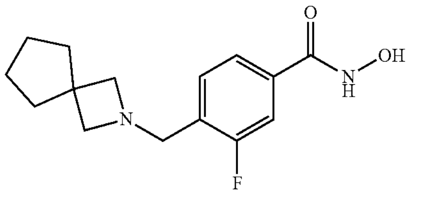

70

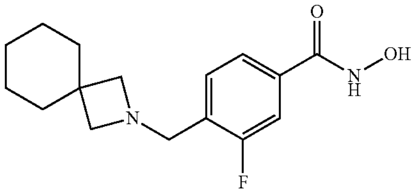

71

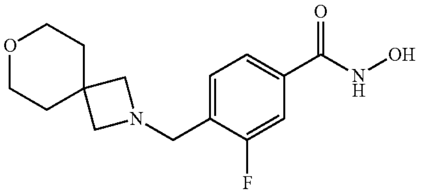

72

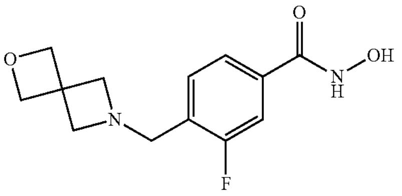

73

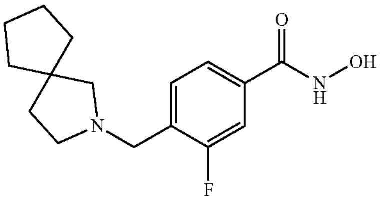

74

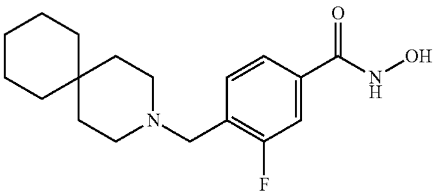

75

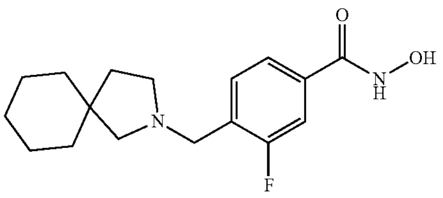

167

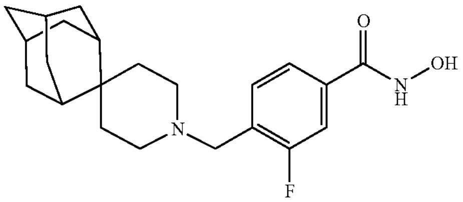

-continued

77

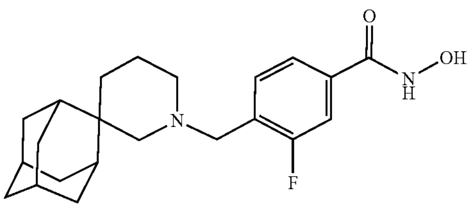

or

78

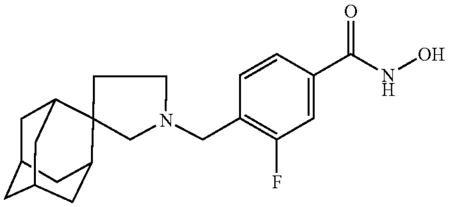

Compounds of Formula (V)

In another aspect, disclosed is a compound of Formula (V):

(V)

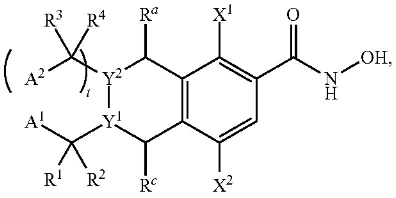

or a pharmaceutically acceptable salt, co-crystal, tautomer, stereoisomer, solvate, hydrate, polymorph, isotopically enriched derivative, or prodrug thereof, wherein:

$X^1$ is hydrogen or fluoro;

$X^2$ is hydrogen or fluoro;

$Y^1$ is nitrogen or $CR^x$;

$Y^2$ is nitrogen, $CR^d$, a bond, —$CH_2$—, or —NH—;

$A^1$ is joined with one of $A^2$, $R^a$, and $R^c$ to form a substituted or unsubstituted ring;

$A^2$ is hydrogen or joined with $A^1$ to form a substituted or unsubstituted ring;

$R^1$ is hydrogen or substituted or unsubstituted alkyl, or $R^1$ is joined with $R^d$, $R^3$, or $R^4$ to form a substituted or unsubstituted ring;

$R^2$ is hydrogen or substituted or unsubstituted alkyl, or $R^2$ is joined with $R^d$, $R^3$, or $R^4$ to form a substituted or unsubstituted ring; or $R^1$ and $R^2$ together form a carbonyl;

$R^3$ is hydrogen or substituted or unsubstituted alkyl, or $R^3$ is joined with $R^1$ or $R^2$ to form a substituted or unsubstituted ring;

$R^4$ is hydrogen or substituted or unsubstituted alkyl, or $R^4$ is joined with $R^1$ or $R^2$ to form a substituted or unsubstituted ring; or $R^3$ and $R^4$ together form a carbonyl;

$R^x$ is hydrogen or substituted or unsubstituted alkyl;

$R^a$ is hydrogen or is joined with $A^1$ to form a substituted or unsubstituted ring;

$R^c$ is hydrogen or is joined with $A^1$ to form a substituted or unsubstituted ring;

$R^d$ is hydrogen or is joined with $R^1$ or $R^2$ to form a substituted or unsubstituted ring; and t is 0 or 1.

$X^1$ and $X^2$

As described herein, $X^1$ is hydrogen or fluoro; and $X^2$ is hydrogen or fluoro. In certain embodiments, $X^1$ is hydrogen or fluoro; and $X^2$ is hydrogen or fluoro; provided that at least one of $X^1$ and $X^2$ is fluoro. In certain embodiments, $X^1$ is hydrogen; and $X^2$ is fluoro. In certain embodiments, $X^1$ is fluoro; and $X^2$ is hydrogen. In certain embodiments, $X^1$ is fluoro; and $X^2$ is fluoro. In certain embodiments, $X^1$ is hydrogen; and $X^2$ is hydrogen.

$Y^1$ and $Y^2$

As described herein, $Y^1$ is nitrogen or CH. In certain embodiments, $Y^1$ is nitrogen. In certain embodiments, $Y^1$ is CH.

As described herein, $Y^2$ is nitrogen, $CR^d$, a bond, —$CH_2$—, or —NH—; and $R^d$ is hydrogen or is joined with $R^3$ or $R^4$ to form a substituted or unsubstituted ring. In certain embodiments, $Y^2$ is nitrogen, CH, or a bond; or $Y^2$ is —$CH_2$— or —NH— when t is 0. In certain embodiments, $Y^2$ is nitrogen, CH, or a bond. In certain embodiments, $Y^2$ is nitrogen or CH. In certain embodiments, $Y^2$ is nitrogen or a bond. In certain embodiments, $Y^2$ is CH or a bond. In certain embodiments, $Y^2$ is nitrogen. In certain embodiments, $Y^2$ is nitrogen; and $A^2$, $R^3$, and $R^4$ are each substituted or unsubstituted alkyl. In certain embodiments, $Y^2$ is nitrogen; and $A^2$, $R^3$, and $R^4$ are each hydrogen. In certain embodiments, $Y^2$ is a bond. In certain embodiments, $Y^2$ is —$CH_2$— when t is 0. In certain embodiments, $Y^2$ is —NH— when t is 0. In certain embodiments, $Y^2$ is $CR^d$; and $R^d$ is hydrogen or is joined with $R^3$ or $R^4$ to form a substituted or unsubstituted ring. In certain embodiments, $Y^2$ is $CR^d$; and $R^d$ is joined with $R^3$ or $R^4$ to form a substituted or unsubstituted ring. In certain embodiments, $Y^2$ is $CR^d$; and $R^d$ is joined with $R^3$ or $R^4$ to form a substituted or unsubstituted bridged ring.

In certain embodiments, $Y^1$ is nitrogen; and $Y^2$ is nitrogen, $CR^d$, a bond, —$CH_2$—, or —NH—; and $R^d$ is hydrogen or is joined with $R^3$ or $R^4$ to form a substituted or unsubstituted ring. In certain embodiments, $Y^1$ is nitrogen; and $Y^2$ is nitrogen, $CR^d$, a bond, —$CH_2$—, or —NH—. In certain embodiments, $Y^1$ is nitrogen; and $Y^2$ is nitrogen, CH, or a bond. In certain embodiments, $Y^1$ is nitrogen; and $Y^2$ is nitrogen. In certain embodiments, $Y^1$ is nitrogen; and $Y^2$ is CH. In certain embodiments, $Y^1$ is nitrogen; and $Y^2$ is a bond. In certain embodiments, $Y^1$ is nitrogen; and $Y^2$ is —$CH_2$— or —NH— when t is 0. In certain embodiments, $Y^1$ is nitrogen; and $Y^2$ is —$CH_2$— when t is 0. In certain embodiments, $Y^1$ is nitrogen; $Y^2$ is $CR^d$; and $R^d$ is joined with $R^3$ or $R^4$ to form a substituted or unsubstituted ring. In certain embodiments, $Y^1$ is nitrogen; $Y^2$ is $CR^d$; and $R^d$ is joined with $R^3$ or $R^4$ to form a substituted or unsubstituted bridged ring.

$A^1$ and $A^2$

As described herein, $A^1$ is joined with one of $A^2$, $R^a$, and $R^c$ to form a substituted or unsubstituted ring. In certain embodiments, $A^1$ is joined with one of $A^2$, $R^a$, and $R^c$ to form a substituted or unsubstituted 5 or 6-membered ring. In certain embodiments, $A^1$ is joined with one of $A^2$, $R^a$, and $R^c$ to form a substituted or unsubstituted 5 or 6-membered heteroaryl, heterocyclyl, or cycloalkyl ring. In certain embodiments, $A^1$ is joined with one of $A^2$, $R^a$, and $R^c$ to form a substituted or unsubstituted 5 or 6-membered heterocyclyl or cycloalkyl ring. In certain embodiments, $A^1$ is joined with one of $A^2$, $R^a$, and $R^c$ to form a substituted or unsubstituted 5 or 6-membered heteroaryl ring. In certain embodiments, $A^1$ is joined with one of $A^2$, $R^a$, and $R^c$ to form a substituted or unsubstituted 5 or 6-membered heterocyclyl ring. In certain embodiments, $A^1$ is joined with one of $A^2$, $R^a$, and $R^c$ to form a substituted or unsubstituted 5 or 6-membered cycloalkyl ring.

In certain embodiments, $A^1$ is joined with $A^2$ to form a substituted or unsubstituted ring. In certain embodiments, $A^1$ is joined with $A^2$ to form a substituted or unsubstituted 5 or 6-membered ring. In certain embodiments, $A^1$ is joined with $A^2$ to form a substituted or unsubstituted 5 or 6-membered heterocyclyl ring. In certain embodiments, $A^1$ is joined with $A^2$ to form a substituted or unsubstituted 5-membered heterocyclyl ring. In certain embodiments, $A^1$ is joined with $A^2$ to form a substituted or unsubstituted 6-membered heterocyclyl ring. In certain embodiments, $A^1$ is joined with $A^2$ to form a substituted or unsubstituted pyrrolidine. In certain embodiments, $A^1$ is joined with $A^2$ to form a substituted or unsubstituted piperidine. In certain embodiments, $A^1$ is joined with $A^2$ to form a substituted or unsubstituted morpholine. In certain embodiments, $A^1$ is joined with $A^2$ to form a substituted or unsubstituted hexahydropyridazine.

In certain embodiments, $A^1$ is joined with $R^a$ to form a substituted or unsubstituted ring. In certain embodiments, $A^1$ is joined with $R^a$ to form a substituted or unsubstituted 5 or 6-membered ring. In certain embodiments, $A^1$ is joined with $R^a$ to form a substituted or unsubstituted 5 or 6-membered heterocyclyl ring. In certain embodiments, $A^1$ is joined with $R^a$ to form a substituted or unsubstituted 5-membered heterocyclyl ring. In certain embodiments, $A^1$ is joined with $R^a$ to form a substituted or unsubstituted 6-membered heterocyclyl ring. In certain embodiments, $A^1$ is joined with $R^a$ to form a substituted or unsubstituted pyrrolidine. In certain embodiments, $A^1$ is joined with $R^a$ to form a substituted or unsubstituted piperidine.

In certain embodiments, $A^1$ is joined with $R^c$ to form a substituted or unsubstituted ring. In certain embodiments, $A^1$ is joined with $R^c$ to form a substituted or unsubstituted 5 or 6-membered ring. In certain embodiments, $A^1$ is joined with $R^c$ to form a substituted or unsubstituted 5 or 6-membered heterocyclyl or heteroaryl ring. In certain embodiments, $A^1$ is joined with $R^c$ to form a substituted or unsubstituted 5 or 6-membered heterocyclyl ring. In certain embodiments, $A^1$ is joined with $R^c$ to form a substituted or unsubstituted 5-membered heterocyclyl ring. In certain embodiments, $A^1$ is joined with $R^c$ to form a substituted or unsubstituted 6-membered heterocyclyl ring. In certain embodiments, $A^1$ is joined with $R^c$ to form a substituted or unsubstituted pyrrolidine. In certain embodiments, $A^1$ is joined with $R^c$ to form a substituted or unsubstituted piperidine. In certain embodiments, $A^1$ is joined with $R^c$ to form a substituted or unsubstituted 5 or 6-membered heteroaryl ring. In certain embodiments, $A^1$ is joined with $R^c$ to form a substituted or unsubstituted 5-membered heteroaryl ring. In certain embodiments, $A^1$ is joined with $R^c$ to form a substituted or unsubstituted 6-membered heteroaryl ring. In certain embodiments, $A^1$ is joined with $R^c$ to form a substituted or unsubstituted pyrrole.

As described herein, $A^2$ is hydrogen or joined with $A^1$ to form a substituted or unsubstituted ring. In certain embodiments, $A^2$ is hydrogen. In certain embodiments, $A^2$ is joined with $A^1$ to form a substituted or unsubstituted ring. In certain embodiments, $A^2$ is joined with $A^1$ to form a substituted or unsubstituted 5 or 6-membered ring. In certain embodiments, $A^2$ is joined with $A^1$ to form a substituted or unsubstituted 5 or 6-membered heterocyclyl ring. In certain embodiments, $A^2$ is joined with $A^1$ to form a substituted or unsubstituted 5-membered heterocyclyl ring. In certain embodiments, $A^2$ is joined with $A^1$ to form a substituted or unsubstituted 6-membered heterocyclyl ring. In certain embodiments, $A^2$ is joined with $A^1$ to form a substituted or unsubstituted pyrrolidine. In certain embodiments, $A^2$ is joined with $A^1$ to form a substituted or unsubstituted piperidine. In certain embodiments, $A^2$ is joined with $A^1$ to form a substituted or unsubstituted morpholine. In certain embodiments, $A^2$ is joined with $A^1$ to form a substituted or unsubstituted hexahydropyridazine.

$R^1$ and $R^2$

As described herein, $R^1$ is hydrogen or substituted or unsubstituted alkyl, or $R^1$ is joined with $R^d$, $R^3$, or $R^4$ to form a substituted or unsubstituted ring. In certain embodiments, $R^1$ is substituted or unsubstituted alkyl. In certain embodiments, $R^1$ is unsubstituted alkyl. In certain embodiments, $R^1$ is unsubstituted $C_{1-6}$ alkyl. In certain embodiments, $R^1$ is unsubstituted $C_{1-4}$ alkyl. In certain embodiments, $R^1$ is hydrogen. In certain embodiments, $R^1$ is joined with $R^d$, $R^3$, or $R^4$ to form a substituted or unsubstituted ring. In certain embodiments, $R^1$ is joined with $R^d$, $R^3$, or $R^4$ to form a substituted or unsubstituted bridged ring. In certain embodiments, $R^1$ is joined with $R^d$, $R^3$, or $R^4$ to form a substituted or unsubstituted 5 or 6-membered bridged ring. In certain embodiments, $R^1$ is joined with $R^d$, $R^3$, or $R^4$ to form a substituted or unsubstituted 5-membered bridged ring. In certain embodiments, $R^1$ is joined with $R^d$, $R^3$, or $R^4$ to form a substituted or unsubstituted 6-membered bridged ring. In certain embodiments, $R^1$ is joined with $R^d$ to form a substituted or unsubstituted ring. In certain embodiments, $R^1$ is joined with $R^d$ to form a substituted or unsubstituted bridged ring. In certain embodiments, $R^1$ is joined with $R^d$ to form a substituted or unsubstituted 5 or 6-membered bridged ring. In certain embodiments, $R^1$ is joined with $R^d$ to form a substituted or unsubstituted 5-membered bridged ring. In certain embodiments, $R^1$ is joined with $R^d$ to form a substituted or unsubstituted 6-membered bridged ring. In certain embodiments, $R^1$ is joined with $R^3$ to form a substituted or unsubstituted ring. In certain embodiments, $R^1$ is joined with $R^3$ to form a substituted or unsubstituted bridged ring. In certain embodiments, $R^1$ is joined with $R^3$ to form a substituted or unsubstituted 5 or 6-membered bridged ring. In certain embodiments, $R^1$ is joined with $R^3$ to form a substituted or unsubstituted 5-membered bridged ring. In certain embodiments, $R^1$ is joined with $R^3$ to form a substituted or unsubstituted 6-membered bridged ring. In certain embodiments, $R^1$ is joined with $R^4$ to form a substituted or unsubstituted ring. In certain embodiments, $R^1$ is joined with $R^4$ to form a substituted or unsubstituted bridged ring. In certain embodiments, $R^1$ is joined with $R^4$ to form a substituted or unsubstituted 5 or 6-membered bridged ring. In certain embodiments, $R^1$ is joined with $R^4$ to form a substituted or unsubstituted 5-membered bridged ring. In certain embodiments, $R^1$ is joined with $R^4$ to form a substituted or unsubstituted 6-membered bridged ring.

As described herein, $R^2$ is hydrogen or substituted or unsubstituted alkyl, or $R^2$ is joined with $R^d$, $R^3$, or $R^4$ to form a substituted or unsubstituted ring. In certain embodiments, $R^2$ is substituted or unsubstituted alkyl. In certain embodiments, $R^2$ is unsubstituted alkyl. In certain embodiments, $R^2$ is unsubstituted $C_{1-6}$ alkyl. In certain embodiments, $R^2$ is unsubstituted $C_{1-4}$ alkyl. In certain embodiments, $R^2$ is hydrogen. In certain embodiments, $R^2$ is joined with $R^d$, $R^3$, or $R^4$ to form a substituted or unsubstituted ring. In certain embodiments, $R^2$ is joined with $R^d$, $R^3$, or $R^4$ to form a substituted or unsubstituted bridged ring. In certain embodiments, $R^2$ is joined with $R^d$, $R^3$, or $R^4$ to form a substituted or unsubstituted 5 or 6-membered bridged ring. In certain embodiments, $R^2$ is joined with $R^d$, $R^3$, or $R^4$ to form a substituted or unsubstituted 5-membered bridged ring. In certain embodiments, $R^2$ is joined with $R^d$, $R^3$, or $R^4$ to form a substituted or unsubstituted 6-membered bridged ring. In certain embodiments, $R^2$ is joined with $R^d$ to form a substituted or unsubstituted ring. In certain embodiments, $R^2$ is joined with $R^d$ to form a substituted or unsubstituted bridged ring. In certain embodiments, $R^2$ is joined with $R^d$ to form a substituted or unsubstituted 5 or 6-membered bridged ring. In certain embodiments, $R^2$ is joined with $R^d$ to form a substituted or unsubstituted 5-membered bridged ring. In certain embodiments, $R^2$ is joined with $R^d$ to form a substituted or unsubstituted 6-membered bridged ring. In certain embodiments, $R^2$ is joined with $R^3$ to form a substituted or unsubstituted ring. In certain embodiments, $R^2$ is joined with $R^3$ to form a substituted or unsubstituted bridged ring. In certain embodiments, $R^2$ is joined with $R^3$ to form a substituted or unsubstituted 5 or 6-membered bridged ring. In certain embodiments, $R^2$ is joined with $R^3$ to form a substituted or unsubstituted 5-membered bridged ring. In certain embodiments, $R^2$ is joined with $R^3$ to form a substituted or unsubstituted 6-membered bridged ring. In certain embodiments, $R^2$ is joined with $R^4$ to form a substituted or unsubstituted ring. In certain embodiments, $R^2$ is joined with $R^4$ to form a substituted or unsubstituted bridged ring. In certain embodiments, $R^2$ is joined with $R^4$ to form a substituted or unsubstituted 5 or 6-membered bridged ring. In certain embodiments, $R^2$ is joined with $R^4$ to form a substituted or unsubstituted 5-membered bridged ring. In certain embodiments, $R^2$ is joined with $R^4$ to form a substituted or unsubstituted 6-membered bridged ring.

In certain embodiments, $R^1$ and $R^2$ together form a carbonyl. In certain embodiments, $R^1$ is hydrogen; and $R^2$ is hydrogen.

$R^3$ and $R^4$

As described herein, $R^3$ is hydrogen or substituted or unsubstituted alkyl, or $R^3$ is joined with $R^1$ or $R^2$ to form a substituted or unsubstituted ring. In certain embodiments, $R^3$ is substituted or unsubstituted alkyl. In certain embodiments, $R^3$ is unsubstituted alkyl. In certain embodiments, $R^3$ is unsubstituted $C_{1-6}$ alkyl. In certain embodiments, $R^3$ is unsubstituted $C_{1-4}$ alkyl. In certain embodiments, $R^3$ is hydrogen. In certain embodiments, $R^3$ is joined with $R^1$ or $R^2$ to form a substituted or unsubstituted ring. In certain embodiments, $R^3$ is joined with $R^1$ or $R^2$ to form a substituted or unsubstituted bridged ring. In certain embodiments, $R^3$ is joined with $R^1$ or $R^2$ to form a substituted or unsubstituted 5 or 6-membered bridged ring. In certain embodiments, $R^3$ is joined with $R^1$ or $R^2$ to form a substituted or unsubstituted 5-membered bridged ring. In certain embodiments, $R^3$ is joined with $R^1$ or $R^2$ to form a substituted or unsubstituted 6-membered bridged ring. In certain embodiments, $R^3$ is joined with $R^1$ to form a substituted or unsubstituted ring. In certain embodiments, $R^3$ is joined with $R^1$ to form a substituted or unsubstituted bridged ring. In certain embodiments, $R^3$ is joined with $R^1$ to form a substituted or unsubstituted 5 or 6-membered bridged ring. In certain embodiments, $R^3$ is joined with $R^1$ to form a substituted or unsubstituted 5-membered bridged ring. In certain embodiments, $R^3$ is joined with $R^1$ to form a substituted or unsubstituted 6-membered bridged ring. In certain embodiments, $R^3$ is joined with $R^1$ to form a substituted or unsubstituted ring. In certain embodiments, $R^3$ is joined with $R^1$ to form a substituted or unsubstituted bridged ring. In certain embodiments, $R^3$ is joined with $R^1$ to form a substituted or unsubstituted 5 or 6-membered bridged ring. In certain embodiments, $R^3$ is joined with $R^1$ to form a substituted or unsubstituted 5-membered bridged ring. In certain embodiments, $R^3$ is joined with $R^1$ to form a substituted or unsubstituted 6-membered bridged ring. In certain embodiments, $R^3$ is joined with $R^2$ to form a substituted or unsubstituted ring. In certain embodiments, $R^3$ is joined with $R^2$ to form a substituted or unsubstituted bridged ring. In certain embodiments, $R^3$ is joined with $R^2$ to form a substituted or unsubstituted 5 or 6-membered bridged ring. In certain embodiments, $R^3$ is joined with $R^2$ to form a substituted or unsubstituted 5-membered bridged ring. In certain embodiments, $R^3$ is joined with $R^2$ to form a substituted or unsubstituted 6-membered bridged ring.

As described herein, $R^2$ is hydrogen or substituted or unsubstituted alkyl, or $R^2$ is joined with $R^d$, $R^3$, or $R^4$ to form a substituted or unsubstituted ring. In certain embodiments, $R^2$ is substituted or unsubstituted alkyl. In certain embodiments, $R^2$ is unsubstituted alkyl. In certain embodiments, $R^2$ is unsubstituted $C_{1-6}$ alkyl. In certain embodiments, $R^2$ is unsubstituted $C_{1-4}$ alkyl. In certain embodiments, $R^2$ is hydrogen. In certain embodiments, $R^2$ is joined with $R^d$, $R^3$, or $R^4$ to form a substituted or unsubstituted ring. In certain embodiments, $R^2$ is joined with $R^d$, $R^3$, or $R^4$ to form a substituted or unsubstituted bridged ring. In certain embodiments, $R^2$ is joined with $R^d$, $R^3$, or $R^4$ to form a substituted or unsubstituted 5 or 6-membered bridged ring. In certain embodiments, $R^2$ is joined with $R^d$, $R^3$, or $R^4$ to form a substituted or unsubstituted 5-membered bridged ring. In certain embodiments, $R^2$ is joined with $R^d$, $R^3$, or $R^4$ to form a substituted or unsubstituted 6-membered bridged ring. In certain embodiments, $R^2$ is joined with $R^d$ to form a substituted or unsubstituted ring. In certain embodiments, $R^2$ is joined with $R^d$ to form a substituted or unsubstituted bridged ring. In certain embodiments, $R^2$ is joined with $R^d$ to form a substituted or unsubstituted 5 or 6-membered bridged ring. In certain embodiments, $R^2$ is joined with $R^d$ to form a substituted or unsubstituted 5-membered bridged ring. In certain embodiments, $R^2$ is joined with $R^d$ to form a substituted or unsubstituted 6-membered bridged ring. In certain embodiments, $R^2$ is joined with $R^3$ to form a substituted or unsubstituted ring. In certain embodiments, $R^2$ is joined with $R^3$ to form a substituted or unsubstituted bridged ring. In certain embodiments, $R^2$ is joined with $R^3$ to form a substituted or unsubstituted 5 or 6-membered bridged ring. In certain embodiments, $R^2$ is joined with $R^3$ to form a substituted or unsubstituted 5-membered bridged ring. In certain embodiments, $R^2$ is joined with $R^3$ to form a substituted or unsubstituted 6-membered bridged ring. In certain embodiments, $R^2$ is joined with $R^4$ to form a substituted or unsubstituted ring. In certain embodiments, $R^2$ is joined with $R^4$ to form a substituted or unsubstituted bridged ring. In certain embodiments, $R^2$ is joined with $R^4$ to form a substituted or unsubstituted 5 or 6-membered bridged ring. In certain embodiments, $R^2$ is joined with $R^4$ to form a substituted or unsubstituted 5-membered bridged ring. In certain embodiments, $R^2$ is joined with $R^4$ to form a substituted or unsubstituted 6-membered bridged ring.

In certain embodiments, $R^3$ and $R^4$ together form a carbonyl. In certain embodiments, $R^3$ is hydrogen; and $R^4$ is hydrogen.

$R^a$, $R^c$, $R^d$, $R^x$, and t

As described herein, $R^x$ is hydrogen or substituted or unsubstituted alkyl; $R^a$ is hydrogen or is joined with $A^1$ to form a substituted or unsubstituted ring. In certain embodiments, $R^a$ is hydrogen. In certain embodiments, $R^a$ is joined with $A^1$ to form a substituted or unsubstituted ring. In certain embodiments, $R^a$ is joined with $A^1$ to form a substituted or unsubstituted 5 or 6-membered ring. In certain embodiments, $R^a$ is joined with $A^1$ to form a substituted or unsubstituted 5 or 6-membered heterocyclyl ring. In certain embodiments, $R^a$ is joined with $A^1$ to form a substituted or unsubstituted 5-membered heterocyclyl ring. In certain embodiments, $R^a$ is joined with $A^1$ to form a substituted or unsubstituted 6-membered heterocyclyl ring. In certain embodiments, $R^a$ is joined with $A^1$ to form a substituted or unsubstituted pyrrolidine. In certain embodiments, $R^a$ is joined with $A^1$ to form a substituted or unsubstituted piperidine.

In certain embodiments, $R^x$ is hydrogen. In certain embodiments, $R^x$ is substituted or unsubstituted alkyl. In certain embodiments, $R^x$ is substituted or unsubstituted $C_{1-6}$ alkyl. In certain embodiments, $R^x$ is substituted or unsubstituted $C_{1-4}$ alkyl. In certain embodiments, $R^x$ is substituted or unsubstituted $C_{1-3}$ alkyl. In certain embodiments, $R^x$ is substituted alkyl. In certain embodiments, $R^x$ is substituted $C_{1-6}$ alkyl. In certain embodiments, $R^x$ is substituted $C_{1-4}$ alkyl. In certain embodiments, $R^x$ is substituted $C_{1-3}$ alkyl. In certain embodiments, $R^x$ is unsubstituted alkyl. In certain embodiments, $R^x$ is unsubstituted $C_{1-6}$ alkyl. In certain embodiments, $R^x$ is unsubstituted $C_{1-4}$ alkyl. In certain embodiments, $R^x$ is unsubstituted $C_{1-3}$ alkyl.

As described herein, $R^c$ is hydrogen or is joined with $A^1$ to form a substituted or unsubstituted ring. In certain embodiments, $R^c$ is hydrogen. In certain embodiments, $R^c$ is joined with $A^1$ to form a substituted or unsubstituted ring. In certain embodiments, $R^c$ is joined with $A^1$ to form a substituted or unsubstituted 5 or 6-membered ring. In certain embodiments, $R^c$ is joined with $A^1$ to form a substituted or unsubstituted 5 or 6-membered heterocyclyl ring. In certain embodiments, $R^c$ is joined with $A^1$ to form a substituted or unsubstituted 5-membered heterocyclyl ring. In certain embodiments, $R^c$ is joined with $A^1$ to form a substituted or unsubstituted 6-membered heterocyclyl ring. In certain embodiments, $R^c$ is joined with $A^1$ to form a substituted or unsubstituted pyrrolidine. In certain embodiments, $R^c$ is joined with $A^1$ to form a substituted or unsubstituted piperidine.

In certain embodiments, $R^d$ is joined with $R^1$ to form a substituted or unsubstituted ring. In certain embodiments, $R^d$ is joined with $R^1$ to form a substituted or unsubstituted bridged ring. In certain embodiments, $R^d$ is joined with $R^1$ to form a substituted or unsubstituted 5 or 6-membered bridged ring. In certain embodiments, $R^d$ is joined with $R^1$ to form a substituted or unsubstituted 5-membered bridged ring. In certain embodiments, $R^d$ is joined with $R^1$ to form a substituted or unsubstituted 6-membered bridged ring.

In certain embodiments, $R^d$ is joined with $R^2$ to form a substituted or unsubstituted ring. In certain embodiments, $R^d$ is joined with $R^2$ to form a substituted or unsubstituted bridged ring. In certain embodiments, $R^d$ is joined with $R^2$ to form a substituted or unsubstituted 5 or 6-membered bridged ring. In certain embodiments, $R^d$ is joined with $R^2$ to form a substituted or unsubstituted 5-membered bridged ring. In certain embodiments, $R^d$ is joined with $R^2$ to form a substituted or unsubstituted 6-membered bridged ring.

As described herein, t is 0 or 1. In certain embodiments, t is 0. In certain embodiments, t is 1.

Certain Embodiments

In certain embodiments, the compound of Formula (V) is of Formula (V-a):

(V-a)

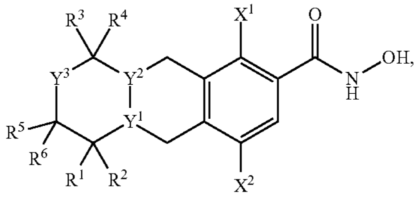

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, $R^4$, $Y^1$, $Y^2$, $X^1$, and $X^2$ are as defined herein;

$Y^3$ is a bond, —$CH_2$—, —O—, —S—, or —$NR^e$—;

$R^e$ is hydrogen, substituted or unsubstituted alkyl, or a protecting group; and $R^5$ and $R^6$ are each independently hydrogen, substituted or unsubstituted alkyl, or together form a substituted or unsubstituted cycloalkyl.

In certain embodiments of the compound of Formula (V-a), $Y^3$ is a bond, —$CH_2$—, or —O—. In certain embodiments of the compound of Formula (V-a), $Y^3$ is —$CH_2$— or —O—. In certain embodiments of the compound of Formula (V-a), $Y^3$ is —$CH_2$—. In certain embodiments of the compound of Formula (V-a), $Y^3$ is —O—. In certain embodiments of the compound of Formula (V-a), $Y^3$ is —O—; and $R^1$ and $R^2$ together form a carbonyl.

In certain embodiments of the compound of Formula (V-a), $Y^3$ is a bond, —$CH_2$—, or —O—; and $R^5$ and $R^6$ are each independently hydrogen, or together form a substituted or unsubstituted cycloalkyl. In certain embodiments of the compound of Formula (V-a), $Y^3$ is —$CH_2$— or —O—; and $R^5$ and $R^6$ are each independently hydrogen, or together form a substituted or unsubstituted cycloalkyl. In certain embodiments of the compound of Formula (V-a), $Y^3$ is —$CH_2$—; and $R^5$ and $R^6$ are each independently hydrogen, or together form a substituted or unsubstituted cycloalkyl. In certain embodiments of the compound of Formula (V-a), $Y^3$ is —O—; and $R^5$ and $R^6$ are each independently hydrogen, or together form a substituted or unsubstituted cycloalkyl.

In certain embodiments, the compound of Formula (V-a) is of Formula (V-a-1):

(V-a-1)

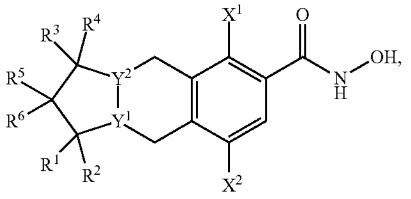

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, $R^4$, $Y^1$, $Y^2$, $X^1$, and $X^2$ are as defined herein; and $R^5$ and $R^6$ are each independently hydrogen, substituted or unsubstituted alkyl, or together form a substituted or unsubstituted cycloalkyl.

In certain embodiments, the compound of Formula (V) is of Formula (V-b):

(V-b)

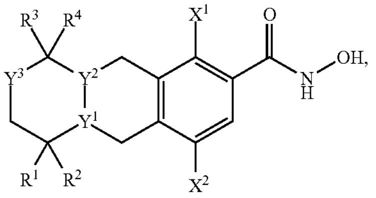

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, $R^4$, $Y^1$, $Y^2$, $X^1$, and $X^2$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-b), $Y^3$ is a bond, —$CH_2$—, or —O—. In certain embodiments of the compound of Formula (V-b), $Y^3$ is —$CH_2$— or —O—. In certain embodiments of the compound of Formula (V-b), $Y^3$ is —$CH_2$—. In certain embodiments of the compound of Formula (V-b), $Y^3$ is —O—. In certain embodiments of the compound of Formula (V-b), $Y^3$ is —O—; and $R^1$ and $R^2$ together form a carbonyl.

In certain embodiments, the compound of Formula (V) is of Formula (V-c):

(V-c)

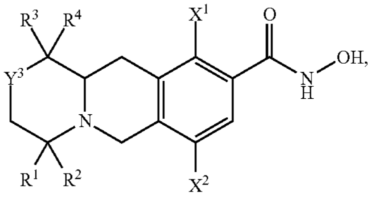

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, $R^4$, $X^1$, and $X^2$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-c), $Y^3$ is a bond, —$CH_2$—, or —O—. In certain embodiments of the compound of Formula (V-c), $Y^3$ is —$CH_2$— or —O—. In certain embodiments of the compound of Formula (V-c), $Y^3$ is —$CH_2$—. In certain embodiments of the compound of Formula (V-c), $Y^3$ is —O—. In certain embodiments of the compound of Formula (V-c), $Y^3$ is —O—; and $R^1$ and $R^2$ together form a carbonyl.

In certain embodiments, the compound of Formula (V) is of Formula (V-d):

(V-d)

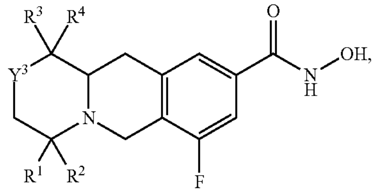

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, and $R^4$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-d), $Y^3$ is a bond, —$CH_2$—, or —O—. In certain embodiments of the compound of Formula (V-d), $Y^3$ is —$CH_2$— or —O—. In certain embodiments of the compound of Formula (V-d), $Y^3$ is —$CH_2$—. In certain embodiments of the compound of Formula (V-d), $Y^3$ is —O—. In certain embodiments of the compound of Formula (V-d), $Y^3$ is —O—; and $R^1$ and $R^2$ together form a carbonyl.

In certain embodiments, the compound of Formula (V) is of Formula (V-e):

(V-e)

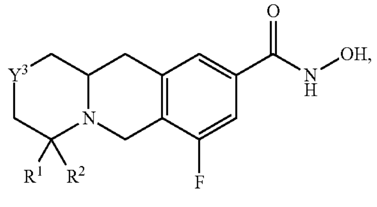

or a pharmaceutically acceptable salt, co-crystal, tautomer, stereoisomer, solvate, hydrate, polymorph, isotopically enriched derivative, or prodrug thereof; wherein $R^1$ and $R^2$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-e), $Y^3$ is a bond, —$CH_2$—, or —O—. In certain embodiments of the compound of Formula (V-e), $Y^3$ is —$CH_2$— or —O—. In certain embodiments of the compound of Formula (V-e), $Y^3$ is —$CH_2$—. In certain embodiments of the compound of Formula (V-e), $Y^3$ is —O—. In certain embodiments of the compound of Formula (V-e), $Y^3$ is —O—; and $R^1$ and $R^2$ together form a carbonyl.

In certain embodiments, the compound of Formula (V) is of Formula (V-f):

(V-f)

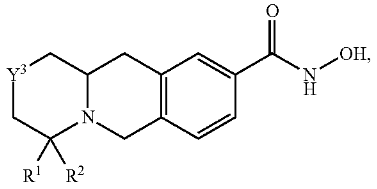

or a pharmaceutically acceptable salt, co-crystal, tautomer, stereoisomer, solvate, hydrate, polymorph, isotopically enriched derivative, or prodrug thereof; wherein $R^1$ and $R^2$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-f), $Y^3$ is a bond, —$CH_2$—, or —O—. In certain embodiments of the compound of Formula (V-f), $Y^3$ is —$CH_2$— or —O—. In certain embodiments of the compound of Formula (V-f), $Y^3$ is —$CH_2$—. In certain embodiments of the compound of Formula (V-f), $Y^3$ is —O—. In certain embodiments of the compound of Formula (V-f), $Y^3$ is —O—; and $R^1$ and $R^2$ together form a carbonyl.

In certain embodiments, the compound of Formula (V) is of Formula (V-g):

(V-g)

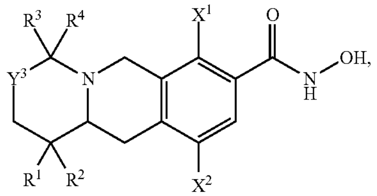

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, $R^4$, $X^1$, and $X^2$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-g), $Y^3$ is a bond or —$CH_2$—. In certain embodiments of the compound of Formula (V-g), $Y^3$ is a bond. In certain embodiments of the compound of Formula (V-g), $Y^3$ is —$CH_2$—.

In certain embodiments, the compound of Formula (V) is of Formula (V-h):

(V-h)

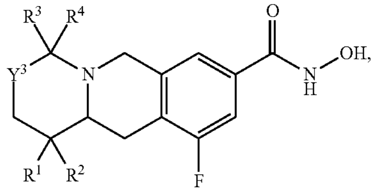

or a pharmaceutically acceptable salt, co-crystal, tautomer, stereoisomer, solvate, hydrate, polymorph, isotopically enriched derivative, or prodrug thereof; wherein $R^1$, $R^2$, $R^3$, and $R^4$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-h), $Y^3$ is a bond or —$CH_2$—. In certain embodiments of the compound of Formula (V-h), $Y^3$ is a bond. In certain embodiments of the compound of Formula (V-h), $Y^3$ is —$CH_2$—.

In certain embodiments, the compound of Formula (V) is of Formula (V-i):

(V-i)

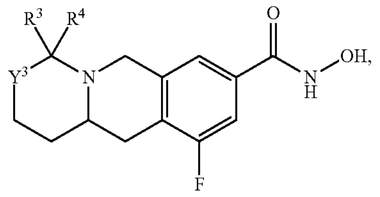

or a pharmaceutically acceptable salt, co-crystal, tautomer, stereoisomer, solvate, hydrate, polymorph, isotopically enriched derivative, or prodrug thereof; wherein $R^3$ and $R^4$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-i), $Y^3$ is a bond or —$CH_2$—. In certain embodiments of the compound of Formula (V-i), $Y^3$ is a bond. In certain embodiments of the compound of Formula (V-i), $Y^3$ is —$CH_2$—.

In certain embodiments, the compound of Formula (V) is of Formula (V-j):

(V-j)

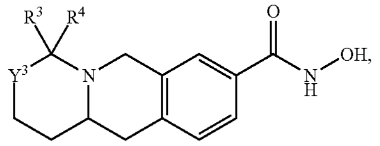

or a pharmaceutically acceptable salt, co-crystal, tautomer, stereoisomer, solvate, hydrate, polymorph, isotopically enriched derivative, or prodrug thereof; wherein $R^3$ and $R^4$ are as defined herein;

$Y^3$ is a bond, —$CH_2$—, —O—, —S—, or —$NR^e$—; and $R^e$ is hydrogen, substituted or unsubstituted alkyl, or a protecting group.

In certain embodiments of the compound of Formula (V-j), $Y^3$ is a bond or —$CH_2$—. In certain embodiments of the compound of Formula (V-j), $Y^3$ is a bond. In certain embodiments of the compound of Formula (V-j), $Y^3$ is —$CH_2$—.

In certain embodiments, the compound of Formula (V) is of Formula (V-k):

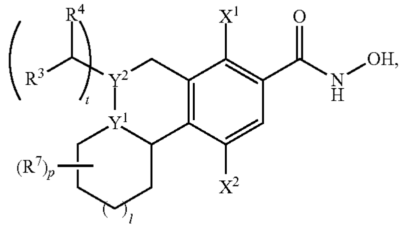

or a pharmaceutically acceptable salt, co-crystal, tautomer, stereoisomer, solvate, hydrate, polymorph, isotopically enriched derivative, or prodrug thereof; wherein $R^3$, $R^4$, t, $Y^1$, $Y^2$, $X^1$, and $X^2$ are as defined herein; each $R^7$ is independently substituted or unsubstituted alkyl, halogen, or two instances of $R^7$ together form a substituted or unsubstituted cycloalkyl, or substituted or unsubstituted heterocyclyl; p is 0, 1, 2, or 3; and l is 0 or 1.

In certain embodiments, the compound of Formula (V) is of Formula (V-l):

(V-l)

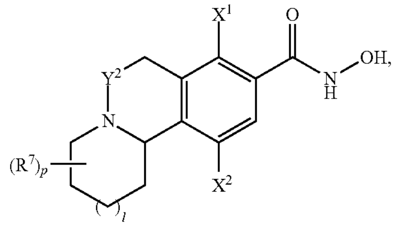

or a pharmaceutically acceptable salt, co-crystal, tautomer, stereoisomer, solvate, hydrate, polymorph, isotopically enriched derivative, or prodrug thereof; wherein $Y^2$, $X^1$, and $X^2$ are as defined herein; each $R^7$ is independently substituted or unsubstituted alkyl, halogen, or two instances of $R^7$ together form a substituted or unsubstituted cycloalkyl, or substituted or unsubstituted heterocyclyl; p is 0, 1, 2, or 3; and l is 0 or 1.

In certain embodiments, the compound of Formula (V-l) is of Formula (V-l-1):

(V-l-1)

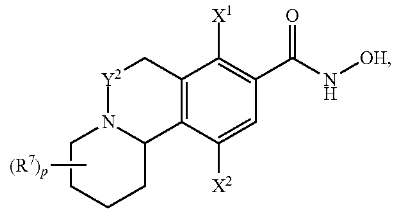

or a pharmaceutically acceptable salt, co-crystal, tautomer, stereoisomer, solvate, hydrate, polymorph, isotopically enriched derivative, or prodrug thereof; wherein $Y^2$, $X^1$, and $X^2$ are as defined herein; each $R^7$ is independently substituted or unsubstituted alkyl, halogen, or two instances of $R^7$ together form a substituted or unsubstituted cycloalkyl, or substituted or unsubstituted heterocyclyl; and p is 0, 1, 2, or 3.

In certain embodiments, the compound of Formula (V-l) is of Formula (V-l-2):

(V-l-2)

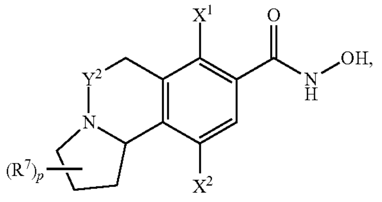

or a pharmaceutically acceptable salt, co-crystal, tautomer, stereoisomer, solvate, hydrate, polymorph, isotopically enriched derivative, or prodrug thereof; wherein $Y^2$, $X^1$, and $X^2$ are as defined herein; each $R^7$ is independently substituted or unsubstituted alkyl, halogen, or two instances of $R^7$ together form a substituted or unsubstituted cycloalkyl, or substituted or unsubstituted heterocyclyl; and p is 0, 1, 2, or 3.

In certain embodiments, the compound of Formula (V-l) is of Formula (V-l-3):

(V-l-3)

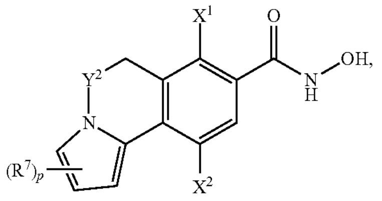

or a pharmaceutically acceptable salt, co-crystal, tautomer, stereoisomer, solvate, hydrate, polymorph, isotopically enriched derivative, or prodrug thereof; wherein $Y^2$, $X^1$, and $X^2$ are as defined herein; each $R^7$ is independently substituted or unsubstituted alkyl, halogen, or two instances of $R^7$ together form a substituted or unsubstituted cycloalkyl, or substituted or unsubstituted heterocyclyl; and p is 0, 1, 2, or 3.

In certain embodiments of the compound of Formula (V-l), $Y^2$ is —NH—, —NMe-, —$CH_2$—, or a bond. In certain embodiments of the compound of Formula (V-l), $Y^2$ is —NMe-, —$CH_2$—, or a bond. In certain embodiments of the compound of Formula (V-l), $Y^2$ is —NMe-. In certain embodiments of the compound of Formula (V-l), $Y^2$ is —$CH_2$—. In certain embodiments of the compound of Formula (V-l), $Y^2$ is a bond.

In certain embodiments, the compound of Formula (V) is of Formula (V-m):

(V-m)

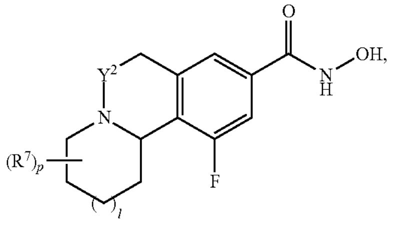

or a pharmaceutically acceptable salt, co-crystal, tautomer, stereoisomer, solvate, hydrate, polymorph, isotopically enriched derivative, or prodrug thereof; wherein $Y^2$ is as defined herein; each $R^7$ is independently substituted or unsubstituted alkyl, halogen, or two instances of $R^7$ together form a substituted or unsubstituted cycloalkyl, or substituted or unsubstituted heterocyclyl; p is 0, 1, 2, or 3; and l is 0 or 1.

In certain embodiments, the compound of Formula (V-m) is of Formula (V-m-1):

(V-m-1)

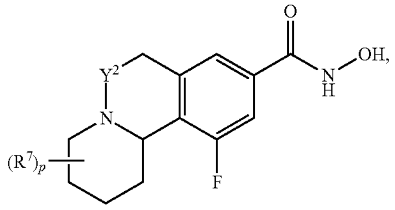

or a pharmaceutically acceptable salt, co-crystal, tautomer, stereoisomer, solvate, hydrate, polymorph, isotopically enriched derivative, or prodrug thereof; wherein $Y^2$, $R^7$, and p are as defined herein.

In certain embodiments, the compound of Formula (V-m) is of Formula (V-m-2):

(V-m-2)

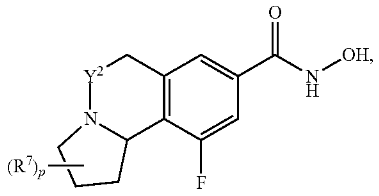

or a pharmaceutically acceptable salt, co-crystal, tautomer, stereoisomer, solvate, hydrate, polymorph, isotopically enriched derivative, or prodrug thereof; wherein $Y^2$, $R^7$, and p are as defined herein.

In certain embodiments, the compound of Formula (V-m) is of Formula (V-m-3):

(V-m-3)

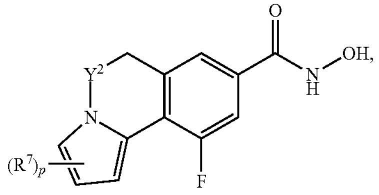

or a pharmaceutically acceptable salt, co-crystal, tautomer, stereoisomer, solvate, hydrate, polymorph, isotopically enriched derivative, or prodrug thereof; wherein $Y^2$, $R^7$, and p are as defined herein.

In certain embodiments of the compound of Formula (V-m), $Y^2$ is —NH—, —NMe-, —$CH_2$—, or a bond. In certain embodiments of the compound of Formula (V-m), $Y^2$ is —NMe-, —$CH_2$—, or a bond. In certain embodiments of the compound of Formula (V-m), $Y^2$ is —NMe-. In certain embodiments of the compound of Formula (V-m), $Y^2$ is —$CH_2$—. In certain embodiments of the compound of Formula (V-m), $Y^2$ is a bond.

In certain embodiments, the compound of Formula (V) is of Formula (V-n):

(V-n)

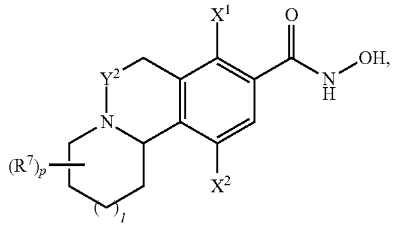

or a pharmaceutically acceptable salt, co-crystal, tautomer, stereoisomer, solvate, hydrate, polymorph, isotopically enriched derivative, or prodrug thereof; wherein $Y^2$ is as defined herein; each $R^7$ is independently substituted or unsubstituted alkyl, halogen, or two instances of $R^7$ together form a substituted or unsubstituted cycloalkyl, or substituted or unsubstituted heterocyclyl; p is 0, 1, 2, or 3; and 1 is 0 or 1.

In certain embodiments, the compound of Formula (V) is of Formula (V-n-1):

(V-n-1)

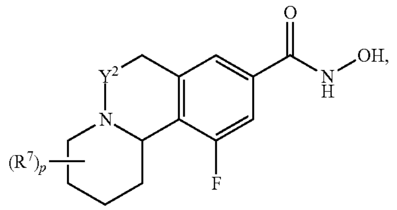

or a pharmaceutically acceptable salt, co-crystal, tautomer, stereoisomer, solvate, hydrate, polymorph, isotopically enriched derivative, or prodrug thereof; wherein $Y^2$ is as defined herein.

In certain embodiments, the compound of Formula (V) is of Formula (V-n-2):

(V-n-2)

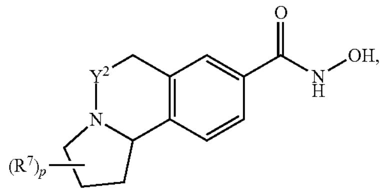

or a pharmaceutically acceptable salt, co-crystal, tautomer, stereoisomer, solvate, hydrate, polymorph, isotopically enriched derivative, or prodrug thereof; wherein $Y^2$, $R^7$, and p are as defined herein.

In certain embodiments, the compound of Formula (V) is of Formula (V-n-3):

(V-n-3)

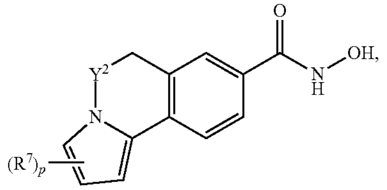

or a pharmaceutically acceptable salt, co-crystal, tautomer, stereoisomer, solvate, hydrate, polymorph, isotopically enriched derivative, or prodrug thereof; wherein $Y^2$, $R^7$, and p are as defined herein.

In certain embodiments of the compound of Formula (V-n), $Y^2$ is —NH—, —NMe-, —$CH_2$—, or a bond. In certain embodiments of the compound of Formula (V-n), $Y^2$ is —NMe-, —$CH_2$—, or a bond. In certain embodiments of the compound of Formula (V-n), $Y^2$ is —NMe-. In certain embodiments of the compound of Formula (V-n), $Y^2$ is —$CH_2$—. In certain embodiments of the compound of Formula (V-n), $Y^2$ is a bond.

In certain embodiments, the compound of Formula (V) is one of the following compounds, or a pharmaceutically acceptable salt, co-crystal, tautomer, stereoisomer, solvate, hydrate, polymorph, isotopically enriched derivative, or prodrug thereof:

79

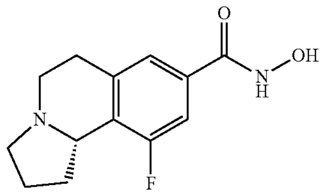

80

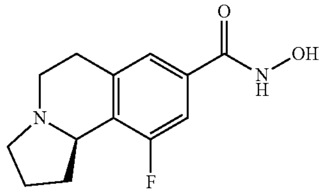

119

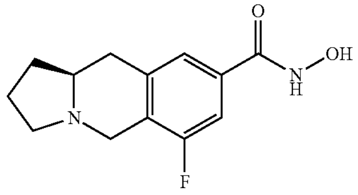

120

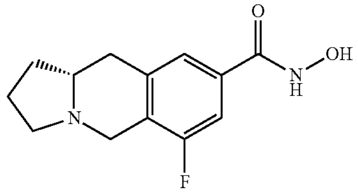

-continued
140
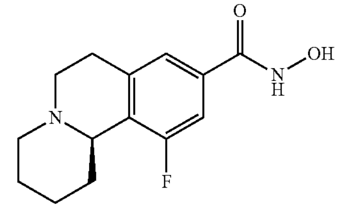
139
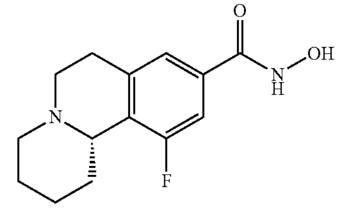
134
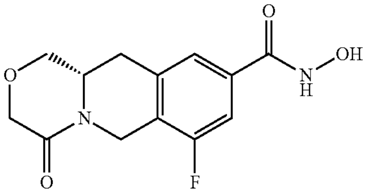
133
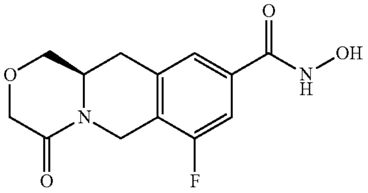
135
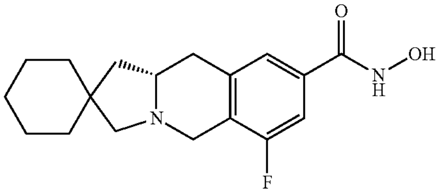
136
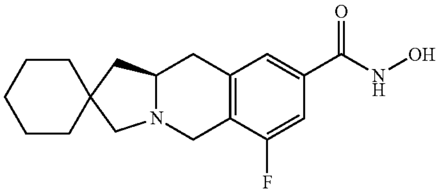
90
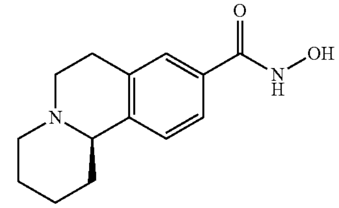
-continued
89
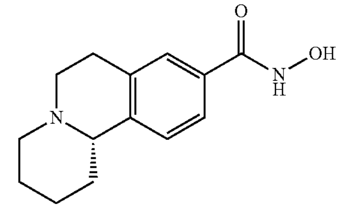
130
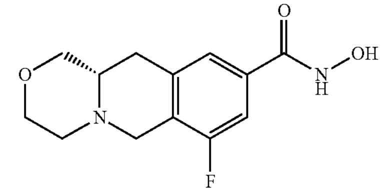
129
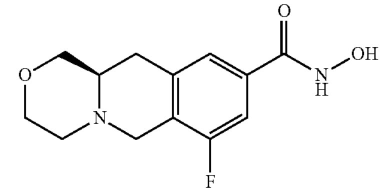
93
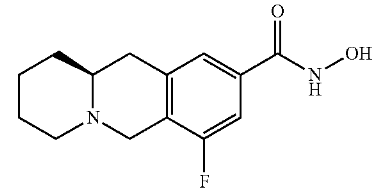
94
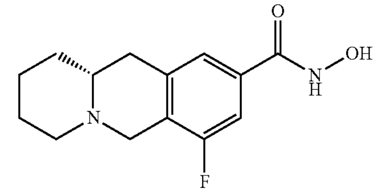
95
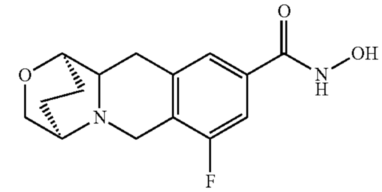
96
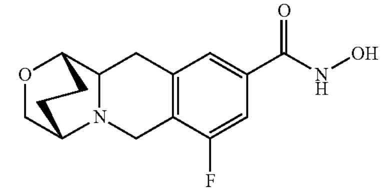
97
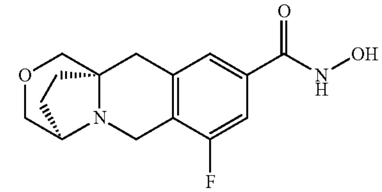

-continued
98
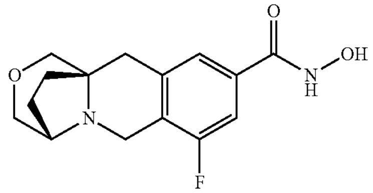
132
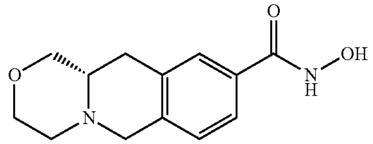
131
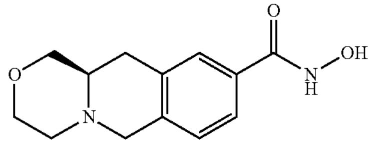
121
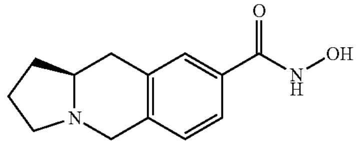
122
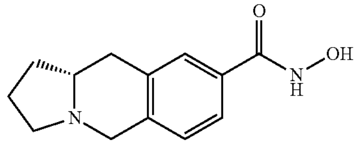
103
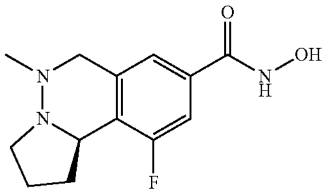
104
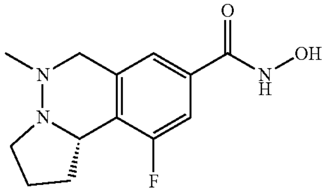
105
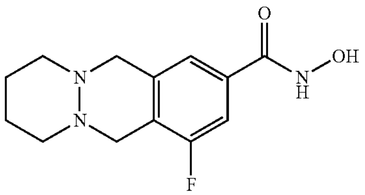
106
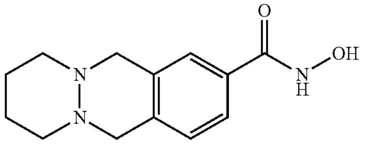
-continued
124
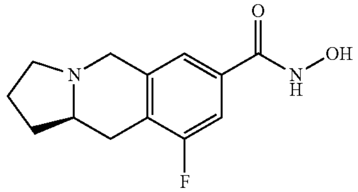
123
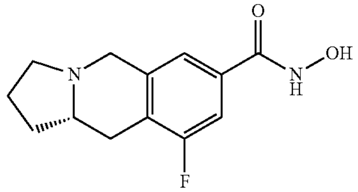
144
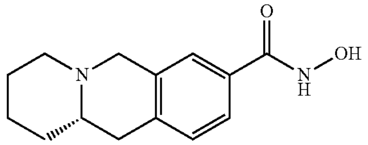
143
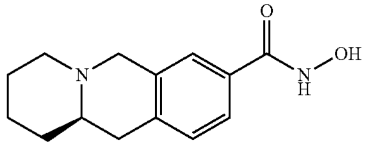
146
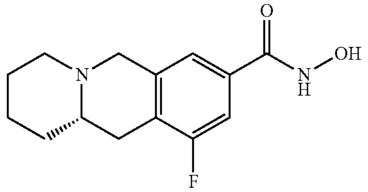
145
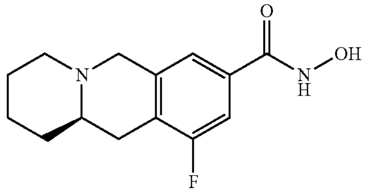
180
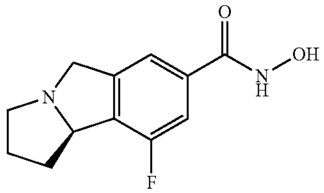
181
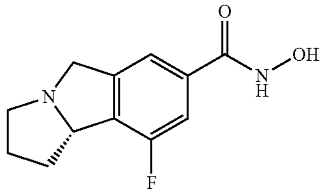

-continued
137
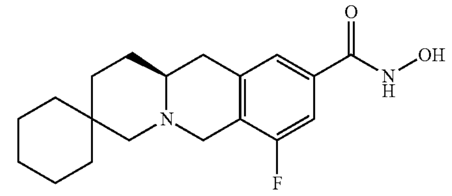
138
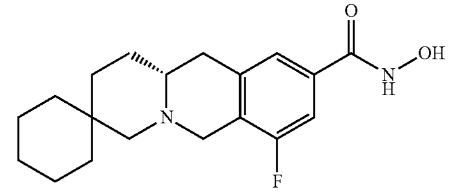
125
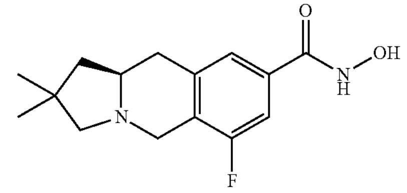
126
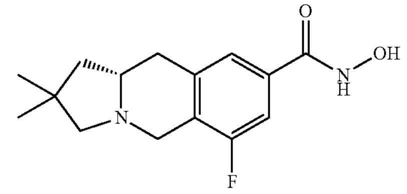
127
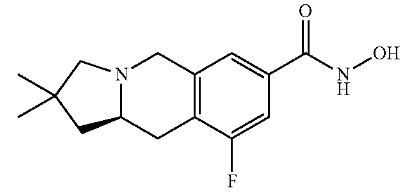
128
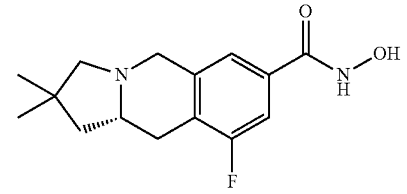
147
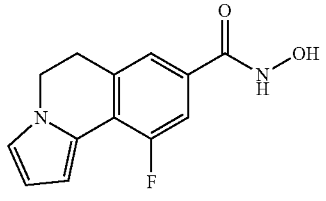
148
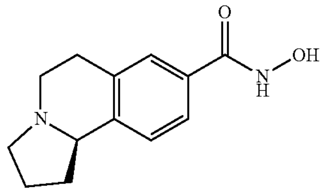
-continued
149
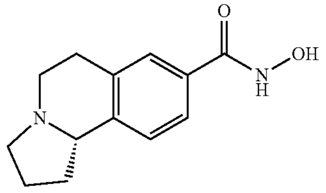
150
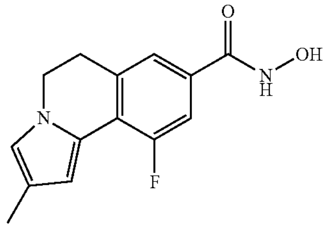
151
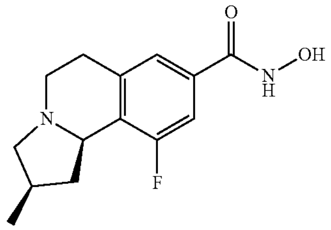
152
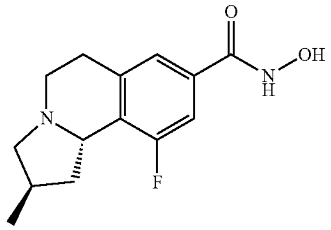
153
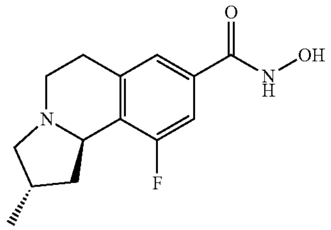
154
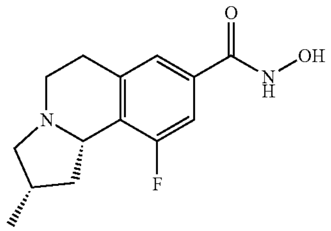
155
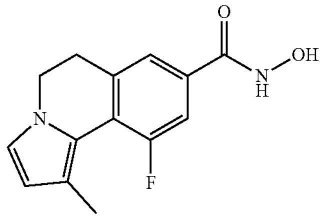

-continued
156
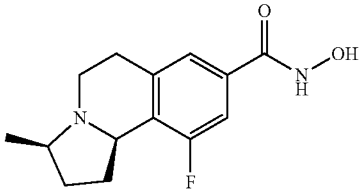
157
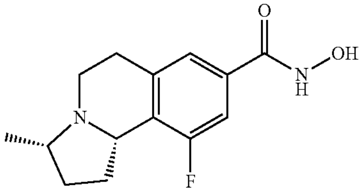
158
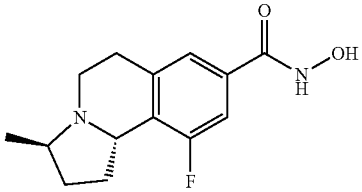
159
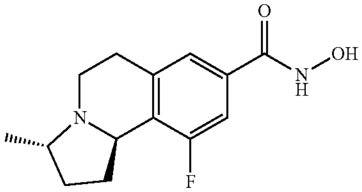
160
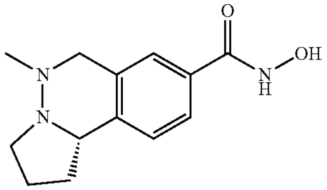
161
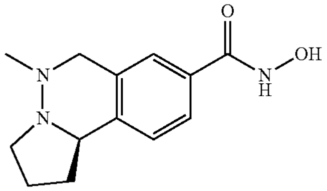
162
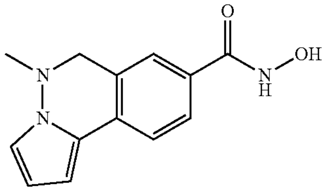
163
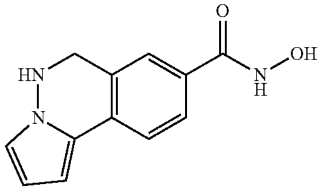
-continued
164
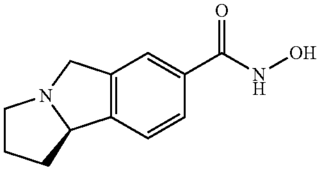
165
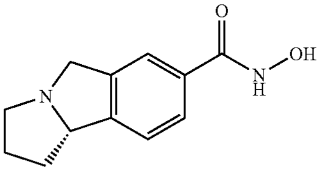
166
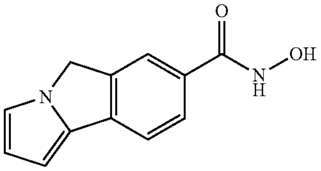
In certain embodiments, the compound of Formula (V) is one of the following compounds, or a pharmaceutically acceptable salt, co-crystal, tautomer, stereoisomer, solvate, hydrate, polymorph, isotopically enriched derivative, or prodrug thereof:
79
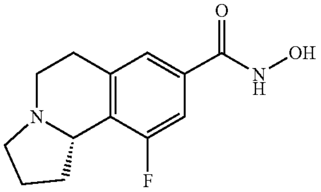
80
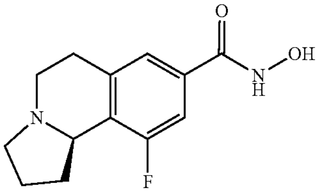
119
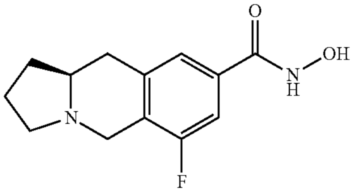
120
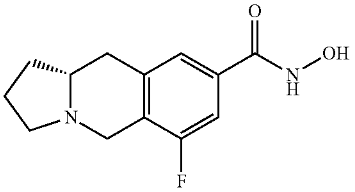

-continued
140
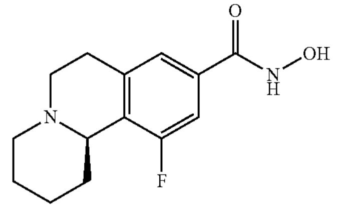
139
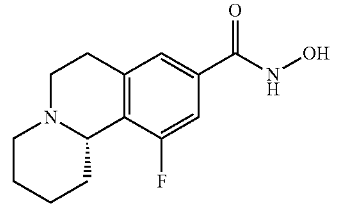
134
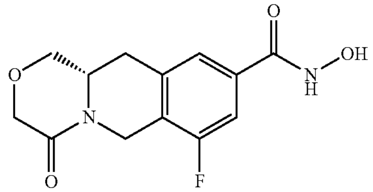
133
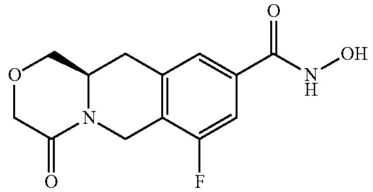
135
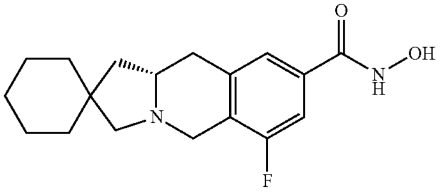
136
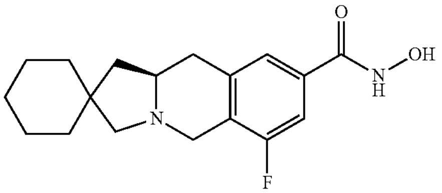
90
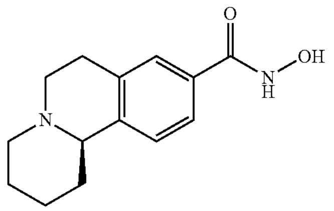
-continued
89
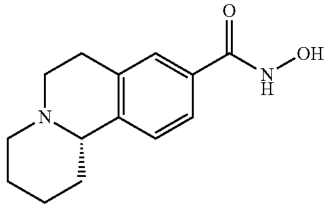
130
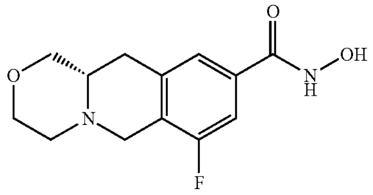
129
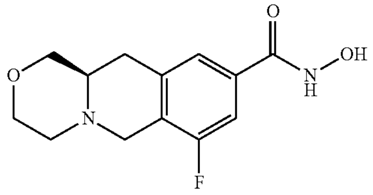
93
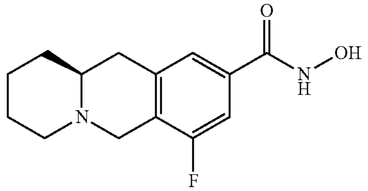
94
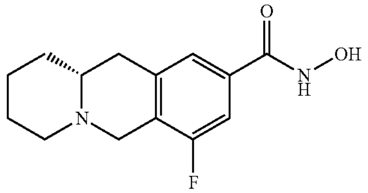
132
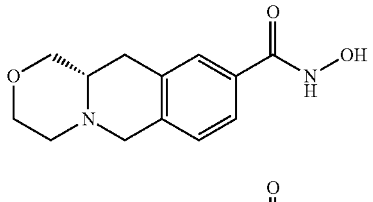
131
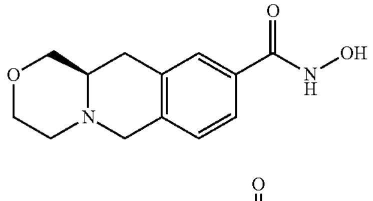
121
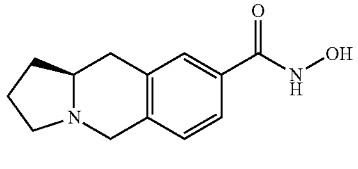

-continued
122
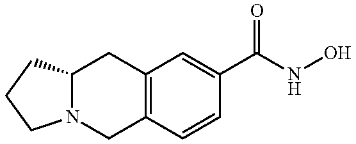
106
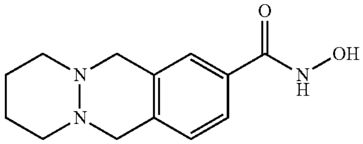
124
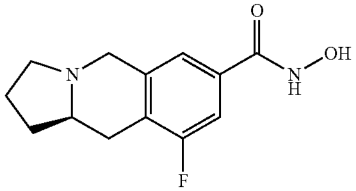
123
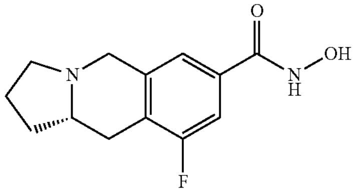
144
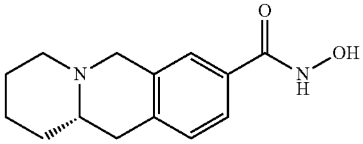
143
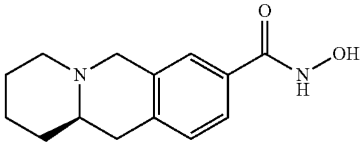
146
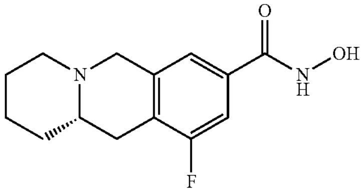
145
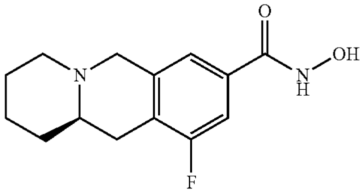
137
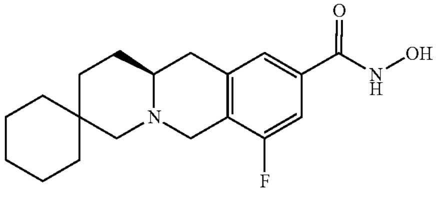
-continued
138
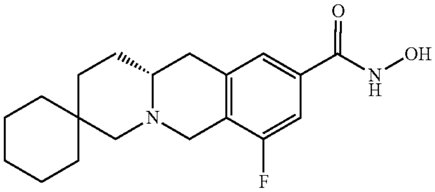
125
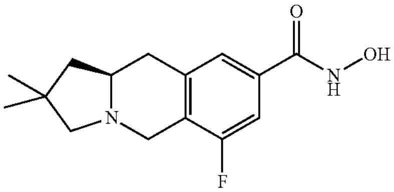
126
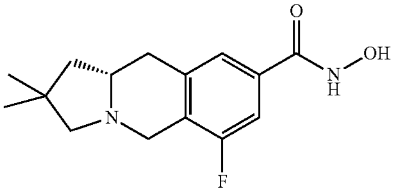
127
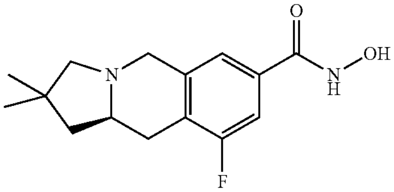
128
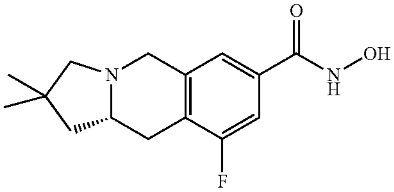
147
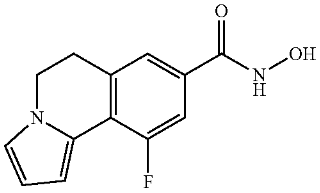
148
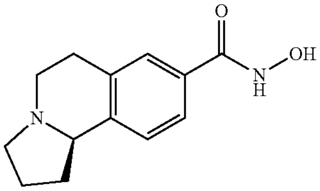
149
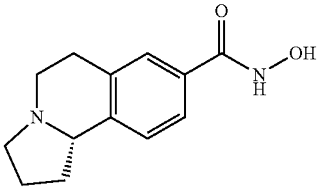

150
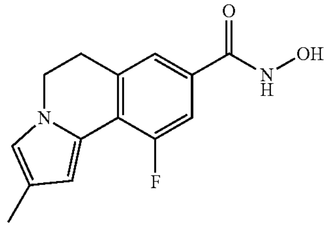
151
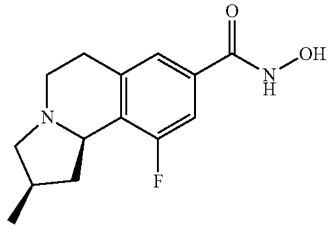
152
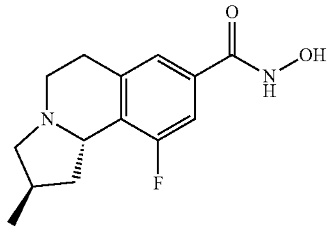
153
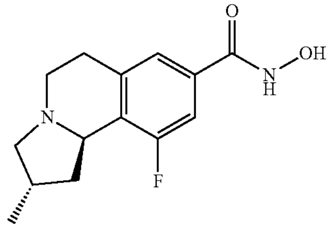
154
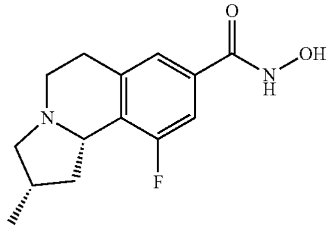
155
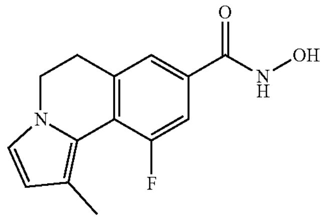
156
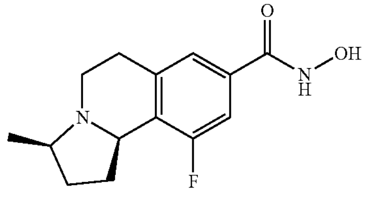
157
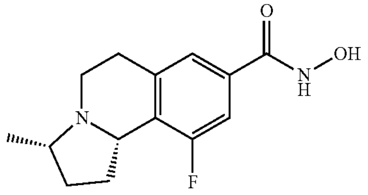
158
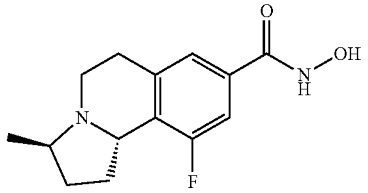
159
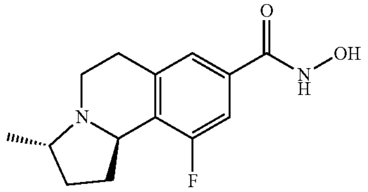
160
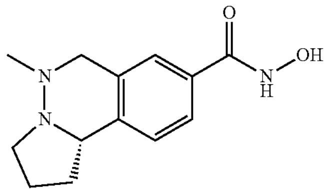
161
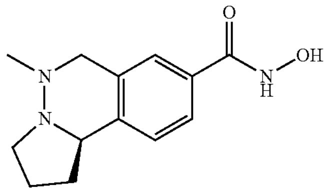
162
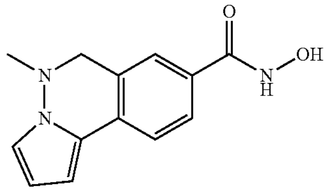
163
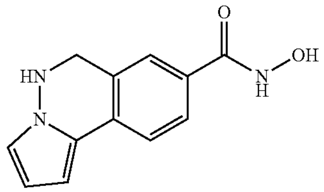
164
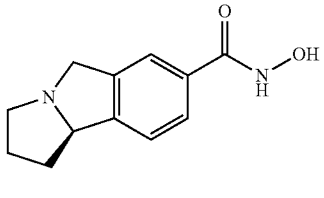

-continued

165

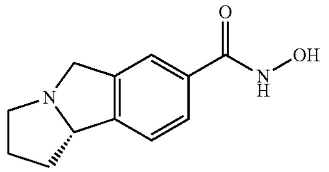

166

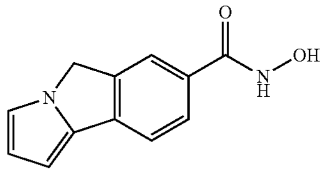

Compound of Formula (VI)

In another aspect, disclosed is a compound of Formula (VI):

(VI)

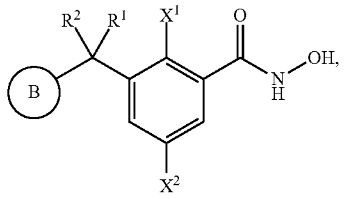

or a pharmaceutically acceptable salt, co-crystal, tautomer, stereoisomer, solvate, hydrate, polymorph, isotopically enriched derivative, or prodrug thereof, wherein:

$X^1$ is hydrogen or fluoro;

$X^2$ is hydrogen or fluoro;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl; and B is a substituted or unsubstituted heterocyclyl, substituted or unsubstituted carbocyclyl, a substituted or unsubstituted polycyclic spiro ring system, or a substituted or unsubstituted bridged ring system.

$X^1$ and $X^2$

As described herein, $X^1$ is hydrogen or fluoro; and $X^2$ is hydrogen or fluoro. In certain embodiments, $X^1$ is hydrogen or fluoro; and $X^2$ is hydrogen or fluoro; provided that at least one of $X^1$ and $X^2$ is fluoro. In certain embodiments, $X^1$ is hydrogen; and $X^2$ is fluoro. In certain embodiments, $X^1$ is fluoro; and $X^2$ is hydrogen. In certain embodiments, $X^1$ is fluoro; and $X^2$ is fluoro. In certain embodiments, $X^1$ is hydrogen; and $X^2$ is hydrogen.

$R^1$ and $R^2$

In certain embodiments, $R^1$ is hydrogen; and $R^2$ is unsubstituted $C_{1-4}$ alkyl; or $R^1$ and $R^2$ together form an unsubstituted cycloalkyl. In certain embodiments, $R^1$ is hydrogen; and $R^2$ is unsubstituted $C_{1-4}$ alkyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted $C_{3-6}$ cycloalkyl. In certain embodiments, $R^1$ is hydrogen; and $R^2$ is methyl or ethyl; or $R^1$ and $R^2$ together form an unsubstituted cyclobutyl. In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ is unsubstituted $C_{1-4}$ alkyl; and $R^2$ is hydrogen; or $R^1$ and $R^2$ together form an unsubstituted cycloalkyl. In certain embodiments, $R^1$ is unsubstituted $C_{1-4}$ alkyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted $C_{3-6}$ cycloalkyl. In certain embodiments, $R^1$ is methyl or ethyl; and $R^2$ is hydrogen; or $R^1$ and $R^2$ together form an unsubstituted cyclobutyl.

In certain embodiments, $R^1$ is unsubstituted $C_{1-4}$ alkyl; and $R^2$ is hydrogen. In certain embodiments, $R^1$ is methyl or ethyl; and $R^2$ is hydrogen. In certain embodiments, $R^1$ is methyl; and $R^2$ is hydrogen. In certain embodiments, $R^1$ is ethyl; and $R^2$ is hydrogen.

In certain embodiments, $R^1$ is hydrogen; and $R^2$ is unsubstituted $C_{1-4}$ alkyl. In certain embodiments, $R^1$ is hydrogen; and $R^2$ is methyl or ethyl. In certain embodiments, $R^1$ is hydrogen; and $R^2$ is methyl. In certain embodiments, $R^1$ is hydrogen; and $R^2$ is ethyl.

In certain embodiments, $R^1$ and $R^2$ together form a substituted or unsubstituted cycloalkyl. In certain embodiments, $R^1$ and $R^2$ together form an unsubstituted cycloalkyl. In certain embodiments, $R^1$ and $R^2$ together form an unsubstituted $C_{3-6}$ cycloalkyl. In certain embodiments, $R^1$ and $R^2$ together form an unsubstituted cyclobutyl.

In certain embodiments, $R^1$ is hydrogen; and $R^2$ is hydrogen.

B

As described herein, B is a substituted or unsubstituted heterocyclyl, substituted or unsubstituted carbocyclyl, a substituted or unsubstituted polycyclic spiro ring system, or a substituted or unsubstituted bridged ring system.

In certain embodiments, B is a substituted or unsubstituted polycyclic spiro ring system, a substituted or unsubstituted bridged ring system,

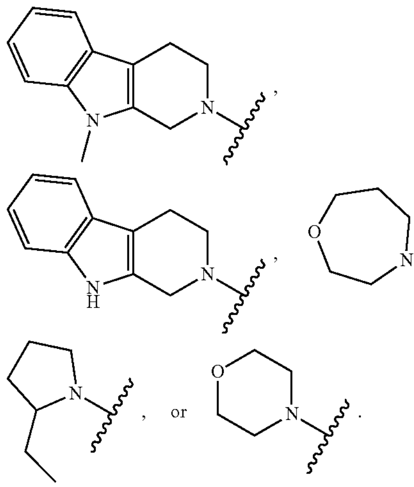

In certain embodiments, B is a substituted or unsubstituted bridged ring system. In certain embodiments, B is a substituted or unsubstituted heterocyclic bridged ring system.

In certain embodiments, B is of formula:

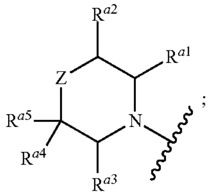
;

wherein Z is —O—, —$NCH_3$—, —C(═O)—, —C(═NOH)—, or —$CHR^{a6}$—; $R^{a1}$ is hydrogen or is joined with $R^{a5}$ or $R^{a4}$ to form a 1-4 carbon bridge; $R^{a2}$ is hydrogen or is joined with $R^{a3}$ or $R^{a4}$ to form a 1-4 carbon bridge; $R^{a5}$ is hydrogen or is joined with $R^{a1}$ or $R^{a2}$ to form a 1-4 carbon bridge; $R^{a4}$ is hydrogen or is joined with $R^{a1}$ or $R^{a2}$ to form a 1-4 carbon bridge; $R^{a}$ is hydrogen or is joined with $R^{a6}$ to form a substituted or unsubstituted cycloalkyl; and $R^{a6}$ is hydrogen or is joined with $R^{a5}$ to form a substituted or unsubstituted cycloalkyl.

In certain embodiments, B is of formula:

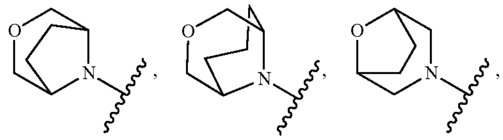

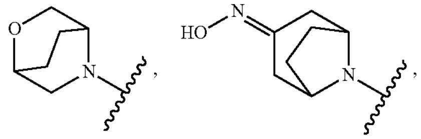

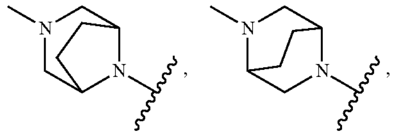

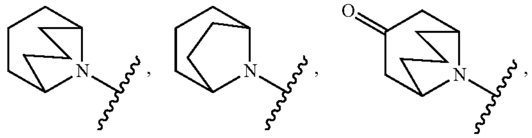

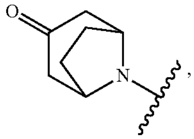
or
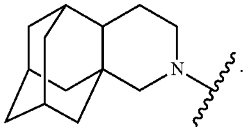
.

In certain embodiments B is of formula:

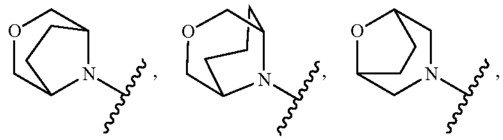

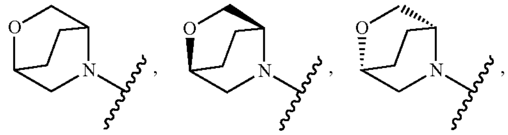

-continued

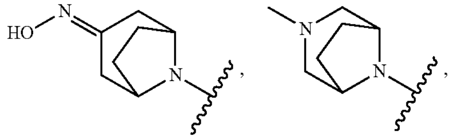

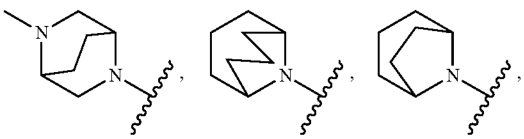

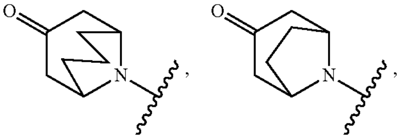

or
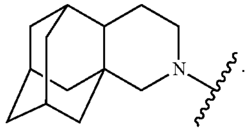
.

In certain embodiments, B is of formula:

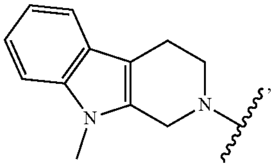

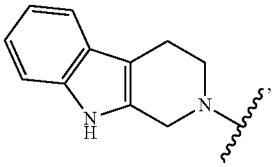

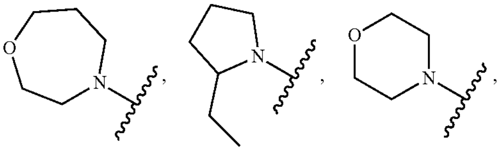

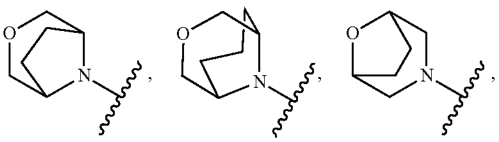

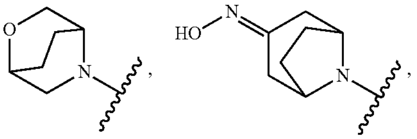

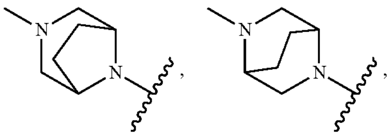

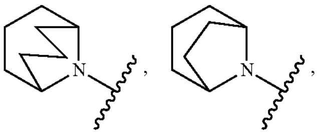

-continued

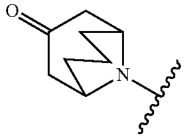,
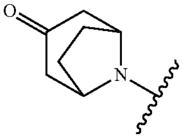, or
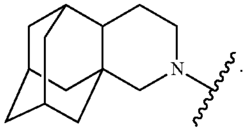.

In certain embodiments, B is of formula:

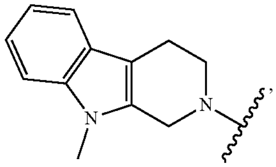,
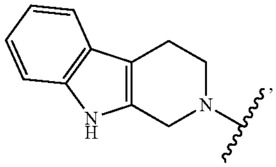,
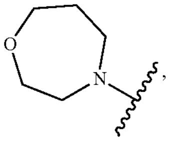,
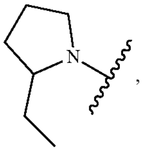,
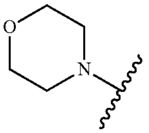,
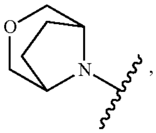,
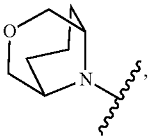,
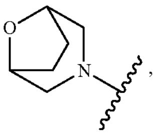,
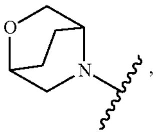,
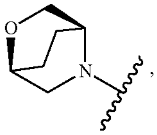,
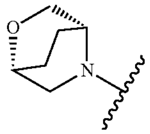,
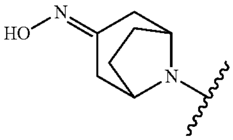,
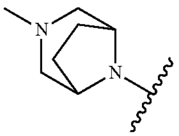,
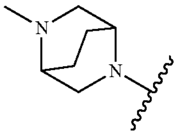,
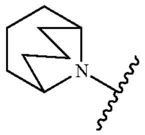,
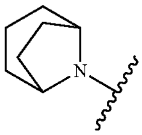,
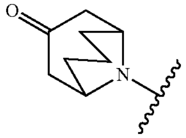,
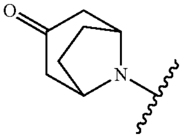, or
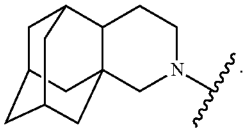.

In certain embodiments, B is of formula:

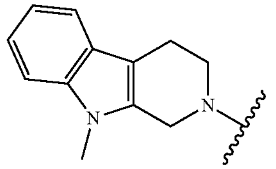

or

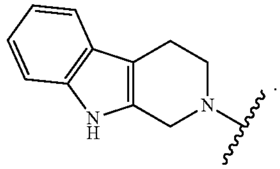.

In certain embodiments, B is of formula:

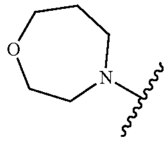,
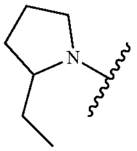, or

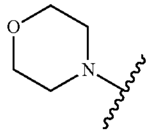.

In certain embodiments, B is a substituted or unsubstituted polycyclic spiro ring system.

In certain embodiments,

B is

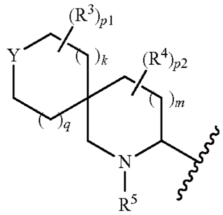, wherein

Y is —O—, —S—, —$NR^{a1}$—, or —($CR^3R^4$)—;

each occurrence of $R^3$ and $R^4$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroalkyl, —$N(R^{a1})_2$, —$OR^{b1}$, —$SR^{c1}$, or —CN; wherein two or three $R^3$ groups are optionally joined to form a substituted or unsubstituted bridged ring; wherein two or three $R^4$ groups are optionally joined to form a substituted or unsubstituted bridged ring;

$R^5$ is hydrogen, substituted or unsubstituted acyl, substituted or unsubstituted alkyl, or a nitrogen protecting group;

each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group, or two $R^{a1}$ groups are joined to form a substituted or unsubstituted heterocyclic ring;

each occurrence of $R^{b1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or an oxygen protecting group;

each occurrence of $R^{c1}$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, or a sulfur protecting group;

m, k, and q are each independently 0, 1, or 2; and p1 and p2 are each independently 0, 1, 2, 3, or 4.

In certain embodiments, Y is —O—, —($CR^3R^4$)—, or —$NR^{a1}$—; and $R^3$, $R^4$, and $R^{a1}$ are as defined herein. In certain embodiments, Y is —O—. In certain embodiments, Y is —($CR^3R^4$)—; and $R^3$, $R^4$, and $R^{a1}$ are as defined herein. In certain embodiments, Y is —$NR^{a1}$—; and $R^{a1}$ is as defined herein.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; and each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; each occurrence of $R^{a1}$ is, independently, hydrogen, substituted or unsubstituted acyl, substituted or unsubstituted alkyl, substituted or unsubstituted heteroalkyl, substituted or unsubstituted carbocyclyl, substituted or unsubstituted heterocyclyl, or a nitrogen protecting group; the sum of m and n is 0, 1, or 2; and the sum of k and q is 0, 1, or 2.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; and each occurrence of $R^{a1}$ is, independently, hydrogen, substituted or unsubstituted acyl, substituted or unsubstituted alkyl, or a nitrogen protecting group.

In certain embodiments, Y is —O—, —($CR^3R^4$)—, or —$NR^{a1}$—; each occurrence of $R^3$ and $R^4$ is, independently, hydrogen, halogen, substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; each occurrence of $R^{a1}$ is, independently, hydrogen, substituted or unsubstituted acyl, substituted or unsubstituted alkyl, or a nitrogen protecting group; the sum of m and n is 0, 1, or 2; and the sum of k and q is 0, 1, or 2.

In certain embodiments, Y is —O—, —($CR^3R^4$)—, or —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; and each occurrence of $R^{a1}$ is, independently, hydrogen, substituted or unsubstituted acyl, substituted or unsubstituted alkyl, or a nitrogen protecting group.

In certain embodiments, Y is —O—, —($CR^3R^4$)—, or —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; each occurrence of $R^{a1}$ is, independently, hydrogen, substituted or unsubstituted acyl, substituted or unsubstituted alkyl, or a nitrogen protecting group; the sum of m and n is 0, 1, or 2; and the sum of k and q is 0, 1, or 2.

In certain embodiments, Y is —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; and each occurrence of $R^{a1}$ is, independently, hydrogen, substituted or unsubstituted acyl, substituted or unsubstituted alkyl, or a nitrogen protecting group.

In certain embodiments, Y is —$NR^{a1}$—; each occurrence of $R^3$ and $R^4$ is, independently, hydrogen, or substituted or unsubstituted alkyl; wherein two or three $R^3$ groups are optionally joined to form a substituted or unsubstituted bridged ring; each occurrence of $R^{a1}$ is, independently, hydrogen, substituted or unsubstituted acyl, substituted or unsubstituted alkyl, or a nitrogen protecting group; the sum of m and n is 0, 1, or 2; and the sum of k and q is 0, 1, or 2.

In certain embodiments, Y is —O— or —($CR^3R^4$)—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —O— or —($CR^3R^4$)—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —O— or —($CR^3R^4$)—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —O— or —($CR^3R^4$)—; each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, Y is —O—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —O—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —O—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —O—; and each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, Y is —$(CR^3R^4)$—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —$(CR^3R^4)$—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —$(CR^3R^4)$—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —$(CR^3R^4)$—; each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, Y is —$(CHR^3)$—; and each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring.

In certain embodiments, Y is —$(CHR^3)$—; each occurrence of $R^3$ and $R^4$ is, independently, hydrogen, halogen, or substituted or unsubstituted alkyl; wherein two or three $R^3$ groups are optionally joined to form a substituted or unsubstituted bridged ring; wherein two or three $R^4$ groups are optionally joined to form a substituted or unsubstituted bridged ring; the sum of m and n is 0, 1, or 2; and the sum of k and q is 0, 1, or 2.

In certain embodiments, Y is —$(CHR^3)$—; and each occurrence of $R^3$ and $R^4$ is, independently, hydrogen, or substituted or unsubstituted alkyl; wherein two or three $R^3$ groups are optionally joined to form a substituted or unsubstituted bridged ring.

In certain embodiments, Y is —$(CHR^3)$—; and each occurrence of $R^3$ and $R^4$ is, independently, hydrogen, or substituted or unsubstituted alkyl; wherein two or three $R^3$ groups are optionally joined to form a substituted or unsubstituted bridged ring; the sum of m and n is 0, 1, or 2; and the sum of k and q is 0, 1, or 2.

In certain embodiments, the sum of m and n is 0, 1, or 2. In certain embodiments, m is 0; and n is 0. In certain embodiments, m is 1; and n is 0. In certain embodiments, m is 2; and n is 0. In certain embodiments, m is 0; and n is 1. In certain embodiments, m is 1; and n is 1. In certain embodiments, m is 0; and n is 2.

In certain embodiments, the sum of k and q is 0, 1, or 2. In certain embodiments, k is 0; and q is 0. In certain embodiments, k is 1; and q is 0. In certain embodiments, k is 2; and q is 0. In certain embodiments, k is 0; and q is 1. In certain embodiments, k is 1; and q is 1. In certain embodiments, k is 0; and q is 2.

In certain embodiments, B is of formula:

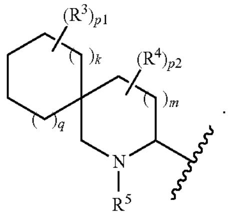

In certain embodiments, B is of formula:

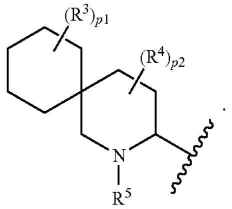

In certain embodiments, B is of formula:

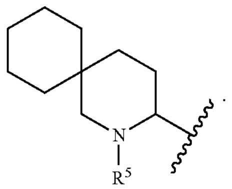

In certain embodiments, B is of formula:

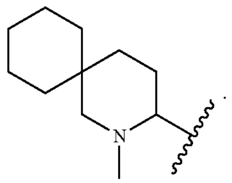 [SMILES: *C1CCC2(CCCCC2)CN1C]

In certain embodiments, B is of formula:

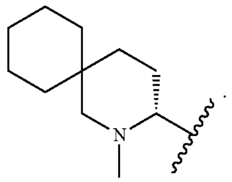 [SMILES: *[C@H]1CCC2(CCCCC2)CN1C]

In certain embodiments, B is of formula:

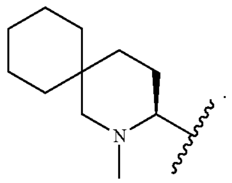 [SMILES: *[C@@H]1CCC2(CCCCC2)CN1C]

In certain embodiments, B is of formula:

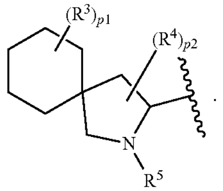

In certain embodiments, B is of formula:

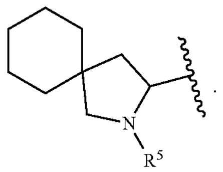

In certain embodiments, B is of formula:

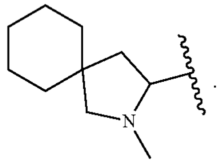 [SMILES: *C1CC2(CCCCC2)CN1C]

In certain embodiments, B is of formula:

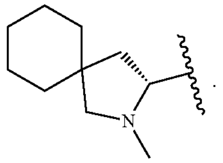 [SMILES: *[C@H]1CC2(CCCCC2)CN1C]

In certain embodiments, B is of formula:

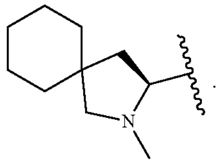 [SMILES: *[C@@H]1CC2(CCCCC2)CN1C]

Certain Embodiments

In certain embodiments, the compound of Formula (VI) is of Formula (VI-a):

(VI-a)

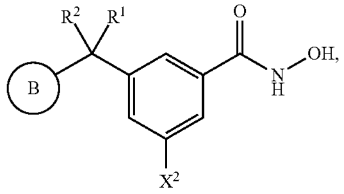

or a pharmaceutically acceptable salt, co-crystal, tautomer, stereoisomer, solvate, hydrate, polymorph, isotopically enriched derivative, or prodrug thereof; wherein $X^2$, $R^1$, $R^2$, and B are as defined herein.

In certain embodiments, the compound of Formula (VI) is of Formula (VI-b):

(VI-b)

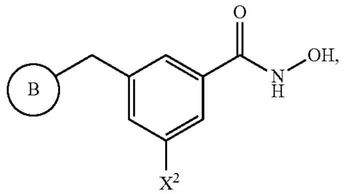

or a pharmaceutically acceptable salt, co-crystal, tautomer, stereoisomer, solvate, hydrate, polymorph, isotopically enriched derivative, or prodrug thereof; wherein $X^2$ and B are as defined herein.

In certain embodiments, the compound of Formula (VI) is of Formula (VI-c):

(VI-c)

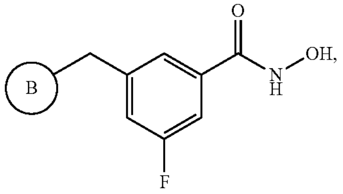

or a pharmaceutically acceptable salt, co-crystal, tautomer, stereoisomer, solvate, hydrate, polymorph, isotopically enriched derivative, or prodrug thereof; wherein B is as defined herein.

In certain embodiments, the compound of Formula (VI) is one of the following compounds, or a pharmaceutically acceptable salt, co-crystal, tautomer, stereoisomer, solvate, hydrate, polymorph, isotopically enriched derivative, or prodrug thereof:

170

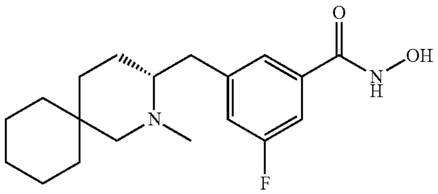

171

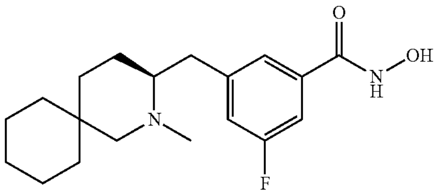

In certain embodiments, the provided compounds (e.g., compounds of Formula (I), (II), (III), (IV), (V), and (VI)) inhibit HDAC6 with an $IC_{50}$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the provided compounds (e.g., compounds of Formula (I), (II), (III), (IV), (V), and (VI)) selectively inhibit HDAC6 over any of HDAC1, HDAC2, HDAC3, HDAC4, HDAC5, HDAC7, HDAC8, HDAC9, HDAC10, and HDAC11. In certain embodiments, the compounds selectively inhibit HDAC6 over each of HDAC1, HDAC2, HDAC3, HDAC4, HDAC5, HDAC7, HDAC8, HDAC9, HDAC10, and HDAC11. In certain embodiments, the compounds are 5-fold, 10-fold, 20-fold, 30-fold, 40-fold, 50-fold, 60-fold, 70-fold, 80-fold, 90-fold, 100-fold, 1,000-fold, or 10,000-fold, more selective inhibitors of HDAC6 over any of HDAC1, HDAC2, HDAC3, HDAC4, HDAC5, HDAC7, HDAC8, HDAC9, HDAC10, and HDAC11. In certain embodiments, the compounds are 5-fold, 10-fold, 20-fold, 30-fold, 40-fold, 50-fold, 60-fold, 70-fold, 80-fold, 90-fold, 100-fold, 1,000-fold, or 10,000-fold, more selective inhibitors of HDAC6 over each of HDAC1, HDAC2, HDAC3, HDAC4, HDAC5, HDAC7, HDAC8, HDAC9, HDAC10, and HDAC11. In certain embodiments, the compounds are 5-fold, 10-fold, 20-fold, 30-fold, 40-fold, 50-fold, 60-fold, 70-fold, 80-fold, 90-fold, 100-fold, 1,000-fold, or 10,000-fold, more selective inhibitors of HDAC6 over HDAC8.

Pharmaceutical Compositions, Kits, and Administration

The present disclosure provides pharmaceutical compositions comprising a disclosed compound (e.g., a compound of Formula (I), (II), (III), (IV), (V), or (VI)), or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound of Formula (I), (II), (III), (IV), (V), or (VI), or a pharmaceutically acceptable salt thereof, and a pharmaceutically acceptable excipient.

In certain embodiments, the compound of Formula (I), (II), (III), (IV), (V), or (VI) is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for treating cancer in a subject in need thereof. In certain embodiments, the effective amount is an amount effective for preventing cancer in a subject in need thereof. In certain embodiments, the effective amount is an amount effective for treating a hematological cancer in a subject in need thereof. In certain embodiments, the effective amount is an amount effective for treating a cancer comprising a solid tumor in a subject in need thereof. In certain embodiments, the effective amount is an amount effective for treating inflammatory disease in a subject in need thereof. In certain embodiments, the effective amount is an amount effective for preventing inflammatory disease in a subject in need thereof. In certain embodiments, the effective amount is an amount effective for treating an infectious disease in a subject in need thereof. In certain embodiments, the effective amount is an amount effective for preventing an infectious disease in a subject in need thereof. In certain embodiments, the effective amount is an amount effective for treating a cardiovascular disease in a subject in need thereof. In certain embodiments, the effective amount is an amount effective for treating a neurological disorder in a subject in need thereof. In certain embodiments, the effective amount is an amount effective for preventing a neurological disorder in a subject in need thereof. In certain embodiments, the effective amount is an amount effective for treating a neurodegenerative, neurodevelopmental, neuropsychiatric, or neuropathy disease in a subject in need thereof.

In certain embodiments, the effective amount is an amount effective for reducing the risk of developing a disease (e.g., proliferative disease, inflammatory disease, infectious disease, a neurological disorder, or cardiovascular disease) in a subject in need thereof.

In certain embodiments, the effective amount is an amount effective for inhibiting the activity (e.g., aberrant activity, such as increased activity) of HDAC6 in a subject, tissue, biological sample, or cell.

In certain embodiments, the subject being treated or administered a compound described herein is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inhibiting the activity of HDAC6 by at least about 10%, at least about 20%, at least about 30%, at least about 40%, at least about 50%, at least about 60%, at least about 70%, at least about 80%, at least about 90%, at least about 95%, at least about 98%, or at least about 99%. In certain embodiments, the effective amount is an amount effective for inhibiting the activity of HDAC6 by a range between a percentage described in this paragraph and another percentage described in this paragraph, inclusive.

The present disclosure provides pharmaceutical compositions comprising a compound that interacts with (e.g., inhibits) HDAC6 for use in treating a HDAC6-related disease or disorder in a subject in need thereof. The present disclosure provides pharmaceutical compositions comprising a compound that interacts with (e.g., inhibits) HDAC6 for use in treating a disease or disorder associated with aberrant activity of HDAC6 in a subject in need thereof. The present disclosure provides pharmaceutical compositions comprising a compound that interacts with (e.g., inhibits) HDAC6 for use in treating a disease or disorder associated with increased activity of HDAC6 in a subject in need thereof.

In certain embodiments, the composition is for use in treating a proliferative disease in a subject in need thereof. In certain embodiments, the composition is for use in treating cancer in a subject in need thereof. In certain embodiments, the composition is for use in treating a hematological cancer. In certain embodiments, the composition is for use in treating a leukemia, T-cell lymphoma, Hodgkin's Disease, non-Hodgkin's lymphoma, or multiple myeloma. In certain embodiments, the composition is for use in treating a cancer comprising a solid tumor. In certain embodiments, the composition is for use in treating glioma, glioblastoma, non-small cell lung cancer, brain tumor, neuroblastoma, bone tumor, soft-tissue sarcoma, head and neck cancer, genitourinary cancer, lung cancer, breast cancer, pancreatic cancer, melanoma, stomach cancer, brain cancer, liver cancer, thyroid cancer, clear cell carcinoma, uterine cancer, or ovarian cancer.

In certain embodiments, the composition is for use in treating an inflammatory disease. In certain embodiments, the composition is for use in treating osteoarthritis, rheumatoid arthritis, lupus, inflammatory bowel disease, Crohn's Disease, ulcerative colitis, anemia, leukocytosis, asthma, chronic obstructive pulmonary disease, appendicitis, bronchitis, bursitis, conjunctivitis, dermatitis, encephalitis, myelitis myocarditis, sinusitis, dermatitis, psoriasis, eczema, or acne.

In certain embodiments, the composition is for use in treating an infectious disease. In certain embodiments, the composition is for use in treating bacterial, fungal, or protozoal infections.

In certain embodiments, the composition is for use in treating autoimmune disease. In certain embodiments, the composition is for use in treating diabetes, thyroiditis, Graves' disease, Guillain-Barre syndrome, Addison's disease, scleroderma, primary biliary cirrhosis, Reiter's syndrome, psoriasis, chronic fatigue, or endometriosis.

In certain embodiments, the composition is for use in treating heteroimmune disease. In certain embodiments, the composition is for use in treating graft versus host disease, transplantation, transfusion, anaphylaxis, allergic conjunctivitis, or allergic rhinitis.

In certain embodiments, the composition is for use in treating a neurological disorder. In certain embodiments, the composition is for use in treating a neurodegenerative, neurodevelopmental, neuropsychiatric, or neuropathy disease. In certain embodiments, the composition is for use in treating Fragile-X syndrome, Charcot-Marie-Tooth disease, Alzheimer's disease, Parkinson's diseases, Huntington's disease, multiple sclerosis, amyotrophic lateral sclerosis, Creutzfeldt-Jakob disease, Lewy body dementia, vascular dementia, muscular atrophy, seizure induced memory loss, schizophrenia, Rubinstein Taybi syndrome, Rett Syndrome, attention deficit hyperactivity disorder, dyslexia, bipolar disorder, social, cognitive and learning disorders associated with autism, attention deficit disorder, schizophrenia, major depressive disorder, peripheral neuropathy, diabetic retinopathy, diabetic peripheral neuropathy, chemotherapy-induced peripheral neuropathy, traumatic brain injury (TBI), chronic traumatic encephalopathy (CTE), or a tauopathy. In certain embodiments, the composition is for use in treating primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, lipofuscinosis, Alzheimer's disease, or argyrophilic grain disease.

In certain embodiments, the composition is for use in treating a disease or disorder mediated by or linked to T-cell dysregulation. In certain embodiments, the composition is for use in treating arthritis, colitis, allograft rejection, lupus, asthma, psoriasis, inflammation, allergy, allergic encephalomyelitis, autoimmune lymphoproliferative disorder, autoimmune polyglandular syndrome type II, type I diabetes, lymphoma, Wiskott-Aldrich syndrome, or myasthenia gravis.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, and/or in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological cancer, chemo-induced neuropathy, neurological disorder, autoimmune disease, and/or inflammatory disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, and immunosuppressants. In certain embodiments, the additional pharmaceutical agent is an anti-inflammatory agent. In certain embodiments, the additional pharmaceutical agent is an immunotherapy. In certain embodiments, the additional pharmaceutical agent is an anti-proliferative agent. In certain embodiments, the additional pharmaceutical agent is an anti-cancer agent. In certain embodiments, the anti-cancer agents include, but are not limited to, epigenetic or transcriptional modulators (e.g., DNA methyltransferase inhibitors, HDAC inhibitors, lysine methyltransferase inhibitors), antimitotic drugs (e.g., taxanes and vinca alkaloids), cell signaling pathway inhibitors (e.g., tyrosine protein kinase inhibitors), modulators of protein stability (e.g., proteasome inhibitors), Hsp90 inhibitors, glucocorticoids, all-trans retinoic acids, anti-estrogens (e.g., tamoxifen, raloxifene, and megestrol), LHRH agonists (e.g., goscrclin and leuprolide), anti-androgens (e.g. flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), antimetabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonuclotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), thalidomide, lenalidomide, pomalidomide, tyrosine kinase inhibitors (e.g., axitinib, bosutinib, cediranib (RECENTIN™), dasatinib (SPRYCEL®), erlotinib (TARCEVA®), gefitinib (IRESSA®), imatinib (Gleevec®), lapatinib (TYKERB®, TYVERB®), lestaurtinib, neratinib, nilotinib (TASIGNA®), semaxanib, sunitinib (SUTENT®), toceranib (PALLADIA®), vandetanib (ZACTIMA®, ZD6474), vatalanib (PTK787), nilotinib (TASIGNA®), sorafenib (NEXAVAR®), everolimus (AFINITOR®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. In certain embodiments, the additional pharmaceutical agent is cisplatin. In certain embodiments, the additional pharmaceutical agent is paclitaxel. In certain embodiments, the additional pharmaceutical agent is vincristine.

In certain embodiments, the additional pharmaceutical agent is an immunotherapy. In certain embodiments, the immunotherapy is useful in the treatment of a cancer. Exemplary immunotherapies include, but are not limited to, T-cell therapies, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies. In certain embodiments, the immunotherapy is a T-cell therapy. In certain embodiments, the T-cell therapy is chimeric antigen receptor T cells (CAR-T). In certain embodiments, the immunotherapy is an antibody. In certain embodiments, the antibody is an anti-PD-1 antibody, an anti-PD-L1 antibody, an anti-CTLA-4 antibody, an anti-TIM3 antibody, an anti-OX40 antibody, an anti-GITR antibody, an anti-LAG-3 antibody, an anti-CD137 antibody, an anti-CD27 antibody, an anti-CD28 antibody, an anti-CD28H antibody, an anti-CD30 antibody, an anti-CD39 antibody, an anti-CD40 antibody, an anti-CD47 antibody, an anti-CD48 antibody, an anti-CD70 antibody, an anti-CD73 antibody, an anti-CD96 antibody, an anti-CD160 antibody, an anti-CD200 antibody, an anti-CD244 antibody, an anti-ICOS antibody, an anti-TNFRSF25 antibody, an anti-TMIGD2 antibody, an anti-DNAM1 antibody, an anti-BTLA antibody, an anti-LIGHT antibody, an anti-TIGIT antibody, an anti-VISTA antibody, an anti-HVEM antibody, an anti-Siglec antibody, an anti-GAL1 antibody, an anti-GAL3 antibody, an anti-GAL9 antibody, an anti-BTNL2 (butrophylins) antibody, an anti-B7-H3 antibody, an anti-B7-H4 antibody, an anti-B7-H5 antibody, an anti-B7-H6 antibody, an anti-KIR antibody, an anti-LIR antibody, an anti-ILT antibody, an anti-MICA antibody, an anti-MICB antibody, an anti-NKG2D antibody, an anti-NKG2A antibody, an anti-TGFβ antibody, an anti-TGFβR antibody, an anti-CXCR4 antibody, an anti-CXCL12 antibody, an anti-CCL2 antibody, an anti-IL-10 antibody, an anti-IL-13 antibody, an anti-IL-23 antibody, an anti-phosphatidylserine antibody, an anti-neuropilin antibody, an anti-GalCer antibody, an anti-HER2 antibody, an anti-VEGFA antibody, an anti-VEGFR antibody, an anti-EGFR antibody, or an anti-Tie2 antibody. In certain embodiments, the antibody is pembrolizumab, nivolumab, pidilizumab, ipilimumab, tremelimumab, durvalumab, atezolizumab, avelumab, PF-06801591, utomilumab, PDR001, PBF-509, MGB453, LAG525, AMP-224, INCSHR1210, INCAGN1876, INCAGN1949, samalizumab, PF-05082566, urelumab, lirilumab, lulizumab, BMS-936559, BMS-936561, BMS-986004, BMS-986012, BMS-986016, BMS-986178, IMP321, IPH2101, IPH2201, varilumab, ulocuplumab, monalizumab, MEDI0562, MEDIO680, MEDI1873, MEDI6383, MEDI6469, MEDI9447, AMG228, AMG820, CC-90002, CDX-1127, CGEN15001T, CGEN15022, CGEN15029, CGEN15049, CGEN15027, CGEN15052, CGEN15092, CX-072, CX-2009, CP-870893, lucatumumab, dacetuzumab, Chi Lob 7/4, RG6058, RG7686, RG7876, RG7888, TRX518, MK-4166, MGA271, IMC-CS4, emactuzumab, pertuzumab, obinutuzumab, cabiralizumab, margetuximab, enoblituzumab, mogamulizumab, carlumab, bevacizumab, trastuzumab (HERCEPTIN®), bevacizumab (AVASTIN®), rituximab (RITUXAN®), cetuximab (ERBITUX®), panitumumab (VECTIBIX®), alemtuzumab (CAMPATH®), or ranibizumab (Lucentis®).

In certain embodiments, the additional pharmaceutical agent is a symptomatic drug, such as cholinesterase inhibitors (e.g., ARICEPT®, EXELON®, RAZADYNE®, donepezil, rivastigmine, and galantamine) and glutamate regulators (e.g., NAMENDA®, memantine). In certain embodiments, the additional pharmaceutical agent is riluzole. In certain embodiments, the additional pharmaceutical agent is edaravone. In certain embodiments, the additional pharmaceutical agent is an anti-amyloid or anti-tau antibody. In certain embodiments, the additional pharmaceutical agent is any agent useful in the treatment of Alzheimer's disease (e.g., small molecule, antibody, polypeptide, antisense oligo, RNA).

In certain embodiments, the compounds or pharmaceutical compositions described herein can be administered in combination with an anti-cancer therapy including, but not limited to, surgery, radiation therapy, and transplantation (e.g., stem cell transplantation, bone marrow transplantation).

In certain embodiments, the compound or pharmaceutical composition is a solid. In certain embodiments, the compound or pharmaceutical composition is a powder. In certain embodiments, the compound or pharmaceutical composition can be dissolved in a liquid to make a solution. In certain embodiments, the compound or pharmaceutical composition is dissolved in water to make an aqueous solution. In certain embodiments, the pharmaceutical composition is a liquid for parental injection. In certain embodiments, the pharmaceutical composition is a liquid for oral administration (e.g., ingestion). In certain embodiments, the pharmaceutical composition is a liquid (e.g., aqueous solution) for intravenous injection. In certain embodiments, the pharmaceutical composition is a liquid (e.g., aqueous solution) for subcutaneous injection.

After formulation with an appropriate pharmaceutically acceptable excipient in a desired dosage, the pharmaceutical compositions of the present disclosure can be administered to humans and other animals orally, parenterally, intracisternally, intraperitoneally, topically, bucally, or the like, depending on the disease or condition being treated.

In certain embodiments, a pharmaceutical composition comprising a compound of Formula (I), (II), (III), (IV), (V), or (VI) is administered, orally or parenterally, at dosage levels of each pharmaceutical composition sufficient to deliver from about 0.001 mg/kg to about 200 mg/kg in one or more dose administrations for one or several days (depending on the mode of administration). In certain embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In certain embodiments, the compounds described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, the composition described herein is administered at a dose that is below the dose at which the agent causes non-specific effects.

In certain embodiments, the pharmaceutical composition is administered at a dose of about 0.001 mg to about 1000 mg per unit dose. In certain embodiments, the pharmaceutical composition is administered at a dose of about 0.01 mg to about 200 mg per unit dose. In certain embodiments, the pharmaceutical composition is administered at a dose of about 0.01 mg to about 100 mg per unit dose. In certain embodiments, pharmaceutical composition is administered at a dose of about 0.01 mg to about 50 mg per unit dose. In certain embodiments, the pharmaceutical composition is administered at a dose of about 0.01 mg to about 10 mg per unit dose. In certain embodiments, the pharmaceutical composition is administered at a dose of about 0.1 mg to about 10 mg per unit dose.

Pharmaceutical compositions described herein can be prepared by any method known in the art of pharmacology. In general, such preparatory methods include the steps of bringing the composition comprising a compound of Formula (I), (II), (III), (IV), (V), or (VI) into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazelnut, hyssop, isopropyl myristate, jojoba, kukui nut, lavandin, lavender, lemon, Litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present disclosure contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits are useful for preventing a disease (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits are useful for reducing the risk of developing a disease (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits are useful for inhibiting the activity (e.g., aberrant activity, such as increased activity) of HDAC6 in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits and instructions provide for preventing a disease (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits and instructions provide for reducing the risk of developing a disease (e.g., proliferative disease, inflammatory disease, infectious disease, autoimmune disease, heteroimmune disease, neurological disorder, metabolic disease, cystic fibrosis, polycystic kidney disease, pulmonary hypertension, cardiac dysfunction, or disease or disorder mediated by or linked to T-cell dysregulation) in a subject in need thereof. In certain embodiments, the kits and instructions provide for inhibiting the activity (e.g., aberrant activity, such as increased activity) of HDAC6 in a subject or cell. A kit described herein may include one or more additional pharmaceutical agents described herein as a separate composition.

Methods of Treatment

HDAC6 is unique in structure and function among all HDAC paralogs. In particular, it possesses two catalytic (deacetylase) domains and a zinc finger ubiquitin-binding domain. HDAC6 does not deacetylate histones, yet interacts with multiple substrates that affect disease-relevant pathways including microtubule stability, axonal and mitochondrial transport, protein aggregation, and autophagy. For example, HDAC6's direct substrates (e.g., tau, tubulin, and HSP90) engage key mechanisms in Alzheimer's disease. As a result of its unique structure and function, selectively targeting and inhibiting HDAC6 activity may avoid the side effects that are typical of existing FDA-approved HDAC inhibitors that result in clinical toxicity due to broad inhibition of multiple HDAC paralogs an/or inhibition of HDACs 1 and/or 2 (which has been shown to cause thrombocytopenia, a dose-limiting toxicity of most FDA-approved pan-HDAC inhibitors). Thus, treatment of HDAC6-related diseases with HDAC6-selective inhibitors may be particularly effective.

The present disclosure provides methods for treating HDAC6-related diseases and disorders. In certain embodiments, the application provides a method of treating a proliferative disease. In certain embodiments, the application provides a method of treating cancer. In certain embodiments, the application provides a method of treating a hematological cancer. In certain embodiments, the application provides a method of treating leukemia, T-cell lymphoma, Hodgkin's Disease, non-Hodgkin's lymphoma, or multiple myeloma. In certain embodiments, the application provides a method of treating a cancer comprising a solid tumor. In certain embodiments, the application provides a method of treating glioma, glioblastoma, non-small cell lung cancer, brain tumor, neuroblastoma, bone tumor, soft-tissue sarcoma, head and neck cancer, genitourinary cancer, lung cancer, breast cancer, pancreatic cancer, melanoma, stomach cancer, brain cancer, liver cancer, thyroid cancer, clear cell carcinoma, uterine cancer, or ovarian cancer.

In certain embodiments, the application provides a method of treating an inflammatory disease. In certain embodiments, the application provides a method of treating osteoarthritis, rheumatoid arthritis, lupus, inflammatory bowel disease, Crohn's Disease, ulcerative colitis, anemia, leukocytosis, asthma, chronic obstructive pulmonary disease, appendicitis, bronchitis, bursitis, conjunctivitis, dermatitis, encephalitis, myelitis myocarditis, sinusitis, dermatitis, psoriasis, eczema, or acne.

In certain embodiments, the application provides a method of treating an infectious disease. In certain embodiments, the application provides a method of treating bacterial, fungal, or protozoal infections.

In certain embodiments, the application provides a method of treating an autoimmune disease. In certain embodiments, the application provides a method of treating diabetes, thyroiditis, Graves' disease, Guillain-Barre syndrome, Addison's disease, scleroderma, primary biliary cirrhosis, Reiter's syndrome, psoriasis, chronic fatigue, or endometriosis.

In certain embodiments, the application provides a method of treating a heteroimmune disease. In certain embodiments, the application provides a method of treating graft versus host disease, transplantation, transfusion, anaphylaxis, allergic conjunctivitis, or allergic rhinitis.

In certain embodiments, the application provides a method of treating a neurological disorder. In certain embodiments, the application provides a method of treating a neurodegenerative, neurodevelopmental, neuropsychiatric, or neuropathy disease. In certain embodiments, the application provides a method of treating Fragile-X syndrome, Charcot-Marie-Tooth disease, Alzheimer's disease, Parkinson's diseases, Huntington's disease, multiple sclerosis, amyotrophic lateral sclerosis, Creutzfeldt-Jakob disease, Lewy body dementia, vascular dementia, muscular atrophy, seizure induced memory loss, schizophrenia, Rubinstein Taybi syndrome, Rett Syndrome, attention deficit hyperactivity disorder, dyslexia, bipolar disorder, social, cognitive and learning disorders associated with autism, attention deficit disorder, schizophrenia, major depressive disorder, peripheral neuropathy, diabetic retinopathy, diabetic peripheral neuropathy, chemotherapy-induced peripheral neuropathy, traumatic brain injury (TBI), chronic traumatic encephalopathy (CTE), or a tauopathy. In certain embodiments, the application provides a method of treating primary age-related tauopathy (PART)/neurofibrillary tangle-predominant senile dementia, chronic traumatic encephalopathy, dementia pugilistica, progressive supranuclear palsy, corticobasal degeneration, Pick's disease, frontotemporal dementia and parkinsonism linked to chromosome 17, Lytico-Bodig disease, ganglioglioma, gangliocytoma, meningioangiomatosis, postencephalitic parkinsonism, subacute sclerosing panencephalitis, lead encephalopathy, tuberous sclerosis, lipofuscinosis, Alzheimer's disease, or argyrophilic grain disease. In certain embodiments, the application provides a method of treating Alzheimer's disease.

In certain embodiments, the application provides a method of treating cystic fibrosis. In certain embodiments, the application provides a method of treating polycystic kidney disease. In certain embodiments, the application provides a method of treating pulmonary hypertension. In certain embodiments, the application provides a method of treating cardiac dysfunction.

The present disclosure provides methods of inhibiting the activity of HDAC. In certain embodiments, the application provides a method of inhibiting the activity of HDAC6. In certain embodiments, the application provides a method of inhibiting the activity of HDAC6 in vitro. In certain embodiments, the application provides a method of inhibiting the activity of HDAC6 in vivo. In certain embodiments, the application provides a method of inhibiting the activity of HDAC6 in a cell. In certain embodiments, the application provides a method of inhibiting the activity of HDAC6 in a human cell.

In certain embodiments, the methods comprise administering to a subject in need thereof (e.g., a subject with a neurological disorder) a compound that interacts with HDAC6, for example, a compound that is an inhibitor of HDAC6, a modulator of HDAC6, a binder of HDAC6, or a compound that modifies HDAC6. In certain embodiments, the methods comprise administering a compound of the disclosure (e.g., a compound of Formula (I), (II), (III), (IV), (V), or (VI)), or a pharmaceutically acceptable salt, co-crystal, tautomer, stereoisomer, solvate, hydrate, polymorph, isotopically enriched derivative, or prodrug, or composition thereof, to a subject in need thereof. In some embodiments, the method comprises administering a pharmaceutical composition comprising a compound of the disclosure (e.g., a compound of Formula (I), (II), (III), (IV), (V), or (VI)), or a pharmaceutically acceptable salt, co-crystal, tautomer, stereoisomer, solvate, hydrate, polymorph, isotopically enriched derivative, or prodrug, or composition thereof, to a subject in need thereof.

Examples

In order that the invention described herein may be more fully understood, the following examples are set forth. The examples described in this application are offered to illustrate the compounds, pharmaceutical compositions, and methods provided herein and are not to be construed in any way as limiting their scope.

Synthetic Methods

General details. All oxygen and/or moisture-sensitive reactions were carried out under nitrogen ($N_2$) atmosphere in glassware that had been flame-dried under vacuum (approximately 0.5 mm Hg) and purged with $N_2$ prior to use. All reagents and solvents were purchased from commercial vendors and used as received, or synthesized according to methods already reported. NMR spectra were recorded on a Bruker 300 (300 MHz $^1$H, 75 MHz $^{13}$C) or Varian UNITY INOVA 500 (500 MHz $^1$H, 125 MHz $^{13}$C) spectrometer. Proton and carbon chemical shifts are reported in ppm (δ) referenced to the NMR solvent. Data are reported as follows: chemical shifts, multiplicity (br=broad, s=singlet, d=doublet, t=triplet, q=quartet, m=multiplet; coupling constant(s) in Hz). Unless otherwise indicated, NMR data were collected at 25° C. Flash chromatography was performed using 40-60 μm Silica Gel (60 Å mesh) on a Teledyne Isco Combiflash $R_f$. Tandem Liquid Chromatography/Mass Spectrometry (LC/MS) was performed on a Waters 2795 separations module and 3100 mass detector. Analytical thin layer chromatography (TLC) was performed on EM Reagent 0.25 mm silica gel 60-F plates.

Compounds of Formula (I) were prepared following the synthetic schemes and procedures described in detail below.

8-fluoro-N-hydroxy-2-((1-methylcyclopropyl)methyl)-1,2,3,4-tetrahydroisoquinoline-6-carboxamide (1)

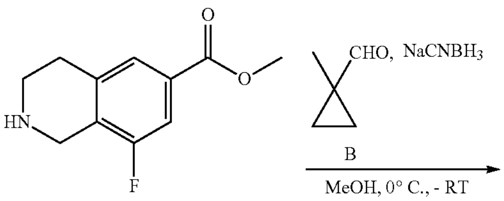

A B

-continued

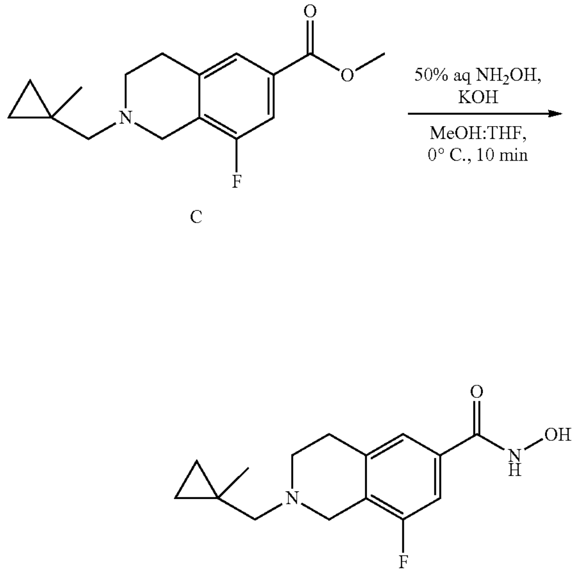

C 1

To a solution of methyl 8-fluoro-1,2,3,4-tetrahydroisoquinoline-6-carboxylate (A, 150 mg, 0.717 mmol. 1 equiv.) in MeOH, 1-methylcyclopropane-1-carbaldehyde (B, 66.3 mg, 0.7894 mmol, 1.1 equiv.) was added and stirred for 15 min and $NaCNBH_3$ (90.11 mg, 1.434 mmol, 2 equiv.) was added. The resulting reaction mixture was stirred at room temperature for 1 hour. After completion of reaction the volatiles were evaporated. The crude material was diluted with dichloromethane (25 ml) and washed with water. The organic layer was dried over sodium sulfate, filtered and concentrated. The crude product was purified by column chromatography to yield methyl 8-fluoro-2-((1-methylcyclopropyl)methyl)-1,2,3,4-tetrahydroisoquinoline-6-carboxylate (C, 98.3 mg, 0.3548 mmol, 50%) as a sticky solid.

To a stirred solution of methyl 8-fluoro-2-((1-methylcyclopropyl)methyl)-1,2,3,4-tetrahydroisoquinoline-6-carboxylate (C, 90 mg, 0.325 mmol, 1 equiv.) in methanol (2 mL) were added 50% aq. $NH_2OH$ (214.4 mg, 6.498 mmol, 20 equiv; 50% aq solution of in $H_2O$) and KOH (35.6 mg, 0.648 mmol, 2 equiv.) at 0° C. The reaction was stirred at 0° C. to room temperature for 10 min then quenched with a saturated solution of $NaHCO_3$ and filtered and washed with n-hexane to obtain compound 1 (0.010 g, 0.0359 mmol, 11%). $^1$H NMR (400 MHz, DMSO-$d_6$) δ 11.23 (bs, 1H), 9.09 (bs, 1H), 7.40 (s, 1H), 7.31 (d, J=10.4 Hz, 1H), 3.57 (s, 2H), 2.88-2.84 (m, 2H), 2.70 (t, J=5.9 Hz, 2H), 2.33 (s, 2H), 1.05 (s, 3H), 0.33 (d, J=10.2 Hz, 4H). MS (ESI): 279 $[M+H]^+$.

The following compounds were prepared in a manner analogous to that used for preparing compound 1. Although compound pairs 8/9, 30/31, 107/108 and 109/110 are designated as the (S) and (R) enantiomers as each enantiomer was prepared and isolated, the absolute stereochemistry of each is unknown.

| Compound | Structure/Name | Characterization |
|---|---|---|
| 2 | 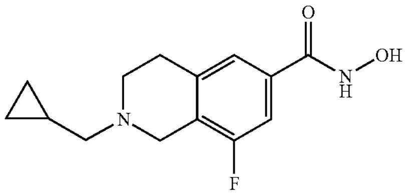 2-(cyclopropylmethyl)-8-fluoro-N-hydroxy-1,2,3,4-tetrahydroisoquinoline-6-carboxamide | $^1$H NMR (400 MHz, DMSO-d6) δ 11.21 (s, 1H), 9.09 (s, 1H), 7.40 (s, 1H), 7.31 (d, J = 10.4 Hz, 1H), 3.63 (s, 2H), 2.86 (t, J = 5.8 Hz, 2H), 2.73 (t, J = 5.8 Hz, 2H), 2.40 (d, J = 6.5 Hz, 2H), 0.51 (dd, J = 5.2, 12.8 Hz, 2H), 0.15 (dd, J = 4.8, 10.0 Hz, 2H). MS (ESI) 265 $[M + H]^+$ |
| 3 | 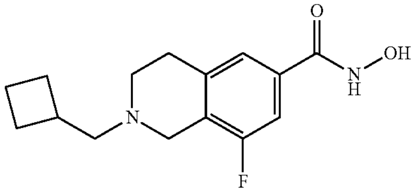 2-(cyclobutylmethyl)-8-fluoro-N-hydroxy-1,2,3,4-tetrahydroisoquinoline-6-carboxamide | $^1$H NMR (400 MHz, DMSO-d6) δ 11.13 (s, 1H), 9.141 (s, 1H), 7.37 (s, 1H), 7.26 (d, J = 10.4 Hz, 1H), 3.5 (s, 1H), 2.54 (s, 2H), 2.62 (t, J = 6.0 Hz, 2H), 2.81 (t, J = 5.6 Hz, 2H), 2.04 - 2.05 (m, 2H), 1.90 - 1.72 (m, 3H), 1.69 - 1.65 (m, 2H). MS (ESI): 279 $[M + H]^+$ |
| 4 | 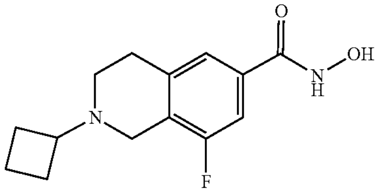 2-cyclobutyl-8-fluoro-N-hydroxy-1,2,3,4-tetrahydroisoquinoline-6-carboxamide | $^1$H NMR (400 MHz, DMSO-d6) δ 8.59 (bs, 2H), 7.40 (s, 1H), 7.31 (d, J = 10.5 Hz, 1H), 3.46 - 3.40 (m, 2H), 2.96 - 2.89 (m, 1H), 2.89 - 2.81 (m, 2H), 2.53 (s, 2H), 2.11 - 2.02 (m, 2H), 1.90 - 1.81 (m, 2H), 1.72 - 1.61 (m, 2H). MS (ESI): 265 $[M + H]^+$ |
| 7 | 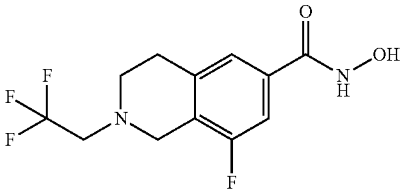 8-fluoro-N-hydroxy-2-(2,2,2-trifluoroethy)-1,2,3,4-tetrahydroisoquinoline-6-carboxamide | 1H NMR (400 MHz, DMSO-d6) δ 11.12 (s, 1H), 9.15 (s, 1H), 7.41 (s, 1H), 7.33 (d, J = 10.6 Hz, 1H), 3.84 (s, 2H), 3.43 (q, J = 10.1 Hz, 2H), 2.93 (t, J = 5.7 Hz, 2H), 2.87 (d, J = 5.8 Hz, 2H). MS (ESI): 291 $[M - H]^-$ |
| 8 | 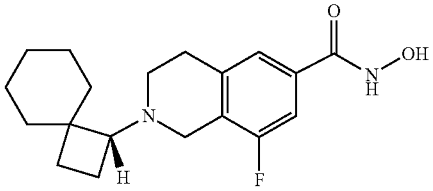 (R)-8-fluoro-N-hydroxy-2-(spiro[3.5]nonan-1-yl)-1,2,3,4-tetrahydroisoquinoline-6-carboxamide | $^1$H NMR (400 MHz, DMSO-d6) δ 11.19 (bs, 1H), 9.01 (bs, 1H), 7.37 (s, 1H), 7.28 (d, J = 10.7 Hz, 1H), 3.48 - 3.22 (m, 2H), 2.802 - 2.70 (m, 3H), 2.60 - 2.25 (m, 2H), 1.99 - 1.92 (m, 1H), 1.75 (t, J = 10.2 Hz, 2H), 1.65 (t, J = 9.9 Hz, 1H), 1.60 - 1.42 (m, 5H), 1.37 - 1.25 (m, 3H), 1.20 - 0.85 (m, 2H). MS (ESI): 333 $[M + H]^+$ Note: absolute stereochemistry is unknown |
| 9 | 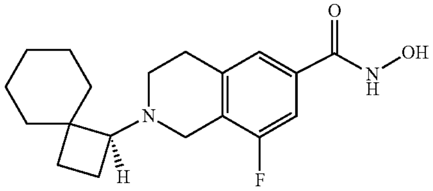 (S)-8-fluoro-N-hydroxy-2-(spiro[3.5]nonan-1-yl)-1,2,3,4-tetrahydroisoquinoline-6-carboxamide | $^1$H NMR (400 MHz, DMSO-d6) δ 11.24 (bs, 1H), 9.10 (s, 1H), 7.38 (s, 1H), 7.28 (d, J = 10.6 Hz, 1H), 3.47 (d, J = 15.9 Hz, 1H), 3.24 (d, J = 16.0 Hz, 1H), 2.85 - 2.75 (m, 3H), 2.61 - 2.57 (m, 1H), 2.42 - 2.36 (m, 1H), 1.94 (t, J = 8.7 Hz, 1H), 1.75 (t, J = 10.1 Hz, 2H), 1.65 (t, J = 9.9 Hz, 1H), 1.59 - 1.40 (m, 5H), 1.31 (dt, J = 18.0, 9.7 Hz, 3H), 1.19 - 1.05 (m, 2H). MS (ESI): 333 $[M + H]^+$ Note: absolute stereochemistry is unknown |

-continued

| Compound | Structure/Name | Characterization |
|---|---|---|
| 13 | 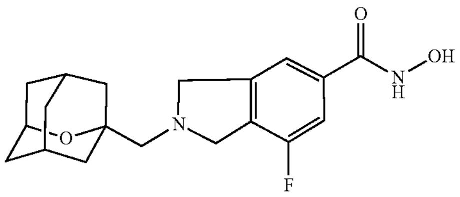 2-(((1r,3s,5R,7S)-2-oxaadamantan-1-yl)methyl)-7-fluoro-N-hydroxyisoindoline-5-carboxamide | MS (ESI): 347 $[M + H]^+$ |
| 14 | 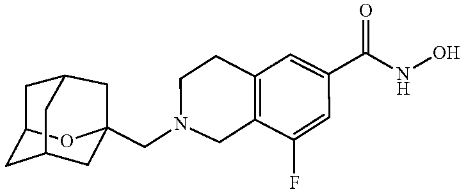 2-(((1r,3s,5R,7S)-2-oxaadamantan-1-yl)methyl)-8-fluoro-N-hydroxy-1,2,3,4-tetrahydroisoquinoline-6-carboxamide | $^1$H NMR (400 MHz, DMSO-$d_6$) δ 7.29 (s, 1H), 7.16 (d, J = 11.3 Hz, 1H), 3.96 (s, 1H), 3.60 (s, 2H), 2.75 (s, 4H), 2.34 (s, 2H), 2.09 (s, 2H), 1.80 (d, J = 11.4 Hz, 6H), 1.55 (t, J = 14.9 Hz, 4H). MS (ESI): 361 $[M + H]^+$ |
| 15 | 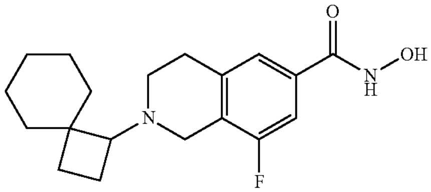 8-fluoro-N-hydroxy-2-(spiro[3.5]nonan-1-yl)-1,2,3,4-tetrahydroisoquinoline-6-carboxamide | $^1$H NMR (400 MHz, DMSO-$d_6$) δ 1.12 (d, J = 9.5 Hz, 2H), 1.26 - 1.35 (m, 3H), 1.54 (t, J = 19.9 Hz, 5H), 1.64 (d, J = 9.3 Hz, 1H), 1.75 (t, J = 9.8 Hz, 2H), 1.95 (d, J = 8.7 Hz, 1H), 2.39 (s, 1H), 2.59 (d, J = 11.9 Hz, 1H), 2.81 (d, J = 13.8 Hz, 3H), 3.25 (d, J = 16.3 Hz, 1H), 3.48 (d, J = 16.0 Hz, 1H), 7.30 (d, J = 10.4 Hz, 1H), 7.39 (s, 1H), 9.14 (bs, 1H), 10.88 (bs, 1H). MS (ESI): 332 $[M + H]^+$ |
| 16 | 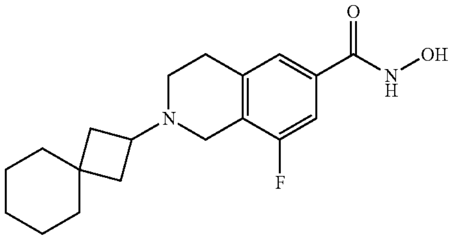 8-fluoro-N-hydroxy-2-(spiro[3.5]nonan-2-yl)-1,2,3,4-tetrahydroisoquinoline-6-carboxamide | $^1$H NMR (400 MHz, DMSO-d6) δ 11.23 (s, 1H), 9.09 (s, 1H), 7.40 (s, 1H), 7.31 (d, J = 10.4 Hz, 1H), 3.41 (s, 2H), 2.84 (q , J = 6.1, 4.8 Hz, 3H), 1.97 (t, J = 9.5 Hz, 2H), 1.53 (dd, J = 11.3, 7.9 Hz, 2H), 1.49 - 1.27 (m, 9H). MS (ESI): 332$[M + H]^+$ |
| 19 | 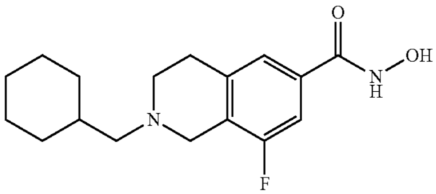 2-(cyclohexylmethyl)-8-fluoro-N-hydroxy-1,2,3,4-tetrahydroisoquinoline-6-carboxamide | $^1$H NMR (400 MHz, DMSO-$d_6$) δ 7.39 (s, 1H), 7.30 (d, J = 10.5 Hz, 1H), 3.51 (s, 2H), 2.84 (t, J = 5.7 Hz, 2H), 2.62 (t, J = 5.8 Hz, 2H), 2.29 (d, J = 7.2 Hz, 2H), 1.75 (d, J = 12.7 Hz, 2H), 1.64 (t, J = 13.3 Hz, 4H), 1.18 (dt, J = 24.9, 12.1 Hz, 3H), 0.86 (q, J = 11.8 Hz, 2H). MS (ESI): 307 $[M + H]^+$ |

-continued

| Compound | Structure/Name | Characterization |
|---|---|---|
| 20 | 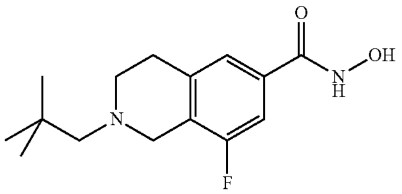 8-fluoro-N-hydroxy-2-neopentyl-1,2,3,4-tetrahydroisoquinoline-6-carboxamide | $^1$H NMR (400 MHz, DMSO-d6) δ 7.40 (s, 1H), 7.30 (d, J = 10.4 Hz, 1H), 3.67 (s, 2H), 2.84 (d, J = 5.7 Hz, 2H), 2.75 (t, J = 5.8 Hz, 2H), 2.27 (s, 2H), 0.88 (s, 9H). MS (ESI): 281 [M + H]$^+$ |
| 21 | 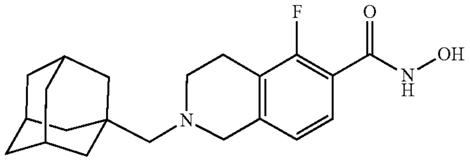 2-(((3r,5r,7r)-adamantan-1-yl)methyl)-5-fluoro-N-hydroxy-1,2,3,4-tetrahydroisoquinoline-6-carboxamide | $^1$H NMR (400 MHz, DMSO-d6) δ 9.24 (bs, 1H), 7.30 (s, 1H), 6.87 (d, J = 8.0 Hz, 1H), 3.59 (s, 2H), 2.78 (s, 2H), 2.69 (d, J = 7.2 Hz, 2H), 2.16 (s, 2H), 1.92 (s, 3H), 1.62 (q, J = 12.5, 12.0 Hz, 6H), 1.50 (s, 6H). MS (ESI): 359 [M + H]$^+$ |
| 24 | 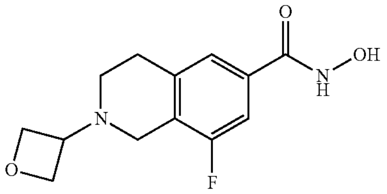 8-fluoro-N-hydroxy-2-(oxetan-3-yl)-1,2,3,4-tetrahydroisoquinoline-6-carboxamide | $^1$H NMR (400 MHz, DMSO-d6) δ 10.83 (s, 1H), 9.35 (s, 1H), 7.42 (s, 1H), 7.33 (d, J = 10.4 Hz, 1H), 4.62 (t, J = 6.5 Hz, 2H), 4.53 (t, J = 6.1 Hz, 2H), 3.66 (p, J = 6.3 Hz, 1H), 3.47 (s, 2H), 2.87 (t, J = 5.9 Hz, 2H), 2.55 (t, J = 5.8 Hz, 2H). MS (ESI): 267 [M + H]$^+$ |
| 25 | 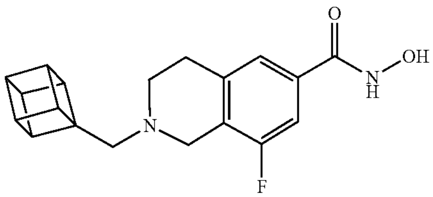 2-(cuban-1-ylmethyl)-8-fluoro-N-hydroxy-1,2,3,4-tetrahydroisoquinoline-6-carboxamide | $^1$H NMR (400 MHz, DMSO-d6) δ 9.01 (bs, 1H), 7.36 (s, 1H), 7.25 (d, J = 10.8 Hz, 1H), 4.03 (bs, 1H), 3.90 - 3.93 (m, 2H), 3.85 - 3.88 (m, 2H), 3.50 (s, 2H), 2.80 - 2.82 (m, 2H), 2.73 (s, 2H), 2.65 - 2.61 (m, 2H). MS (ESI): 327 [M + H]$^+$ |
| 26 | 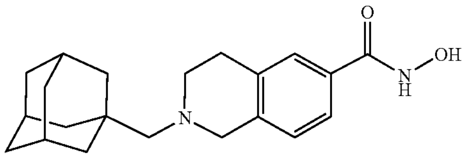 2(((3r,5r,7r)-adamantan-1-yl)methyl)-N-hydroxy-1,2,3,4-tetrahydroisoquinoline-6-carboxamide | $^1$H NMR (400 MHz, DMSO-d6) δ 11.11 (s, 1H), 8.96 (s, 1H), 7.55 - 7.44 (m, 2H), 7.07 (d, J = 7.8 Hz, 1H), 3.64 (s, 2H), 2.85 - 2.76 (m, 2H), 2.73 - 2.70 (m, 2H), 2.11 (s, 2H), 1.92 (s, 3H), 1.68 - 1.56 (m, 6H), 1.50 (s, 6H). MS (ESI): 341 [M + H]$^+$ |
| 27 | 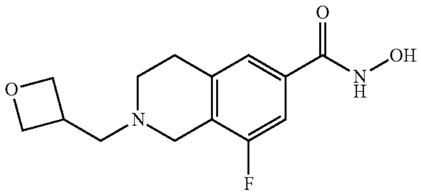 8-fluoro-N-hydroxy-2-(oxetan-3-ylmethyl)-1,2,3,4-tetrahydroisoquinoline-6-carboxamide | $^1$H NMR (400 MHz, DMSO-d6) δ 11.19 (s, 1H), 9.10 (s, 1H), 7.39 (s, 1H), 7.31 (d, J = 10.4 Hz, 1H), 4.66 (dd, J = 7.8, 5.9 Hz, 2H), 4.29 (t, J = 6.0 Hz, 2H), 3.52 (s, 2H), 3.32 - 3.26 (m, 1H), 2.82 (t, J = 6.0 Hz, 4H), 2.63 (t, J = 5.8 Hz, 2H). MS (ESI): 281 [M + H]$^+$ |

-continued

| Compound | Structure/Name | Characterization |
|---|---|---|
| 28 | 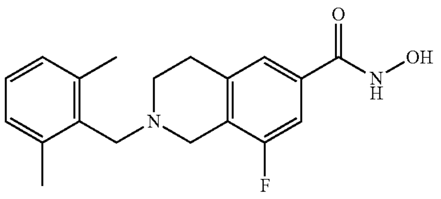 2-(2,6-dimethylbenzyl)-8-fluoro-N-hydroxy-1,2,3,4-tetrahydroisoquinoline-6-carboxamide | $^1$H NMR (400 MHz, DMSO-d6) δ 9.38 (bs, 1H), 7.38 (s, 1H), 7.29 (d, J = 10.6 Hz, 1H), 7.07 - 7.00 (m, 3H), 3.67 (s, 2H), 3.59 (s, 2H), 2.78 (t, J = 5.7 Hz, 2H), 2.68 (t, J = 5.6 Hz, 2H), 2.35 (s, 6H). MS (ESI): 329 $[M + H]^+$ |
| 30 | 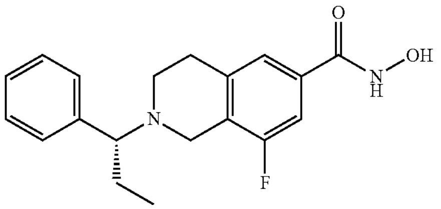 (R)-8-fluoro-N-hydroxy-2-(1-phenylpropyl)-1,2,3,4-tetrahydroisoquinoline-6-carboxamide | $^1$H NMR (400 MHz, DMSO-d6) δ 7.40 - 7.23 (m, 6H), 3.64 (d, J = 16.1 Hz, 1H), 3.53 - 3.43 (m, 2H), 2.80 (t, J = 5.7 Hz, 3H), 2.76 - 2.70 (m, 1H), 1.99 (dt, J = 13.5, 6.7 Hz, 1H), 1.78 (dt, J = 13.6, 7.4 Hz, 1H), 0.74 (t, J = 7.3 Hz, 3H). MS (ESI): 329 $[M + H]^+$ Note: absolute stereochemistry is unknown |
| 31 | 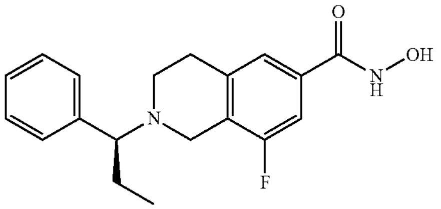 (S)-8-fluoro-N-hydroxy-2-(1-phenylpropyl)-1,2,3,4-tetrahydroisoquinoline-6-carboxamide | $^1$H NMR (400 MHz, DMSO-d6) δ 11.16 (s, 1H), 9.56 - 8.81 (s, 1H), 7.40 - 7.22 (m, 6H), 3.64 (d, J = 16.2 Hz, 1H), 3.54 - 3.42 (m, 2H), 2.77 - 2.71 (m, 4H), 1.99 (dt, J = 13.4, 6.6 Hz, 1H), 1.77 (dd, J = 13.8, 7.2 Hz, 1H), 0.74 (t, J = 7.3 Hz, 3H). MS (ESI): 329 $[M + H]^+$ Note: absolute stereochemistry is unknown |
| 32 | 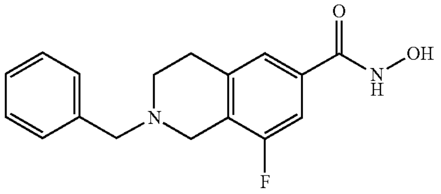 2-benzyl-8-fluoro-N-hydroxy-1,2,3,4-tetrahydroisoquinoline-6-carboxamide | $^1$H NMR (400 MHz, DMSO-d6) δ 11.22 (bs, 1H), 9.10 (bs, 1H), 7.41 (s, 1H), 7.38 - 7.26 (m, 6H), 3.70 (s, 2H), 3.55 (s, 2H), 2.86 (t, J = 5.8 Hz, 2H), 2.69 (t, J = 5.9 Hz, 2H). MS (ESI): 301 $[M + H]^+$ |
| 33 | 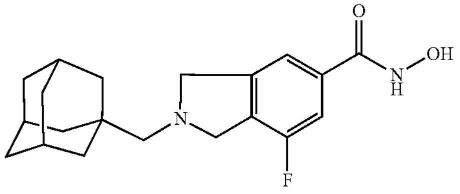 2-(((3r,5r,7r)-adamantan-1-yl)methyl)-7-fluoro-N-hydroxyisoindoline-5-carboxamide | $^1$H NMR (400 MHz, DMSO-d6) δ 7.46 (s, 1H), 7.37 (d, J = 9.8 Hz, 1H), 4.04 (d, J = 5.1 Hz, 4H), 2.41 (s, 2H), 1.94 (s, 3H), 1.64 (q, J = 12.2 Hz, 6H), 1.53 (s, 6H). MS (ESI): 345 $[M + H]^+$ |

-continued

| Compound | Structure/Name | Characterization |
|---|---|---|
| 34 | 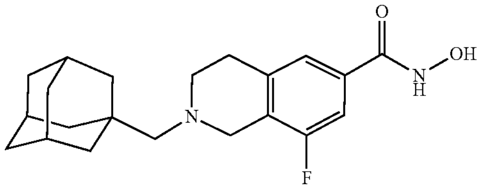 2-(((3r,5r,7r)-adamantan-1-yl)methyl)-8-fluoro-N-hydroxy-1,2,3,4-tetrahydroisoquinoline-6-carboxamide | $^{1}$H NMR (400 MHz, DMSO-d6) δ 9.26 (bs, 1H), 7.33 (s, 1H), 7.22 (d, J = 11.1 Hz, 1H), 3.59 (s, 2H), 2.79 (s, 2H), 2.69 (bs, 2H), 2.14 (bs, 2H), 1.92 (bs, 3H), 1.68 - 1.45 (m, 12H). MS(ESI): 359 [M + H]$^+$ |
| 35 | 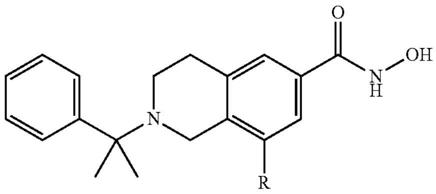 8-fluoro-N-hydroxy-2-(2-phenylpropan-2-yl)-1,2,3,4-tetrahydroisoquinoline-6-carboxamide | $^{1}$H NMR (400 MHz, DMSO-d6) δ 11.27 (bs,1H), 9.08 (s, 1H), 7.53 (d, J = 5.6 Hz, 1H), 7.40 (s, 1H), 7.32 - 7.22 (m, 3H), 3.71 (s, 2H), 2.79 (s, 2H), 1.41 (s, 6H). MS (ESI): 329 [M + H]$^+$ |
| 107 | 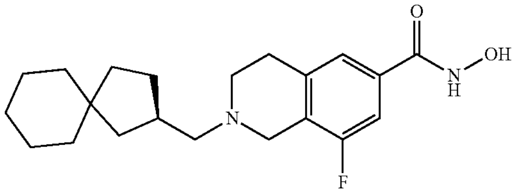 (R)-8-fluoro-N-hydroxy-2-(spiro[4.5]decan-2-ylmethyl)-1,2,3,4-tetrahydroisoquinoline-6-carboxamide | MS (ESI): 361 [M + H]$^+$ Note: absolute stereochemistry is unknown |
| 108 | 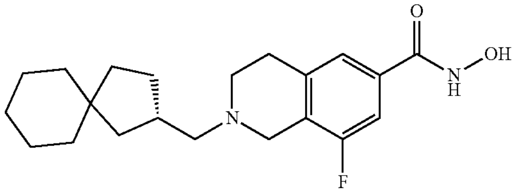 (S)-8-fluoro-N-hydroxy-2-(spiro[4.5]decan-2-ylmethyl)-1,2,3,4-tetrahydroisoquinoline-6-carboxamide | MS (ESI): 361 [M + H]$^+$ Note: absolute stereochemistry is unknown |
| 109 | 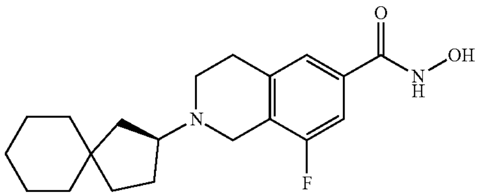 (S)-8-fluoro-N-hydroxy-2-(spiro[4.5]decan-2-yl)-1,2,3,4-tetrahydroisoquinoline-6-carboxamide | MS (ESI): 347 [M + H]$^+$ Note: absolute stereochemistry is unknown |

-continued

| Compound | Structure/Name | Characterization |
|---|---|---|
| 110 | 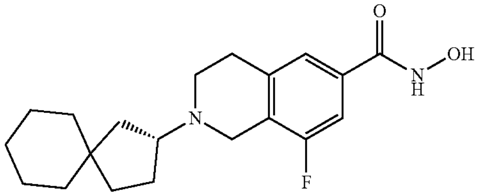 (R)-8-fluoro-N-hydroxy-2-(spiro[4.5]decan-2-yl)-1,2,3,4-tetrahydroisoquinoline-6-carboxamide | MS (ESI): 347 $[M + H]^+$ Note: absolute stereo chemistry is unknown. |
| 111 | 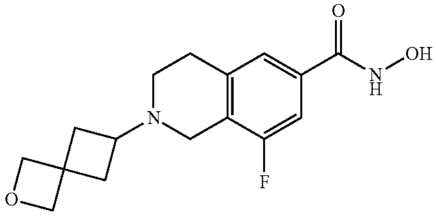 8-fluoro-N-hydroxy-2-(2-oxaspiro[3.3]heptan-6-yl)-1,2,3,4-tetrahydroisoquinoline-6-carboxamide | $^1H$ NMR (400 MHz, Methanol-d4) δ 7.36 (s, 1H), 7.26 (d, J = 10.2 Hz, 1H), 4.74 (s, 2H), 4.60 (s, 2H), 3.53 (s, 2H), 2.93 (t, J = 5.9 Hz, 2H), 2.81 (q, J = 7.8 Hz, 1H), 2.63 (t, J = 6.0 Hz, 2H), 2.53 (ddd, J = 9.9, 7.0, 3.1 Hz, 2H), 2.13 (td, J = 8.8, 3.0 Hz, 2H). MS (ESI): 307 $[M + H]^+$ |
| 112 | 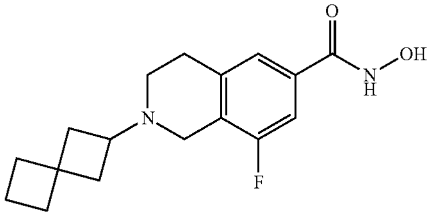 8-fluoro-N-hydroxy-2-(spiro[3.3]heptan-2-yl)-1,2,3,4-tetrahydroisoquinoline-6-carboxamide | $^1H$ NMR (400 MHz, Methanol-d4) δ 7.38 (s, 1H), 7.28 (d, J = 10.2 Hz, 1H), 3.54 (s, 2H), 2.96 (t, J = 6.0 Hz, 2H), 2.86 (q, J = 7.9 Hz, 1H), 2.65 (t, J = 5.9 Hz, 2H), 2.30 (s, 2H), 2.10 (t, J = 7.3 Hz, 2H), 2.00 - 1.84 (m, 6H). MS (ESI): 305 $[M + H]^+$ |

Compounds of Formula (III) and (IV) were prepared following the synthetic schemes and procedures described in detail below.

4-((2-Azaspiro[4.5]decan-2-yl)methyl)-3-fluoro-N-hydroxybenzamide (75)

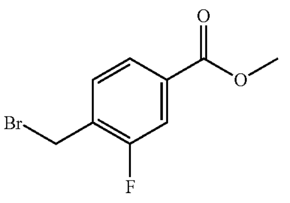

D

+

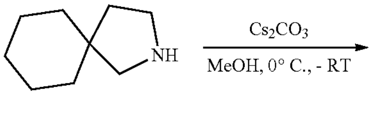

-continued

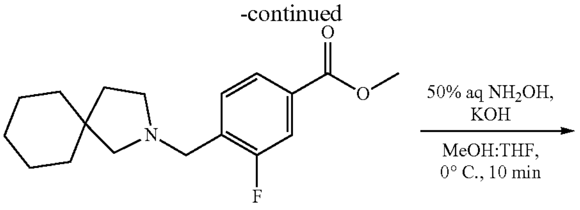

E

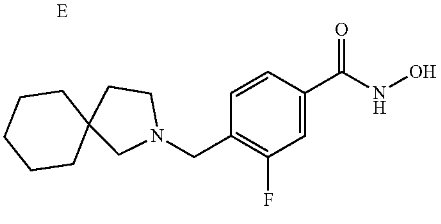

75

To a stirred solution of methyl 4-(bromomethyl)-3-fluorobenzoate (D, 150 mg, 0.6098 mmol, 1 equv) in acetonitrile (5 mL) was added $Cs_2CO_3$ (397 mg, 1.2196 mmol, 2.0 equv) and 2-azaspiro[4.5]decane (84 mg, 0.6098 mmol, 1 equiv) at room temperature. The reaction was stirred at room temperature for 2 h, then quenched with water (10 mL) and extracted with ethyl acetate (10 mL×3). The combined organic phases were washed with brine (10 mL), dried over anhydrous sodium sulphate, filtered and concentrated in vacuo. The residue was purified by a flash silica gel column chromatography. The product was eluted at 5% EtOAc in hexane to give 4-((2-azaspiro[4.5]decan-2-yl)methyl)-3-fluorobenzoate (E) as a colorless oil (110 mg, 0.3604 mmol, 59%). $^1$H NMR (400 MHz, $CDCl_3$) δ 7.81 (dd, J=8.0, 1.7 Hz, 1H), 7.69 (dd, J=10.4, 1.7 Hz, 1H), 7.55 (s, 1H), 3.93 (s, 3H), 3.71 (s, 2H), 2.62 (s, 2H), 2.39 (s, 2H), 1.41 (d, J=18.8 Hz, 12H), 1.27 (t, J=3.5 Hz, 1H). MS (ESI): 305 $[M+H]^+$ To a stirred solution of methyl 4-((2-azaspiro[4.5]decan-2-yl)methyl)-3-fluorobenzoate (E, 110 mg, 0.3604 mmol, 1.0 equiv.) in methanol (1 mL) were added $NH_2OH$ (50% aq.) (0.4 mL, 7.2 mmol, 20.0 equiv) and KOH (40 mg, 0.72 mmol, 2.0 equiv) at 0° C. The reaction was stirred at 0° C. for 10 min then quenched with a saturated solution of $NaHCO_3$ (2 mL). A white compound was precipitated, filtered and washed with n-hexane to obtain the title compound (75) as an off-white solid (55 mg, 0.1795 mmol, 50%). $^1$H NMR (400 MHz, DMSO-d6) δ 11.17 (s, 1H), 9.17 (s, 1H), 7.56 (d, J=7.8 Hz, 1H), 7.52-7.39 (m, 2H), 3.59 (s, 2H), 2.30 (s, 2H), 1.50 (t, J=6.8 Hz, 2H), 1.34 (d, J=13.5 Hz, 10H). MS (ESI): 306.38 $[M+H]^+$ The following compounds were prepared in a manner analogous to that used for preparing compound 75. Although compound pairs 48/49 and 172/173 are designated as the (S) and (R) enantiomers as each enantiomer was prepared and isolated, the absolute stereochemistry of each is unknown.

| Compound | Structure/Name | Characterization |
|---|---|---|
| 45 | 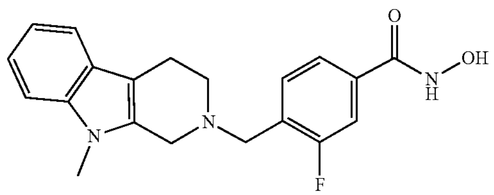 3-fluoro-N-hydroxy-4-((9-methyl-1,3,4,9-tetrahydro-2H-pyrido[3,4-b]indol-2-yl)methyl)benzamide | $^1$H NMR (400 MHz, DMSO-d6) δ 10.40 - 9.19 (m, 1H), 7.61 (d, J = 7.9 Hz, 1H), 7.57 - 7.44 (m, 2H), 7.37 (t, J = 7.3 Hz, 2H), 7.07 (t, J = 7.6 Hz, 1H), 6.97 (t, J = 7.4 Hz, 1H), 3.83 (s, 2H), 3.71 (s, 2H), 3.56 (bs, 3H), 2.82 - 2.75 (m, 2H), 2.75 - 2.63 (m, 2H). MS (ESI): 354 $[M + H]^+$ |
| 46 | 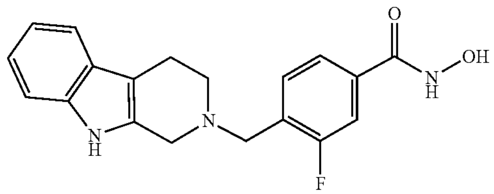 3-fluoro-N-hydroxy-4-((1,3,4,9-tetrahydro-2H-pyrido[3,4-b]indol-2-yl)methyl)benzamide | $^1$H NMR (400 MHz, DMSO-d6) δ 10.68 (s, 1H), 9.03 (bs, 1H), 7.55 (d, J = 7.7 Hz, 1H), 7.49 - 7.31 (m, 3H), 7.24 (d, J = 7.9 Hz, 1H), 6.99 (t, J = 7.5 Hz, 1H), 6.92 (t, J = 7.3 Hz, 1H), 3.77 (s, 2H), 3.59 (s, 2H), 2.82 (t, J = 5.6 Hz, 2H), 2.69 (t, J = 5.8 Hz, 2H). MS(ESI): 340 $[M + H]^+$ |
| 47 | 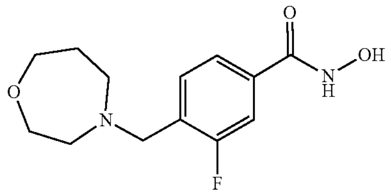 4-((1,4-oxazepan-4-yl)methyl)-3-fluoro-N-hydroxybenzamide | $^1$H NMR (400 MHz, DMSO-d6) δ 11.28 (bs, 1H), 9.16 (bs, 1H), 7.60 - 7.47 (m, 3H), 3.62 - 3.55 (m, 6H), 2.62 (q, J = 5.2, 4.3 Hz, 4H), 1.80 (p, J = 5.9 Hz, 2H). MS(ESI): 269 $[M + H]^+$ |
| 48 | 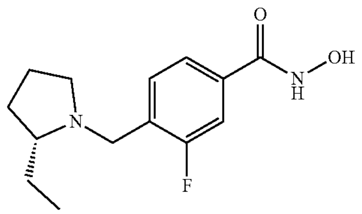 (R)-4-((2-ethylpyrrolidin-1-yl)methyl)-3-fluoro-N-hydroxybenzamide | $^1$H NMR (400 MHz, DMSO-d6) δ 11.28 (bs, 1H), 9.14 (bs, 1H), 7.56 (dd, J = 7.9, 1.7 Hz, 1H), 7.52 - 7.40 (m, 2H), 3.94 (d, J = 13.7 Hz, 1H), 3.30 (d, J = 13.6 Hz, 1H), 2.78 (ddd, J = 9.5, 6.8, 3.3 Hz, 1H), 2.31 (qd, J = 8.0, 3.2 Hz, 1H), 2.09 (q, J = 8.7 Hz, 1H), 1.85 (dq, J = 12.2, 7.8 Hz, 1H), 1.67 (dtd, J = 14.5, 7.3, 3.1 Hz, 1H), 1.58 (tt, J = 9.3, 7.1 Hz, 2H), 1.39 (dq, J = 15.2, 8.9, 8.3 Hz, 1H), 1.30 - 1.20 (m, 1H), 0.85 (t, J = 7.4 Hz, 3H). MS(ESI): 267 $[M + H]^+$ Note: absolute stereochemistry is unknown |

-continued

| Compound | Structure/Name | Characterization |
|---|---|---|
| 49 | 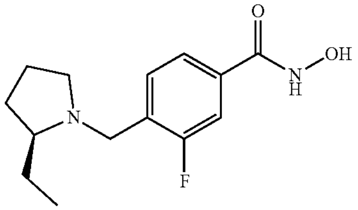 (S)-4-((2-ethylpyrrolidin-1-yl)methyl)-3-fluoro-N-hydroxybenzamide | $^1$H NMR (400 MHz, DMSO-d6) δ 9.14 (bs, 1H), 7.57 (d, J = 7.9 Hz, 1H), 7.53 - 7.40 (m, 2H), 3.95 (d, J = 13.7 Hz, 1H), 3.29 (s, 1H), 2.78 (td, J = 7.8, 6.3, 3.4 Hz, 1H), 2.32 (qd, J = 8.1, 3.2 Hz, 1H), 2.10 (q, J = 8.7 Hz, 1H), 1.86 (dq, J = 12.0, 7.9 Hz, 1H), 1.68 (ddd, J = 13.4, 7.4, 3.2 Hz, 1H), 1.64 - 1.51 (m, 2H), 1.39 (q, J = 7.1, 6.4 Hz, 1H), 1.32 - 1.20 (m, 1H), 0.85 (t, J = 7.4 Hz, 3H). MS(ESI): 267[M + H]$^+$ Note: absolute stereochemistry is unknown |
| 50 | 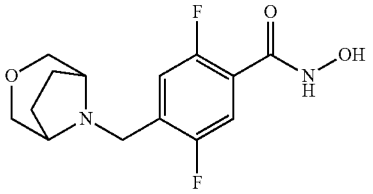 4-((3-oxa-8-azabicyclo[3.2.1]octan-8-yl)methyl)-2,5-difluoro-N-hydroxybenzamide | $^1$H NMR (400 MHz, DMSO-d6) δ 10.74 (bs, 1H), 9.35 (bs, 1H), 7.37 (ddd, J = 32.7, 10.1, 5.6 Hz, 2H), 3.55 (d, J = 10.2 Hz, 2H), 3.50 - 3.38 (m, 4H), 3.00 (d, J = 4.3 Hz, 2H), 1.95 (dd, J = 8.7, 4.2 Hz, 2H), 1.77 (t, J = 6.5 Hz, 2H). MS (ESI): 299 [M + H]$^+$ |
| 51 | 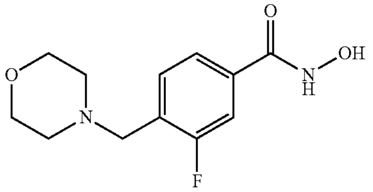 3-fluoro-N-hydroxy-4-(morpholinomethyl)benzamide | $^1$H NMR (400 MHz, DMSO-d6) δ 11.20 (bs, 1H), 9.22 (bs, 1H), 7.58 (dd, J = 7.9, 1.6 Hz, 1H), 7.55 - 7.44 (m, 2H), 3.58 - 3.52 (m, 6H), 2.37 (t, J = 4.5 Hz, 4H). MS(ESI): 255 [M + H]$^+$ |
| 52 | 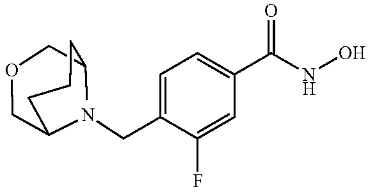 4-((3-oxa-9-azabicyclo[3.3.1]nonan-9-yl)methyl)-3-fluoro-N-hydroxybenzamide | $^1$H NMR (400 MHz, DMSO-d6) δ 8.80 (bs, 1H), 7.56 (s, 2H), 7.48 (d, J = 10.9 Hz, 1H), 3.92 (s, 2H), 3.83 (dt, J = 10.9, 2.4 Hz, 2H), 3.70 (d, J = 10.8 Hz, 2H), 2.21 - 2.01 (m, 2H), 2.09 - 2.01 (m, 3H), 1.76 - 1.47 (m, 4H). MS(ESI): 295 [M + H]$^+$ |
| 53 | 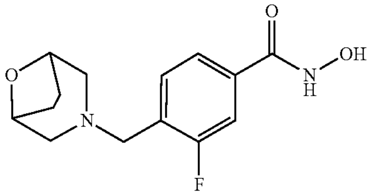 4-((8-oxa-3-azabicyclo+8 3.2.1+9 octan-3-yl)methyl)-3-fluoro-N-hydroxybenzamide | $^1$H NMR (400 MHz, DMSO-d6) δ 9.48 (bs, 1H), 7.61 - 7.55 (m, 1H), 7.52 - 7.45 (m, 2H), 4.19 (d, J = 4.6 Hz, 2H), 3.52 (s, 2H), 2.23 (d, J = 10.4 Hz, 2H), 1.83 (t, J = 6.0 Hz, 2H), 1.71 (d, J = 5.1 Hz, 2H). MS (ESI): 279 [M - H]$^-$ |
| 54 | 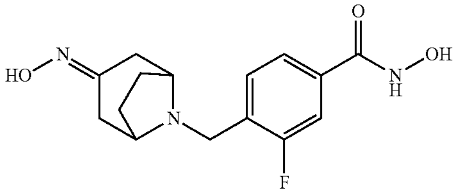 3-fluoro-N-hydroxy-4-((3-(hydroxyimino)-8-azabicyclo[3.2.1]octan-8-yl)methyl)benzamide | $^1$H NMR (400 MHz, DMSO-d6) δ 10.34 (s, 1H), 9.55 (s, 2H), 7.72 - 7.53 (m, 2H), 7.50 (d, J = 11.0 Hz, 1H), 3.66 (s, 2H), 3.27 (d, J = 18.2 Hz, 2H), 2.85 (d, J = 15.0 Hz, 1H), 2.48 - 2.39 (m, 2H), 2.14 - 1.88 (m, 4H), 1.47 (t, J = 9.2 Hz, 1H), 1.34 (t, J = 9.2 Hz, 1H). MS (ESI): 306 [M - H]$^-$ |

-continued

| Compound | Structure/Name | Characterization |
| --- | --- | --- |
| 56 | 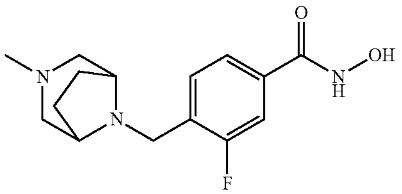 3-fluoro-N-hydroxy-4-((3-methyl-3,8-diazabicyclo[3.2.1]octan-8-yl)methyl)benzamide | $^1H$ NMR (400 MHz, DMSO-d6) δ 11.23 (s, 1H), 9.15 (s, 1H), 7.71 – 7.53 (m, 2H), 7.48 (d, J = 11.0 Hz, 1H), 3.51 (s, 2H), 3.05 (s, 2H), 2.15 (s, 1H), 2.12 (d, J = 5.2 Hz, 4H), 1.88 (dd, J = 8.2, 4.1 Hz, 2H), 1.71 (t, J = 6.2 Hz, 2H). MS (ESI): 292 $[M - H]^-$ |
| 57 | 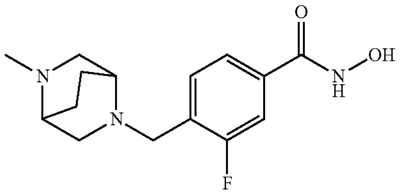 3-fluoro-N-hydroxy-4-((5-methyl-2,5-diazabicyclo[2.2.2]octan-2-yl)methyl)benzamide | 1H NMR (400 MHz, DMSO-d6) δ 7.53 (d, J = 7.8 Hz, 1H), 7.41 (t, J = 8.3 Hz, 2H), 3.75 – 3.63 (m, 2H), 2.89 (t, J = 10.1 Hz, 2H), 2.62 (d, J = 10.1 Hz, 2H), 2.43 (s, 1H), 2.26 (s, 3H), 1.81 (d, J = 11.0 Hz, 2H), 1.65 (s, 1H), 1.52 (h, J = 7.3, 6.5 Hz, 2H). MS (ESI): 294 $[M + H]^+$ |
| 58 | 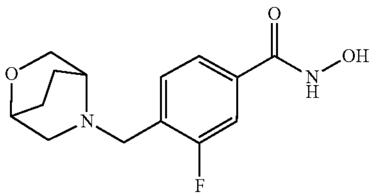 4-((2-oxa-5-azabicyclo[2.2.2]octan-5-yl)methyl)-3-fluoro-N-hydroxybenzamide | $^1H$ NMR (400 MHz, DMSO-d6) δ 11.28 (s, 1H), 9.13 (s, 1H), 7.61 – 7.45 (m, 3H), 4.18 – 4.11 (m, 1H), 3.84 – 3.73 (m, 2H), 3.71 (dd, J = 8.9, 1.7 Hz, 1H), 3.66 (s, 1H), 2.93 (dt, J = 10.6, 2.8 Hz, 1H), 2.85 – 2.77 (m, 1H), 2.61 (s, 1H), 2.00 (d, J = 14.6 Hz, 1H), 1.86 (d, J = 12.6 Hz, 1H), 1.71 – 1.60 (m, 2H). MS(ESI): 281 $[M + H]^+$ |
| 59 | 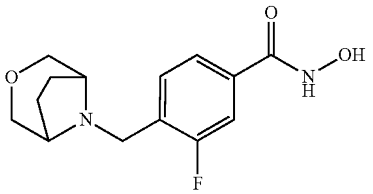 4-((3-oxa-8-azabicyclo[3.2.1]octan-8-yl)methyl)-3-fluoro-N-hydroxybenzamide | $^1H$ NMR (400 MHz, DMSO-d6) δ 8.96 (s, 2H), 7.61 (dt, J = 16.3, 7.8 Hz, 2H), 7.49 (d, J = 10.9 Hz, 1H), 3.53 (d, J = 10.2 Hz, 2H), 3.47 (s, 2H), 3.41 (dd, J = 10.4, 2.0 Hz, 2H), 3.04 – 2.91 (m, 2H), 1.96 (dd, J = 8.6, 4.3 Hz, 2H), 1.77 (t, J = 6.6 Hz, 2H). MS(ESI): 279 $[M - H]^-$ |
| 60 | 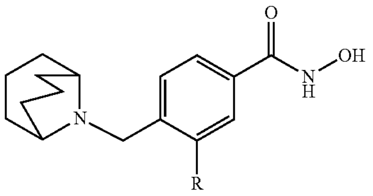 4-((9-azabicyclo[3.3.1]nonan-9-yl)methyl)-3-fluoro-N-hydroxybenzamide | $^1H$ NMR (400 MHz, DMSO-d6) δ 11.21 (bs, 1H), 9.13 (bs, 1H), 7.63 – 7.44 (m, 3H), 3.86 (s, 2H), 2.69 (bs, 2H), 1.96 (dd, J = 7.6, 4.9 Hz, 6H), 1.61 (d, J = 13.2 Hz, 2H), 1.45 (d, J = 8.1 Hz, 4H). MS(ESI): 293 $[M + H]^+$ |
| 61 | 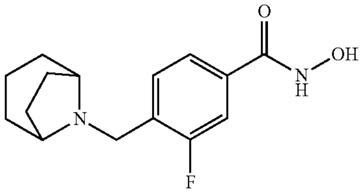 4-((8-azabicyclo[3.2.1]octan-8-yl)methyl)-3-fluoro-N-hydroxybenzamide | $^1H$ NMR (400 MHz, DMSO-d6) δ 11.15 (s, 1H), 9.21 (s, 1H), 7.58 (s, 2H), 7.47 (d, J = 11.0 Hz, 1H), 3.50 (s, 2H), 3.16 – 2.99 (m, 2H), 2.05 – 1.87 (m, 2H), 1.70 – 1.58 (m, 2H), 1.54 (dd, J = 14.9, 8.1 Hz, 2H), 1.39 (q, J = 6.7, 6.0 Hz, 1H), 1.34 – 1.21 (m, 2H). MS(ESI): 279 $[M + H]^+$ |

-continued

| Compound | Structure/Name | Characterization |
| --- | --- | --- |
| 62 | 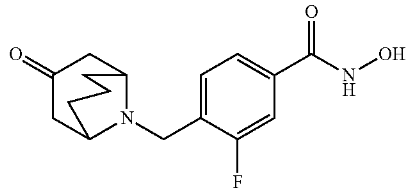 3-fluoro-N-hydroxy-4-((3-oxo-9-azabicyclo[3.3.1]nonan-9-yl)methypbenzamide | MS(ESI): 307 [M + H]$^+$ |
| 63 | 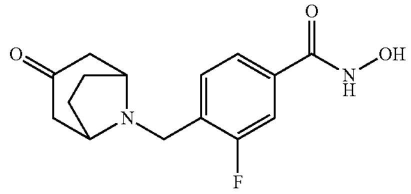 3-fluoro-N-hydroxy-4-((3-oxo-8-azabicyclo[3.2.1]octan-8-yl)methyl)benzamide | $^1$H NMR (400 MHz, DMSO-d6) δ 7.66 (t, J = 7.6 Hz, 1H), 7.63 - 7.56 (m, 1H), 7.51 (d, J = 10.9 Hz, 1H), 6.05 (s, 1H), 3.81 (s, 3H), 3.44 (s, 3H), 2.68 (dd, J = 16.1, 4.3 Hz, 2H), 2.09 (s, 1H), 2.08 - 1.94 (m, 3H), 1.51 (t, J = 7.2 Hz, 2H). MS (ESI): 293 [M + H]$^+$ |
| 64 | 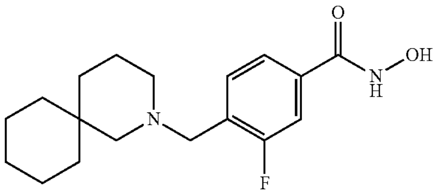 4-((2-azaspiro[5.5]undecan-2-yl)methyl)-3-fluoro-N-hydroxybenzamide | $^1$H NMR (400 MHz, DMSO-d6) δ 11.29 (s, 1H), 9.29 (s, 1H), 7.61 - 7.54 (m, 1H), 7.49 (d, J = 9.7 Hz, 2H), 3.48 (d, J = 3.3 Hz, 2H), 2.33 (s, 2H), 2.09 (s, 2H), 1.49 (p, J = 5.2 Hz, 2H), 1.30 (dd, J = 31.6, 15.4 Hz, 12H). MS(ESI): 321 [M + H]$^+$ |
| 67 | 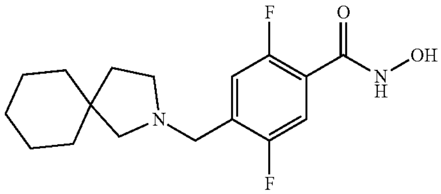 4-((2-azaspiro[4.5]decan-2-yl)methyl)-2,5-difluoro-N-hydroxybenzamide | $^1$H NMR (400 MHz, DMSO-d6) δ 10.00 (bs, 1H), 7.35 - 7.22 (m, 2H), 3.58 (s, 2H), 2.55 (bs, 2H), 2.31 (s, 2H), 1.51 (t, J = 6.8 Hz, 2H), 1.38 - 1.32 (m, 10H). MS (ESI): 325 [M + H]$^+$ |
| 68 | 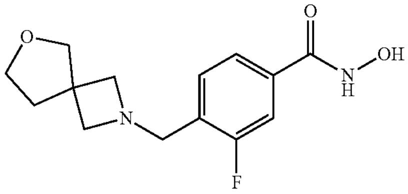 4-((6-oxa-2-azaspiro[3.4]octan-2-yl)methyl)-3-fluoro-N-hydroxybenzamide | $^1$H NMR (400 MHz, DMSO-d6) δ 11.28 (bs, 1H), 9.15 (bs, 1H), 7.72 - 7.42 (m, 3H), 3.69 (s, 2H), 3.65 - 3.55 (m, 4H), 3.17 (d, J = 2.6 Hz, 4H), 1.99 (t, J = 6.8 Hz, 2H). MS(ESI): 279 [M - H]$^-$ |
| 69 | 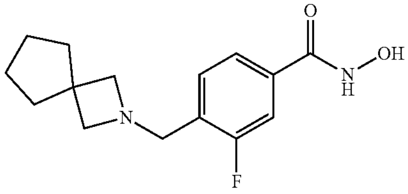 4-((2-azaspiro[3.4]octan-2-yl)methyl)-3-fluoro-N-hydroxybenzamide | $^1$H NMR (400 MHz, DMSO-d6) δ 9.33 (bs, 1H), 7.55 (d, J = 8.0 Hz, 1H), 7.50 - 7.39 (m, 2H), 3.58 (s, 2H), 3.05 (d, J = 2.1 Hz, 4H), 1.66 (d, J = 6.5 Hz, 5H), 1.48 (dt, J = 6.7, 3.7 Hz, 5H). MS(ESI): 279 [M + H]$^+$ |

-continued

| Compound | Structure/Name | Characterization |
|---|---|---|
| 70 | 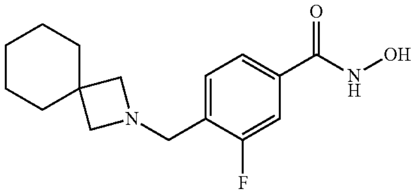 4-((2-azaspiro[3.5]nonan-2-yl)methyl)-3-fluoro-N-hydroxybenzamide | $^1$H NMR (400 MHz, DMSO-d6) δ 11.28 (bs, 1H), 9.15 (bs, 1H), 7.56 (d, J = 8.0 Hz, 1H), 7.52 - 7.37 (m, 2H), 3.61 (s, 2H), 2.91 (s, 4H), 1.54 (d, J = 6.4 Hz, 4H), 1.45 - 1.20 (m, 6H). MS(ESI): 293 [M + H]$^+$ |
| 71 | 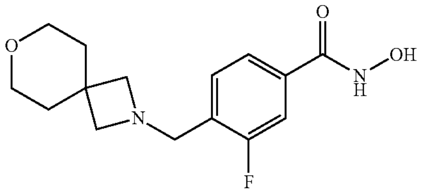 4-((7-oxa-2-azaspiro[3.5]nonan-2-yl)methyl)-3-fluoro-N-hydroxybenzamide | $^1$H NMR (400 MHz, DMSO-d6) δ 11.22 (bs, 1H), 9.14 (s, 1H), 7.56 (dd, J = 7.9, 1.7 Hz, 1H), 7.52 - 7.36 (m, 2H), 3.63 (s, 2H), 3.46 (t, J = 5.2 Hz, 4H), 3.01 (s, 4H), 1.64 (t, J = 5.2 Hz, 4H). MS (ESI): 295 [M + H]$^+$ |
| 72 | 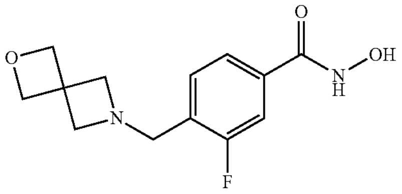 4-((2-oxa-6-azaspiro[3.3]heptan-6-yl)methyl)-3-fluoro-N-hydroxybenzamide | $^1$H NMR (400 MHz, DMSO-d6) δ 11.28 (s, 1H), 9.14 (s, 1H), 7.55 (d, J = 7.9 Hz, 1H), 7.48 (d, J = 10.8 Hz, 1H), 7.41 (t, J = 7.7 Hz, 1H), 4.59 (s, 4H), 3.54 (s, 2H), 3.32 (s, 4H). MS (ESI): 267 [M + H]$^+$ |
| 73 | 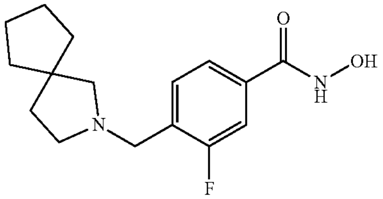 4-((2-azaspiro[4.4]nonan-2-yl)methyl)-3-fluoro-N-hydroxybenzamide | $^1$H NMR (400 MHz, DMSO-d6) δ 11.27 (bs, 1H), 9.14 (bs, 1H), 7.57 (dd, J = 7.9, 1.6 Hz, 1H), 7.54 - 7.44 (m, 2H), 3.62 (s, 2H), 2.54 (t, J = 7.0 Hz, 3H), 2.36 (s, 2H), 1.63 (t, J = 7.0 Hz, 2H), 1.59 - 1.38 (m, 9H). MS(ESI): 293 [M + H]$^+$ |
| 74 | 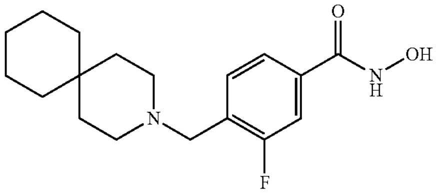 4-((3-azaspiro[5.5]undecan-3-yl)methyl)-3-fluoro-N-hydroxybenzamide | $^1$H NMR (400 MHz, DMSO-d6) δ 11.24 (bs, 1H), 9.14 (bs, 1H), 7.57 - 7.44 (m, 3H), 3.51 (s, 2H), 2.32 (t, J = 11.2 Hz, 4H), 1.38 - 1.28 (m, 14H). MS(ESI): 321 [M + H]$^+$ |
| 77 | 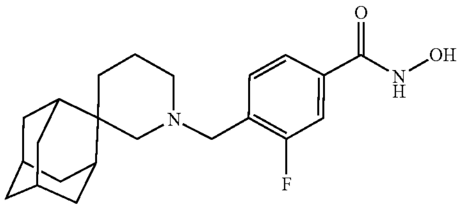 3-fluoro-N-hydroxy-4-(((1r,3r,5r,7r-spiro[adamantane-2,3'-piperidin]-1'-yl)methyl)benzamide | 1H NMR (400 MHz, DMSO-d6) δ 7.52 (d, J = 7.9 Hz, 1H), 7.42 (d, J = 11.4 Hz, 1H), 7.34 (t, J = 7.7 Hz, 1H), 3.45 (s, 2H), 2.40 - 2.25 (m, 4H), 1.97 (d, J = 12.8 Hz, 2H), 1.73 (dd, J = 26.5, 13.2 Hz, 5H), 1.61 (d, J = 17.7 Hz, 5H), 1.51 - 1.34 (m, 8H). MS(ESI): 373 [M + H]$^+$ |

-continued

| Compound | Structure/Name | Characterization |
|---|---|---|
| 78 | 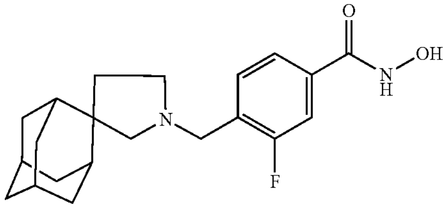 3-fluoro-N-hydroxy-4-(((1r,3r,5r,7r)-spiro[adamantane-2,3'-pyrrolidin]-1'-yl)methyl)benzamide | $^1$H NMR (400 MHz, Methanol-d4) δ 7.54 (d, J = 7.1 Hz, 2H), 7.49 (d, J = 10.4 Hz, 1H), 3.72 (d, J = 1.6 Hz, 2H), 2.64 (s, 2H), 2.61 (t, J = 6.8 Hz, 2H), 1.94 (d, J = 12.9 Hz, 2H), 1.79 (dd, J = 19.8, 11.4 Hz, 8H), 1.67 (t, J = 12.5 Hz, 4H), 1.57 (s, 2H). MS(ESI): 359 [M + H]$^+$ |
| 172 | 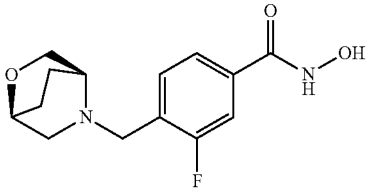 4-(((1S,4S)-2-oxa-5-azabicyclo[2.2.2]octan-5-yl)methyl)-3-fluoro-N-hydroxybenzamide | $^1$H NMR (400 MHz, DMSO-d6) δ 11.27 (s, 1H), 9.13 (s, 1H), 7.60 - 7.53 (m, 2H), 7.50 (d, J = 10.8 Hz, 1H), 4.15 (d, J = 9.0 Hz, 1H), 3.79 (d, J = 6.4 Hz, 2H), 3.74 (d, J = 5.6 Hz, 2H), 3.67 (s, 1H), 2.95 (td, J = 7.6, 3.2 Hz, 1H), 2.82 (d, J = 10.7 Hz, 1H), 2.62 (s, 1H), 1.99 - 1.88 (m, 2H), 1.66 (t, J = 12.2 Hz, 2H). MS (ESI): 281 [M + H]$^+$ Note: absolute stereochemistry is unknown |
| 173 | 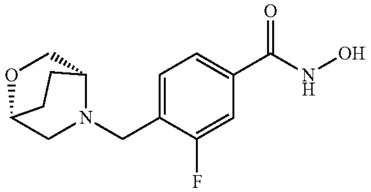 (4-(((1R,4R)-2-oxa-5-azabicyclo[2.2.2]octan-5-yl)methyl)-3-fluoro-N-hydroxybenzamide | HPLC purity: 98.82% MS (ESI):281 [M + H]$^+$ Note: absolute stereochemistry is unknown |

Compounds of Formula (V) were prepared following the synthetic schemes and procedures described in detail below.

(S)-10-fluoro-N-hydroxy-1,2,3,5,6,10b-hexahydro-pyrrolo[2,1-a]isoquinoline-8-carboxamide (79) and (R)-10-fluoro-N-hydroxy-1,2,3,5,6,10b-hexahydro-pyrrolo[2,1-a]isoquinoline-8-carboxamide (80)

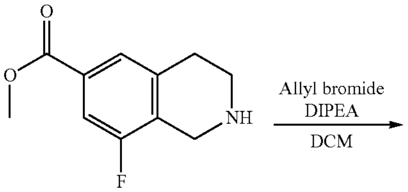

F

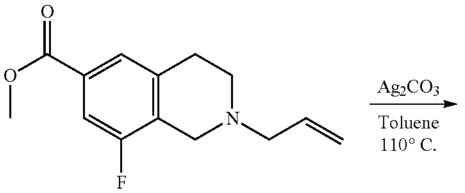

G

-continued

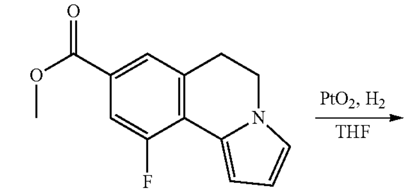

H

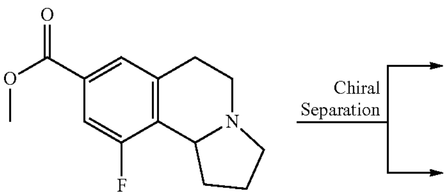

I

-continued

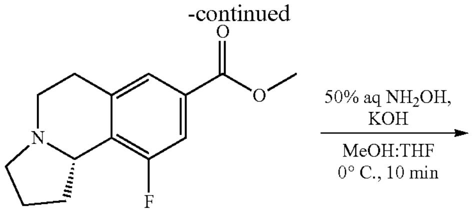

Ia

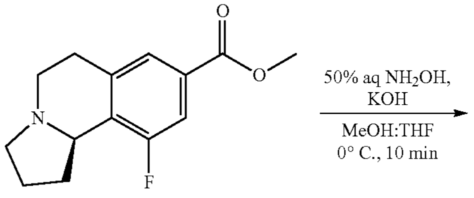

Ib

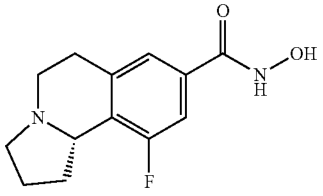

79

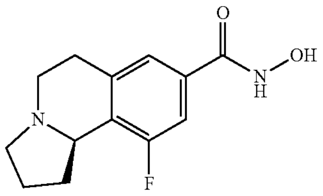

80

Methyl 2-allyl-8-fluoro-1,2,3,4-tetrahydroisoquinoline-6-carboxylate (G): To a solution of methyl 8-fluoro-1,2,3,4-tetrahydroisoquinoline-6-carboxylate (F, 2.0 g, 9.556 mmol, 1.0 equiv.) in DCM (40 mL) were added DIPEA (2.46 g, 19.11 mmol, 2.0 equiv.) and allyl bromide (1.26 g, 10.472 mmol, 1.1 equiv.) at 0° C. The reaction mixture was stirred at rt for 2 h. The reaction was monitored by TLC and mass. After completion of the reaction, the reaction mixture was poured in water and extracted with DCM (3×50 mL). The combined organic layer was dried over $Na_2SO_4$, concentrated under reduced pressure. The crude material was purifying by flash chromatography. The desire compound eluted in 5% (ethylacetate/hexane) to afford methyl 2-allyl-8-fluoro-1,2,3,4-tetrahydroisoquinoline-6-carboxylate (G, 1.6 g, 6.418 mmol, 67%) as a light yellowish solid. MS (ESI): 250 $[M+H]^+$ Methyl 10-fluoro-5,6-dihydropyrrolo[2,1-a]isoquinoline-8-carboxylate (H): To a solution of methyl 2-allyl-8-fluoro-1,2,3,4-tetrahydroisoquinoline-6-carboxylate (G, 1.6 g, 6.418 mmol, 1.0 equiv.) in toluene (20 mL) was added $Ag_2CO_3$ (17.69 g, 64.18 mmol, 10.0 equiv.) at room temperature. The reaction mixture was stirred at 110° C. for 72 h. After completion of the reaction, the reaction mixture was poured in water (20 ml) and extracted with ethyl acetate (3×50 mL). The combined organic layer was dried over $Na_2SO_4$ and concentrated under reduced pressure, to give methyl 10-fluoro-5,6 dihydropyrrolo[2,1-a]isoquinoline-8-carboxylate (H, 400 mg, 1.630 mmol, 25%) as a yellowish oil. MS (ESI): 246 $[M+H]^+$ Methyl 10-fluoro-1,2,3,5,6,10b-hexahydropyrrolo[2,1-a]isoquinoline-8-carboxylate (I): To a stirred solution of methyl 10-fluoro-5,6-dihydropyrrolo[2,1-a]isoquinoline-8-carboxylate (H, 400 mg, 1.630 mmol, 1 equiv.) in THF (5 mL) were added 1N HCl (cat.) and $PtO_2$ (200 mg) with stirring under $H_2$ atmosphere at (200 psi), the mixture was stirred room temperature for 8 h. After completion of the reaction, the catalyst was filtered off with celite by washings of THF. The residue was purified by flash chromatography, and the desired compound eluted in 10% (MeOH/DCM) to give methyl 10-fluoro-1,2,3,5,6,10b-hexahydropyrrolo[2,1-a]isoquinoline-8-carboxylate as yellow oil (I, 190 mg, 0.762 mmol, 47%). The 100 mg of racemic compound was purified on Waters SFC 200 and UV detector. The column was used Chiralpak IG (250*21.0) mm, 5 micron, column flow was 80.0 ml/min and ABPR was 100 bar. Mobile phase were used (A) Liquid Carbon dioxide (Liq. $CO_2$) and (B) 0.1% DEA in Methanol:Acetonitrile (50:50), (Fr-1(Ia): 20 mg LCMS-100%, Fr-2(Ib): 32 mg LCMS-100%). MS (ESI): 250 $[M+H]^+$ (S)-10-fluoro-N-hydroxy-1,2,3,5,6,10b-hexahydropyrrolo[2,1-a]isoquinoline-8-carboxamide (79): To a solution of methyl (S)-10-fluoro-1,2,3,5,6,10b-hexahydropyrrolo[2,1-a]isoquinoline-8-carboxylate (Ia, 20 mg, 0.080 mmol, 1.0 equiv.) in MeOH (1 mL), added the $NH_2OH$ (0.1 mL, 1.606 mmol, 50% aqueous solution, 20.0 equiv.) and KOH (14 mg, 0.240 mmol, 3.0 equiv.) at 0° C. to room temperature and reaction was stirred for 10 min. Completion of reaction was monitored by TLC and LCMS analysis and the reaction was quenched with saturated solution of $NaHCO_3$ and stirred for 10 min. The formed precipitate was filtered, washed with water and n-Hexane to obtain crude product as white residue. The crude compound was purified by Prep. HPLC method using 5 mM ABC+0.1% $NH_3$ in water and $CH_3CN$ as a mobile phase to give (S)-10-fluoro-N-hydroxy-1,2,3,5,6,10b-hexahydropyrrolo[2,1-a]isoquinoline-8-carboxamide, (79, 7.884 mg, 0.031 mmol, 39% yield) as a yellow oil. $^1H$ NMR (400 MHz, DMSO-d6) δ 7.40 (s, 1H), 7.29 (d, J=11.0 Hz, 1H), 3.67 (t, J=8.3 Hz, 1H), 2.99-2.87 (m, 2H), 2.80-2.58 (m, 4H), 2.38-2.30 (m, 1H), 1.86-1.70 (m, 2H), 1.62-1.51 (m, 1H). MS (ESI): 251 $[M+H]^+$ (R)-10-fluoro-N-hydroxy-1,2,3,5,6,10b hexahydropyrrolo[2,1-a]isoquinoline-8-carboxamide (80): To a solution of methyl (R)-10-fluoro-1,2,3,5,6,10b-hexahydropyrrolo[2,1-a]isoquinoline-8-carboxylate (Ib, 32 mg, 0.128 mmol, 1.0 equiv.) in MeOH (1 mL), added the $NH_2OH$ (0.2 mL, 2.567 mmol, 50% aqueous solution, 20.0 equiv.) and KOH (21.56 mg, 0.385 mmol, 3.0 equiv.) at 0° C. to room temperature and reaction was stirred for 10 min. Completion of reaction was monitored by TLC and LCMS analysis and the reaction was quenched with saturated solution of $NaHCO_3$ and stirred for 10 min. The formed precipitate was filtered, washed with water and n-hexane to obtain crude product as a white residue. The crude compound was purified by prep. HPLC method using 5 mM ABC+0.1% $NH_3$ in water and $CH_3CN$ as a mobile phase to give (R)-10-fluoro-N-hydroxy-1,2,3,5,6,10b hexahydropyrrolo[2,1-a]isoquinoline-8-carboxamide, (80, 6.924 mg, 0.027 mmol, 21% yield). $^1H$ NMR (400 MHz, DMSO-d6) δ 7.38 (s, 1H), 7.29 (d, J=11.0 Hz, 1H), 3.67 (t, J=8.3 Hz, 1H), 2.99-2.87 (m, 2H), 2.80-2.58 (m, 4H), 2.38-2.30 (m, 1H), 1.86-1.70 (m, 2H), 1.62-1.51 (m, 1H). MS (ESI): 251 $[M+H]^+$ Although compounds 79 and 80 are designated as the (S) and (R) enantiomers as each enantiomer was prepared and isolated, the absolute stereochemistry of each is unknown.

(S)—N-Hydroxy-1,3,4,6,7,11b-hexahydro-2H-pyrido[2,1-a]isoquinoline-9-carboxamide (89) and (R)—N-Hydroxy-1,3,4,6,7,11b-hexahydro-2H-pyrido[2,1-a]isoquinoline-9-carboxamide (90)

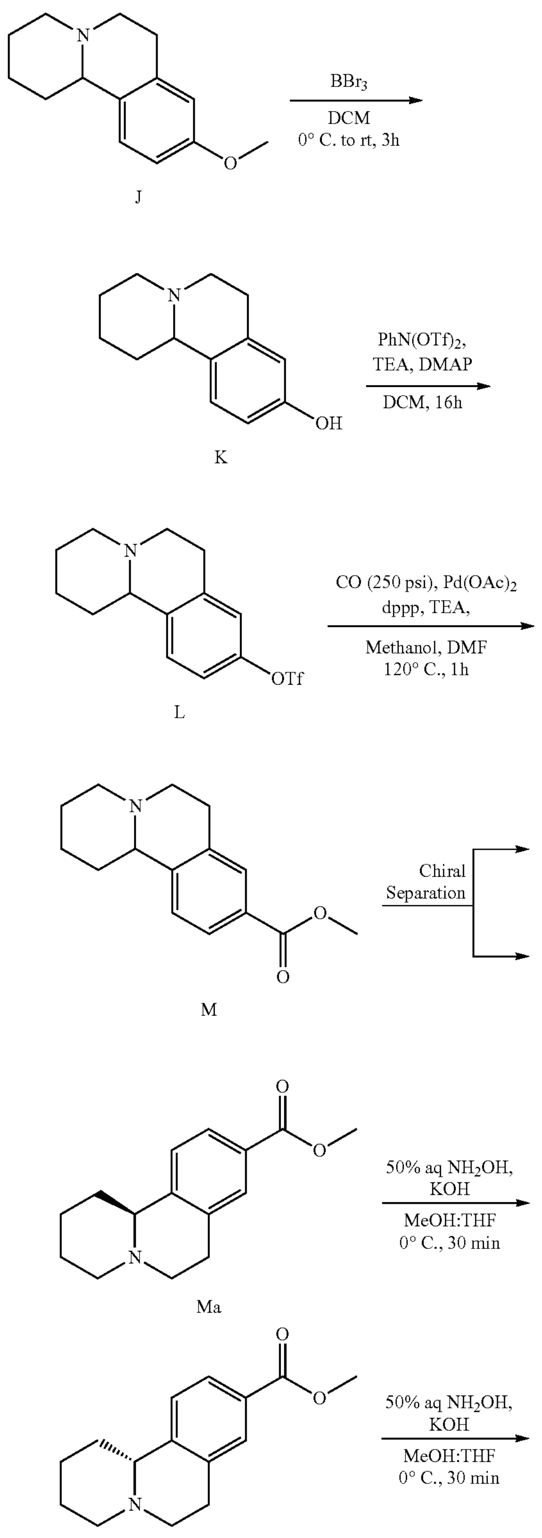

J, K, L, M, Ma, Mb

-continued

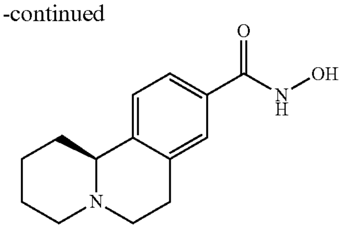

89

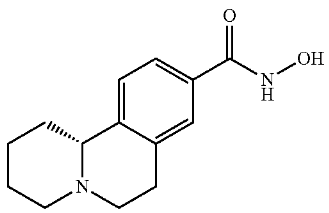

90

1,3,4,6,7,11b-Hexahydro-2H-pyrido[2,1-a]isoquinolin-9-ol (K): To a solution of 9-methoxy-1,3,4,6,7,11b-hexahydro-2H-pyrido[2,1-a]isoquinoline (J, 1.2 g, 5.52 mmol, 1.0 equiv.) in dichloromethane (15 mL), was added 1M $BBr_3$ in DCM (14 ml, 13.81 mmol, 2.0 equiv.) at 0° C. and stirred at room temperature for 3 hrs. After completion of reaction cold water (10 ml) was added to reaction mixture, the formed precipitate was filtered through Buchner funnel, washed with ice cold DCM (15 mL). The solid was taken up 5% methanol in DCM (150 mL) and gave wash of saturated bicarbonate solution (100 mL). The organic layer separated, dried over $Na_2SO_4$ and evaporated to dryness to give 1,3,4,6,7,11b-hexahydro-2H-pyrido[2,1-a]isoquinolin-9-ol (K, 1.0 g, 4.92 mmol, 89% yield). MS (ESI): 204 $[M+H]^+$ 1,3,4,6,7,11b-Hexahydro-2H-pyrido[2,1-a]isoquinolin-9-yl trifluoromethanesulfonate (L): To a stirred solution of 1,3,4,6,7,11b-hexahydro-2H-pyrido[2,1-a]isoquinolin-9-ol (K, 1.0 g, 4.92 mmol, 1.0 equiv.) in dry DCM (15 mL) was added triethylamine (1.6 ml, 12.31 mmol, 2.5 equiv.) and 4-dimethylamino)pyridine (60 mg, 0.49 mmol, 0.1 equiv.). After about 20 minutes, N-phenylbis(trifluoromethanesulfonimide) (2.63 g, 7.38 mmol, 1.5 equiv.) was added in portions. Upon complete addition, the reaction mixture was stirred at room temperature for 8 h and monitored with TLC and LC-MS. After completion of the reaction solvents were removed under reduced pressure and the product thus obtained was purified with silica gel chromatography using 70% EtOAc in hexanes to afford 1,3,4,6,7,11b-hexahydro-2H-pyrido[2,1-a]isoquinolin-9-yl trifluoromethanesulfonate (L, 1.35 g, 4.0 mmol, 82% yield) as a brown oil. MS (ESI): 336 $[M+H]^+$ Methyl 1,3,4,6,7,11b-hexahydro-2Hpyrido[2,1-a]isoquinoline-9-carboxylate (M): To a stirred solution of 1,3,4,6,7,11b-hexahydro-2H-pyrido[2,1-a]isoquinolin-9-yl trifluoromethanesulfonate (3, 0.9 g, 2.68 mmol, 1.0 equiv.) in dry methanol (20 mL), DMF (2 ml) was degassed with $N_2$ gas for 10 min. Palladium acetate (9 mg, 0.040 mmol. 0.15 equiv.), 1,3-Bis(diphenylphosphino)propane (0.221 g, 0.53 mmol, 0.2 equiv.), TEA (1.12 mL, 8.05 mmol, 3 equiv.) were added to the above reaction mixture. The reaction mixture was stirred under an atmosphere of CO (250 psi) at 120° C. for 1 h. The mixture was cooled to room temperature and the solids were removed by filtration. The filtrate was concentrated in reduced pressure and the residue was purified by silica gel flash chromatography (70% EtOAc/Haxane) to provide methyl 1,3,4,6,7,11b-hexahydro-2Hpyrido[2,1-a]

isoquinoline-9-carboxylate (M, 0.38 g, 1.55 mmol, 58% yield). The enantiomers of M were separated on 120 mg scale on Waters SFC 200 and UV detector. The column was used Chiralpak IG (250*21.0) mm, 5 micron, column flow was 80.0 ml/min and ABPR was 100 bar. Mobile phase were used (A) Liquid Carbon dioxide (Liq. $CO_2$) and (B) 0.1% DEA in Methanol. The UV spectra were recorded at 236 nm Lambdamax. (Fr-1(Ma): 40 mg LCMS-100%, Fr-2(Mb): 57 mg LCMS-100%). MS (ESI): 246 $[M+H]^+$ (S)—N-hydroxy-1,3,4,6,7,11b-hexahydro-2H-pyrido[2,1-a]isoquinoline-9-carboxamide (89): To a solution of methyl (R)-1,3,4,6,7,11b-hexahydro-2H-pyrido[2,1-a]isoquinoline-9-carboxylate (Ma, 40 mg, 0.163 mmol, 1.0 equiv.) in methanol (1.5 mL) added the $NH_2OH$ (0.215 mL, 3.26 mmol, 50% aqueous solution, 20.0 equiv.) and KOH (27.46 mg, 0.489 mmol, 3.0 equiv.) at 0° C. stirred at room temperature for 1 h. Completion of reaction was confirmed by TLC. The reaction mixture was evaporated to dryness; the crude material was purified by Prep HPLC purification using (A) 5 mM ammonium bicarbonate+0.1% ammonia in water (2) 100% acetonitrile. The solvents were lyophilized to give (S)—N-hydroxy-1,3,4,6,7,11b-hexahydro-2H-pyrido[2,1-a]isoquinoline-9-carboxamide, (89.9 mg, 0.036 mmol, 22% yield). $^1H$ NMR (400 MHz, DMSO-d6) δ 11.06 (s, 1H), 8.96 (s, 1H), 7.58-7.38 (m, 2H), 7.30 (d, J=8.1 Hz, 1H), 3.14-2.84 (m, 4H), 2.67 (d, J=15.0 Hz, 1H), 2.35-2.18 (m, 3H), 1.83 (d, J=12.2 Hz, 1H), 1.64-1.39 (m, 3H), 1.29-1.17 (m, 1H). MS (ESI): $245[M-H]^-$ (R)—N-hydroxy-1,3,4,6,7,11b-hexahydro-2H-pyrido[2,1-a]isoquinoline-9-carboxamide (90): To a solution of methyl (S)-1,3,4,6,7,11b-hexahydro-2H-pyrido[2,1-a]isoquinoline-9-carboxylate (Mb, 57 mg, 0.23 mmol, 1.0 equiv.) in methanol (1.5 mL), were added $NH_2OH$ (0.307 mL, 4.65 mmol, 50.00% aqueous solution, 20.0 equiv.) and KOH (39.16 mg, 0.69 mmol, 3.0 equiv.) at 0° C. stirred at room temperature for 1 hr. Completion of reaction was confirmed by TLC. The reaction mixture was evaporated to dryness; the crude material was purified by Prep HPLC purification using (A) 5 mM ammonium bicarbonate+0.1% ammonia in water (2) 100% acetonitrile. The solvents was lyophilized to give (R)—N-hydroxy-1,3,4,6,7,11b-hexahydro-2H-pyrido[2,1-a]isoquinoline-9-carboxamide (90, 16.8 mg, 0.068 mmol, 29%). $^1H$ NMR (400 MHz, DMSO-d6) δ 10.83 (s, 1H), 8.96 (s, 1H), 7.64-7.38 (m, 2H), 7.30 (d, J=8.1 Hz, 1H), 3.09-2.88 (m, 4H), 2.68 (m, 1H), 2.33-2.23 (m, 3H), 1.83 (d, J=12.4 Hz, 1H), 1.62-1.39 (m, 3H), 1.24-1.18 (m, 1H). MS (ESI): $245[M-H]^-$ Although compounds 89 and 90 are designated as the (S) and (R) enantiomers as each enantiomer was prepared and isolated, the absolute stereochemistry of each is unknown.

(S)-7-fluoro-N-hydroxy-1,3,4,6,11,11a-hexahydro-2H-pyrido[1,2-b]isoquinoline-9-carboxamide (93) and (R)-7-fluoro-N-hydroxy-1,3,4,6,11,11a-hexahydro-2H-pyrido[1,2-b]isoquinoline-9-carboxamide (94)

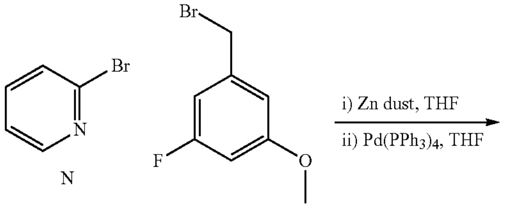

N

O

-continued

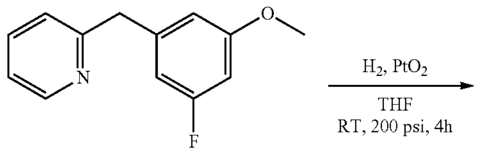

P

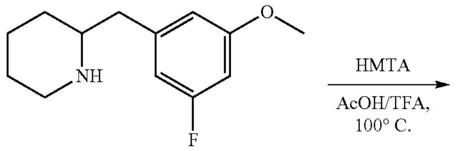

Q

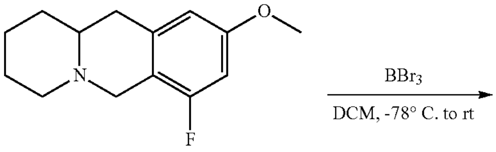

R

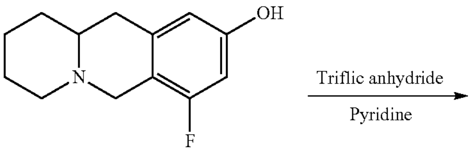

S

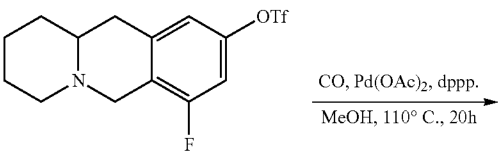

T

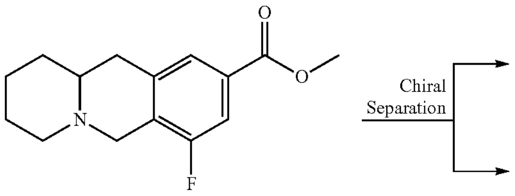

U

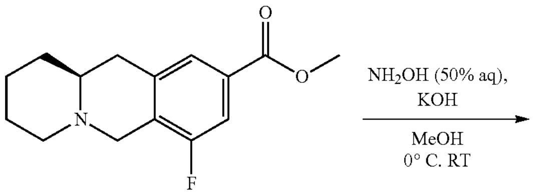

Ua

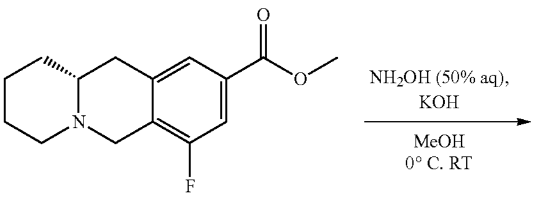

Ub

-continued

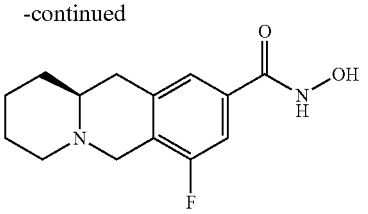

93

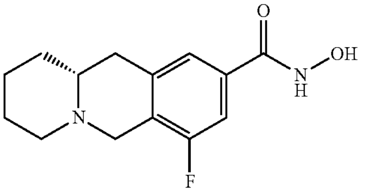

94

2-(3-Fluoro-5-methoxybenzyl)pyridine (P): A solution of 1-(bromomethyl)-3-fluoro-5-methoxybenzene, (0, 5.3 g, 24.2 mmol, 1 equiv.) in dry THF (10 mL) was added drop wise to a suspension of zinc dust (7.86 g, 121.0 mmol) (activated by washing with aq. HCl) in dry THF (40 mL) under nitrogen. As soon as the flask reached room temperature, the resulting solution was added to a stirred mixture of 2-bromopyridine (N, 3.82 g, 24.2 mmol, 1 equiv.) and $Pd(PPh_3)_4$ (0.2796 g, 0.242 mmol, 1 mol %) in dry THF (40 mL). The mixture was stirred overnight. The solvent was evaporated, and the residue was purified by column chromatography using AcOEt-hexane as eluents to give 2-(3-fluoro-5-methoxybenzyl)pyridine (P, 4.1 g, 78.1%) as a colorless oil. MS (ESI): 218 $[M+H]^+$ 2-(3-Fluoro-5-methoxybenzyl)piperidine (Q): To a stirred solution of 2-(3-fluoro-5-methoxybenzyl)pyridine (P, 4.0 g, 18.430 mmol, 1 equiv.) in THF (15 mL) were added 1N HCl (0.5 mL) and $PtO_2$ (100 mg) with stirring. The reaction mixture was stirred under $H_2$ atmosphere, (200 psi) at room temperature for 4 h, and the catalyst was filtered off with celite and washed with THF. The solvents were evaporated under reduced pressure to give 2-(3-fluoro-5-methoxybenzyl)piperidine as a white solid (Q, 2.3 g, 10.31 mmol, 56%) and used for the next reaction without further purification. MS (ESI): 224 $[M+H]^+$ 7-Fluoro-9-methoxy-1,3,4,6,11,11a-hexahydro-2H-pyrido[1,2-b]isoquinoline (Ra) and 9-fluoro-7-methoxy 1,3,4,6,11,11a-hexahydro-2H-pyrido[1,2-b]isoquinoline (Rb): To a stirred solution of 2-(3-fluoro-5-methoxybenzyl)piperidine (Q, 2.3 g, 10.31 mmol, 1 equiv.) in acetic acid/trifluoroacetic acid (4:1) (10 mL) was added hexamethylentetramine (2.908 g, 20.62 mmol, 2 equiv.) in a sealed tube. The reaction mixture was stirred at 100° C. for 4 hours and monitored by TLC analysis. After completion of the reaction, the mixture was carefully quenched by the addition of aqueous sodium bicarbonate (20 mL) and extracted with ethyl acetate (2×20 mL) and dried over sodium sulfate. The organic layer was concentrated under reduced pressure and purified by column chromatography to yield mixture of 7-fluoro-9-methoxy-1,3,4,6,11,11a-hexahydro-2H-pyrido[1,2-b]isoquinoline (Ra) and 9-fluoro-7-methoxy 1,3,4,6,11,11a-hexahydro-2H-pyrido[1,2-b]isoquinoline as a white solid (Rb) (1.5 g, 6.383 mmols, 62%). The mixture of Ra and Rb was used for the next step without further purification. A small fraction of $R^a$ was purified and characterized by $^1H$ NMR. $^1H$ NMR (400 MHz, Chloroform-d) δ 6.44 (d, J=12.4 Hz, 1H), 4.03 (d, J=15.5 Hz, 1H), 3.77 (s, 2H), 3.25-3.07 (m, 1H), 2.75 (q, J=10.0, 8.1 Hz, 1H), 2.34-2.12 (m, 1H), 1.38 (s, 2H), 1.31-1.18 (m, 1H). MS (ESI): 236 $[M+H]^+$ 7-Fluoro-1,3,4,6,11,11a-hexahydro-2H-pyrido[1,2-b]isoquinolin-9-ol (Sa) and 9-fluoro-1,3,4,6,11,11a-hexahydro-2H-pyrido[1,2-b]isoquinolin-7-ol (Sb): To a stirred solution of Sa and Sb (1.2 g, 5.106 mmol, 1 equiv.) in DCM (25 mL) was added $BBr_3$ solution (3.19 g, 12.76 mmol, 2.5 equiv.). The reaction mixture was allowed to warm to rt and monitored with TLC analysis. After completion of reaction the reaction mixture was carefully quenched by the addition of aqueous sodium bicarbonate (25 mL) and extracted with ethyl acetate (5×25 mL) and dried over sodium sulfate. The organic layer was concentrated to yield a mixture of 7-fluoro-1,3,4,6,11,11a-hexahydro-2H-pyrido[1,2-b]isoquinolin-9-ol (Sa) and 9-fluoro-1,3,4,6,11,11a-hexahydro-2H-pyrido[1,2-b]isoquinolin-7-ol (Sb) as a brown solid (890 mg, 4.022 mmol, 79%). The mixture of Sa and Sb was used in the next step without further purification. MS (ESI): 222 $[M+H]^+$ 7-fluoro-1,3,4,6,11,11a-hexahydro-2H-pyrido[1,2-b]isoquinolin-9-yl trifluoromethanesulfonate (Ta) and 8-fluoro-1,3,4,6,11,11a-hexahydro-2H-pyrido[1,2-b]isoquinolin-10-yl trifluoromethanesulfonate (Tb): To a stirred solution of Sa and Sb (450 g, 2.036 mmol, 1 equiv.) in pyridine (5 mL) was added $Tf_2O$ (851.7 mg, 3.108 mmol, 1.5 equiv.). The reaction mixture was allowed to warm to rt and monitored with TLC analysis. After completion of the reaction, the reaction mixture was carefully quenched by the addition of water and extracted with ethyl acetate (3×25 mL) and dried over sodium sulfate. The organic layer was concentrated to yield a mixture of Ta and Tb as a sticky solid (710 mg, 2.011 mmols, 99%). The mixture of Ta and Tb was used in the next step without further purification. MS (ESI): 354 $[M+H]^+$ Methyl 7-fluoro-1,3,4,6,11,11a-hexahydro-2H-pyrido[1,2-b]isoquinoline-9-carboxylate (Ua): To a solution of Ta and Tb (700 mg, 1.9830 mmol, 1 equiv.) in MeOH (25 mL), was added $Pd(OAc)_2$ (64 mg, 0.285 mmol, 0.15 equiv.), triethylamine (0.9595 mg, 9.5 mmol, 5 equiv.) and DPPP (156.5 mg, 0.38 mmol, 0.2 equiv.). The resulting mixture was degassed using nitrogen gas. The reaction mixture was stirred at 110° C. under carbon monoxide pressure (350 psi) for 24 h. The reaction mixture was filtered through a celite pad and the filtrate was concentrated under reduced pressure. The crude reaction mixture was purified by column chromatography to yield U (175 mg, 0.6653 mmol, 34% yield). 100 mg of U was purified by prep HPLC (Shimadzu LC-20AP and UV detector). The column used was CHIRALPAK IG (250*21.0) mm, 5 micron; column flow was 12.0 ml/min. Mobile phase: (A) 0.1% DEA in HEXANE (B) 0.1% DEA IN IPA: MEOH (50:50) to provide individual enantiomers. (Fr-1(Ua): 42 mg LCMS-100%, Fr-2(Ub): 32 mg LCMS-100%). Ua: $^1H$ NMR (400 MHz, Chloroform-d) δ 7.60 (s, 1H), 7.51 (d, J=10.0 Hz, 1H), 4.17 (d, J=17.0 Hz, 1H), 3.92 (s, 3H), 3.33 (s, 1H), 3.20 (s, 1H), 2.86 (s, 2H), 2.27 (s, 2H), 1.91 (s, 2H), 1.79 (s, 2H), 1.28 (s, 1H). MS (ESI): 264 $[M+H]^+$ (S)-7-fluoro-N-hydroxy-1,3,4,6,11,11a-hexahydro-2H-pyrido[1,2-b]isoquinoline-9-carboxamide (93): To a stirred solution of methyl (S)-7-fluoro-1,3,4,6,11,11a-hexahydro-2H-pyrido[1,2-b]isoquinoline-9-carboxylate (Ua, 42 mg, 0.1597 mmol, 1 equiv.) in methanol (2 mL) were added 50% aq. $NH_2OH$ (0.0210 mL, 3.194 mmol, 20 equiv; 50% aq solution of in $H_2O$) and KOH (17.88 mg, 0.3194 mmol, 2 equiv.) at 0° C. The reaction was stirred at 0° C. to rt for 10 min then quenched with saturated solution of $NaHCO_3$ and filtered and wash with n-hexane to obtain white residue which was purified by Prep-HPLC purification using an mobile phase ACN and water to get pure (S)-7-fluoro-N-hydroxy-1,3,4,6,11,11a-hexahydro-2H-pyrido[1,2-b]isoquinoline-9-carboxamide (93, 18.2 mg, 0.0688 mmol, 43%). $^1$H NMR (400 MHz, DMSO-$d_6$) δ 11.20 (s, 1H), 9.10 (s, 1H), 7.36 (s, 1H), 7.30 (d, J=10.0 Hz, 1H), 3.93 (d, J=16.4 Hz, 1H), 3.12 (d, J=16.5 Hz, 1H), 3.01 (d, J=11.5 Hz, 1H), 2.80 (dd, J=17.1, 3.7 Hz, 1H), 2.16 (t, J=6.6 Hz, 1H), 2.05 (td, J=11.8, 2.8 Hz, 1H), 1.80 (d, J=11.4 Hz, 1H), 1.76-1.59 (m, 2H), 1.51 (d, J=13.1 Hz, 1H), 1.25 (q, J=13.6 Hz, 2H). MS (ESI): 265 $[M+H]^+$ (R)-7-fluoro-N-hydroxy-1,3,4,6,11,11a-hexahydro-2H-pyrido[1,2-b]isoquinoline-9-carboxamide (94): To a stirred solution of methyl (R)-7-fluoro-1,3,4,6,11,11a-hexahydro-2H-pyrido[1,2-b]isoquinoline-9-carboxylate (Ub, 38 mg, 0.1444 mmol, 1 equiv.) in methanol (2 mL) were added 50% aq. $NH_2OH$ (0.0190 mL, 2.889 mmol, 20 equiv; 50% aq solution of in $H_2O$) and KOH (16.19 mg, 0.2889 mmol, 2 equiv.) at 0° C. The reaction was stirred at 0° C. to rt for 10 min then quenched with saturated solution of $NaHCO_3$ and filtered and wash with n-hexane to obtain white residue which was purified by Prep-HPLC purification using an mobile phase ACN and water to get pure (R)-7-fluoro-N-hydroxy-1,3,4,6,11,11a-hexahydro-2H-pyrido[1,2-b]isoquinoline-9-carboxamide (94, 19.482 mg, 0.07407 mmol, 51%). $^1$H NMR (400 MHz, DMSO-$d_6$) δ 11.22 (s, 1H), 9.10 (s, 1H), 7.35 (s, 1H), 7.30 (d, J=10.0 Hz, 1H), 3.93 (d, J=16.8 Hz, 1H), 3.12 (d, J=16.6 Hz, 1H), 3.01 (d, J=11.2 Hz, 1H), 2.80 (d, J=17.1 Hz, 1H), 2.16 (s, 1H), 2.05 (t, J=11.7 Hz, 1H), 1.80 (d, J=11.1 Hz, 1H), 1.76-1.59 (m, 2H), 1.51 (m, 1H), 1.25 (m, 2H). MS (ESI): 265 $[M+H]^+$.

Although compounds 93 and 94 are designated as the (S) and (R) enantiomers as each enantiomer was prepared and isolated, the absolute stereochemistry of each is unknown.

N-hydroxy-1,2,3,4,6,11-hexahydropyridazino[1,2-b]phthalazine-8-carboxamide (106)

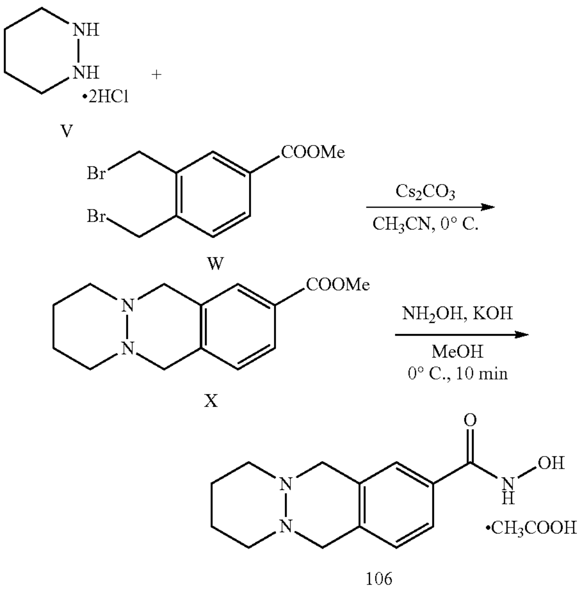

V

W

X

106

Methyl 1,2,3,4,6,11-hexahydropyridazino[1,2-b]phthalazine-8-carboxylate (X): To a solution of hexahydropyridazine hydrogen chloride (V, 98 mg, 0.616 mmol, 1.0 equiv.) in acetonitrile (ACN) (5 mL) were added methyl 3,4-bis(bromomethyl)benzoate (W, 198.4 mg, 0.616 mmol, 1.0 equiv.) and $Cs_2CO_3$ (803 mg, 2.46 mmol, 4.0 equiv.). The reaction mixture was stirred at room temperature for 2 h. Completion of reaction was monitored by TLC and LCMS. The reaction mixture was filtered and concentrated. The crude methyl 1,2,3,4,6,11-hexahydropyridazino[1,2-b]phthalazine-8-carboxylate (X, 150 mg, 0.608 mmol, 99%) was used as such for the next step. MS (ESI): 247 $[M+H]^+$ N-hydroxy-1,2,3,4,6,11-hexahydropyridazino[1,2-b]phthalazine-8-carboxamide (106): To a solution of methyl 1,2,3,4,6,11-hexahydropyridazino[1,2-b]phthalazine-8-carboxylate (X, 150 mg, 0.608 mmol, 1.0 equiv.) in MeOH (3 mL) was added $NH_2OH$ (0.8 mL, 12.16 mmol, 50% aqueous solution, 20.0 equiv.) and KOH (102.1 mg, 1.824 mmol, 3.0 equiv.) at 0° C. The reaction was stirred for 10 min at RT. Completion of reaction was monitored by TLC and LCMS analysis. The reaction mixture was concentrated and purified by prep. HPLC. Mobile phase (A: 5 mM AA+0.1% $NH_3$ in water, B:100% ACN) to afford N-hydroxy-1,2,3,4,6,11-hexahydropyridazino[1,2-b]phthalazine-8-carboxamide (106, 19.9 mg, 0.065 mmol, 11% yield). $^1$H NMR (400 MHz, DMSO-$d_6$) δ 7.77-7.74 (m, 2H), 7.42 (d, J=7.8 Hz, 1H), 5.13-5.01 (m, 4H), 3.72-3.70 (m, 2H), 3.12 (s, 2H), 1.96 (s, 2H), 1.74 (s, 3H), 1.61 (s, 2H). MS (ESI): 248 $[M+H]^+$ Compounds of Formula (II) were prepared following the synthetic schemes and procedures described in detail below.

2-(((3r,5r,7r)-adamantan-1-yl)methyl)-5-fluoro-N-hydroxy-1,2,3,4-tetrahydroisoquinoline-7-carboxamide (113)

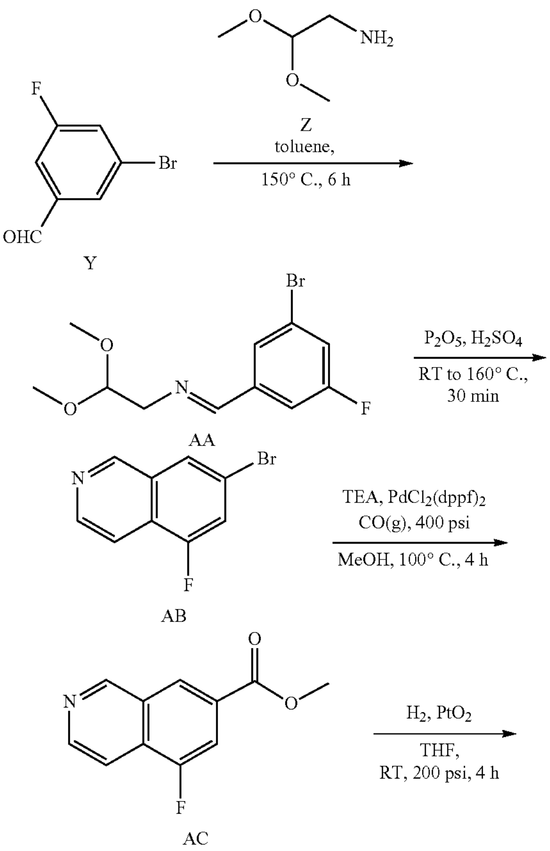

Z

Y

AA

AB

AC

-continued

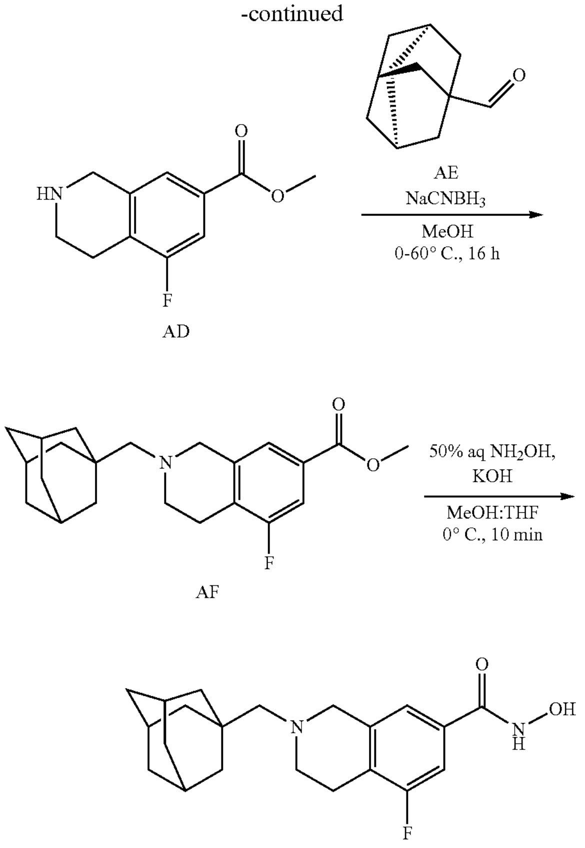

AD

AF

113

(E)-1-(3-bromo-5-fluorophenyl)-N-(2,2-dimethoxyethyl) methanimine (AA): A stirred solution of 3-bromo-5-fluorobenzaldehyde (Y, 5.0 g, 24.293 mmol, 1.0 equiv.) and 2,2-dimethoxyethan-1-amine (Z, 3.103 g, 29.555 mmol, 1.2 equiv.) in toluene (50 mL) was refluxed using Dean-Stark apparatus at 120° C. for 6 h. Completion of reaction was monitored by TLC. The reaction the mixture was then concentrated under vacuum. The solid residue was triturated with pentane to give (E)-1-(3-bromo-5-fluorophenyl)-N-(2, 2-dimethoxyethyl)methanimine (AA, 7.5 g, 25.850 mmol, 91%) was used as such in the next step. MS (ESI): 290 $[M+H]^+$.

7-bromo-5-fluoroisoquinolinemethanimine (AB): Phosphorous pentoxide (10.0 g) and concentrated sulfuric acid (3 mL) were mixed and stirred until thick brown coloured gum was formed. Next, (E)-1-(3-bromo-5-fluorophenyl)-N-(2,2-dimethoxyethyl)methanimine (AA, 7.5 g, 25.85 mmol) was dissolved in cold (5° C.) concentrated sulfuric acid (30 mL) and added slowly to the mixture of Phosphorous pentoxide and concentrated sulfuric acid prepared above. The resulting dark coloured reaction mixture was vigorously stirred and heated at 160° C. for 30 minutes. After cooling to room temperature, the dark brown viscous reaction mixture was carefully poured into ice water (500 mL) with vigorous stirring. The pH was adjusted to 7 using 1N NaOH and the black tarry precipitate were filtered. The pH was then further increased to 9 using 1N NaOH. This basic aqueous phase was extracted with EtOAc (3×500 mL). The combined organic layers were washed with brine dried over $MgSO_4$ and evaporated to afford 7 g of brown oil. The crude product was purified by Prep. HPLC to afford 7-bromo-5-fluoroisoquinoline (AB, 1.5 g, 6.6371 mmol, 38%). MS (ESI): 227 $[M+H]^+$.

methyl 5-fluoroisoquinoline-7-carboxylate (AC): To a stirred solution of 7-bromo-5-fluoroisoquinoline (AB, 1.1 g, 4.8672 mmol, 1 equiv.) in a methanol (20 mL), were added TEA (3.3 mL, 24.336 mmol, 5 equiv.) and $PdCl_2$(dppf) (177 mg, 0.2433 mmol, 0.05 equiv.) under nitrogen. The reaction mixture was heated to 100° C. under (400 psi) carbon monoxide for 4 h. Reaction was monitored by TLC. The reaction mixture was filtered through celite, washed with methanol (50 mL) and combined filtrate was concentrated under vacuum and the resulting residue was purified by combi flash chromatography eluting with 42% EtOAc: hexane to afford methyl 7-fluoroisoquinoline-5-carboxylate (AC, 770 mg, 3.7551 mmol, 73%) as a solid. MS (ESI): 206 $[M+H]^+$.

methyl 5-fluoro-1,2,3,4-tetrahydroisoquinoline-7-carboxylate (AD): To a stirred solution of methyl 7-fluoroisoquinoline-5-carboxylate (AC, 770 mg, 3.75 mmol) in THF (15 mL) were added 1N HCl (2.0 mL) and $PtO_2$ (300 mg) at room temperature. The resulting mixture was stirred at room temperature under $H_2$ gas (200 psi) for 4 h. Reaction was monitored by TLC. Reaction mixture was then filtered through celite washed with THF (30 mL) and combined filtrate was concentrated to afford methyl 5-fluoro-1,2,3,4-tetrahydroisoquinoline-7-carboxylat (AD, 581 mg, 2.78 mmol, 74%) as brown solid. MS (ESI): 210 $[M+H]^+$.

methyl 2-(((3r,5r,7r)-adamantan-1-yl)methyl)-5-fluoro-1,2,3,4 tetrahydroisoquinoline-7-carboxylate (AF): To a stirred solution of methyl 5-fluoro-1,2,3,4-tetrahydroisoquinoline-7-carboxylat (AD, 200 mg, 0.9559 mmol, 1.0 equiv.) in methanol (10 mL) were added acetic acid (cat.), adamantane-1-carbaldehyde (AE, 313 mg, 1.9118 mmol, 2.0 equiv.) and $NaCNBH_3$ (118 mg, 1.9118 mmol, 2.0 equiv.) at 0° C. Reaction mixture was stirred at 60° C. for 16 h. Reaction was monitored by TLC. The reaction was quenched with sodium bicarbonate solution (50 mL) and extracted with EtOAc (3×50 mL). The combined organic layers were dried over anhydrous $Na_2SO_4$ and concentrated under reduced pressure to obtain the crude material. It was purified by silica gel column. Compound was eluted at 3.4% EtOAc in hexane to afford methyl2-(((3r,5r,7r)-adamantan-1-yl)methyl)-5-fluoro-1,2,3,4-tetrahydroisoquinoline-7-carboxylate (AF, 45 mg, 0.1256 mmol, 13%). MS (ESI): 358 $[M+H]^+$.

2-(((3r,5r,7r)-adamantan-1-yl)methyl)-5-fluoro-N-hydroxy-1,2,3,4-tetrahydroisoquinoline-7-carboxamide (113): To a solution of methyl2-(((3r,5r,7r)-adamantan-1-yl)methyl)-5-fluoro-1,2,3,4-tetrahydroisoquinoline-7-carboxylate (AF, 40 mg, 0.1120 mmol, 1.0 equiv.) in MeOH (1 mL) were added $NH_2OH$ (0.1 mL, 1.6806 mmol, 50% aqueous solution, 15.0 equiv.) and KOH (18 mg, 0.336 mmol, 3.0 equiv.) at 0° C. The reaction was stirred for 10 min at room temperature. Completion of reaction was monitored by TLC and LCMS analysis. The reaction mixture was concentrated and purified by prep. HPLC. Mobile phase (A: 5 mM ammonium acetate+0.1% $NH_3$ in water, B: 100% ACN) to afford 2-(((3r,5r,7r)-adamantan-1-yl)methyl)-5-fluoro-N-hydroxy-1,2,3,4-tetrahydroisoquinoline-7-carboxamide (113, 4.1 mg, 0.011 mmol, 10.22% yield). $^1H$ NMR (400 MHz, Methanol-d4) δ 7.27-7.25 (m, 2H), 3.70 (s, 2H), 2.81 (dt, J=9.3, 4.6 Hz, 4H), 2.17 (s, 2H), 1.95 (s, 3H), 1.75 (d, J=12.3 Hz, 3H), 1.68 (d, J=12.4 Hz, 3H), 1.59 (d, J=2.8 Hz, 6H). MS (ESI): 359 $[M+H]^+$.

The following compounds were prepared in a manner analogous to that used for preparing compound 113.

| | | |
|---|---|---|
| 114 | 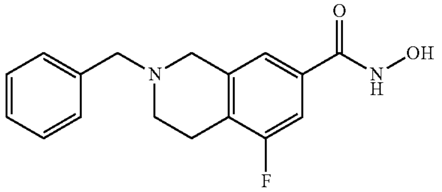 [SMILES: O=C(NO)c1cc(F)c2c(c1)CN(Cc1ccccc1)CC2]<br>2-benzyl-5-fluoro-N-hydroxy-1,2,3,4-tetrahydroisoquinoline-7-carboxamide | $^1$H NMR (400 MHz, DMSO-$d_6$) δ 11.23-10.05 (bs, 1H), 9.35 (bs, 1H), 7.37-7.32 (m, 5H), 7.31-7.23 (m, 2H), 3.67 (s, 2H), 3.57 (s, 2H), 2.75 (d, J = 5.6 Hz, 2H), 2.70 (t, J = 5.8 Hz, 2H).<br>MS (ESI): 301 $[M + H]^+$ |
| 115 | 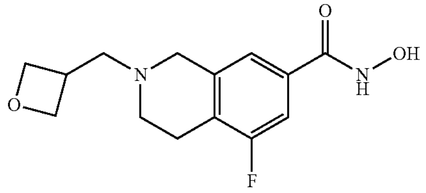 [SMILES: O=C(NO)c1cc(F)c2c(c1)CN(CC1COC1)CC2]<br>5-fluoro-N-hydroxy-2-(oxetan-3-ylmethyl)-1,2,3,4-tetrahydroisoquinoline-7-carboxamide | $^1$H NMR (400 MHz, DMSO-$d_6$) δ 11.18 (s, 1H), 9.09 (s, 1H), 7.32 (d, J = 15.8 Hz, 2H), 4.66 (t, J = 6.9 Hz, 2H), 4.29 (t, J = 6.1 Hz, 2H), 3.54 (s, 2H), 3.30-3.23 (m, 1H), 2.79 (d, J = 7.4 Hz, 2H), 2.72 (d, J = 6.1 Hz, 2H), 2.65 (s, 2H).<br>MS (ESI): 281 $[M + H]^+$ |
| 116 | 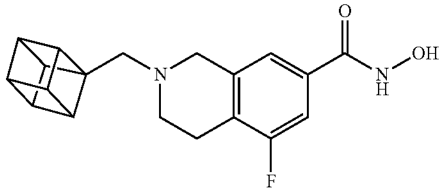 [SMILES: O=C(NO)c1cc(F)c2c(c1)CN(CC13C4C5C6C4C1C6C53)CC2]<br>2-(cuban-1-ylmethyl)-5-fluoro-N-hydroxy-1,2,3,4-tetrahydroisoquinoline-7-carboxamide | $^1$H NMR (400 MHz, DMSO-$d_6$) δ 11.17 (bs, 1H), 9.09 (bs, 1H), 7.35-7.30 (m, 2H), 4.03 (s, 1H), 3.98-3.84 (m, 6H), 3.55 (s, 2H), 2.76-2.64 (m, 6H).<br>MS (ESI): 327 $[M + H]^+$ |

3-benzyl-N-hydroxy-2-methyl-1,2,3,4-tetrahydrophthalazine-6-carboxamide (117) and 2-benzyl-N-hydroxy-3-methyl-1,2,3,4-tetrahydrophthalazine-6-carboxamide (118)

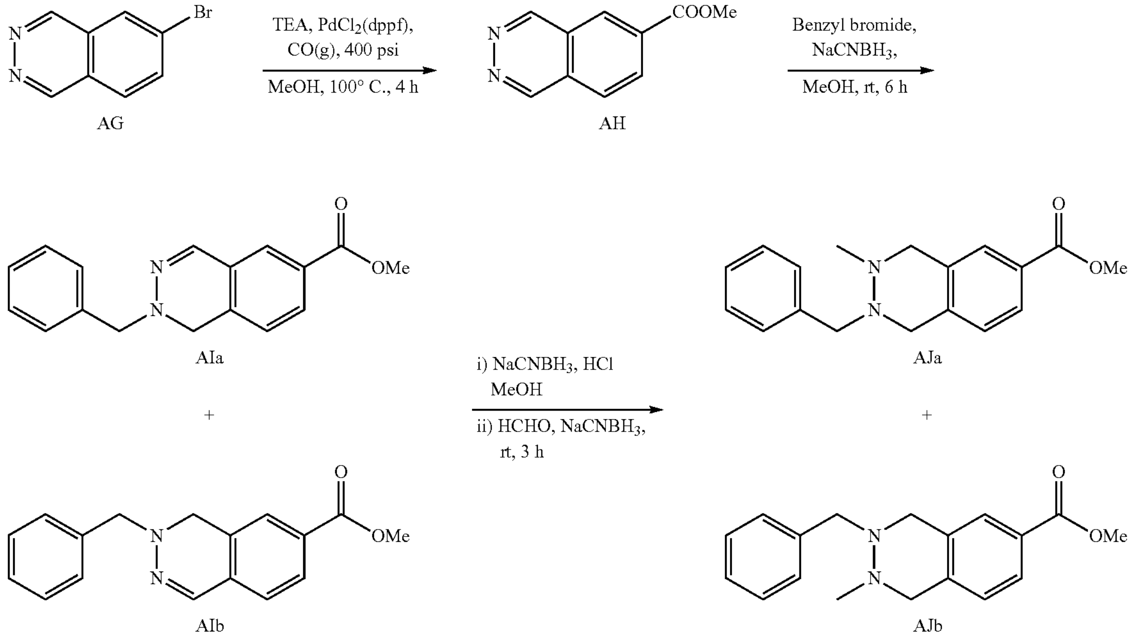

AG AH

AIa + AIb

AJa + AJb

-continued

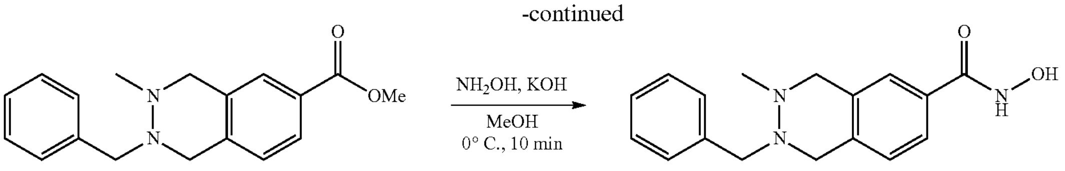

AJa 118

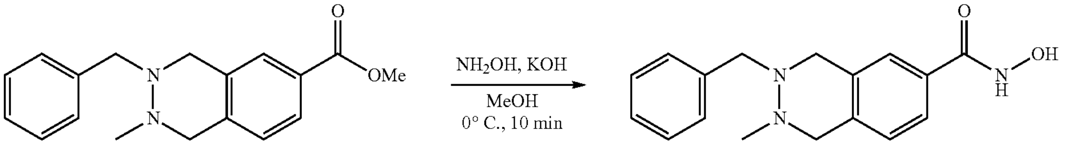

AJb 117 methyl phthalazine-6-carboxylate (AH): To a stirred solution of 6-bromophthalazine (AG, 800 mg, 3.8277 mmol, 1 equiv.) in a methanol were added TEA (2.66 mL, 19.1385 mmol, 5.0 equiv.) and $PdCl_2$(dppf) (139.90 mg, 0.1913 mmol, 0.05 equiv.) at room temperature under nitrogen atmosphere. The mixture was heated to 100° C. under carbon monoxide (400 psi) for 3 h. Reaction was monitored by TLC. Reaction mixture was filtered through celite and washed with methanol. Filtrate was concentrated in vacuum and purified by combi flash chromatography eluting with 50% EtOAc: hexane to afford methyl phthalazine-6-carboxylate (AH, 250 mg, 1.3297 mmol, 35%) as a white solid. MS (ESI): 189 $[M+H]^+$.

methyl 2-benzyl-1,2-dihydrophthalazine-6-carboxylate (Ala) and methyl-3-benzyl-3,4-dihydrophthalazine-6-carboxylate (AIb): To a stirred solution of methyl phthalazine-6-carboxylate (AH, 250 mg, 1.3297 mmol, 1.0 equiv.) in MeOH (10 mL) were added benzylbromide (2.3 mL, 1.5937 mmol, 1.5 equiv.) and $NaBH_3CN$ (329 mg, 5.3191 mmol, 4.0 equiv.). The solution was stirred at room temperature for 6 h. Reaction was monitored with TLC. The reaction was quenched with water (10 mL) and extracted with EtOAc (3×10 mL). The combined organic layers were dried over anhydrous $Na_2SO_4$ and concentrated under reduced pressure to obtain the crude AIa+AIb (300 mg) which was immediately used for next step. MS (ESI): 281 $[M+H]^+$.

methyl 2-benzyl-3-methyl-1,2,3,4-tetrahydrophthalazine-6-carboxylate (AJa) and methyl 3-benzyl-2-methyl-1,2,3,4-tetrahydrophthalazine-6-carboxylate (AJb): To a stirred solution of methyl 2-benzyl-1,2-dihydrophthalazine-6-carboxylate and methyl3-benzyl-3,4-dihydrophthalazine-6-carboxylate (AIa+AIb, 300 mg, 1.0714 mmol, 1.0 equiv.) in MeOH (15 mL) was added $NaBH_3CN$ (66.42 mg, 2.1428 mmol, 2.0 equiv.) and added Con. HCl (0.05 mL). The solution was stirred at room temperature for 1 h and monitored with TLC. After 1 hours, further added $NaBH_3CN$ (66.42 mg, 2.1428 mmol, 2.0 equiv.) and formaldehyde solution (10 mL). Reaction mixture was stirred at room temperature for 2 h. The reaction was then quenched with water (100 mL) extracted with EtOAc (3×100 mL). The combined organic layers were dried over anhydrous $Na_2SO_4$, and the organic layer was concentrated under reduced pressure to obtain the crude material. It was purified by combi flash chromatography eluting with 50% EtOAc: hexane to gate mixture of regio isomers (88 mg). The regio isomers were further separated using CHIRAL PREP HPLC using 0.1% DEA in MeOH on CHIRAL pack AD-H (250×4.6 mm) 5μ column.) to provide individual isoomers. (Fr-1 (AJb): 32 mg, Fr-2 (AJa): 25 mg. MS (ESI): 297 $[M+H]^+$. AJa and AJb isolated pure and confirmed by NOE experiment. Fraction-2 was found to be (AJa).

3-benzyl-N-hydroxy-2-methyl-1,2,3,4-tetrahydrophthalazine-6-carboxamide (117): To a stirred solution of methyl 3-benzyl-2-methyl-1,2,3,4-tetrahydrophthalazine-6-carboxylate (AJa, 25 mg, 0.08446 mmol, 1.0 equiv.) in MeOH (2 mL) were added the $NH_2OH$ (0.1 mL, 1.26689 mmol, 50% aqueous solution, 15.0 equiv.) and KOH (23 mg, 0.4223 mmol, 5.0 equiv.) at 0° C. The reaction mixture was stirred at room temperature for 10 min. Completion of reaction was monitored by TLC and LCMS. The reaction was quenched with saturated $NaHCO_3$ solution and stirred for 10 min. The precipitates were filtered and washed with water and n-hexane. White residue was purified by PREP HPLC. Mobile phase (A: 0.1% formic acid in water, B 100% ACN) to afford 3-benzyl-N-hydroxy-2-methyl-1,2,3,4-tetrahydrophthalazine-carboxamide. (117, 4.094 mg, 0.01378 mmol, 13%). MS (ESI): 298 $[M+H]^+$.

2-benzyl-N-hydroxy-3-methyl-1,2,3,4-tetrahydrophthalazine-6-carboxamide (118): This compound was prepared from AJb in a manner analogous to that used for 117. $^1H$ NMR (400 MHz, DMSO-$d_6$) δ 11.14 (bs, 1H), 9.01 (bs, 1H), 7.55-7.50 (m, 2H), 7.30 (d, J=4.3 Hz, 4H), 7.23 (dt, J=8.7, 4.3 Hz, 1H), 7.13 (d, J=8.0 Hz, 1H), 3.89 (s, 2H), 3.72 (d, J=8.7 Hz, 4H), 2.40 (s, 3H). MS (ESI): 298 $[M+H]^+$.

Compounds of Formula (V) were prepared following the synthetic schemes and procedures described in detail below.

(S)-6-fluoro-N-hydroxy-1,2,3,5,10,10a-hexahydro-pyrrolo[1,2-b]isoquinoline-8-carboxamide (119) and (R)-6-fluoro-N-hydroxy-1,2,3,5,10,10a-hexahydro-pyrrolo[1,2-b]isoquinoline-8-carboxamide (120)

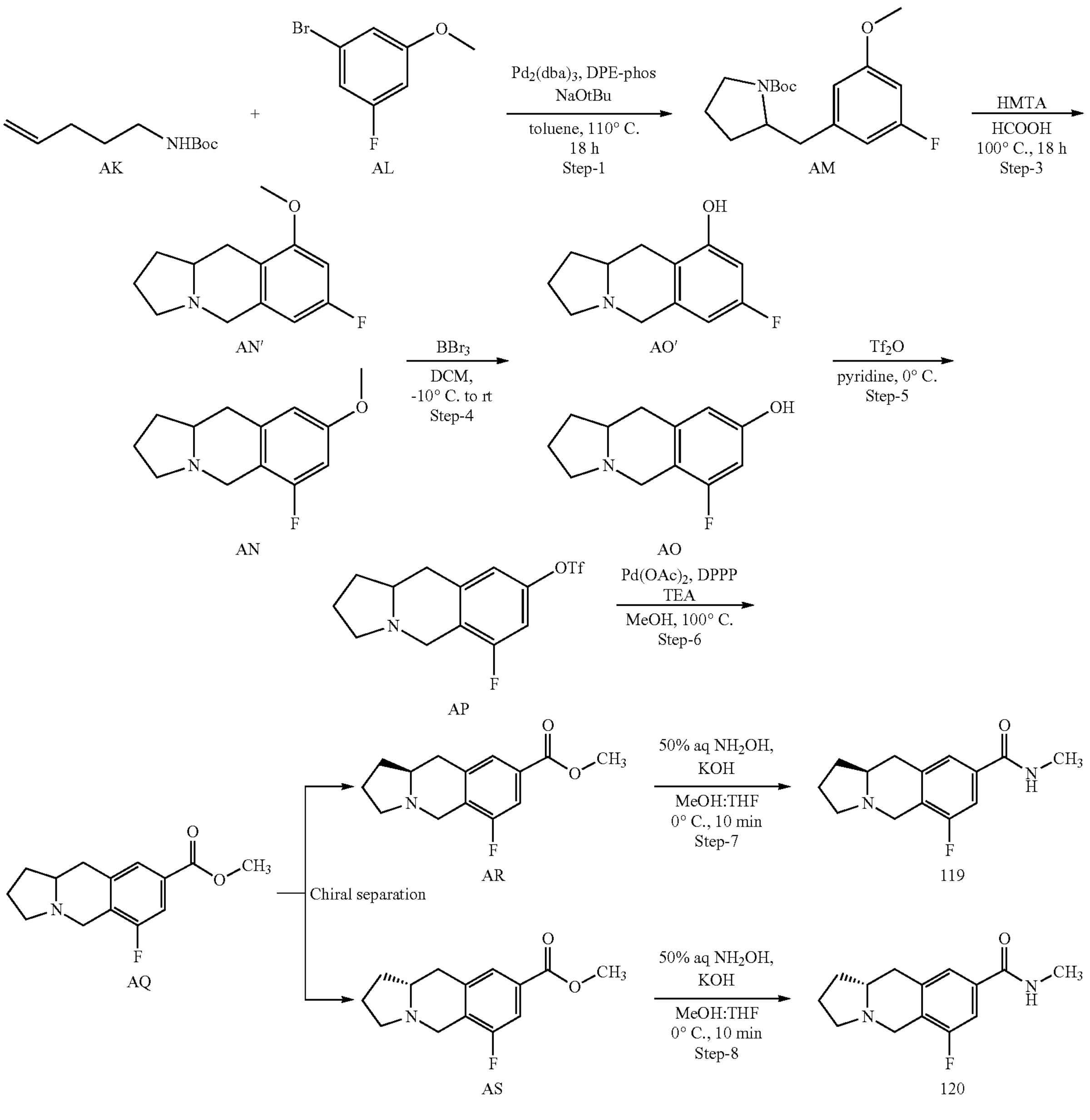

AK AL AM AN' AN AO' AO AP AQ AR AS 119 120 tert-butyl 2-(3-fluoro-5-methoxybenzyl)pyrrolidine-1-carboxylate (AM): A stirred solution of tert-butyl pent-4-en-1-ylcarbamate (AK, 0.99 g, 5.39 mmol, 1.1 equiv.) and 1-bromo-3-fluoro-5-methoxybenzene (AL, 1.0 g, 4.90 mmol, 1.0 equiv.) in toluene (15 mL) was degassed using nitrogen for 15 min, following which DPE-Phos (52 mg, 0.098 mmol, 0.02 equiv.), NaOtBu (0.706 g, 7.35 mmol, 1.5 equiv.) and $Pd_2(dba)_3$ (44 mg, 0.049 mmol, 0.01 equiv.) were added. The reaction mixture was refluxed for 18 h and was monitored by TLC. The reaction mixture was poured on water (100 mL) and extracted with ethyl acetate (2×100 mL). The combine organic layer dried over sodium sulfate, concentrated under reduced pressure to obtain crude mixture. The crude material was purified by column chromatography using ethyl acetate/hexane (2:8), to get tert-butyl 2-(3-fluoro-5-methoxybenzyl) pyrrolidine-1-carboxylate (AM, 1.2 g, 3.88 mmol, 79%) as a yellow oil. MS (ESI): 310 $[M+H]^+$ Subsequent steps for the preparation of 119 and 120 were performed in a manner analogous to that used for preparation of compound 93 and 94.

(S)-6-fluoro-N-hydroxy-1,2,3,5,10,10a-hexahydropyrrolo[1,2-b]isoquinoline-8-carboxamide (119)$^1$H NMR (400 MHz, DMSO-$d_6$) δ 11.22 (s, 1H), 9.08 (s, 1H), 7.41-7.31 (m, 2H), 4.19 (d, J=16.0 Hz, 1H), 3.42 (m, 1H), 3.03 (d, J=15.6 Hz, 2H), 2.22 (m, 1H), 2.62 (m, 2H), 2.04 (m, 1H), 1.77 (m, 2H), 1.45 (m, 1H). MS (ESI): 251 $[M+H]^+$ (R)-6-fluoro-N-hydroxy-1,2,3,5,10,10a-hexahydropyrrolo [1,2-b]isoquinoline-8-carboxamide (120)$^1$H NMR (400 MHz, DMSO-$d_6$) δ 11.21 (s, 1H), 9.19 (s, 1H), 7.40 (s, 1H), 7.32 (d, J=10.4 Hz, 1H), 4.16 (d, J=16.0 Hz, 1H), 3.17 (d, J=6.8 Hz, 2H), 2.99 (dd, J=16.0, 3.2 Hz, 1H), 2.62-2.56 (m, 1H), 2.27-2.19 (m, 2H), 2.05-2.00 (m, 1H), 1.81-1.77 (m, 2H), 1.49-1.42 (i, 1H). MS(ESI): 251.2 [M+H]

Although compounds 119 and 120 are designated as the (S) and (R) enantiomers as each enantiomer was prepared and isolated, the absolute stereochemistry of each is unknown.

The following compounds were prepared in a manner analogous to that used for preparing compound 119 and 120. Although compound pairs 121/122, 123/124, 125/126, and 127/128 are designated as the (S) and (R) enantiomers as each enantiomer was prepared and isolated, the absolute stereochemistry of each is unknown.

| | | |
|---|---|---|
| 121 | 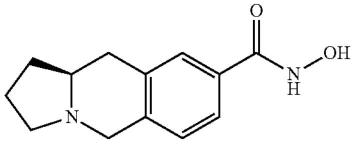 [SMILES: O=C(NO)c1ccc2c(c1)C[C@@H]1CCCN1C2] (S)-N-hydroxy-1,2,3,5,10,10a-hexahydropyrrolo[1,2-b]isoquinoline-8-carboxamide | MS(ESI): 233 [M + H]$^+$ Note: absolute stereochemistry is unknown |
| 122 | 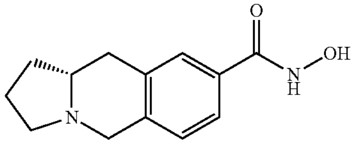 [SMILES: O=C(NO)c1ccc2c(c1)C[C@H]1CCCN1C2] (R)-N-hydroxy-1,2,3,5,10,10a-hexahydropyrrolo[1,2-b]isoquinoline-8-carboxamide | MS(ESI): 233 [M + H]$^+$ Note: absolute stereochemistry is unknown |
| 123 | 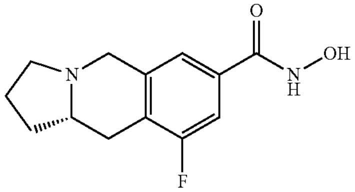 [SMILES: O=C(NO)c1cc(F)c2c(c1)CN1CCC[C@H]1C2] (S)-9-fluoro-N-hydroxy-1,2,3,5,10,10a-hexahydropyrrolo[1,2-b]isoquinoline-7-carboxamide | $^1$H NMR (400 MHz, DMSO-d6) δ 7.67 (bs, 1H), 7.40 (s, 1H), 7.32 (d, J = 10.5 Hz, 1H), 4.17 (d, J = 15.9 Hz, 1H), 3.25-3.14 (m, 2H), 3.00 (dd, J = 16.2, 3.5 Hz, 1H), 2.61 (d, J = 10.9 Hz, 1H), 2.27-2.16 (m, 2H), 2.11-1.99 (m, 1H), 1.81-1.73 (m, 2H), 1.44 (p, J = 10.1 Hz, 1H). MS (ESI): 251 [M + H]$^+$ Note: absolute stereochemistry is unknown. |
| 124 | 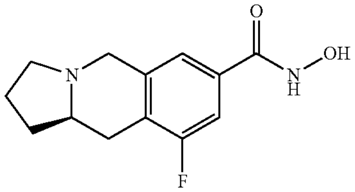 [SMILES: O=C(NO)c1cc(F)c2c(c1)CN1CCC[C@@H]1C2] (R)-9-fluoro-N-hydroxy-1,2,3,5,10,10a-hexahydropyrrolo[1,2-b]isoquinoline-7-carboxamide | $^1$H NMR (400 MHz, DMSO-d6) δ 11.12 (bs, 1H), 9.10 (bs, 1H), 7.40 (s, 1H), 7.32 (d, 7 = 10.5 Hz, 1H), 4.16 (d, J = 15.9 Hz, 1H), 3.24-3.15 (m, 2H), 3.00 (dd, J = 16.1, 3.5 Hz, 1H), 2.61 (d, J = 10.8 Hz, 1H), 2.27-2.16 (m, 2H), 2.10-2.00 (m, 1H), 1.81-1.73 (m, 2H), 1.44 (p, J = 9.8 Hz, 1H). MS (ESI): 251 [M + H]$^+$ Note: absolute stereochemistry is unknown |
| 125 | 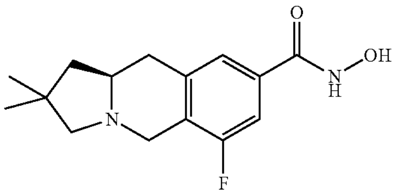 [SMILES: CC1(C)C[C@H]2Cc3cc(C(=O)NO)cc(F)c3CN2C1] (R)-6-fluoro-N-hydroxy-2,2-dimethyl-1,2,3,5,10,10a-hexahydropyrrolo[1,2-b]isoquinoline-8-carboxamide | $^1$H NMR (400 MHz, DMSO-d6) δ 10.95 (bs, 1H), 9.13 (bs, 1H), 7.36 (s, 1H), 7.33 (d, J = 10.0 Hz, 1H), 4.03 (d, J = 15.2 Hz, 1H), 3.26 (d, J = 15.2 Hz, 1H), 2.98-2.89 (m, 2H), 2.44-2.38 (m, 2H), 2.05 (d, J = 8.8 Hz, 1H), 1.87 (dd, J = 12.4, 5.6 Hz, 1H), 1.35 (dd, J = 11.6, 9.2 Hz, 1H), 1.12 (s, 3H), 1.08 (s, 3H). MS (ESI): 279 [M + H]$^+$ Note: absolute stereochemistry is unknown |

-continued

| | | |
|---|---|---|
| 126 | 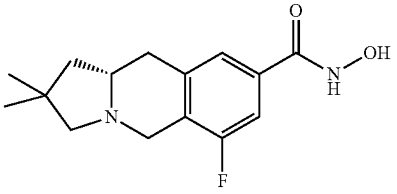 [SMILES: CC1(C)C[C@@H]2Cc3cc(C(=O)NO)cc(F)c3CN2C1]<br>(S)-6-fluoro-N-hydroxy-2,2-dimethyl-1,2,3,5,10,10a-hexahydropyrrolo[1,2-b]isoquinoline-8-carboxamide | $^1H$ NMR (400 MHz, DMSO-d6) δ 11.22 (bs, 1H), 9.09 (bs, 1H), 7.36 (s, 1H), 7.33 (d, J = 10.8 Hz, 1H), 4.03 (d, J = 14.8 Hz, 1H), 3.26 (d, J = 15.6 Hz, 1H), 2.98-2.89 (m, 2H), 2.41-2.38 (m, 2H), 2.05 (d, J = 8.8 Hz, 1H), 1.87 (dd, J = 14.4, 5.6 Hz, 1H), 1.37 (d, J = 10.0 Hz, 1H), 1.13 (s, 3H), 1.08 (s, 3H). MS (ESI): 279 $[M + H]^+$ Note: absolute stereochemistry is unknown |
| 127 | 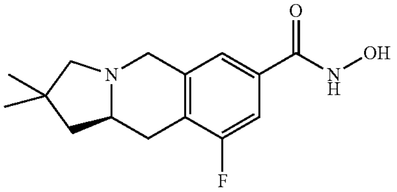 [SMILES: CC1(C)C[C@@H]2Cc3c(F)cc(C(=O)NO)cc3CN2C1]<br>(R)-9-fluoro-N-hydroxy-2,2-dimethyl-1,2,3,5,10,10a-hexahydropyrrolo[1,2-b]isoquinoline-7-carboxamide | $^1H$ NMR (400 MHz, DMSO-d6) δ 11.25 (s, 1H), 9.12 (s, 1H), 7.41 (s, 1H), 7.34 (d, 7 = 10.4 Hz, 1H), 4.12 (d, J = 15.9 Hz, 1H), 3.18 (d, J = 15.8 Hz, 1H), 3.03-2.89 (m, 2H), 2.67-2.58 (m, 2H), 2.11 (d, J = 8.8 Hz, 1H), 1.87 (dd, J = 12.3, 6.8 Hz, 1H), 1.35 (dd, J = 12.3, 9.1 Hz, 1H), 1.15 (s, 3H), 1.10 (s, 3H). MS (ESI): 279 $[M + H]^+$ Note: absolute stereochemistry is unknown |
| 128 | 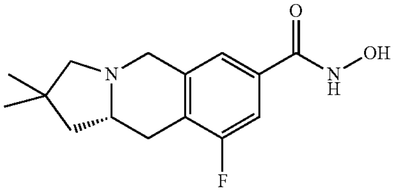 [SMILES: CC1(C)C[C@H]2Cc3c(F)cc(C(=O)NO)cc3CN2C1]<br>((S)-9-fluoro-N-hydroxy-2,2-dimethyl-1,2,3,5,10,10a-hexahydropyrrolo[1,2-b]isoquinoline-7-carboxamide | $^1H$ NMR (400 MHz, DMSO-d6) δ 11.25 (s, 1H), 9.12 (s, 1H), 7.41 (s, 1H), 7.33 (d, J = 10.5 Hz, 1H), 4.11 (d, J = 15.8 Hz, 1H), 3.18 (d, J = 15.4 Hz, 1H), 3.04-2.85 (m, 2H), 2.63 (s, 2H), 2.11 (d, J = 8.8 Hz, 1H), 1.87 (dd, J = 12.4, 6.7 Hz, 1H), 1.35 (dd, J =12.3, 9.2 Hz, 1H), 1.15 (s, 3H), 1.10 (s, 3H). MS (ESI): 279 $[M + H]^+$ Note: absolute stereochemistry is unknown |

(R)-7-fluoro-N-hydroxy-1,3,4,6,11,11a-hexahydro-[1,4]oxazino[4,3-b]isoquinoline-9-carboxamide (129) and (S)-7-fluoro-N-hydroxy-1,3,4,6,11,11a-hexahydro-[1,4]oxazino[4,3-b]isoquinoline-9-carboxamide (130)

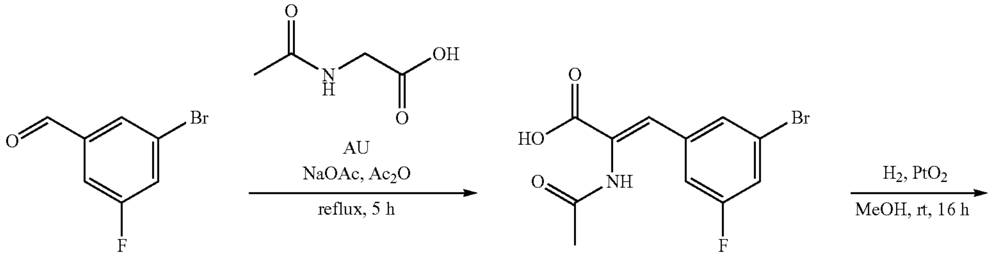

AT AV

-continued

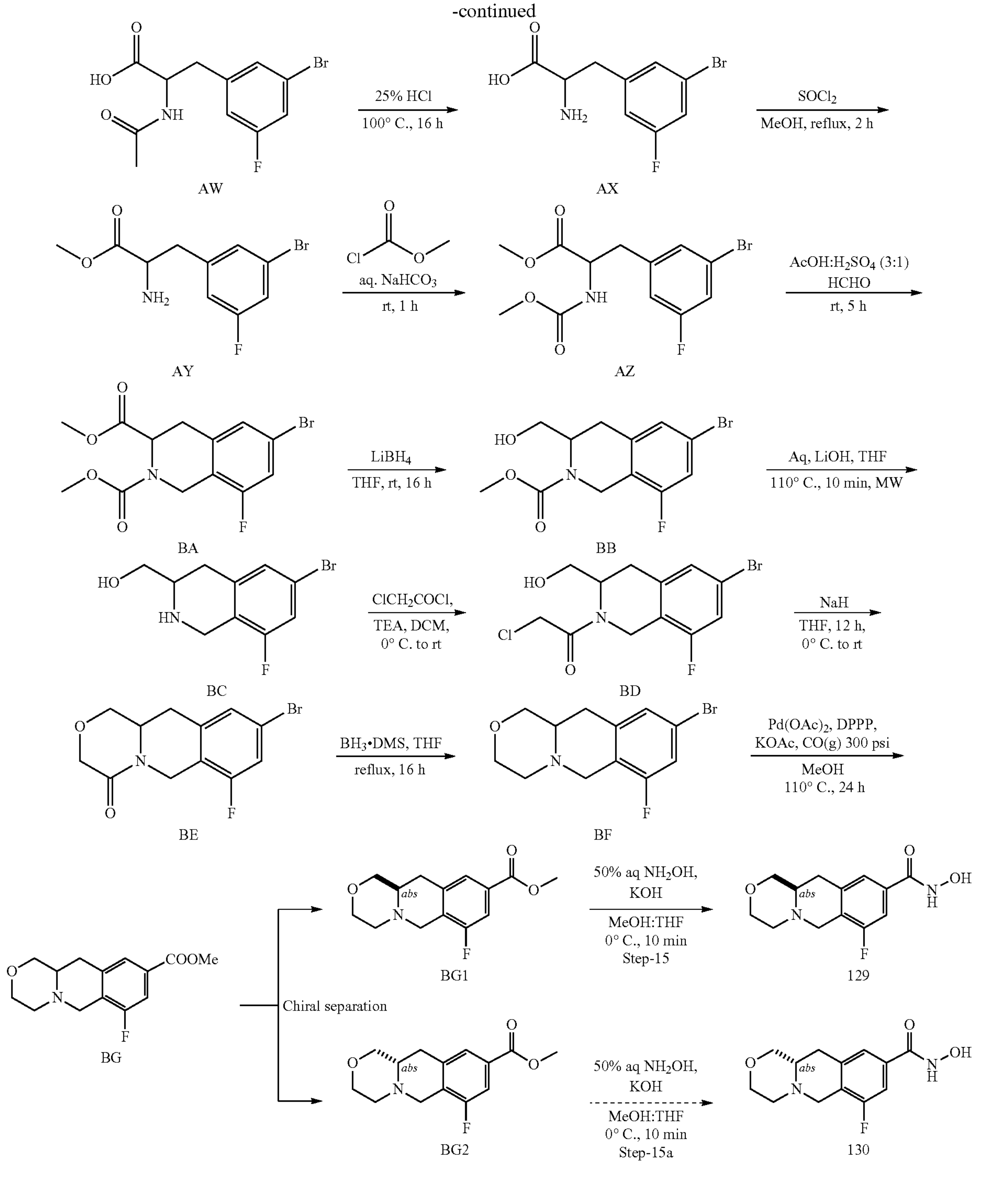

(Z)-2-acetamido-3-(3-bromo-5-fluorophenyl)acrylic acid (AV): To a solution of 3-bromo-5-fluorobenzaldehyde (AT, 15 g, 73.892 mmol, 1.0 equiv.) in acetic anhydride (24 mL) was added N-acetyl glycine (AU, 8.6 g, 73.892 mmol, 1.0 equiv.) and NaOAc (6 g, 73.892 mmol, 1.0 equiv.). The reaction mixture was stirred at 120° C. for 5 h. The completion of reaction was monitored by TLC and LCMS. The resulting solution solidified upon cooling to room temperature and was quenched with ice-cold water and filtered. The solids were washed with water (50 mL), dried under reduced pressure to get product (Z)-2-acetamido-3-(3-bromo-5-fluorophenyl)acrylic acid (AV, 9.0 g, 29.903 mmol, 40%) as a brown solid. MS (ESI): 302 $[M+H]^+$ 2-acetamido-3-(3-bromo-5-fluorophenyl)propanoic acid (AW): To a solution of (Z)-2-acetamido-3-(3-bromo-5-fluorophenyl)acrylic acid (AV, 7 g, 23.258 mmol, 1.0 equiv.) in MeOH (70 mL) was added $PtO_2$ (2 g), The mixture was stirred at room temperature for 16 h in hydrogenator under 200 psi $H_{2(g)}$ and was monitored using TLC. The reaction mixture was filtered through celite and filtrate was concentrated under reduced pressure to obtain 2-acetamido-3-(3-bromo-5-fluorophenyl)propanoic acid (AW, 7.0 g, 23.02 mmol, 99%) as a sticky brown solid. MS (ESI): 304 $[M+H]^+$ 2-amino-3-(3-bromo-5-fluorophenyl)propanoic acid (AX): To an round-bottom flask containing 2-acetamido-3-(3-bromo-5-fluorophenyl)propanoic acid (AW, 7 g, 23.02 mmol, 1.0 equiv.), 25% HCl solution (100 mL) was added. The reaction mixture was refluxed at 100° C. for 16 h and was monitored by LCMS. Upon completion of reaction, it was concentrated under reduced pressure, ethyl acetate was added to obtain white solid. It was filtered and dried under reduce pressure to get 2-amino-3-(3-bromo-5-fluorophenyl) propanoic acid (AX, 6.0 g, 22.99 mmol, 99%). MS (ESI): 263 $[M+H]^+$ Methyl 2-amino-3-(3-bromo-5-fluorophenyl)propanoate (AY): To a stirred solution of 2-amino-3-(3-bromo-5-fluorophenyl)propanoic acid (AX, 6.0 g, 22.99 mmol, 1.0 equiv.) in MeOH (140 mL) was added thionyl chloride (2.0 mL, 27.58 mmol, 1.2 equiv.) at −10° C. Then, solution was refluxed at 90° C. for 2 h and was monitored by TLC and LCMS. Upon completion of reaction, it was concentrated under reduce pressure and triturated with diethyl ether to obtain methyl 2-amino-3-(3-bromo-5-fluorophenyl)propanoate (AY, 5.0 g, 18.11 mmol, 79%) as a white solid. MS (ESI): 277 $[M+H]^+$ Methyl 3-(3-bromo-5-fluorophenyl)-2-((methoxycarbonyl)amino)propanoate (AZ): To stirred a solution of methyl 2-amino-3-(3-bromo-5-fluorophenyl)propanoate (AY, 5.0 g, 18.11 mmol, 1.0 equiv.) in satd. $NaHCO_3$ solution (100 mL), was added methyl chloroformate (2.79 mL, 36.23 mmol, 2.0 equiv.) at room temperature, reaction mixture was stirred at room temperature for 1 h and was monitored by TLC and LCMS. The reaction mixture was poured onto water (100 mL) and extracted with ethyl acetate (3×100 mL). The combined organic layer was dried over sodium sulfate and concentrated under reduce pressure to get methyl 3-(3-bromo-5-fluorophenyl)-2-((methoxycarbonyl)amino)propanoate (AZ, 4.8 g, 14.36 mmol, 79%). MS (ESI): 335 $[M+H]^+$ Dimethyl 6-bromo-8-fluoro-3,4-dihydroisoquinoline-2,3(1H)-dicarboxylate (BA): To a stirred solution of methyl 3-(3-bromo-5-fluorophenyl)-2-((methoxycarbonyl)amino) propionate (AZ, 4.8 g, 14.36 mmol, 1.0 equiv.) in AcOH: conc. $H2SO_4$ (14.4 mL: 4.8 mL) was added paraformaldehyde (2.1 g, 71.83 mmol, 5.0 equiv.) at room temperature. The reaction mixture was stirred at room temperature for 5 h and was monitored by TLC and LCMS. Upon completion, reaction mixture was poured into ice water (50 mL) and extracted with ethyl acetate (3×50 mL). The combined organic layer was dried over sodium sulfate and concentrated under reduce pressure to get crude compound which was purified by silica gel column chromatography using DCM:MeOH (9.5:5) to get dimethyl 6-bromo-8-fluoro-3,4-dihydroisoquinoline-2,3-(1H)-dicarboxylate (BA, 3.0 g, 8.67 mmol, 60%). MS (ESI): 346 $[M+H]^+$ Methyl-6-bromo-8-fluoro-3-(hydroxymethyl)-3,4-dihydroisoquinoline-2(1H)-carboxylate (BB): To a stirred solution of dimethyl 6-bromo-8-fluoro-3,4-dihydroisoquinoline-2,3(1H)-dicarboxylate (BA, 850 mg, 2.46 mmol, 1.0 equiv.) in THF (10 mL), was added $LiBH_4$ (64 mg, 2.95 mmol, 1.2 equiv.). The reaction mixture was stirred at room temperature for 16 h, completion of reaction was monitored by TLC and LCMS. Upon completion, reaction mixture was poured onto water (10 mL) and extracted with ethyl acetate (3×12 mL). The combined organic layer was dried over sodium sulfate and concentrated under reduce pressure to get crude compound which was purified by silica gel column chromatography using DCM:MeOH (9:1) to get methyl-6-bromo-8-fluoro-3-(hydroxymethyl)-3,4-dihydroisoquinoline-2(1H)-carboxylate (BB, 500 mg, 1.57 mmol, 64%). MS (ESI): 319 $[M+H]^+$ (6-bromo-8-fluoro-1,2,3,4-tetrahydroisoquinolin-3-yl) methanol (BC): A stirred solution of methyl 6-bromo-8-fluoro-3-(hydroxymethyl)-3,4-dihydroisoquinoline-2(1H)-carboxylate (BB, 2 g, 6.29 mmol, 1.0 equiv.) in MeOH: THF:2M LiOH solution (1:1:1) (20 mL) was prepared at room temperature. The resulting mixture was heated in microwave at 120° C. for 10 min. Completion of reaction was monitored by TLC, after completion of reaction added ethyl acetate (20 mL) and filtered, filtrate was dried over sodium sulfate and concentrated under reduce pressure to get (6-bromo-8 fluoro-1,2,3,4-tetrahydroisoquinolin-3-yl) methanol (BC, 1.5 g, 5.77 mmol, 92%). MS (ESI): 261 $[M+H]^+$ 1-(6-bromo-8-fluoro-3-(hydroxymethyl)-3,4-dihydroisoquinolin-2(1H)-yl)-2-chloroethan-1-one (BD): To a stirred solution of (6-bromo-1,2,3,4-tetrahydroisoquinolin-3-yl) methanol (BC, 1.5 g, 5.77 mmol, 1.0 equiv.) in DCM (75 mL), added TEA (0.8 mL, 5.77 mmol, 1.0 equiv.). Then, it was cooled to 0° C. and chloroacetyl chloride (0.45 mL, 5.77 mmol, 1.0 equiv.) was added dropwise. The reaction mixture was stirred at room temperature for 2 h. Upon completion of reaction, the reaction mixture was washed with dil. HCl (80 mL) and water (100 mL). The organic layer was dried over anhydrous sodium sulfate, filtered and concentration under reduce pressure to get crude compound which was purified by column chromatography using DCM:MeOH (9.5:5) to get 1-(6-bromo-8-fluoro3-(hydroxymethyl)-3,4-dihydroisoquinolin-2(1H)-yl)-2-chloroethan-1-one (BD, 1.2 g, 3.57 mmol, 62%) as a colourless semi-solid. MS (ESI): 337 $[M+H]^+$.

9-bromo-7-fluoro-1,6,11,11a-tetrahydro-[1,4]oxazino[4,3-b]isoquinolin-4(3H)-one (BE): To a stirred solution of 1-(6-bromo-8-fluoro-3-(hydroxymethyl)-3,4-dihydroisoquinolin-2(1H)-yl)-2-chloroethan-1-one (BD, 1.2 g, 3.57 mmol, 1.0 equiv.) in THF (60 mL), sodium hydride (55%) (0.47 g, 10.71 mmol, 3.0 equiv.) was added at 0° C. The reaction mixture was allowed to come to room temperature and stirred for 2 h. The excess reagent was decomposed by the addition of water and pH was adjusted to 5-6 with 3 N aqueous hydrochloric acid. The solution was extracted with ethyl acetate (3×70 mL). The organic layer was washed with brine solution (100 mL) and dried over Sodium sulfate. It was concentrated under reduce pressure to get crude compound which was purified by column chromatography using n-Hexane: Ethyl acetate (7:3) to get 9-bromo-7-fluoro-1,6,11,11a-tetrahydro-[1,4]-oxazino-[4,3-b]isoquinolin-4(3H)-one (BE, 0.8 g, 2.67 mmol, 75%) as an off-white solid. MS (ESI): 301 $[M+H]^+$.

9-bromo-7-fluoro-1,3,4,6,11,11a-hexahydro-[1,4]oxazino[4,3-b]isoquinoline (BF): To a stirred solution of 9-bromo-7-fluoro-1,6,11,11a-tetrahydro-[1,4]oxazino[4,3-b]isoquinolin-4(3H)-one (BE, 800 mg, 2.67 mmol, 1 equiv.) in THF (5.0 mL) was added $BH_3$-DMS (0.7 mL, 7.99 mmol, 3.0 equiv.) at 0° C. Then, reaction mixture was stirred at 80° C. for 16 h and completion of reaction monitored by TLC. Upon completion of reaction, methanol (8 mL) was added slowly at 0° C., followed by 6 N HCl solution (3 mL). The resulting mixture was refluxed at 80° C. for 16 h. The reaction mixture was concentrated under reduced pressure and triturated with diethylether to get 9-bromo-7-fluoro-1,3,4,6,11,11a-hexahydro-[1,4]oxazino[4,3-b]isoquinoline (BF, 800 mg, 2.79 mmol, 96%). MS (ESI): 286 $[M+H]^+$.

Methyl 7-fluoro-1,3,4,6,11,11a-hexahydro-[1,4]oxazino[4,3-b]isoquinoline-9-carboxylate (BG): To an autoclave containing a magnetic stirrer bar, 9-bromo-7-fluoro-1,3,4,6,11,11a-hexahydro-[1,4]oxazino[4,3-b]isoquinoline (BE, 600 mg, 2.097 mmol, 1.0 equiv.), methanol (15 mL) and KOAc (617 mg, 6.29 mmol, 3.0 equiv.) were added. The solution was degassed with $N_{2(g)}$ for 30 min. Then, $Pd(OAc)_2$ (94 mg, 0.4193 mmol, 0.2 equiv.) and DPPP (303 mg, 0.7338 mmol, 0.35 equiv.) were added. The reaction mixture was then heated at 110° C. under carbon monoxide pressure (350 psi) for 48 h and was monitored by TLC and LCMS. After completion of reaction, reaction mixture was filtered through cilite, washed with methanol (25 mL). The combined filtrate was concentrated under reduce pressure and the residue was purified by column chromatography using n-hexane: ethyl acetate (7:3) to get racemic methyl 7-fluoro-1,3,4,6,11,11a-hexahydro-[1,4]oxazino[4,3-b]isoquinoline-9-carboxylate (BG) which was separated by chiral prep-HPLC.

Subsequent steps for the preparation of 129 and 130 were performed in a manner analogous to that used for preparation of compound 93 and 94.

(R)-7-fluoro-N-hydroxy-1,3,4,6,11,11a-hexahydro-[1,4]oxazino[4,3-b]isoquinoline-9-carboxamide.TFA (129). MS (ESI): 267 $[M+H]^+$ (S)-7-fluoro-N-hydroxy-1,3,4,6,11,11a-hexahydro-[1,4]oxazino[4,3-b]isoquinoline-9-carboxamide.TFA (130) HPLC purity: 100%, MS (ESI): 267$[M+H]^+$ Although compounds 129 and 130 are designated as the (S) and (R) enantiomers as each enantiomer was prepared and isolated, the absolute stereochemistry of each is unknown.

The following compounds were prepared in a manner analogous to that used for preparing compound 129 and 130. Although compound pairs 131/132 and 133/134 are designated as the (S) and (R) enantiomers as each enantiomer was prepared and isolated, the absolute stereochemistry of each is unknown.

| | | |
|---|---|---|
| 131 | 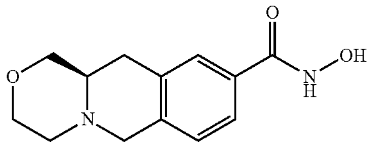 [SMILES: O=C(NO)c1ccc2c(c1)C[C@@H]1COCCN1C2]<br>((R)-N-hydroxy-1,3,4,6,11,11a-hexahydro-[1,4]oxazino[4,3-b] isoquinoline-9-carboxamide | MS (ESI): 249 $[M + H]^+$<br>Note:<br>absolute stereochemistry is unknown |
| 132 | 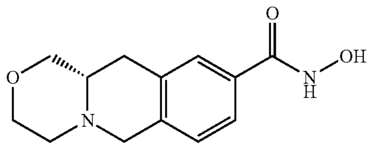 [SMILES: O=C(NO)c1ccc2c(c1)C[C@H]1COCCN1C2]<br>((S)-N-hydroxy-1,3,4,6,11,11a-hexahydro-[1,4]oxazino[4,3-b]isoquinoline-9-carboxamide | MS (ESI): 249 $[M + H]^+$<br>Note:<br>absolute stereochemistry is unknown |
| 133 | 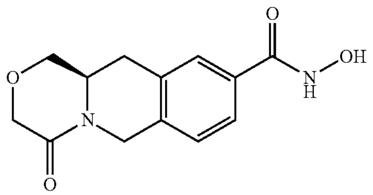 [SMILES: O=C(NO)c1ccc2c(c1)C[C@@H]1COCC(=O)N1C2]<br>(R)-N-hydroxy-4-oxo-1,3,4,6,11,11a-hexahydro-[1,4]oxazino[4,3-b]isoquinoline-9-carboxamide | $^1H$ NMR (400 MHz, DMSO-$d_6$) δ 7.58-7.56 (m, 2H), 7.29 (d, J = 8.2 Hz, 1H), 5.18 (d, J = 17.8 Hz, 1H), 4.24 (d, J = 17.8 Hz, 1H), 4.11 (d, J = 2.5 Hz, 2H), 4.08-4.04 (m, 1H), 3.78-3.73 (m, 2H), 2.94-2.81 (m, 2H).<br>MS (ESI): 263 $[M + H]^+$<br>Note:<br>absolute stereochemistry is unknown |
| 134 | 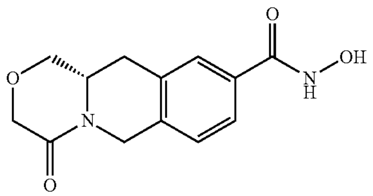 [SMILES: O=C(NO)c1ccc2c(c1)C[C@H]1COCC(=O)N1C2]<br>(S)-N-hydroxy-4-oxo-1,3,4,6,11,11a-hexahydro-[1,4]oxazino[4,3-b]isoquinoline-9-carboxamide | $^1H$ NMR (400 MHz, DMSO-$d_6$) δ 7.58-7.56 (m, 2H), 7.28 (d, J = 8.2 Hz, 1H), 5.18 (d, J = 17.7 Hz, 1H), 4.23 (d, J = 17.7 Hz, 1H), 4.11 (d, J = 2.5 Hz, 2H), 4.08-4.04 (m, 1H), 3.78-3.71 (m, 2H), 2.94-2.81 (m, 2H).<br>MS (ESI): 263 $[M + H]^+$<br>Note:<br>absolute stereochemistry is unknown |

(R)-6'-fluoro-N-hydroxy-1',5',10',10a'-tetrahydro-3'H-spiro[cyclohexane-1,2'-pyrrolo[1,2-b]isoquinoline]-8'-carboxamide (135) and (S)-6'-fluoro-N-hydroxy-1',5',10',10a'-tetrahydro-3'H-spiro[cyclohexane-1,2'-pyrrolo[1,2-b]isoquinoline]-8'-carboxamide (136)

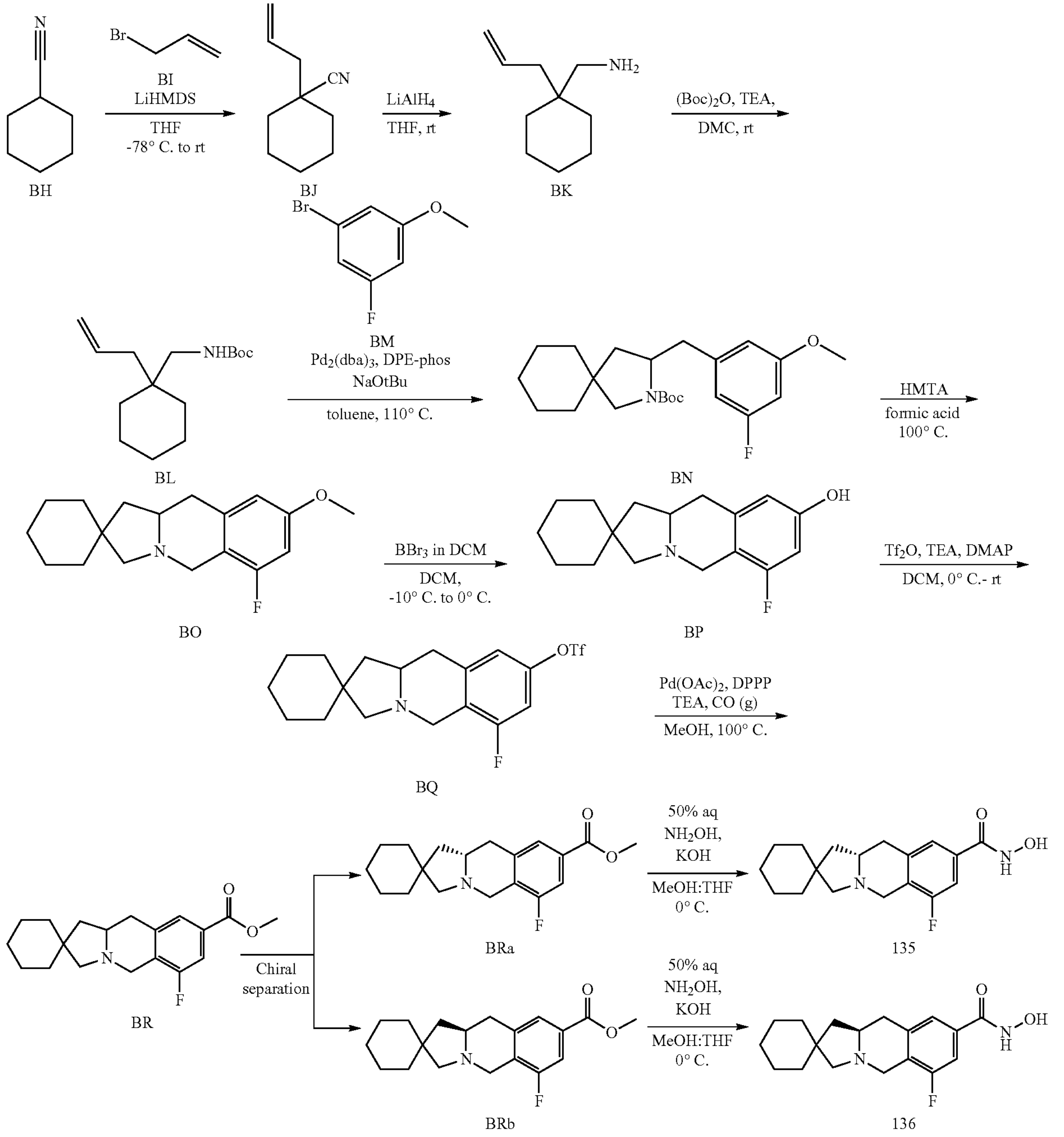

1-allylcyclohexane-1-carbonitrile (BJ): To a stirred solution of cyclohexanecarbonitrile (BH, 3.0 g, 27.50 mmol, 1.0 equiv.) in THF (30 mL) at −78° C., was added dropwise 1 M LiHMDS in hexane (30.25 mL, 30.25 mmol, 1.1 equiv.). The resulting reaction mixture was stirred for 30 min at same temperature. To this reaction mixture allyl bromide (BI, 8.32 g, 68.75 mmol, 2.5 equiv.) was added dropwise. The reaction mixture was stirred at room temperature for 18 h. After completion of the reaction, it was quenched by the addition of ice cold water (100 mL) and extracted with DCM (2×100 mL). The combined organic layer was dried over sodium sulfate and concentrated to give 1-allylcyclohexane-1-carbonitrile (BJ, 3.0 g, 20.10 mmol, 73%). $^1$H NMR (400 MHz, Chloroform-d) δ 5.93 (ddt, J=17.3, 10.3, 7.4 Hz, 1H), 5.33-5.13 (m, 2H), 2.32 (d, J=7.3 Hz, 2H), 2.06-1.92 (m, 2H), 1.78 (ddt, J=11.2, 7.3, 3.4 Hz, 2H), 1.70-1.59 (m, 2H), 1.36-1.14 (m, 2H).

(1-allylcyclohexyl)methanamine (BK): To a stirred solution of 1-allylcyclohexane-1-carbonitrile (BJ, 3.0 g, 20.10 mmol, 1.0 equiv.) in THF (30 mL) at 0° C., was added dropwise 1 M LiAlH$_4$ in THF (22.11 mL, 22.11 mmol, 1.1 equiv.). The resulting reaction mixture was stirred for 3 hours at room temperature. After completion of the reaction, the reaction mixture was quenched by the careful addition of ethyl acetate (50 mL) and water (10 mL). The resulting suspension was filtered through celite bed, washed with ethylacetate (50 mL) and concentrated under reduced pressure to give (1-allylcyclohexyl) methanamine (BK, 1.7 g, 11.10 mmol, 55%). $^1$H NMR (400 MHz, Chloroform-d) δ 5.86 (tt, J=17.0, 9.5 Hz, 1H), 5.25-4.90 (m, 2H), 2.56 (s, 2H), 2.24-2.01 (m, 2H), 1.44-1.11 (m, 10H).

tert-butyl ((1-allylcyclohexyl)methyl)carbamate (BL): To a solution of (1-allylcyclohexyl)methanamine (BK, 1.7 g, 11.10 mmol, 1.0 equiv.) in DCM (17 mL), were added TEA (4.64 mL, 33.30 mmol, 3.0 equiv.), DMAP (0.135 g, 1.11 mmol, 0.1 equiv.) and Di-tert-butyl dicarbonate (3.35 g, 27.75 mmol, 2.5 equiv.). The resulting reaction mixture was stirred at room temperature for 2 h. After completion of the reaction, the reaction mixture was diluted with DCM (100 mL), washed with water (100 mL). The organic layer was dried over sodium sulfate and concentrated under reduced pressure. The residue was purified by column chromatography eluting the product in 10% ethyl acetate in hexane to yield tert-butyl ((1-allylcyclohexyl)methyl)carbamate (BL, 1.6 g, 6.31 mmol, 57%) as sticky liquid. $^1$H NMR (400 MHz, Chloroform-d) δ 5.95-5.82 (m, 1H), 5.15-5.01 (m, 2H), 4.56 (s, 1H), 3.08 (d, J=6.5 Hz, 2H), 2.08 (d, J=7.4 Hz, 2H), 1.48 (s, 9H), 1.38-1.18 (m, 10H).

Subsequent steps for the preparation of 135 and 136 were performed in a manner analogous to that used for preparation of compound 119 and 120. Although compounds 135 and 136 are designated as the (S) and (R) enantiomers as each enantiomer was prepared and isolated, the absolute stereochemistry of each is unknown.

| | | |
|---|---|---|
| 135 | 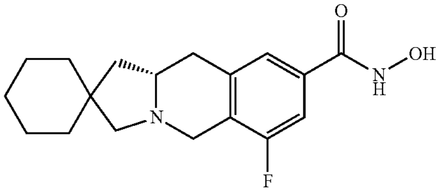 [SMILES: O=C(NO)c1cc(F)c2c(c1)C[C@H]1CC3(CCCCC3)CN1C2]<br>(R)-6'-fluoro-N -hydroxy-1',5',10',10a'-tetrahydro-3'H-spiro [cyclohexane-1,2'-pyrrolo[1,2-b]isoquinoline]-8'-carboxamide (135). | $^1$H NMR (400 MHz, DMSO-$d_6$) δ 9.19 (s, 2H), 7.40 (s, 1H), 7.31 (d, J = 10.4 Hz, 1H), 4.10 (d, J = 15.7 Hz, 1H), 3.15-3.07 (m, 2H), 2.96 (dd, J = 16.3, 3.4 Hz, 1H), 2.59 (m, 1H), 2.39 (m, 2H), 2.01 (d, J = 9.0 Hz, 1H), 1.94-1.86 (m, 1H), 1.44-1.36 (m, 9H), 1.29-1.24 (m, 1H). MS (ESI): 319 [M + H]$^+$<br>Note:<br>absolute stereochemistry is unknown |
| 136 | 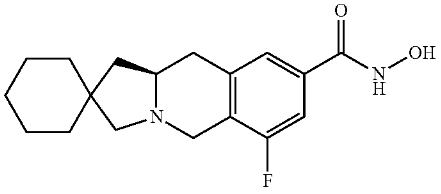 [SMILES: O=C(NO)c1cc(F)c2c(c1)C[C@@H]1CC3(CCCCC3)CN1C2]<br>(S)-6'-fluoro-N -hydroxy-1',5',10',10a'-tetrahydro-3'H-spiro [cyclohexane-1,2'-pyrrolo[1,2-b]isoquinoline]-8'-carboxamide (135). | $^1$H NMR (400 MHz, DMSO-$d_6$) δ 9.38 (s, 2H), 7.40 (s, 1H), 7.32 (d, J = 10.4 Hz, 1H), 4.11 (d, J = 15.7 Hz, 1H), 3.16-3.07 (m, 2H), 2.97 (dd, J = 16.4, 3.6 Hz, 1H), 2.61-2.59 (m, 1H), 2.43-2.39 (m, 2H), 2.01 (d, J = 9.0 Hz, 1H), 1.93-1.87 (m, 1H), 1.45-1.37 (m, 9H), 1.27 (dd, J = 12.5, 9.5 Hz, 1H). MS (ESI): 319 [M + H]$^+$<br>Note:<br>absolute stereochemistry is unknown |

The following compounds were prepared in a manner analogous to that used for preparation of compound 135. Although compounds 137 and 138 are designated as the (S) and (R) enantiomers as each enantiomer was prepared and isolated, the absolute stereochemistry of each is unknown.

| | | |
|---|---|---|
| 137 | 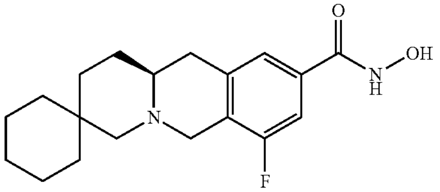 [SMILES: O=C(NO)c1cc(F)c2c(c1)C[C@@H]1CCC3(CCCCC3)CN1C2]<br>(S)-7'-fluoro-N-hydroxy-1',6',11',11a'-tetrahydro-2'H,4'H-spiro[cyclohexane-1,3'-pyrido[1,2-b]isoquinoline]-9'-carboxamide | $^1$H NMR (400 MHz, DMSO-$d_6$) δ 11.21 (s, 1H), 9.09 (s, 1H), 7.32 (d, J = 12.4 Hz, 2H), 3.79 (d, J = 15.8 Hz, 1H), 3.16 (d, J = 15.8 Hz, 1H), 2.84 (t, J = 11.3 Hz, 2H), 2.44-2.34 (m, 2H), 2.05 (s, 1H), 1.76-1.55 (m, 4H), 1.40 (d, J = 19.4 Hz, 8H), 1.20 (s, 2H), 1.07 (t, J = 13.1 Hz, 1H).<br>MS (ESI): 333 [M + H]$^+$<br>Note:<br>absolute stereochemistry is unknown |

-continued

| | | |
|---|---|---|
| 138 | 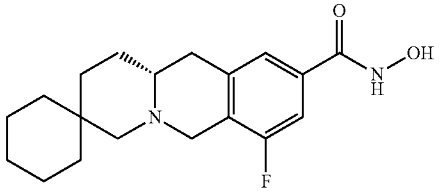 [SMILES: O=C(NO)c1cc(F)c2c(c1)C[C@H]1CCC3(CCCCC3)CN1C2] (R)-7'-fluoro-N-hydroxy-1',6',11',11a'-tetrahydro-2'H,4'H-spiro[cyclohexane-1,3'-pyrido[1,2-b]isoquinoline]-9'-carboxamide | $^1$H NMR (400 MHz, DMSO-$d_6$) δ 11.21 (s, 1H), 9.13 (s, 2H), 7.32 (d, J = 12.4 Hz, 2H), 3.80 (d, J = 15.8 Hz, 1H), 3.17 (d, J = 15.7 Hz, 1H), 2.84 (d, J = 17.2 Hz, 2H), 2.44-2.34 (m, 2H), 2.06 (s, 1H), 1.82-1.55 (m, 4H), 1.39 (s, 8H), 1.21 (s, 2H), 1.08 (s, 1H). MS (ESI): 333 [M + H]$^+$ Note: absolute stereochemistry is unknown |

(S)-11-fluoro-N-hydroxy-1,3,4,6,7,11b-hexahydro-2H-pyrido[2,1-a]isoquinoline-9-carboxamide (139) and (R)-11-fluoro-N-hydroxy-1,3,4,6,7,11b-hexahydro-2H-pyrido[2,1-a]isoquinoline-9-carboxamide (140)

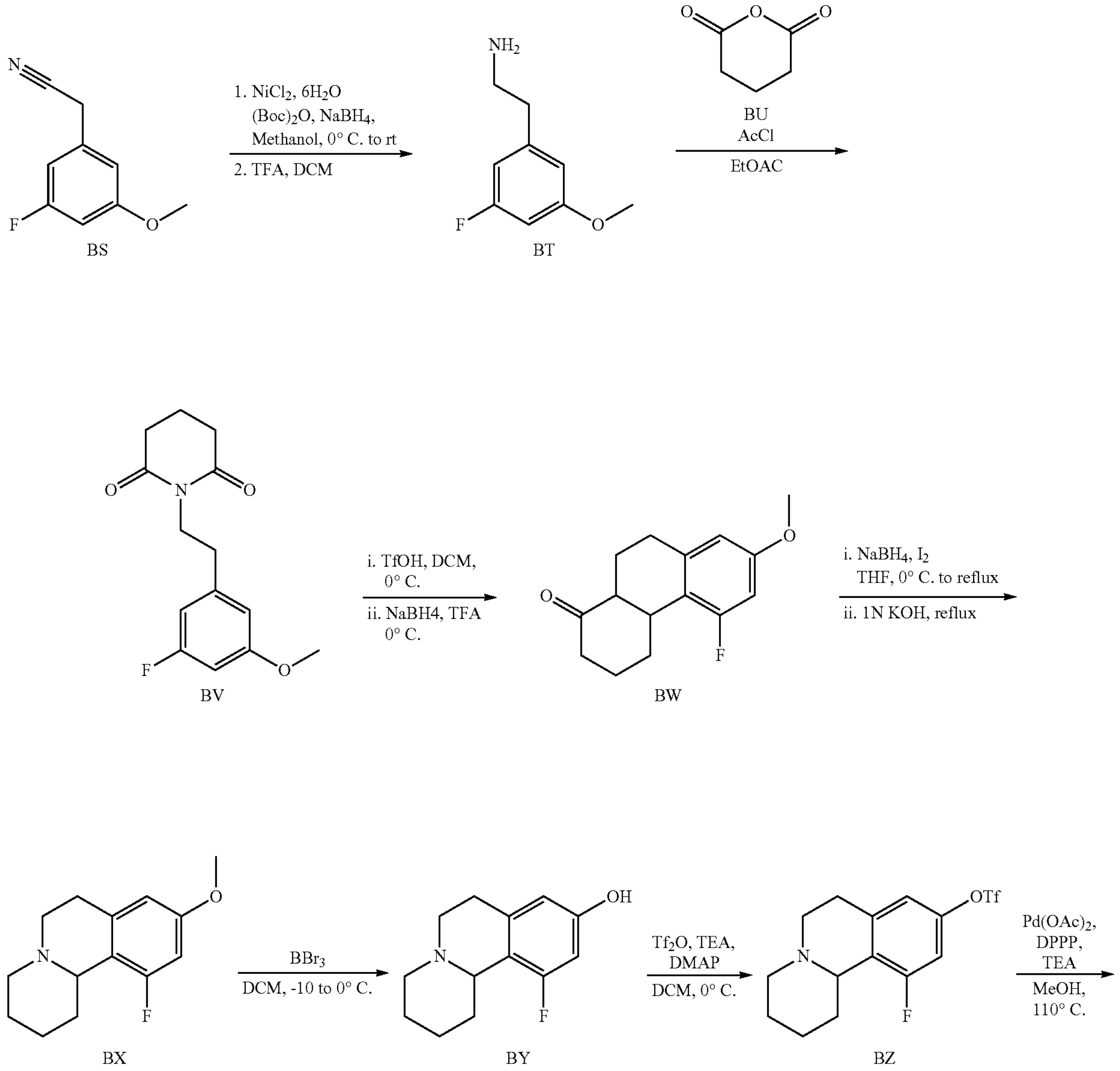

-continued

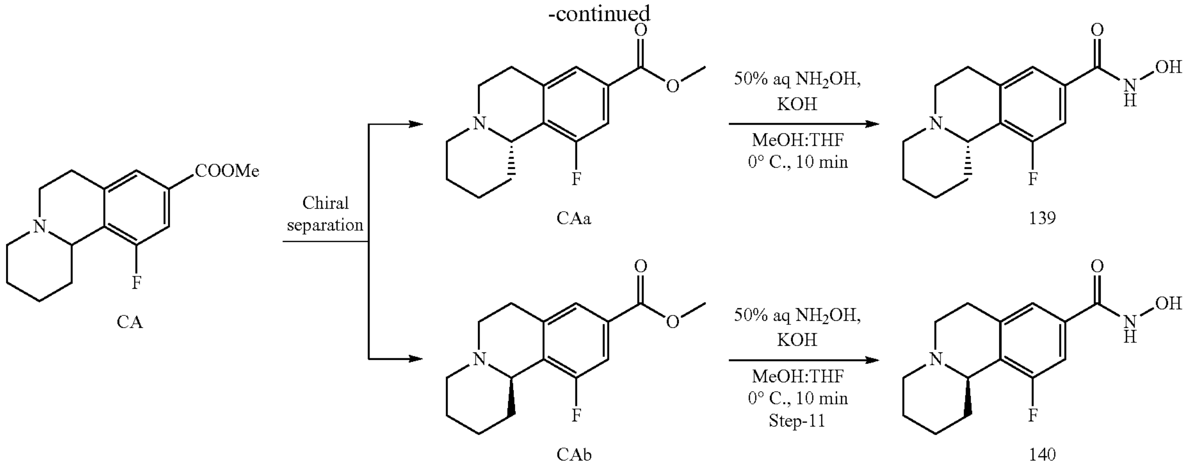

CA

CAa

139

CAb

140

2-(3-fluoro-5-methoxyphenyl)ethan-1-amine (BT): To a solution of 2-(3-fluoro-5-methoxyphenyl)acetonitrile (BS, 8.0 g, 48.46 mmol, 1.0 equiv.) in methanol (150 mL) were added the $NiCl_2 \cdot 6H_2O$ (5.76 g, 24.23 mmol, 0.5 equiv.), Boc anhydride (31.69 g, 0.145 mmol, 3.0 equiv.) and sodium borohydride (portion wise) (5.50 g, 0.145 mmol, 3.0 equiv.) at 0° C. The resulting mixture was stirred at room temperature for 1 h. The reaction was monitored by TLC. Reaction mixture was filtered through celite, washed with methanol (100 mL). The combined filtrate was evaporated and residue was dissolved in ethyl acetate (250 mL) insoluble particles were filtered through celite, washed with ethyl acetate (100 mL). The combined filtrate was evaporated to dryness. Residue was purified by Combi flash using 10% ethyl acetate in hexane as eluent. Pure fractions were evaporated to give tert-butyl (3-fluoro-5-methoxyphenethyl)carbamate (10.5 g, 39.02 mmol, 80%). MS (ESI): 270 $[M+H]^+$. To a solution of tert-butyl (3-fluoro-5-methoxyphenethyl)carbamate (10.5 g, 39.02 mmol, 1.0 equiv.) in DCM (80 mL) added the TFA (390.20 mmol, 29.65 mL, 10 equiv.) at 0° C. The resulting mixture was stirred at room temperature for 16 h. Reaction mixture was then poured in saturated bicarbonate solution (100 mL) and extracted with DCM (3×100 mL). Combined organics were dried over sodium sulfate and evaporated to give 2-(3-fluoro-5-methoxyphenyl)ethan-1-amine (BT, 4.5 g, 26.21 mmol, 67%). MS (ESI): 170 $[M+H]^+$.

1-(3-fluoro-5-methoxyphenethyl)piperidine-2,6-dione (BV): A solution of 2-(3-fluoro-5-methoxyphenyl)ethan-1-amine (BT, 2.2 g, 13.01 mmol, 1.0 equiv.) and glutaric anhydride (BU, 1.78 mmol, 1.2 equiv.) in dry Ethyl acetate (20 mL) was stirred at room temperature for 30 min. Ethyl acetate was removed under reduced pressure and the resulting residue is dissolved in toluene (20 mL). To this reaction mixture was added, acetyl chloride (5.1 g, 65.05 mmol, 5 equiv.) and refluxed for 1 h. The reaction mixture was washed with aqueous $Na_2CO_3$, and dried over anhydrous $Na_2SO_4$. The organic layer was concentrated under reduced pressure followed by silica gel column purification using 30% ethyl acetate in hexane as eluent to afford 1-(3-fluoro-5-methoxyphenethyl)piperidine-2,6-dione (BV, 2.7 g, 10.18 mmol, 78%) as colorless liquid. $^1H$ NMR (400 MHz, Chloroform-d) δ 6.74-6.39 (m, 3H), 4.09-3.90 (m, 2H), 3.81 (s, 3H), 2.78 (t, J=7.9 Hz, 2H), 2.66 (t, J=6.4 Hz, 4H), 1.95 (h, J=7.4, 6.6 Hz, 2H).

11-fluoro-9-methoxy-1,2,3,6,7,11b-hexahydro-4H-pyrido[2,1-a]isoquinolin-4-one (BW): A solution of 1-(3-fluoro-5-methoxyphenethyl)piperidine-2,6-dione (BV, 2.7 g, 10.18 mmol, 1.0 equiv.) in dry dichloromethane (30 mL) was cooled to 0° C. To this solution, was added TfOH (6.11 g, 40.73 mmol, 4.0 equiv.) with stirring. After 45 min, the contents were warmed to room temperature, and $NaBH_4$ (1.54 g, 40.73 mmol, 4.0 equiv.) was added followed by TFA (3.11 mL, 40.73 mmol, 4.0 equiv.). The resulting solution was stirred until the color disappeared. (Additional $NaBH_4$ and TFA were used if the color persisted for a long time). The reaction mixture was evaporated to dryness under reduced pressure. The solid residue was dissolved in dichloromethane (180 mL), and the insoluble material was removed by filtration. The filtrate was washed with saturated $NaHCO_3$ solution (250 mL). Organic layer was dried over anhydrous $Na_2SO_4$ and filtered. The solvent was evaporated under vacuum to give 11-fluoro-9-methoxy-1,2,3,6,7,11b-hexahydro-4H-pyrido[2,1-a]isoquinolin-4-one (BW, 2.54 g, 10.18 mmol, 100%). MS (ESI): 250.4 $[M+H]^+$.

11-fluoro-9-methoxy-1,3,4,6,7,11b-hexahydro-2H-pyrido[2,1-a]isoquinoline (BX): To a solution of 11-fluoro-9-methoxy-1,2,3,6,7,11b-hexahydro-4H-pyrido[2,1-a]isoquinolin-4-one (BW, 2.54 g, 10.18 mmol, 1.0 equiv.) in dry THF (25 mL) was added sodium borohydride (0.963 g, 25.45 mmol, 2.5 equiv.) at 0° C. A solution of iodine (0.661 g, 5.21 mmol, 0.51 equiv.) in Dry THF was added drop wise via syringe and stirred at same temperature for 2 h. The mixture was then refluxed for 24 h. The reaction was brought to room temperature and quenched with methanol (30 mL), after which the solvents were evaporated. The residue obtained was refluxed with 5 M KOH (50 mL) for 18 h and the reaction mixture was extracted with DCM (2×150 mL). The organic layer was dried over anhydrous $Na_2SO_4$ and evaporated to give (BX, 1.2 g, 5.10 mmol, 50%). MS (ESI): 222 $[M+H]^+$.

Subsequent steps for the preparation of 139 and 140 were performed in a manner analogous to that used for preparation of compound 119 and 120.

(S)-11-fluoro-N-hydroxy-1,3,4,6,7,11b-hexahydro-2H-pyrido[2,1-a]isoquinoline-9-carboxamide (139). $^1H$ NMR (400 MHz, DMSO-$d_6$) δ 11.19 (s, 1H), 9.11 (s, 1H), 7.37 (s, 1H), 7.29 (d, J=11.9 Hz, 1H), 3.55 (d, J=10.9 Hz, 1H), 3.29-3.11 (m, 1H), 3.03-2.75 (m, 3H), 2.73-2.60 (m, 2H), 2.11 (d, J=12.6 Hz, 1H), 1.80 (d, J=11.4 Hz, 1H), 1.49-1.33 (m, 4H). MS (ESI): 265 $[M+H]^+$.

(R)-11-fluoro-N-hydroxy-1,3,4,6,7,11b-hexahydro-2H-pyrido[2,1-a]isoquinoline-9-carboxamide (140). $^1$H NMR (400 MHz, DMSO-d6) δ 11.17 (s, 1H), 9.10 (s, 1H), 7.37 (s, 1H), 7.29 (d, J=12.2 Hz, 1H), 3.28-3.317 (m, 1H), 3.55 (d, J=10.4 Hz, 1H), 3.03-2.86 (m, 3H), 2.73-2.55 (m, 2H), 2.12 (d, J=12.5 Hz, 1H), 1.81 (d, J=11.5 Hz, 1H), 1.61-1.34 (m, 4H). MS (ESI): 265 [M+H]$^+$ Although compounds 139 and 140 are designated as the (S) and (R) enantiomers as each enantiomer was prepared and isolated, the absolute stereochemistry of each is unknown.

The following compounds were prepared in a manner analogous to that used for preparation of compound 93. Although compound pairs 143/144 and 145/146 are designated as the (S) and (R) enantiomers as each enantiomer was prepared and isolated, the absolute stereochemistry of each is unknown.

| | | |
|---|---|---|
| 143 | 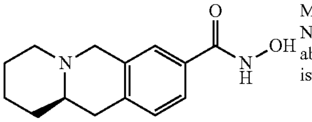 (R)-N-hydroxy-1,3,4,6,11,11a-hexahydro-2H-pyrido[1,2-b]isoquinoline-8-carboxamide | MS (ESI): 247 [M + H]$^+$ Note: absolute stereochemistry is unknown |
| 144 | 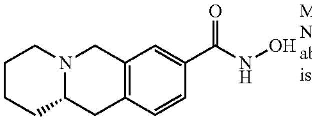 (S)-N-hydroxy-1,3,4,6,11,11a-hexahydro-2H-pyrido[1,2-b]isoquinoline-8-carboxamide | MS (ESI): 247 [M + H]$^+$ Note: absolute stereochemistry is unknown |
| 145 | 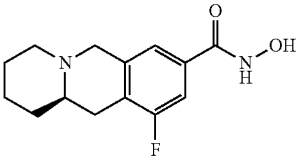 [SMILES: O=C(NO)c1cc(F)c2c(c1)CN1CCCC[C@@H]1C2] (R)-10-fluoro-N-hydroxy-1,3,4,6,11,11a-hexahydro-2H-pyrido[1,2-b]isoquinoline-8-carboxamide | $^1$H NMR (400 MHz, DMSO-d6) δ 11.15 (s, 1H), 9.08 (s, 1H), 7.33-7.30 (m, 2H), 3.83 (d, J = 16.0 Hz, 1H), 3.23 (d, J = 15.6 Hz, 1H), 2.98 (d, J = 11.6 Hz, 1H), 2.82 (d, J = 18.4 Hz, 1H), 2.41-2.34 (m, 1H), 2.20-2.08 (m, 1H), 2.01 (t, J = 12.0 Hz, 1H), 1.85-1.49 (m, 4H), 1.33-1.23 (m, 2H). MS (ESI): 265 [M + H]$^+$ Note: absolute stereochemistry is unknown. |
| 146 | 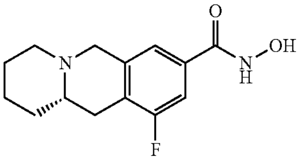 [SMILES: O=C(NO)c1cc(F)c2c(c1)CN1CCCC[C@H]1C2] (S)-10-fluoro-N-hydroxy-1,3,4,6,11,11a-hexahydro-2H-pyrido[1,2-b]isoquinoline-8-carboxamide | $^1$H NMR (400 MHz, DMSO-d6) δ 11.13 (s, 1H), 9.11 (s, 1H), 7.33-7.29 (m, 2H), 3.83 (d, J = 16.0 Hz, 1H), 3.23 (d, J = 15.6 Hz, 1H), 2.98 (d, J = 11.6 Hz, 1H), 2.82 (d, J = 18.4 Hz, 1H), 2.41-2.34 (m, 1H), 2.20-2.08 (m, 1H), 2.01 (t, J = 12.0 Hz, 1H), 1.85-1.49 (m, 4H), 1.33-1.23 (m, 2H). MS (ESI): 265 [M + H]$^+$ Note: absolute stereochemistry is unknown. |

The following compounds were prepared in a manner analogous to that used for preparing compound 79 and 80. Although compound pairs 148/149, 151/152, and 153/154 are designated as the (S) and (R) enantiomers as each enantiomer was prepared and isolated, the absolute stereochemistry of each is unknown.

| | | |
|---|---|---|
| 147 | 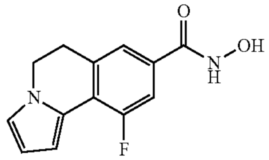 [SMILES: O=C(NO)c1cc(F)c2c(c1)CCn1cccc1-2] 10-fluoro-N-hydroxy-5,6-dihydropyrrolo[2,1-a]isoquinoline-8-carboxamide | $^1$H NMR (400 MHz, DMSO-$d_6$) δ 11.24 (s, 1H), 9.11 (s, 1H), 7.54-7.45 (m, 2H), 6.99 (s, 1H), 6.59 (s, 1H), 6.19 (s, 1H), 4.12 (t, J = 6.6 Hz, 2H), 3.10 (t, J = 6.6 Hz, 2H). MS (ESI): 247 [M + H]$^+$ |
| 148 | 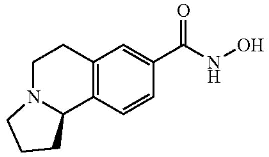 [SMILES: O=C(NO)c1ccc2c(c1)CCN1CCC[C@H]21] (R)-N-hydroxy-1,2,3,5,6,10b-hexahydropyrrolo[2,1-a]isoquinoline-8-carboxamide | MS (ESI): 233 [M + H]$^+$ Note: absolute stereochemistry is unknown |
| 149 | 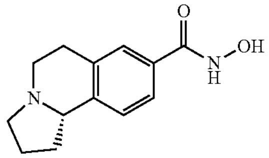 [SMILES: O=C(NO)c1ccc2c(c1)CCN1CCC[C@@H]21] (S)-N-hydroxy-1,2,3,5,6,10b-hexahydropyrrolo[2,1-a]isoquinoline-8-carboxamide | $^1$H NMR (400 MHz, DMSO-$d_6$) δ 11.10 (s, 1H), 8.95 (s, 1H), 7.52 (s, 2H), 7.14 (dd, J = 8.9, 4.1 Hz, 1H), 3.11-3.08 (m, 1H), 2.99 (s, 2H), 2.79 (d, J = 16.8 Hz, 2H), 2.61-2.51 (m, 1H), 2.45-2.38 (m, 2H), 1.80-1.76 (m, 2H), 1.55 (d, J = 10.8 Hz, 1H) MS (ESI): 233 [M + H]$^+$ Note: absolute stereochemistry is unknown |
| 150 | 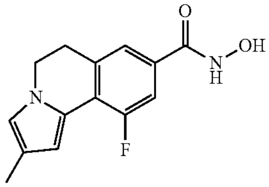 [SMILES: Cc1cc2n(c1)CCc1cc(C(=O)NO)cc(F)c1-2] 10-fluoro-N-hydroxy-2-methyl-5,6-dihydropyrrolo[2,1-a]isoquinoline-8-carboxamide | $^1$H NMR (400 MHz, DMSO-d6) δ 11.24 (s, 1H), 9.13 (s, 1H), 7.53-7.43 (m, 2H), 6.74 (d, J = 5.2 Hz, 1H), 6.43 (s, 1H), 4.04-3.99 (m, 2H), 3.11-2.97 (m, 2H), 2.05 (d, J = 5.2 Hz, 3H). MS (ESI): 261 [M + H]$^+$. |
| 151 | 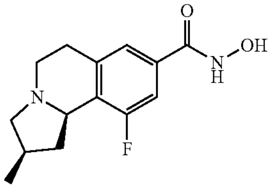 [SMILES: C[C@@H]1C[C@@H]2c3c(F)cc(C(=O)NO)cc3CCN2C1] (2R,10bR)-10-fluoro-N-hydroxy-2-methyl-1,2,3,5,6,10b-hexahydropyrrolo[2,1-a]isoquinoline-8-carboxamide | MS (ESI): 265 [M + H]$^+$ Note: absolute stereochemistry is unknown |

152
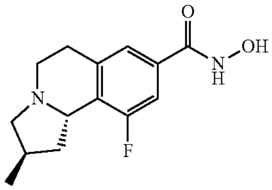 [SMILES: C[C@@H]1C[C@H]2c3c(F)cc(C(=O)NO)cc3CCN2C1]
(2R,10bS)-10-fluoro-N-hydroxy-2-methyl-1,2,3,5,6,10b-hexahydropyrrolo[2,1-a] isoquinoline-8-carboxamide

$^1$H NMR (400 MHz, DMSO-$d_6$) δ 11.21 (s, 1H), 9.11 (s, 1H), 7.39 (s, 1H), 7.31 (d, J = 10.8 Hz, 1H), 3.87 (t, J = 8.0 Hz, 1H), 3.10-3.06 (m, 1H), 2.95-2.91 (m, 1H), 2.74 (t, J = 8.4 Hz, 1H), 2.66-2.59 (m, 2H), 2.26 (m, 1H), 1.16 (q, J = 10.0 Hz, 1H), 0.99 (d, J = 6.8 Hz, 3H). MS (ESI): 265 $[M + H]^+$ Note: absolute stereochemistry is unknown 153
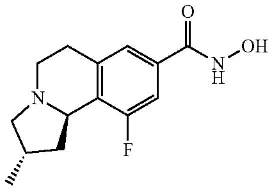 [SMILES: C[C@H]1C[C@@H]2c3c(F)cc(C(=O)NO)cc3CCN2C1]
(2S,10bR)-10-fluoro-N-hydroxy-2-methyl-1,2,3,5,6,10b-hexahydropyrrolo[2,1-a] isoquinoline-8-carboxamide MS (ESI): 265 $[M + H]^+$ Note: absolute stereochemistry is unknown 154
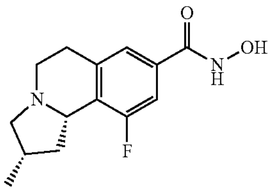 [SMILES: C[C@H]1C[C@H]2c3c(F)cc(C(=O)NO)cc3CCN2C1]
(2S,10bS)-10-fluoro-N-hydroxy-2-methyl-1,2,3,5,6,10b-hexahydropyrrolo[2,1-a] isoquinoline-8-carboxamide

$^1$H NMR (400 MHz, DMSO-$d_6$) δ 10.64 (s, 1H), 9.19 (s, 1H), 7.39 (s, 1H), 7.31 (d, J = 10.8 Hz, 1H), 3.76 (t, J = 8.0 Hz, 1H), 3.11 (t, J = 6.4 Hz, 1H), 2.98-2.91 (m, 2H), 2.78-2.72 (m, 1H), 2.66-2.59 (m, 1H), 2.29-2.20 (m, 2H), 1.95-1.81 (m, 2H), 0.89 (d, J = 6.8 Hz, 3H). MS (ESI): 265 $[M + H]^+$ Note: absolute stereochemistry is unknown 155
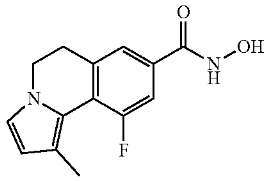 [SMILES: Cc1ccn2c1-c1c(F)cc(C(=O)NO)cc1CC2]
10-fluoro-N-hydroxy-1-methyl-5,6-dihydropyrrolo[2,1-a] isoquinoline-8-carboxamide

$^1$H NMR (400 MHz, DMSO-$d_6$) δ 11.24 (s, 1H), 9.10 (s, 1H), 7.55 (s, 1H), 7.47 (d, J = 12.0 Hz, 1H), 6.90 (d, J = 2.8 Hz, 1H), 5.98 (d, J = 2.8 Hz, 1H), 4.01 (t, J = 6.0 Hz, 2H), 2.96 (t, J = 6.0 Hz, 2H), 2.16 (d, J = 8.0 Hz, 3H). MS (ESI): 261 $[M + H]^+$.

(3R,10bR)-10-fluoro-N-hydroxy-3-methyl-1,2,3,5,6,10b-hexahydropyrrolo[2,1-a]isoquinoline-8-carboxamide (156) and (3S,10bS)-10-fluoro-N-hydroxy-3-methyl-1,2,3,5,6,10b-hexahydropyrrolo[2,1-a] isoquinoline-8-carboxamide (157)

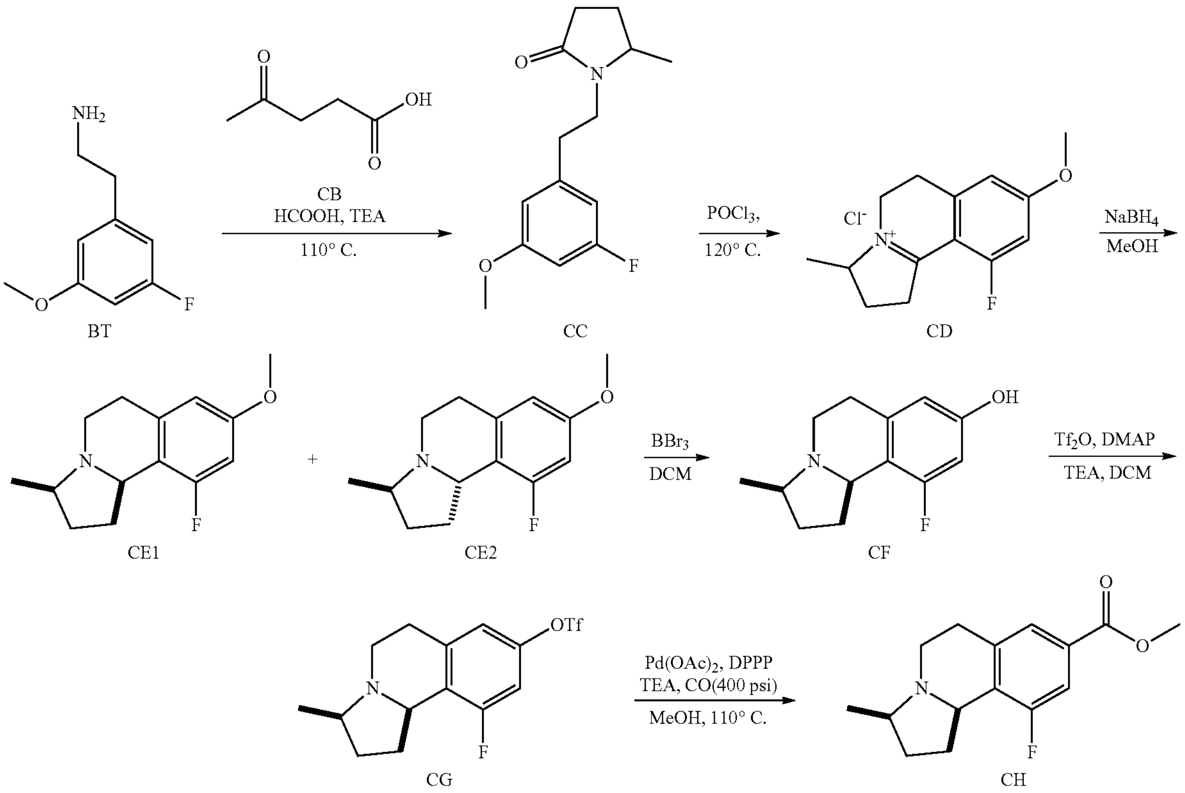

-continued

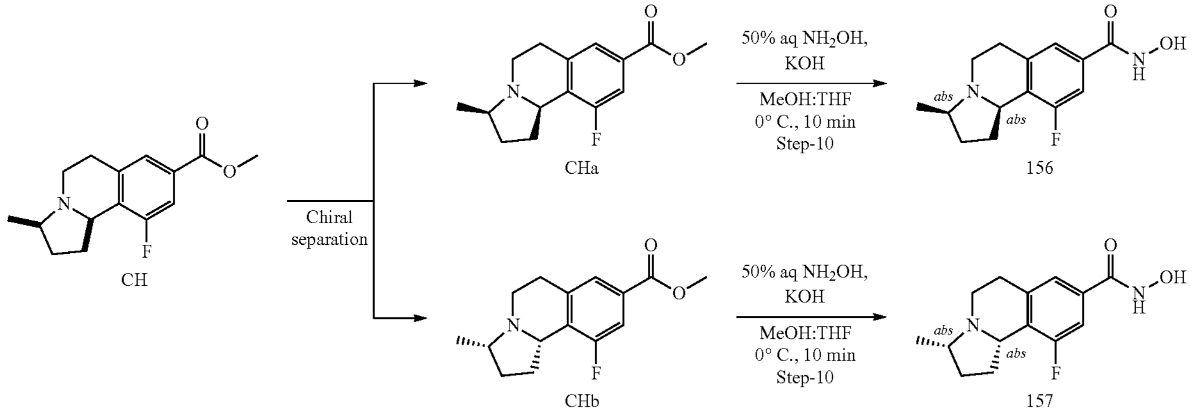

CH

CHa

CHb

156

157

1-(3-fluoro-5-methoxyphenethyl)-5-methylpyrrolidin-2-one (CC): 2-(3-fluoro-5-methoxyphenyl) ethan-1-amine (BT, 7.0 g, 41.38 mmol, 1.5 equiv.) and levulinic acid (CB, 3.2 g, 27.58 mmol, 1.0 equiv.) were placed in a pressure tube. To the mixture was injected DMSO (78 mL), formic acid (5.2 mL, 137.93 mmol, 5.0 equiv.), and $NEt_3$ (3.84 mL, 27.58 mmol, 1.0 equiv.). The mixture was bubbled with argon for 15 min, and then stirred at 100° C. for 5 h. After cooling to room temperature, the reaction was basified with saturated NaOH solution (150 mL) and extracted with DCM (3×100 mL). The organic layers were washed with brine (100 mL), and dried over $Na_2SO_4$. The organic solvent was removed under reduced pressure and the product was purified by flash chromatography using 30% ethyl acetate with 0.1% triethylamine as elute. Pure fraction was evaporated to give 1-(3-fluoro-5-methoxyphenethyl)-5-methylpyrrolidin-2-one (CC, 6.0 g, 23.89 mmol, 87%). MS (ESI): 252 $[M+H]^+$ 10-fluoro-8-methoxy-3-methyl-2,3,5,6-tetrahydro-1H-pyrrolo[2,1-a]isoquinolin-4-ium (CD): To a solution of 1-(3-fluoro-5-methoxyphenethyl)-5-methylpyrrolidin-2-one (CC, 6.0 g, 23.89 mmol, 1.0 equiv.) in acetonitrile (240 mL) was added phosphorus oxychloride (11.16 mL, 119.46 mmol, 5.0 equiv.) at 0° C. The combined reaction mixture was heated reflux at 120° C. for 3 h. The completion of reaction was confirmed by TLC and LCMS. Reaction was cooled to room temperature. Solvent was evaporated to dryness. The residue was washed with diethyl ether (50 mL) to give 10-fluoro-8-methoxy-3-methyl-2,3,5,6-tetrahydro-1H-pyrrolo[2,1-a] isoquinolin-4-ium (CD, 6.0 g, 25.62 mmol). MS (ESI): 234 $[M]^+$.

10-fluoro-8-methoxy-3-methyl-1,2,3,5,6,10b-hexahydropyrrolo[2,1-a]isoquinoline (CE1) and 10-fluoro-8-methoxy-3-methyl-1,2,3,5,6,10b-hexahydropyrrolo[2,1-a]isoquinoline (CE2): To a solution of 10-fluoro-8-methoxy-3-methyl-2,3,5,6-tetrahydro-1H-pyrrolo[2,1-a]isoquinolin-4-ium (CD, 6.0 g, 25.62 mmol, 1 equiv.) in methanol (240 mL) was added $NaBH_4$ (2.42 g, 64.10 mmol, 2.5 equiv.) at 0° C. The reaction mixture was stirred for 3 h at room temperature. The completion of reaction was confirmed by TLC. Methanol was evaporated to dryness and water (100 mL) was added. The resulting emulsion was extracted with ethyl acetate (2×100 mL). The organic layer was separated, dried over $Na_2SO_4$ and evaporated. The residue was purified by Combi flash. The product was eluted at 10% ethyl acetate with 0.1% TEA in hexane. The diastereomers were further separated by prep HPLC to afford 10-fluoro-8-methoxy-3-methyl-1,2,3,5,6,10b-hexahydropyrrolo[2,1-a]isoquinoline (CE1, 0.65 g, 2.76 mmol, 12%) as oil. $^1H$ NMR (400 MHz, Chloroform-d) δ 6.57-6.33 (m, 2H), 3.75 (d, J=4.1 Hz, 3H), 3.36-2.97 (m, 3H), 2.84 (d, J=16.6 Hz, 1H), 2.53-2.35 (m, 2H), 2.29 (q, J=6.8 Hz, 1H), 2.04 (d, J=8.0 Hz, 2H), 1.80-1.68 (m, 1H), 1.50 (tdd, J=12.2, 8.6, 3.7 Hz, 1H), 1.20 (d, J=6.1 Hz, 4H), MS (ESI): 236 $[M+H]^+$. and 10-fluoro-8-methoxy-3-methyl-1,2,3,5,6,10b-hexahydropyrrolo[2,1-a]isoquinoline (CE2, 0.2 g, 0.85 mmol, 4%). $^1H$ NMR (400 MHz, DMSO-$d_6$) δ 6.64 (dd, J=12.2, 2.5 Hz, 1H), 6.57 (d, J=2.5 Hz, 1H), 4.35 (t, J=7.7 Hz, 1H), 3.73 (s, 3H), 3.05 (q, J=10.1, 9.2 Hz, 2H), 2.88-2.72 (m, 2H), 2.43-2.34 (m, 1H), 1.94 (dt, J=9.9, 7.1 Hz, 1H), 1.53 (q, J=11.2, 10.2 Hz, 1H), 1.38 (p, J=8.8 Hz, 1H), 1.10 (d, J=6.1 Hz, 3H), MS (ESI): 236 $[M+H]^+$. The stereochemistry of CE1 was confirmed by NOE experiment.

Subsequent steps for the preparation of 156, 157, 158 and 159 were performed in a manner analogous to that used for preparation of compound 119 and 120. Although compound pairs 156/157 and 158/159 are designated as the (S) and (R) enantiomers as each enantiomer was prepared and isolated, the absolute stereochemistry of each is unknown.

156
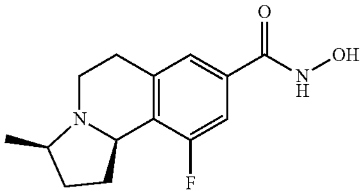 [SMILES: C[C@@H]1CC[C@@H]2c3c(F)cc(C(=O)NO)cc3CCN12]
(3R,10bR)-10-fluoro-N-hydroxy-3-methyl-1,2,3,5,6,10b-hexahydropyrrolo[2,1-a]isoquinoline-8-carboxamide $^1$H NMR (400 MHz, DMSO-$d_6$) δ 11.23 (s, 1H), 9.11 (s, 1H), 7.41 (s, 1H), 7.30 (d, J = 11.2 Hz, 1H), 3.27-3.17 (m, 2H), 3.00-2.97 (m, 1H), 2.88-2.83 (m, 1H), 2.40-2.23 (m, 3H), 2.00 (s, 1H), 1.59-1.54 (m, 1H), 1.37-1.35 (m, 1H), 1.12 (d, J = 5.9 Hz, 3H).
MS (ESI): 265 $[M + H]^+$
Note:
absolute stereo chemistry is unknown 157
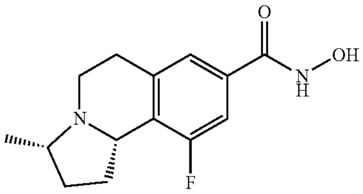 [SMILES: C[C@H]1CC[C@H]2c3c(F)cc(C(=O)NO)cc3CCN12]
(3S,10bS)-10-fluoro-N-hydroxy-3-methyl-1,2,3,5,6,10b-hexahydropyrrolo[2,1-a]isoquinoline-8-carboxamide $^1$H NMR (400 MHz, DMSO-$d_6$) δ 11.17 (s, 1H), 9.11 (s, 1H), 7.41-7.28 (m, 2H), 3.27-3.17 (m, 2H), 3.00-2.97 (m, 1H), 2.88-2.83 (m, 1H), 2.40-2.21 (m, 3H), 2.00 (s, 1H), 1.59-1.56 (m, 1H), 1.37-1.34 (m, 1H), 1.11 (t, J = 7.1 Hz, 3H).
MS (ESI): 265 $[M + H]^+$
Note:
absolute stereo chemistry is unknown 158
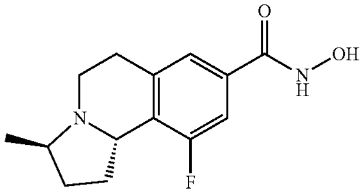 [SMILES: C[C@@H]1CC[C@H]2c3c(F)cc(C(=O)NO)cc3CCN12]
(3R,10bS)-10-fluoro-N-hydroxy-3-methyl-1,2,3,5,6,10b-hexahydropyrrolo[2,1-a]isoquinoline-8-carboxamide $^1$H NMR (400 MHz, DMSO-$d_6$) δ 7.38 (s, 1H), 7.31 (d, J = 10.9 Hz, 1H), 4.39 (t, J = 7.7 Hz, 1H), 3.10-3.03 (m, 1H), 2.94 (q, J = 6.6 Hz, 1H), 2.82-2.73 (m, 2H), 2.60 (m, 2H), 2.42-2.38 (m, 1H), 1.96-1.93-1.86 (m, 1H), 1.49 (p, J = 8.6 Hz, 1H), 1.42-1.30 (m, 1H), 1.07 (d, J = 6.0 Hz, 3H).
MS (ESI): 265 $[M + H]^+$
Note:
absolute stereo chemistry is unknown 159
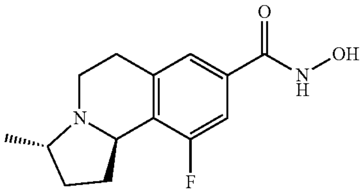 [SMILES: C[C@H]1CC[C@@H]2c3c(F)cc(C(=O)NO)cc3CCN21]
(3S,10bR)-10-fluoro-N-hydroxy-3-methyl-1,2,3,5,6,10b-hexahydropyrrolo[2,1-a]isoquinoline-8-carboxamide $^1$H NMR (400 MHz, DMSO-$d_6$) δ 9.13 (s, 1H), 7.38 (s, 1H), 7.32 (d, J = 10.8 Hz, 1H), 4.39 (t, J = 7.8 Hz, 1H), 3.06 (d, J = 11.1 Hz, 1H), 2.94 (d, J = 7.2 Hz, 1H), 2.82-2.73 (m, 2H), 2.61 (m, 2H), 2.46-2.38 (m, 1H), 1.90 (m, 1H), 1.53-1.48 (m, 1H), 1.40-1.33 (m, 1H), 1.07 (d, J = 6.0 Hz, 3H).
MS (ESI): 265 $[M + H]^+$
Note:
absolute stereo chemistry is unknown (S)—N-hydroxy-5-methyl-1,2,3,5,6,10b-hexahydro-pyrrolo[2,1-a]phthalazine-8-carboxamide (160) and (R)—N-hydroxy-5-methyl-1,2,3,5,6,10b-hexahydro-pyrrolo[2,1-a]phthalazine-8-carboxamide (161)
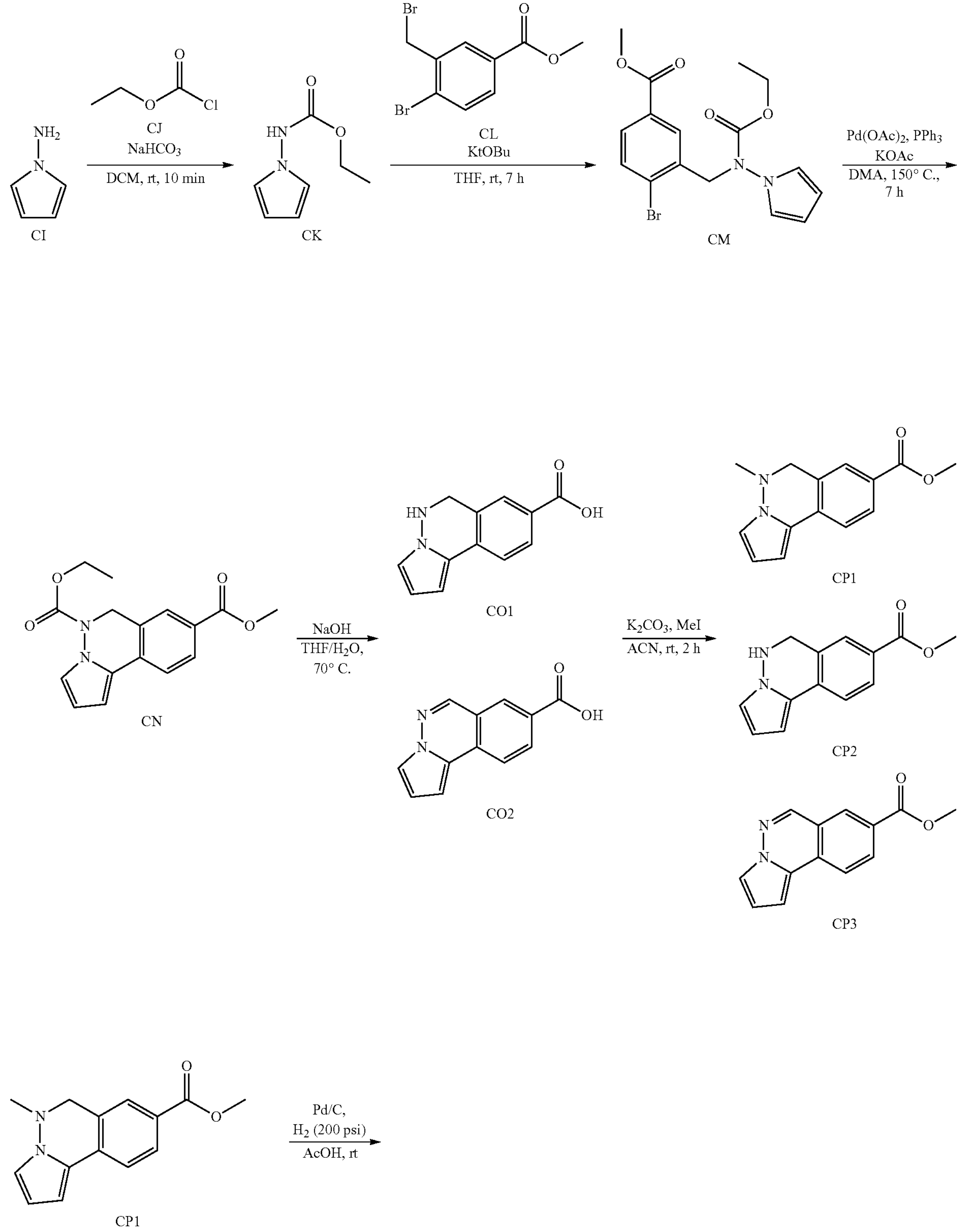

-continued

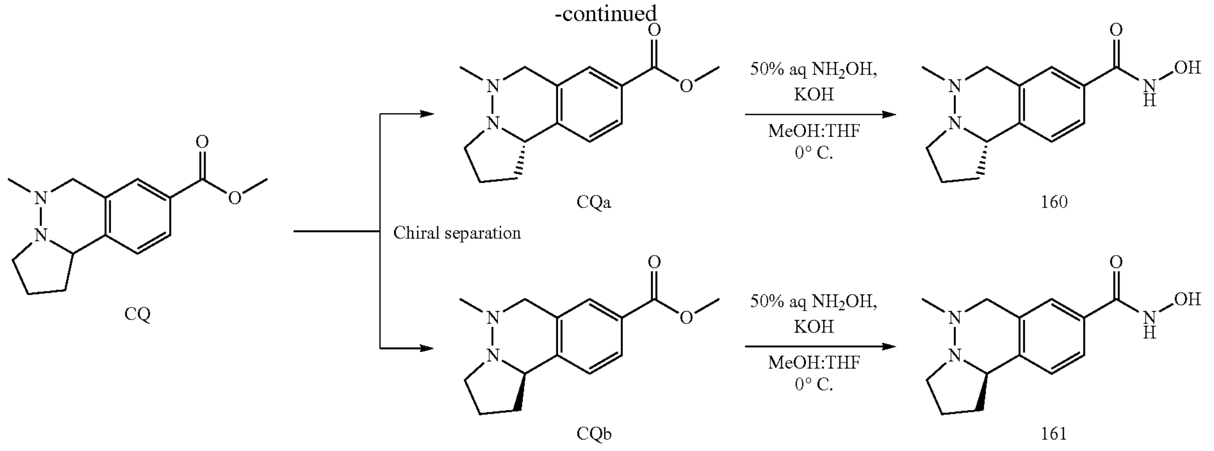

CQ CQa 160 CQb 161

Methyl 4-bromo-3-(bromomethyl)benzoate (CK): To a stirred solution of 1H-pyrrol-1-amine (CI, 3 g, 36.54 mmol, 1.0 equiv.) in 25% $NaHCO_3$ solution (5 mL), ethyl chloroformate (CJ, 6.96 mL, 73.074 mmol, 2.0 equiv.) was added at room temperature. The reaction mixture was stirred at room temperature for 10 min and was monitored by TLC. The reaction was diluted with water (20 mL) and extracted with EtOAc (3×25 mL). The combined organic layers were dried over anhydrous sodium sulfate and was concentrated under reduced pressure to obtain the crude material ethyl (1H-pyrrol-1-yl)carbamate (CK, 3.2 g, 20.756 mmol, 85%). MS (ESI): 155 $[M+H]^+$.

Methyl 4-bromo-3-(((ethoxycarbonyl)(1H-pyrrol-1-yl)amino)methyl)benzoate (CM): To a solution of (CK, 0.5 g, 3.24 mmol, 1.0 equiv.) in THF (25 mL), KOtBu (0.40 g, 3.5674 mmol, 1.1 equiv.) was added and the mixture was stirred at 5° C. for one hour. Following which, CL (0.99 g, 3.2431 mmol, 1.0 equiv.) was added and stirred at 5° C. for 1 h and at room temperature for 7 h. The mixture was poured onto ice-cold water (25 mL) and stirred for five minutes and extracted with ethyl acetate (2×25 mL). The organic layer was dried over sodium sulfate, concentrated under reduced pressure and purified by silica gel column chromatography using EtOAc: hexanes (3:7) to obtain methyl 4-bromo-3-(((ethoxycarbonyl)(1H-pyrrol-1-yl)amino)methyl)benzoate (CM, 1.1 g, 2.885 mmol, 89%). MS (ESI): 382 $[M+H]^+$.

5-Ethyl 8-methyl pyrrolo[2,1-a]phthalazine-5,8(6H)-dicarboxylate (CN): To a solution of methyl 4-bromo-3-(((ethoxycarbonyl)(1H-pyrrol-1-yl)amino)methyl)benzoate (CM, 1.1 g, 2.88 mmol, 1.0 equiv.) in DMA (10 mL) were added, triphenyl phosphine (0.151 g, 0.5774 mmol, 0.2 equiv.), $Pd(OAc)_2$ (0.064 g, 0.2887 mmol, 0.1 equiv.) and potassium acetate (0.566 g, 5.7742 mmol, 2 equiv.) at room temperature under nitrogen. The reaction was stirred at 150° C. for 7 h, then quenched with water (30 mL) and extracted with ethyl acetate (3×20 mL). The combined organic phases were washed with brine (20 mL), dried over anhydrous sodium sulfate, filtered and concentrated in vacuo. The residue was purified by a flash silica gel column chromatography EtOAc:Hexane (5:5) to give 5-ethyl 8-methyl pyrrolo[2,1-a]phthalazine-5,8(6H)-dicarboxylate as off white solid (CN, 0.812 g, 2.71 mmol, 93%). MS (ESI): 301 $[M+H]^+$.

5,6-Dihydropyrrolo[2,1-a]phthalazine-8-carboxylic acid (CO1) and pyrrolo[2,1-a]phthalazine-8-carboxylic acid (CO2): To a stirred solution of 5-ethyl 8-methyl pyrrolo[2,1-a]phthalazine-5,8(6H)-dicarboxylate (CN, 0.812 g, 2.70 mmol, 1.0 equiv.) in THF and water (3 mL) sodium hydroxide (0.270 g, 6.76 mmol, 2.5 equiv.) was added at room temperature. The reaction mixture was heated to 90° C. and reaction was monitored by TLC. After completion of reaction, it was acidified using dilute HCl to obtain the product CO1, CO2 as precipitates which were dried under vacuum. The formation of products was confirmed by LCMS and used the mixture of compounds as such for next step without further purification. CO2: MS (ESI): 213 $[M+H]^+$, CO1: MS (ESI): 215 $[M+H]^+$ Methyl 5,6-dihydropyrrolo[2,1-a]phthalazine-8-carboxylate (CP1): To a stirred solution of mixture (CO1 & CO2, 200 mg, 0.93 mmol, 1 equiv.) in ACN (2 mL), $K_2CO_3$ (0.516 g, 3.74 mmol, 4.0 equiv.) and MeI (0.397 mg, 2.7969 mmol, 3 equiv.) were added dropwise at room temperature under nitrogen. The reaction was stirred at room temperature for 2 h and was monitored using TLC. Upon completion of reaction, it was diluted with water (30 mL) and extracted with ethyl acetate (3×20 mL). The combined organic phase was washed with brine (20 mL), dried over anhydrous sodium sulfate, filtered and concentrated in vacuum. The residue was purified by a flash silica gel column chromatography EtOAc:Hexane (2.5:7.5) to give CP1 (32 mg, 0.1322 mmol, 14%), CP2 (43 mg, 0.1842 mmol, 20%), CP3 (39 mg, 0.1725 mmol, 18%). CP1: MS (ESI): 243 $[M+H]^+$, CP2: MS (ESI): 229 $[M+H]^+$, CP3: MS (ESI): 227$[M+H]^+$ Methyl 5-methyl-1,2,3,5,6,10b-hexahydropyrrolo[2,1-a]phthalazine-8-carboxylate (CQ): To an oven-dried autoclave, methyl 5-methyl-5,6-dihydropyrrolo[2,1-a]phthalazine-8-carboxylate (CP1, 0.054 g, 0.222 mmol, 1 equiv.), AcOH (3 mL) and Pd/C (0.05 g) were added. The autoclave was pressurized with $H_{2(g)}$ (100 psi) and stirred at room temperature for 48 h and was monitored by TLC. After completion of the reaction, the reaction mixture was filtered through celite and washed with THF (20 mL). The filtrate obtained was concentrated under reduced pressure and purified by Prep. HPLC to obtain greenish oil (CQ, 32 mg, 58%). MS (ESI): 247 $[M+H]^+$ Subsequent steps for the preparation of 160, 161, 162 and 163 were performed in a manner analogous to that used for preparation of compound 79. Although compounds 160 and 161 are designated as the (S) and (R) enantiomers as each enantiomer was prepared and isolated, the absolute stereochemistry of each is unknown.

-continued

160

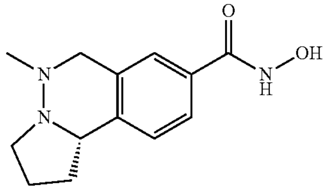 [SMILES: CN1Cc2cc(C(=O)NO)ccc2[C@@H]2CCCN21]

MS (ESI): 248 [M + H]+
Note: absolute stereochemistry is unknown (S)-N-Hydroxy-5-methyl-1,2,3,5,6,10b-hexahydropyrrolo[2,1-a]phthalazine-8-carboxamide

161

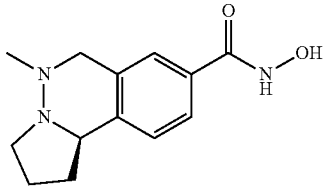

MS (ESI): 248 [M + H]+
Note: absolute stereochemistry is unknown (R)-N-Hydroxy-5-methyl-1,2,3,5,6,10b-hexahydropyrrolo[2,1-a]phthalazine-8-carboxamide

162

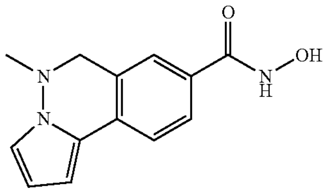 [SMILES: CN1Cc2cc(C(=O)NO)ccc2-c2cccn21]

MS (ESI): 244 [M + H]+

N-hydroxy-5-methyl-5,6-dihydropyrrolo[2,1-a]phthalazine-8-carboxamide

163

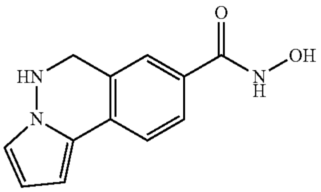 [SMILES: O=C(NO)c1ccc2c(c1)CNn1cccc1-2]

$^1$H NMR (400 MHz, DMSO-$d_6$) δ 7.67-7.64 (m, 2H), 7.56 (d, J = 8.0 Hz, 1H), 6.87 (t, J = 2.2 Hz, 1H), 6.57 (dd, J = 4.1, 1.7 Hz, 1H), 6.37 (t, J = 8.3 Hz, 1H), 6.02 (t, J = 3.2 Hz, 1H), 4.13 (d, J = 8.4 Hz, 2H). MS (ESI): 230 [M + H]+.

N-hydroxy-5,6-dihydropyrrolo[2,1-a]phthalazine-8-carboxamide

(R)—N-hydroxy-2,3,5,9b-tetrahydro-1H-pyrrolo[2,1-a]isoindole-7-carboxamide (164) and (S)—N-hydroxy-2,3,5,9b-tetrahydro-1H-pyrrolo[2,1-a]isoindole-7-carboxamide (165)

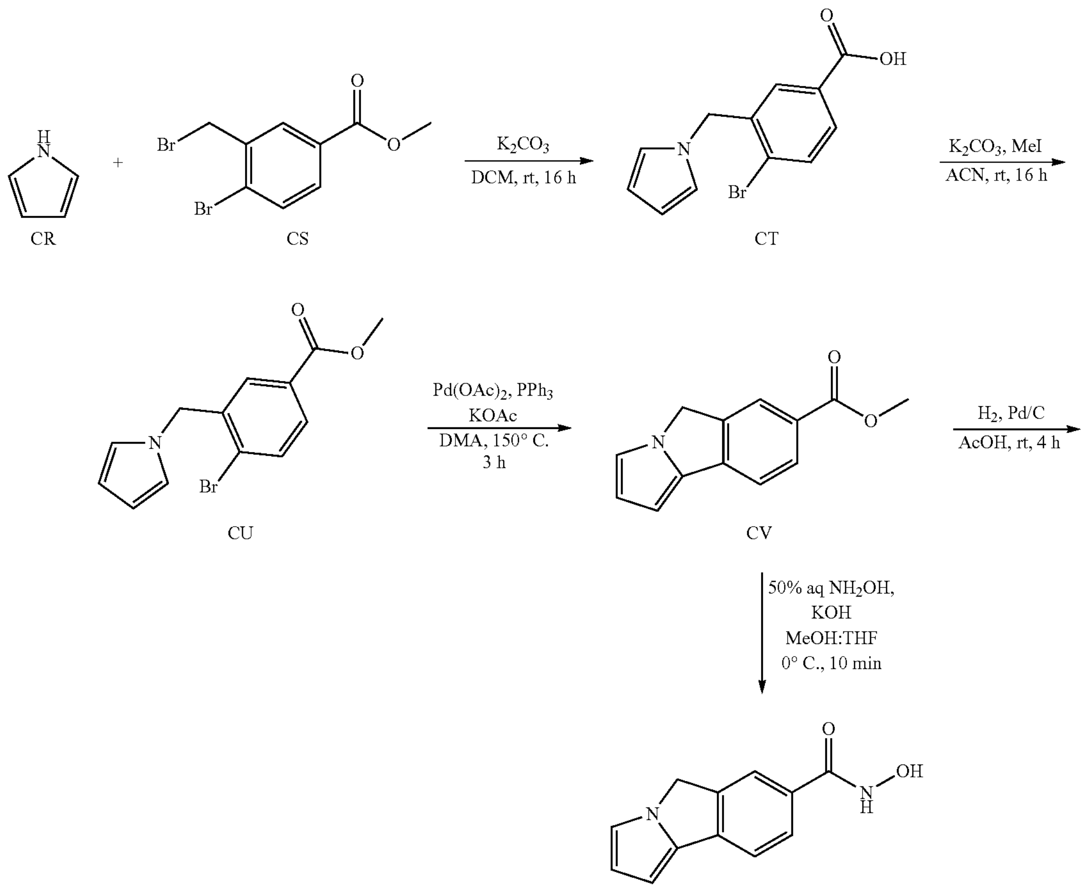

CR CS CT CU CV 166

-continued

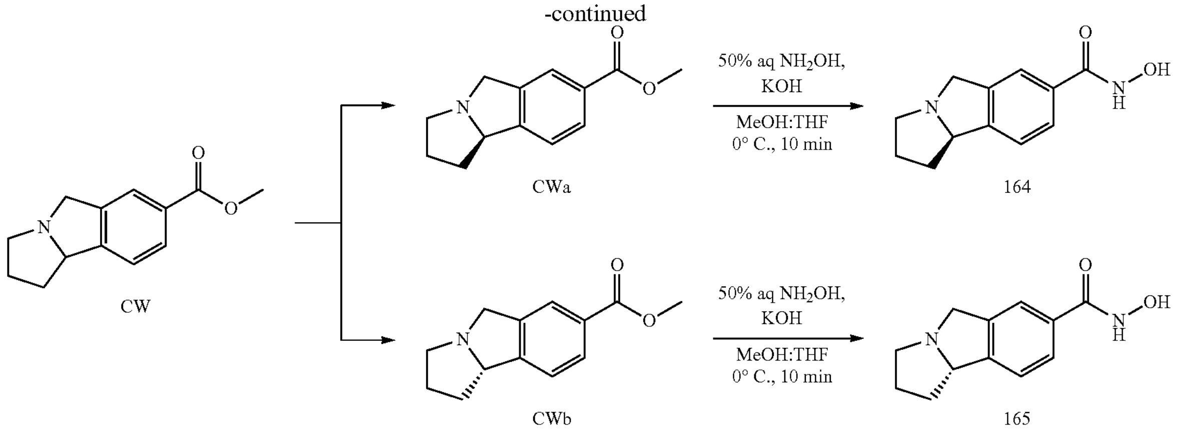

3-((1H-pyrrol-1-yl)methyl)-4-bromobenzoic acid (CT): To a stirred solution of methyl 4-bromo-3-(bromomethyl) benzoate (CS, 2.0 g, 6.4935 mmol, 1.0 equiv.) in DMF (20 mL), was added sodium hydride (55%) (611 mg, 12.987 mmol, 2.0 equiv.) at 0° C., followed pyrrole (CR, 522 mg, 7.7922 mmol, 1.2 equiv.) The reaction mixture was stirred at 110° C. for 16 h. The completion of reaction was monitored by TLC and LCMS. Excess reagent was decomposed by the addition of water and pH was adjusted to 5-6 with 1N aqueous hydrochloric acid. It was then extracted with ethyl acetate (3x70 mL) and organic layer was washed with brine solution (100 mL) and dried over sodium sulfate and concentrated under reduce pressure to get 3-((1H-pyrrol-1-yl) methyl)-4-bromobenzoic acid (CT, 1.5 g, 5.38 mmol, 82%) as crude compound which was used further next step without purification. MS (ESI): 280 $[M+H]^+$.

Methyl 3-((1H-pyrrol-1-yl)methyl)-4-bromobenzoate (CU): To a stirred solution of 3-((1H-pyrrol-1-yl)methyl)-4-bromobenzoic acid (CT, 1.5 g, 5.35 mmol, 1.0 equiv.) in acetonitrile (20 mL), was added potassium carbonate (2.2 g, 16.0 mmol, 3 equiv.) and methyl iodide (1.1 g, 8.03 mmol, 1.5 equiv.) at room temperature. The reaction mixture was stirred at room temperature for 16 h. The completion of reaction was monitored by TLC and LCMS. Upon completion of reaction, it was diluted with water (20 mL) and extracted with ethyl acetate (40 mL) and organic layer was washed with brine solution (20 mL) and dried over Sodium sulfate and concentrated under reduce pressure to get crude mixture. It was then purified by silica gel column chromatography using EtOAc: hexanes (5%) to obtain (CU, methyl 3-((1H-pyrrol-1-yl)methyl)-4-bromobenzoate (1.3 g, 4.28 mmol, 82%) as a white solid. MS (ESI): 294 $[M+H]^+$ Methyl 5H-pyrrolo[2,1-a]isoindole-7-carboxylate (CV): To a schlenk-tube containing methyl 3-((1H-pyrrol-1-yl) methyl)-4-bromobenzoate (CU, 1.3 g, 4.436 mmol, 1.0 equiv.), potassium acetate (879 mg, 8.872 mmol, 2.0 equiv.) was added DMF (10 mL) under $N_{2(g)}$ atmosphere. The resulting solution was degassed with $N_{2(g)}$ for 20 min and then, palladium acetate (0.099 g, 0.44 mmol, 0.1 equiv.) and triphenylphosphine (0.23 g, 0.88 mmol, 0.2 equiv.) were added. The reaction mixture was heated at 150° C. for 3 h and was monitored by TLC and LCMS. Upon completion of reaction, it was cooled to room temperature, diluted with ice-cold water (20 mL) and extracted with ethyl acetate (40 mL). The organic layer was washed with brine solution (20 mL), dried over Sodium sulfate and concentrated under reduce pressure to get crude mixture. It was then purified by silica gel column chromatography using EtOAc: hexanes (6%) to obtain methyl 5H-pyrrolo[2,1-a]isoindole-7-carboxylate (CV, 0.49 g, 2.1596 mmol, 52%) as a solid. MS (ESI): 214 $[M+H]^+$ Methyl 2,3,5,9b-tetrahydro-1H-pyrrolo[2,1-a]isoindole-7-carboxylate (CW): To a stirred solution of methyl 5H-pyrrolo[2,1-a]isoindole-7-carboxylate (CV, 0.3 g, 1.38 mmol, 1.0 equiv.) in acetic acid (1 mL) was added palladium on carbon (50%) (0.30 g). The reaction mixture was purged continuously with $H_{2(g)}$ at room temperature for 4 h. and was monitored by TLC and LCMS. Upon completion of reaction, it was filtered through celite and concentrated under reduce pressure to get crude mixture. It was then purified by silica gel column chromatography using EtOAc: hexanes (60%) to obtain methyl 2,3,5,9b-tetrahydro-1H-pyrrolo[2,1-a]isoindole-7-carboxylate (CW, 0.096 g, 0.442 mmol, 47%) as a solid. MS (ESI): 216 $[M-H]^-$ Subsequent steps for the preparation of 164, 165 and 166 were performed in a manner analogous to that used for preparation of compound 94. Although compounds 164 and 165 are designated as the (S) and (R) enantiomers as each enantiomer was prepared and isolated, the absolute stereochemistry of each is unknown.

| | | |
|---|---|---|
| 164 | 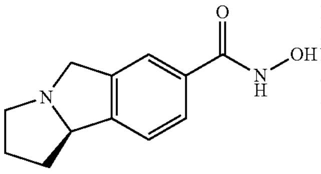<br>(R)-N-hydroxy-2,3,5,9b-tetrahydro-1H-pyrrolo[2,1-a]isoindole-7-carboxamide | HPLC purity: 95.74%<br>MS (ESI): 219 $[M + H]^+$<br>Note:<br>absolute stereochemistry is unknown |
| 165 | 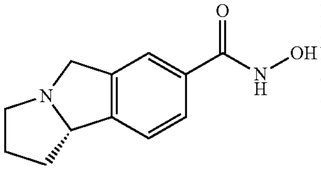<br>(S)-N-hydroxy-2,3,5,9b-tetrahydro-1H-pyrrolo[2,1-a]isoindole-7-carboxamide | HPLC purity: 96.10%<br>MS (ESI): 219 $[M + H]^+$<br>Note:<br>absolute stereochemistry is unknown |

-continued

| | | |
|---|---|---|
| 166 | 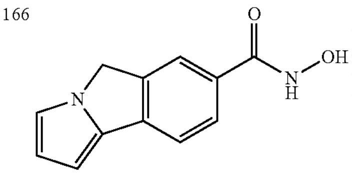 N-hydroxy-5H-pyrrolo[2,1-a]isoindole-7-carboxamide | $^1$H NMR (400 MHz, DMSO-$d_6$) δ 11.12 (s, 1H), 9.02 (s, 1H), 7.83 (s, 1H), 7.73 (d, J = 7.9 Hz, 1H), 7.52 (d, J = 7.9 Hz, 1H), 7.14 (d, J = 2.4 Hz, 1H), 6.33 (d, J = 3.2 Hz, 1H), 6.26 (t, J = 2.8 Hz, 1H), 5.05 (s, 2H). MS (ESI): 213 [M − H]$^-$ |

Compounds of Formula (III) were prepared following the synthetic schemes and procedures described in detail below.

3-fluoro-N-hydroxy-4-(((1r,3r,5r,7r)-spiro[adamantane-2,4'-piperidin]-1'-yl)methyl)benzamide (167)

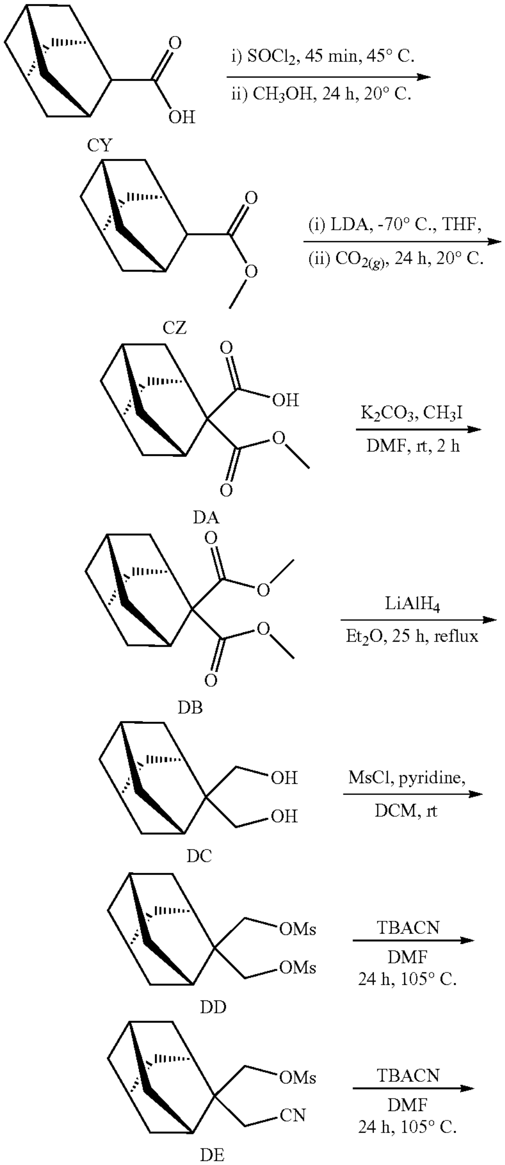

CY, CZ, DA, DB, DC, DD, DE

-continued

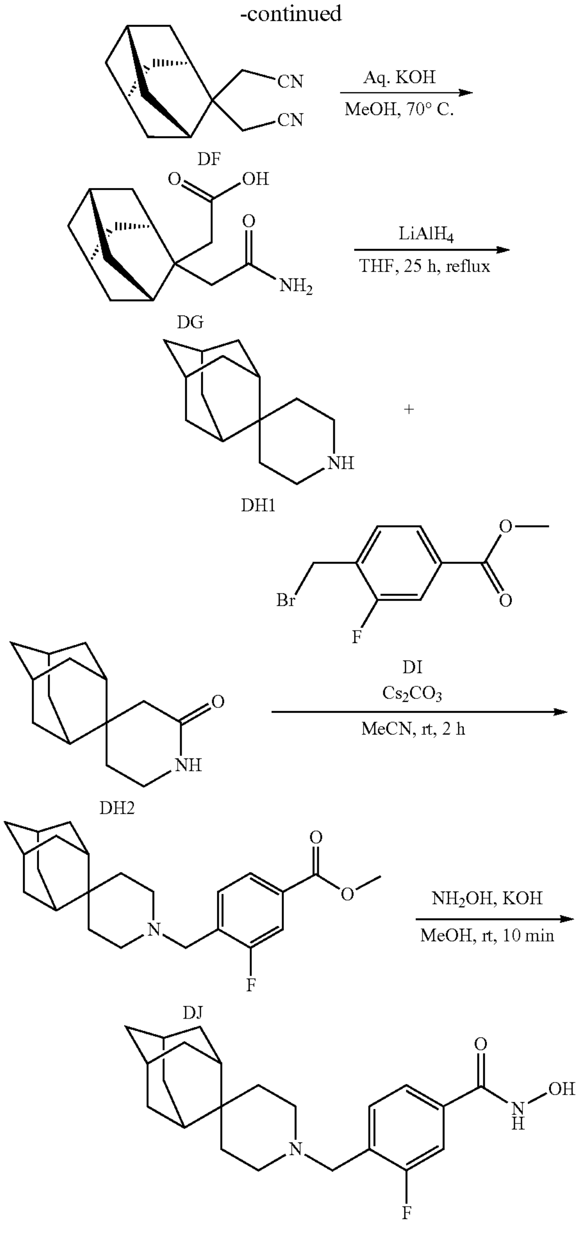

DF, DG, DH1, DH2, DJ

167

Methyl (1r,3r,5r,7r)-adamantane-2-carboxylate (CZ): To a stirred solution of (1r,3r,5r,7r)-adamantane-2-carboxylic acid (CY, 24 g, 133.48 mmol, 1.0 equiv.) in toluene (150 mL) was added thionyl chloride (150 mL, 2135.6 mmol, 16 equiv.) at 0° C. The reaction mixture was stirred at 45° C. for 45 min and was monitored by TLC. Upon consumption of starting material, the reaction mixture was concentrated under reduced pressure to obtain crude mixture. In the crude material methanol was added slowly drop wise at 0° C., then the reaction mixture was stirred at 20° C. for 24 h. The reaction was monitored by TLC and upon completion of reaction; the reaction mixture was concentrated under reduced pressure to obtain crude mixture. The crude material was purified by silica gel flash chromatography, using ethyl acetate/hexane (5:5) to afford methyl (1r,3r,5r,7r)-adamantane-2-carboxylate (CZ, 23 g, 118.39 mmol, 89%). $^1$H NMR (400 MHz, Chloroform-d) δ 3.69 (s, 3H), 2.59-2.61 (m, 1H), 2.32 (d, J=3.9 Hz, 2H), 1.83-1.90 (m, 6H), 1.72-1.76 (m, 4H), 1.60-1.64 (m, 3H).

(1r,3r,5r,7r)-2-(Methoxycarbonyl)adamantane-2-carboxylic acid (DA): To a stirred solution of methyl (1r,3r,5r,7r)-adamantane-2-carboxylate (CZ, 23 g, 118.39 mmol, 1.0 equiv.) in THF (230 mL) was added LDA (177 mL, 177.58 mmol, 1.5 equiv.) at −78° C. under $N_{2(g)}$ atmosphere. The reaction mixture was stirred at −78° C. to −40° C. for 1 h, then $CO_{2(g)}$ was purged in reaction mixture for 1 h at −78° C. to −40° C. The reaction mixture was further stirred for 24 h at 20° C. Upon completion of reaction as monitored by TLC, the reaction mixture was poured in water (150 mL) and extracted with ethyl acetate (3×200 mL). The aqueous layer was acidified using 1N HCl to obtain white precipitates which were filtered and dried under vacuum to give (1r,3r,5r,7r)-2-(methoxycarbonyl)adamantane-2-carboxylic acid (DA, 25 g, 104.91 mmol, 89%) as a white solid. $^1$H NMR (400 MHz, DMSO-$d_6$) δ 12.90 (s, 1H), 3.64 (s, 3H), 2.55 (s, 2H), 1.83 (d, J=13.0 Hz, 2H), 1.74 (d, J=11.3 Hz, 4H), 1.65 (d, J=12.9 Hz, 6H).

Dimethyl (1r,3r,5r,7r)-adamantane-2,2-dicarboxylate (DB): To a stirred solution of (1r,3r,5r,7r)-2-(methoxycarbonyl)adamantane-2-carboxylic acid (DA, 25 g, 104.91 mmol, 1.0 equiv.) in DMF (250 mL) were added $K_2CO_3$ (28.9 g, 209.83 mmol, 2.0 equiv.) and methyl iodide (74.4 g, 524.59 mmol, 5.0 equiv.) at room temperature. The reaction mixture was stirred at room temperature for 2 h and was monitored by TLC. Upon completion of reaction, the reaction mixture was poured on ice-cold water (500 mL) to obtain white precipitates, which were filtered and dried under vacuum to give dimethyl (1r,3r,5r,7r)-adamantane-2,2-dicarboxylate (DB, 23 g, 91.157 mmol, 87%) as a white solid. $^1$H NMR (400 MHz, Chloroform-d) δ 3.72 (s, 6H), 2.72 (m, 2H), 1.87-1.83 (m, 6H), 1.74-1.70 (m, 6H).

((1r,3r,5r,7r)-adamantane-2,2-diyl)dimethanol (DC): To a stirred solution of dimethyl (1r,3r,5r,7r)-adamantane-2,2-dicarboxylate (DB, 1.0 g, 3.978 mmol, 1.0 equiv.) in THF (10 mL) was added lithium aluminium hydride (1.0 M in THF) (20 mL) at 0° C. The mixture was reflux for 25 h. The reaction was monitoring by TLC and LCMS. Upon completion of reaction, reaction mixture was poured on ice-cold water (20 mL) and extracted with ethyl acetate (100 mL). The organic layer was dried over sodium sulfate and concentrated under reduced pressure to afford ((1r,3r,5r,7r)-adamantane-2,2-diyl)dimethanol (DC, 700 mg, 3.566 mmol, 90%) as a white solid. $^1$H NMR (400 MHz, DMSO-$d_6$) δ 4.20 (t, J=5.2 Hz, 2H), 3.61 (d, J=5.2 Hz, 4H), 1.98 (d, J=12.7 Hz, 4H), 1.82-1.80 (m, 2H), 1.62 (dt, J=5.8, 3.1 Hz, 4H), 1.48-1.42 (m, 4H).

((1r,3r,5r,7r)-Adamantane-2,2-diyl)bis(methylene) dimethanesulfonate (DD): To a stirred solution of ((1r,3r,5r,7r)-adamantane-2,2-diyl)dimethanol (DC, 370 mg, 1.887 mmol, 1.0 equiv.) in DCM (5 mL) were added methane sulfonyl chloride (324.3 mg, 2.831 mmol, 1.5 equiv.), N,N-dimethylaminopyridine (46.12 mg, 0.3775 mmol, 0.2 equiv.) and pyridine (299 mg, 3.775 mmol, 2.0 equiv.). The reaction mixture was stirred at room temperature for 16 h and was monitored by TLC and LCMS. Upon completion of reaction, the reaction mixture was poured on water, extracted with ethyl acetate (3×50 mL) and combined organic layer was concentrated under reduced pressure to obtain crude mixture. The crude mixture was purified by silica gel flash chromatography using 15% (ethyl acetate/hexane) to afford ((1r,3r,5r,7r)-adamantane-2,2-diyl)bis(methylene) dimethanesulfonate (DD, 250 mg, 0.709 mmol, 37%) as a white solid. $^1$H NMR (400 MHz, DMSO-$d_6$) δ 4.36 (s, 4H), 3.22 (s, 6H), 1.99 (d, J=13.2 Hz, 4H), 1.87 (s, 2H), 1.69 (d, J=8.6 Hz, 4H), 1.60 (d, J=13.2 Hz, 4H).

((1r,3r,5r,7r)-2-(cyanomethyl)adamantan-2-yl)methyl methanesulfonate (DE): To a stirred solution of ((1r,3r,5r,7r)-adamantane-2,2-diyl)bis(methylene) dimethanesulfonate (DD, 250 mg, 0.709 mmol, 1.0 equiv.) in DMF (3 mL) was added tetrabutyl ammonium cyanide (952 mg, 3.546 mmol, 5.0 equiv.). The reaction mixture was stirred at 105° C. for 24 h and was monitored by TLC. Upon completion of reaction, the reaction mixture was poured on water (10 mL), extracted with ethyl acetate (3×30 mL) and combined organic layer was concentrated under reduced pressure to give ((1r,3r,5r,7r)-2-(cyanomethyl)adamantan-2-yl) methyl methanesulfonate (DE, 250 mg, 0.882 mmol) as a yellow oil. $^1$H NMR (400 MHz, DMSO-$d_6$) δ 4.37 (s, 2H), 3.26 (s, 3H), 2.88 (s, 1H), 2.69 (s, 1H), 2.04-1.91 (m, 4H), 1.89-1.83 (d, J=8.2 Hz, 2H), 1.72-1.54 (m, 8H).

2,2'-((1r,3r,5r,7r)-adamantane-2,2-diyl)diacetonitrile (DF): To a stirred solution of ((1r,3r,5r,7r)-2-(cyanomethyl) adamantan-2-yl)methyl methanesulfonate (DE, 250 mg, 0.882 mmol, 1.0 equiv.) in DMF (3 mL) was added tetrabutyl ammonium cyanide (1.19 g, 4.410 mmol, 5.0 equiv.). The reaction mixture was stirred at 105° C. for 24 hand was monitored by TLC. Upon completion of reaction, the reaction mixture was poured on water (10 mL), extracted with ethyl acetate (3×30 mL) and combined organic layer was concentrated under reduced pressure to give crude mixture. The crude mixture was purified by silica gel flash chromatography using 5% (ethyl acetate/hexane) to give 2,2'-((1r,3r,5r,7r)-adamantane-2,2-diyl)diacetonitrile (DF, 120 mg, 0.559 mmol, 64%) as an off-white solid. $^1$H NMR (400 MHz, DMSO-$d_6$) δ 2.94 (s, 4H), 1.97 (d, J=13.1 Hz, 4H), 1.81 (s, 2H), 1.65-1.59 (m, 8H).

2-((1r,3r,5r,7r)-2-(2-amino-2-oxoethyl)adamantan-2-yl) acetic acid (DG): To a stirred solution of 2,2'-((1r,3r,5r,7r)-adamantane-2,2-diyl)diacetonitrile (DF, 100 mg, 0.466 mmol, 1.0 equiv.) in MeOH (1 mL) was added KOH (35% soln. in water, 7.5 mL). The reaction mixture was stirred at 70° C. for 24 h and was monitored by TLC and LCMS. The reaction mixture was poured on water (5 mL) to get white precipitates. The precipitates were filtered and dried under vacuum to give 2-((1r,3r,5r,7r)-2-(2-amino-2-oxoethyl)adamantan-2-yl)acetic acid (DG, 70 mg, 0.278 mmol, 60%) as a white solid. MS (ESI): 252 $[M+H]^+$, $^1$H NMR (400 MHz, DMSO-$d_6$) δ 12.34 (s, 1H), 7.35 (s, 1H), 6.97 (s, 1H), 2.79 (s, 2H), 2.56 (d, J=8.8 Hz, 2H), 2.08 (t, J=17.0 Hz, 4H), 1.79-1.64 (m, 6H), 1.51 (d, J=13.0 Hz, 4H).

(1r,3r,5r,7r)-spiro[adamantane-2,4'-piperidine] (DH): To a stirred solution of 2-((1r,3r,5r,7r)-2-(2-amino-2-oxoethyl) adamantan-2-yl)acetic acid (DG, 70 mg, 0.278 mmol, 1.0 equiv.) in THF (1 mL) was added lithium aluminium hydride (1.0 M in THF) (1.39 mL) at 0° C. The mixture was refluxed for 25 h and was monitored by TLC and LCMS. Upon completion of reaction, reaction mixture was cooled to 0° C. and diluted with water (1 mL), 15% sodium hydroxide solution (1 mL) and filtered off. The filtrate was concentrated under reduced pressure to get (1r,3r,5r,7r)-spiro[adamantane-2,4'-piperidine] (DH, 70 mg, 0.34 mmol, 100%) which was directly used for next step. MS (ESI): 206 $[M+H]^+$ Methyl 3-fluoro-4-(((1r,3r,5r,7r)-spiro[adamantane-2,4'-piperidin]-1'-yl)methyl)benzoate (DJ): To a stirred solution of (1r,3r,5r,7r)-spiro[adamantane-2,4'-piperidine] (DH, 70 mg, 0.340 mmol, 1.0 equiv.) in ACN (1 mL) were added methyl 4-(bromomethyl)-3-fluorobenzoate (84.2 mg, 0.340 mmol, 1.0 equiv.) and $Cs_2CO_3$ (333 mg, 1.022 mmol, 3.0 equiv.). The reaction mixture was stirred at room temperature for 2 h and was monitored by TLC and LCMS. The reaction mixture was poured on water to get white precipitates which were filtered and dried under vacuum to afford methyl 3-fluoro-4-(((1r,3r,5r,7r)-spiro[adamantane-2,4'-piperidin]-1'-yl)methyl)benzoate (DJ, 40 mg, 0.107 mmol, 32%) as a white solid. MS (ESI): 372 $[M+H]^+$ 3-fluoro-N-hydroxy-4-(((1r,3r,5r,7r)-spiro[adamantane-2,4'-piperidin]-1'-yl)methyl)benzamide (167). This step for the preparation of 167 was performed in a manner analogous to that used for preparation of compound 75. $^1$H NMR (400 MHz, DMSO-$d_6$) δ 11.26 (s, 1H), 9.14 (s, 1H), 7.56 (d, J=8.2 Hz, 1H), 7.49 (m, 2H), 3.50 (s, 2H), 2.33 (s, 4H), 1.97 (d, J=12.6 Hz, 4H), 1.79 (m, 2H), 1.63 (m, 6H), 1.55 (m, 2H), 1.47 (d, J=12.6 Hz, 4H). MS (ESI): 373 $[M+H]^+$ (S)-4-((1-ethyl-2-azaspiro[3.4]octan-2-yl)methyl)-3-fluoro-N-hydroxybenzamide (168) and (R)-4-((1-ethyl-2-azaspiro[3.4]octan-2-yl)methyl)-3-fluoro-N-hydroxybenzamide (169)

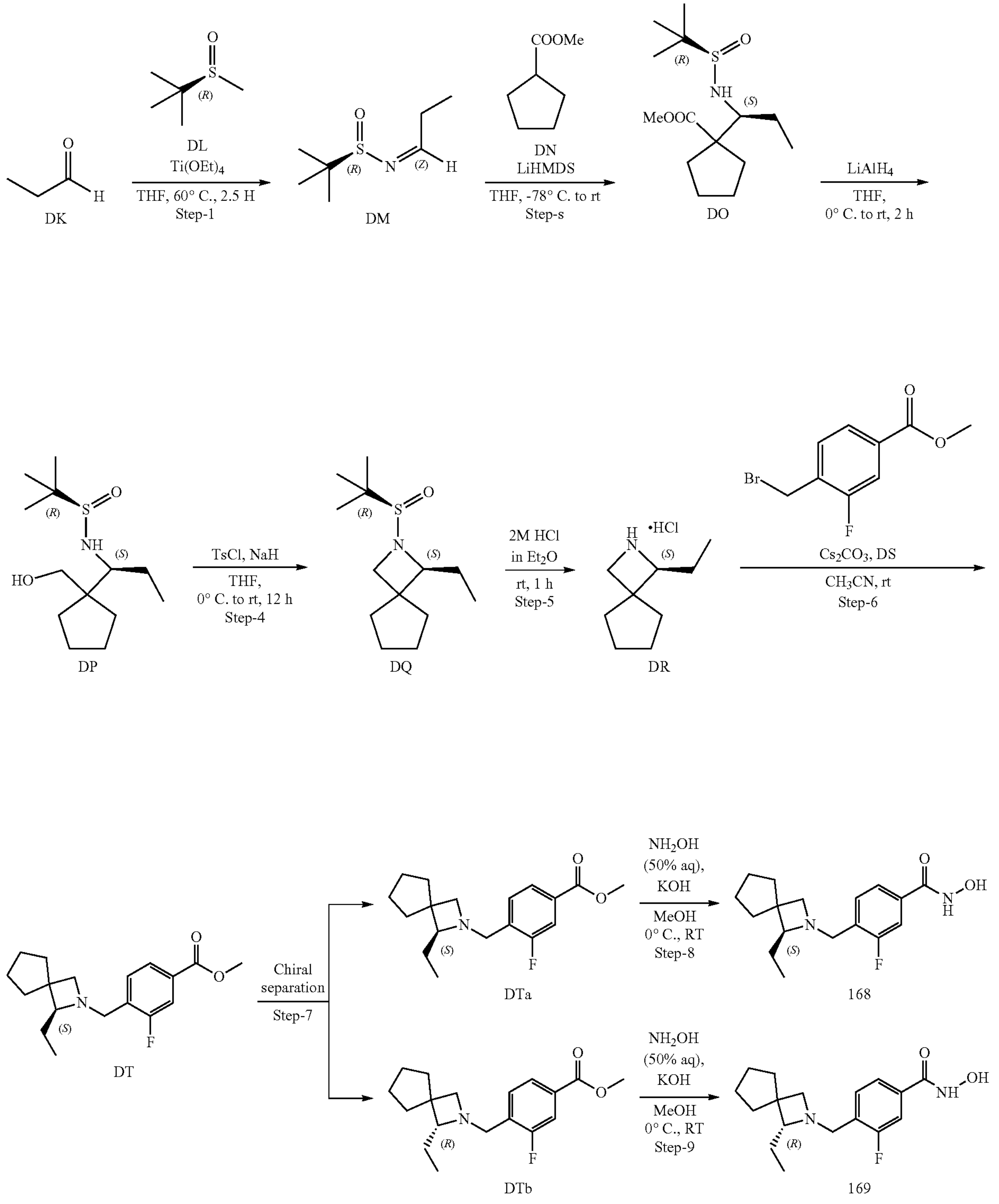

(R, Z)-2-methyl-N-propylidenepropane-2-sulfinamide (DM): To a stirred solution of propionaldehyde (DK, 1.5 g, 25.83 mmol, 1.0 equiv.) in anhydrous THF (10 mL) was added $Ti(OEt)_4$ (1.09 mL, 38.74 mmol, 1.5 equiv.) dropwise under $N_{2(g)}$ followed by (R) tert-butyl sulphinamide (DL, 3.44 g, 28.41 mmol, 1.1 equiv.) at room temperature. The resulting mixture was heated at 60° C. for 2.5 h. After 2.5 h the reaction was cooled to room temperature and poured onto brine solution (60 mL) and extracted with ethyl acetate (3×30 mL). The combined organic layer was dried over sodium sulfate and concentrated under reduced pressure to give (R)-2-methyl-N-propylidenepropane-2-sulfinamide as a yellow oil, which was purified by silica gel chromatography (EtOAc/hexane, 1:4) to afford (R, Z)-2-methyl-N-propylidenepropane-2-sulfinamide (DM, 3.5 g, 21.70 mmol, 84%) as a clear oil. MS (ESI): 162 $[M+H]^+$ Methyl 1-(1-(((R)-tert-butylsulfinyl)amino)propyl)cyclopentane-1-carboxylate (DO): To a stirred solution of (R)-2-methyl-N-propylidenepropane-2-sulfinamide (DM, 1.7 g, 10.54 mmol, 1 equiv.) and methyl cyclopentane carboxylate (DN, 6.76 g, 52.71 mmol, 5 equiv.) in anhydrous THF (17 mL) was added LiHMDS (53 mL, 1 M solution in THF, 52.71 mmol, 5 equiv.) drop wise at −78° C. under $N_{2(g)}$ atmosphere. The reaction was stirred at −78° C. for 3 h, then, at room temperature for 12 h. After completion of the reaction, it was quenched with water (10 mL). The reaction mixture was extracted with EtOAc (3×30 mL) and the combined organic layer was dried over anhydrous sodium sulfate. The solvent was concentrated under reduced pressure to obtain crude product, which was purified by silica gel column chromatography (1:3, EtOAc/hexane) to obtain pure product as methyl 1-(1-(((R)-tert-butylsulfinyl)amino)propyl)cyclopentane-1-carboxylate (DO, 2.0 g, 6.91 mmol, 65%) as a sticky oil. $^1$H NMR (400 MHz, Chloroform-d) δ 4.61 (d, J=7.8 Hz, 1H), 3.72 (s, 3H), 2.99 (t, J=8.5 Hz, 1H), 2.34 (dd, J=12.9, 6.3 Hz, 1H), 2.06-1.98 (m, 2H), 1.71-1.70 (m, 3H), 1.29-1.23 (m, 13H), 0.94 (t, J=7.3 Hz, 3H).

(R)—N-(1-(1-(hydroxymethyl)cyclopentyl)propyl)-2-methylpropane-2-sulfinamide (DP): To a solution of methyl 1-(1-(((R)-tert-butylsulfinyl)amino)propyl)cyclopentane-1-carboxylate (DO, 2.0 g, 6.91 mmol, 1.0 equiv.) in anhydrous THF (20 mL) was added lithium aluminium hydride (1.0 M in THF, 13.84 mL, 13.84 mmol, 2 equiv.) slowly at 0° C., and stirred for 2 h under $N_{2(g)}$ atmosphere. After completion of the reaction, it was quenched with water (10 mL) and extracted with EtOAc (3×30 mL). The combined organic layer was dried over anhydrous sodium sulfate and concentrated under reduced pressure to obtain crude mixture. The crude mixture was purified by silica gel column chromatography to yield (R)—N-(1-(1-(hydroxymethyl)cyclopentyl)propyl)-2-methylpropane-2-sulfinamide (DP, 1.1 g, 4.20 mmol, 61%) as a colorless liquid. $^1$H NMR (400 MHz, Chloroform-d) δ 4.01 (d, J=7.2 Hz, 1H), 3.80 (d, J=6.6 Hz, 1H), 3.60-3.56 (m, 1H), 3.41-3.37 (m, 1H), 3.10-2.94 (m, 1H), 1.50-1.20 (m, 19H), 0.97 (dt, J=12.0, 7.3 Hz, 3H).

2-((R)-tert-butylsulfinyl)-1-ethyl-2-azaspiro[3.4]octane (DQ): To a stirred solution of (R)—N-(1-(1-(hydroxymethyl)cyclopentyl)propyl)-2-methylpropane-2-sulfinamide (DP, 1.0 g, 3.83 mmol, 1.0 equiv.) in anhydrous THF (10 mL) was added tosyl chloride (1.09 g, 5.74 mmol, 1.5 equiv.) followed by addition of 60% NaH (0.459 g, 11.48 mmol, 3.0 equiv.) at 0° C. The resulting mixture was stirred at room temperature for 12 h under $N_{2(g)}$ atmosphere. After completion of the reaction, it was quenched with water (10 mL) and extracted with EtOAc (3×30 mL). The combined organic layer was concentrated under reduced pressure to obtain crude mixture which was purified by silica gel column chromatography (1:3, EtOAc/hexane) to obtain 2-((R)-tert-butylsulfinyl)-1-ethyl-2-azaspiro[3.4]octane (DQ, 0.600 g, 2.46 mmol, 64%) as a colourless liquid. $^1$H NMR (400 MHz, Chloroform-d) δ 3.99 (d, J=7.5 Hz, 1H), 3.83 (t, J=7.1 Hz, 1H), 2.92 (d, J=7.5 Hz, 1H), 1.81-1.69 (m, 3H), 1.63-1.50 (m, 4H), 1.15 (s, 10H), 0.88 (t, J=7.5 Hz, 3H).

1-ethyl-2-azaspiro[3.4]octane (DR): To a stirred solution of 2-((R)-tert-butylsulfinyl)-1-ethyl-2-azaspiro[3.4]octane (DQ, 0.6 g, 2.46 mmol, 1 equiv.) in diethyl ether (1 mL) was added HCl (2.0 M solution in 1,4-Dioxane, 5.0 mmol) at room temperature and stirred for 1 h. After completion of the reaction, it was concentrated under vacuum to dryness to obtain 1-ethyl-2-azaspiro[3.4]octane (DR, 0.225 g, 1.28 mmol, 52%) as a crude product which was used as such without further purification.

Methyl-4-((1-ethyl-2-azaspiro[3.4]octan-2-yl)methyl)-3-fluorobenzoate (DT): To a stirred solution of methyl 4-(bromomethyl)-3-fluorobenzoate (DR, 0.317 g, 1.28 mmol, 1 equiv.) in ACN (15 mL) was added $Cs_2CO_3$ (0.834 g, 2.56 mmol, 2.0 equiv.) and (S)-1-ethyl-2-azaspiro[3.4]octane hydrochloride (DS, 0.225 g, 1.28 mmol, 1 equiv.) at room temperature. The reaction was stirred at room temperature for 2 h, then quenched water (30 mL) and extracted with ethyl acetate (3×20 mL). The combined organic layer was washed with brine (20 mL), dried over anhydrous sodium sulfate and concentrated under reduced pressure to obtain crude mixture which was purified by flash silica gel column chromatography (5% EtOAc:Hexane) to obtain methyl-4-((1-ethyl-2-azaspiro[3.4]octan-2-yl)methyl)-3-fluorobenzoate (DT, 0.220 g, 0.7203 mmol, 56%) as a sticky liquid. Mass (ESI): 306 $[M+H]^+$; $^1$H NMR (400 MHz, Chloroform-d) δ 7.79 (dd, J=7.9, 1.7 Hz, 1H), 7.68 (dd, J=10.3, 1.7 Hz, 1H), 7.50 (s, 1H), 3.93 (m, 4H), 3.61 (d, J=14.0 Hz, 1H), 3.25 (s, 1H), 3.04 (s, 1H), 2.67 (s, 1H), 1.76 (d, J=7.6 Hz, 3H), 1.65-1.42 (m, 10H), 1.27 (s, 2H), 0.85 (t, J=7.5 Hz, 3H).

Subsequent steps for the preparation of 168 and 169 were performed in a manner analogous to that used for preparation of compound 75. Although compounds 168 and 169 are designated as the (S) and (R) enantiomers as each enantiomer was prepared and isolated, the absolute stereochemistry of each is unknown.

| | | |
|---|---|---|
| 168 | 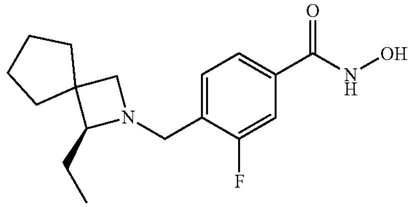 [SMILES: CC[C@@H]1N(Cc2ccc(C(=O)NO)cc2F)CC12CCCC2] (S)-4-((1-ethyl-2-azaspiro[3.4]octan-2-yl)methyl)-3-fluoro-N-hydroxybenzamide | 1H NMR (400 MHz, DMSO-$d_6$) δ 11.19 (s, 1H), 9.12 (s, 1H), 7.54 (d, J = 7.9 Hz, 1H), 7.48-7.41 (m, 2H), 3.78 (d, J = 13.8 Hz, 1H), 3.44 (d, J = 13.8 Hz, 1H), 3.03 (d, J = 6.3 Hz, 1H), 2.94 (t, J = 7.0 Hz, 1H), 2.58-2.54 (m, 2H), 1.67-1.51 (m, 4H), 1.48-1.38 (m, 5H), 0.78 (t, J = 7.5 Hz, 3H). MS (ESI): 307 $[M + H]^+$ Note: absolute stereochemistry is unknown |
| 169 | 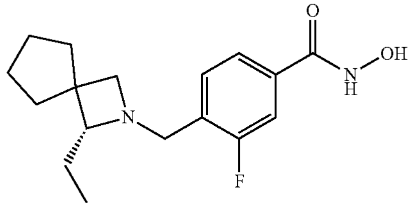 [SMILES: CC[C@H]1N(Cc2ccc(C(=O)NO)cc2F)CC12CCCC2] (R)-4-((1-ethyl-2-azaspiro[3.4]octan-2-yl)methyl)-3-fluoro-N-hydroxybenzamide | $^1$H NMR (400 MHz, DMSO-$d_6$) δ 11.24 (s, 1H), 9.12 (s, 1H), 7.54 (d, J = 7.8 Hz, 1H), 7.48-7.41 (m, 2H), 3.78 (d, J = 13.7 Hz, 1H), 3.44 (d, J = 13.7 Hz, 1H), 3.03 (d, J = 6.3 Hz, 1H), 2.94 (t, J = 7.0 Hz, 1H), 2.57 (d, J = 6.3 Hz, 2H), 1.64-1.60 (m, 2H), 1.58-1.51 (m, 3H), 1.48-1.34 (m, 5H), 0.78 (t, J = 7.5 Hz, 3H). MS (ESI): 307 $[M + H]^+$ Note: absolute stereochemistry is unknown |

(R)-3-fluoro-N-hydroxy-5-((2-methyl-2-azaspiro[5.5]undecan-3-yl)methyl)benzamide (170) and (S)-3-fluoro-N-hydroxy-5-((2-methyl-2-azaspiro[5.5]undecan-3-yl)methyl)benzamide (171)

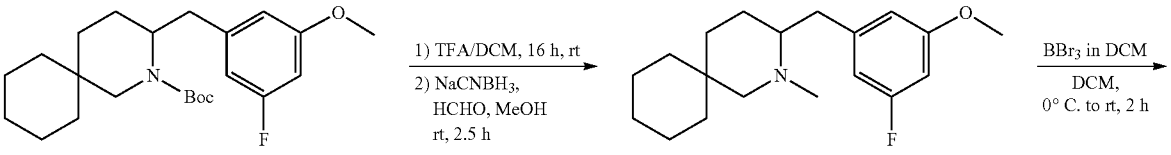

DU DV

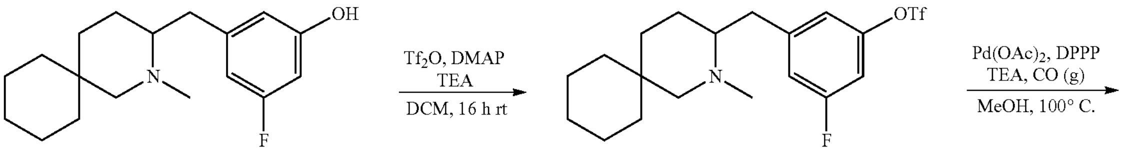

DW DX

-continued

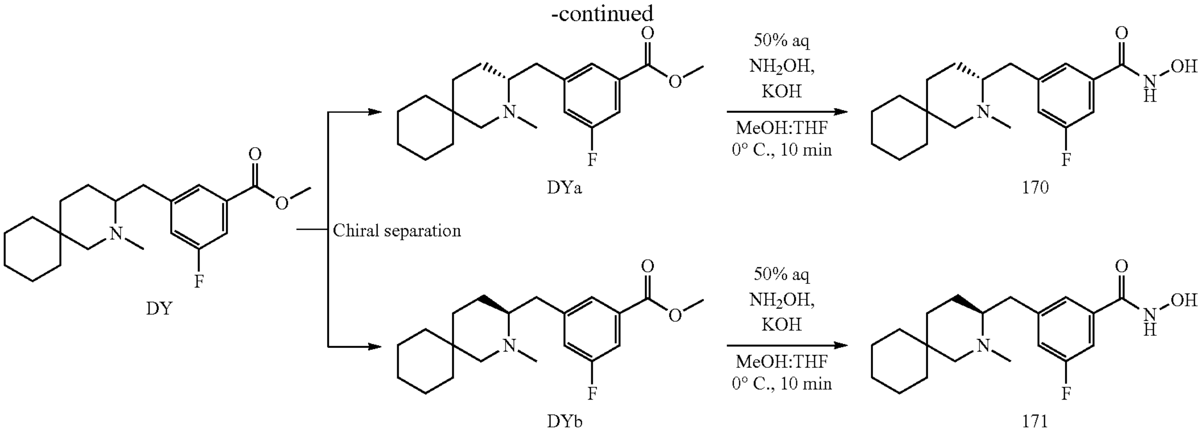

tert-butyl 3-(3-fluoro-5-methoxybenzyl)-2-azaspiro[5.5]undecane-2-carboxylate (DU). This compound was prepared in a manner analogous to that used for preparation of Intermediate BN in compound 135. MS (ESI): 392 $[M+H]^+$ 3-(3-fluoro-5-methoxybenzyl)-2-methyl-2-azaspiro[5.5]undecane (DV): To a stirred solution of tert-butyl 3-(3-fluoro-5-methoxybenzyl)-2-azaspiro[5.5]undecane-2-carboxylate (DU, 1.3 g, 3.325 mmol, 1.0 equiv.) in DCM (15 mL) was added TFA (1.4 mL, 13.299 mmol, 4.0 equiv.) at 0° C. The reaction mixture was stirred at 0° C. for 16 h and was monitored by TLC and LCMS. Upon completion of reaction, it was concentrated under reduced pressure to get crude mixture. It was dissolved in methanol (15 mL) and p-formaldehyde (1.4 g, 44.61 mmol, 10 equiv.) was added to it at 0° C. The reaction mixture was stirred at 0° C. for 30 min following which sodium cyanoborohydride (596 mg, 9.6218 mmol, 2.0 equiv.) was added. The reaction mixture was stirred at room temperature for 6 h. Upon completion of reaction concentrated under reduce pressure and to get crude mixture which was then purified by silica gel column chromatography using EtOAc: hexanes (1:9) to obtain 3-(3-fluoro-5-methoxybenzyl)-2-methyl-2-azaspiro[5.5]undecane (DV, (670 mg, 2.1967 mmol, 66%) as solid. MS (ESI): 306 $[M+H]^+$ Subsequent steps for the preparation of 170 and 171 were performed in a manner analogous to that used for preparation of compound 94. Although compounds 170 and 171 are designated as the (S) and (R) enantiomers as each enantiomer was prepared and isolated, the absolute stereochemistry of each is unknown.

| | | |
|---|---|---|
| 170 | 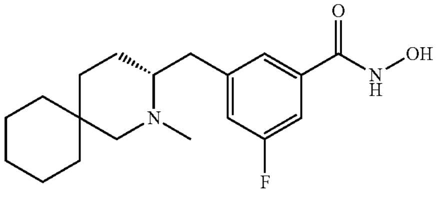 [SMILES: CN1CC2(CCCCC2)CC[C@@H]1Cc1cc(F)cc(C(=O)NO)c1] (R)-3-fluoro-N-hydroxy-5-((2-methyl-2-azaspiro[5.5]undecan-3-yl)methyl)benzamide | $^1H$ NMR (400 MHz, DMSO-$d_6$) δ 11.08 (s, 1H), 9.15 (s, 1H), 7.54-7.50 (m, 2H), 7.40 (t, J = 7.6 Hz, 1H), 3.11 (d, J = 12.9 Hz, 1H), 2.61-2.59 (m, 3H), 2.28 (s, 3H), 2.03 (s, 1H), 1.76-1.70 (m, 1H), 1.48 (m, 2H), 1.36 (s, 5H), 1.24-1.68 (m, 4H), 0.88 (t, J = 13.9 Hz, 2H). MS (ESI): 335 $[M + H]^+$ Note: absolute stereochemistry is unknown |
| 171 | 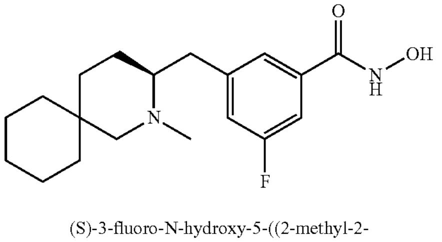 (S)-3-fluoro-N-hydroxy-5-((2-methyl-2-azaspiro[5.5]undecan-3-yl)methyl)benzamide | HPLC purity: 94.76% MS (ESI): 335 $[M + H]^+$ Note: absolute stereochemistry is unknown |

Biological Assay Data and Procedures

Caliper Endpoint Assay for HDAC Enzymatic Activity

HDAC reactions were assembled in 384 well plates (Greiner) in a total volume of 20 μL as follows: HDAC proteins (and their regulatory subunit, if applicable) were pre-diluted in the assay buffer comprising: 100 mM HEPES, pH 7.5, 0.1% BSA, 0.01% Triton $X^-$ 100, 25 mM KCl and dispensed into a 384 well plate (10 μL per well). An example of enzyme concentrations used in each assay is listed in the table below.

Control samples (0%-inhibition in the absence of inhibitor, DMSO only) and 100%-inhibition (in the absence of enzyme) were assembled in replicates of four (for each caliper sipper) and used to calculate the %-inhibition in the presence of compounds. At this step compounds were pre-incubated with enzyme for 30 minutes at room temperature (20-23° C.). The reactions were initiated by addition of 10 μL of the FAM-labeled substrate peptide (see table above) pre-diluted in the same assay buffer. Final concentration of substrate peptide was 1 μM (HDAC1-10) and 2 μM

| Assay | Expression Construct | Regulatory subunit | [Enzyme] nM | Substrate Peptide | Substrate Conc (μM) | Incubation Time (hr) |
|---|---|---|---|---|---|---|
| HDAC1 | Full length Human HDAC1 with C-terminal His-tag and C-terminal FLAG-tag, expressed in baculovirus expression system. | None | 5 | FAM-TSRHK(Ac) KL-NH2 | 1 | 17 |
| HDAC2 | Full length Human HDAC2 with C-terminal FLAG-tag, expressed in baculovirus expression system. | None | 7.5 | FAM-TSRHK(Ac) KL-NH2 | 1 | 17 |
| HDAC3 | Full length Human HDAC3 with C-terminal His-tag, co-expressed with Human NCOR2 , a.a. 395-489, N-terminal GST-tag, in baculovirus expression system. | NCOR2 | 0.5 | FAM-RHKK(Ac)-NH2 | 1 | 3 |
| HDAC4 | Human HDAC4 aa 101-1084(end) with C-terminal GST-tag, expressed in baculovirus expression system. | None | 1 | FAM-RHKK (TFAc)-NH2 | 1 | 1.5 |
| HDAC5 | Full length Human HDAC5 with N-terminal GST-tag, expressed in baculovirus expression system. | None | 0.25 | FAM-RHKK (TFAc)-NH2 | 1 | 3 |
| HDAC6 | Full length Human HDAC6 with C-terminal FLAG-tag, expressed in baculovirus expression system. | None | 60 | FAM-RHKK (TFAc)-NH2 | 1 | 5 |
| HDAC7 | Human HDAC7 aa 518-end with N-terminal GST-tag, expressed in baculovirus expression system. | None | 0.2 | FAM-RHKK (TFAc)-NH2 | 1 | 3 |
| HDAC8 | Full length Human HDAC8 with N-terminal HIS-tag, expressed in baculovirus expression system. | None | 5 | FAM-RHKK (TFAc)-NH2 | 1 | 3 |
| HDAC9 | Human HDAC9 a.a. 604-1066 with C-terminal His-tag, expressed in baculovirus expression system. | None | 0.5 | FAM-RHKK (TFAc)-NH2 | 1 | 3 |
| HDAC10 | Full length Human HDAC10 with N-terminal HIS-tag, expressed in baculovirus expression system. | None | 450 | FAM-TSRHK(Ac) KL-NH2 | 1 | 17 |
| HDAC11 | Full length Human HDAC11 with N-terminal HIS-tag, expressed in baculovirus expression system. | None | 10 | FAM-RHKK (TFA-c)-NH2 | 2 | 17 |

Test compounds were serially pre-diluted in 100% DMSO using 3-fold dilution steps and added to the protein samples by acoustic dispensing (Labcyte Echo). Concentration of DMSO was equalized to 1% in all samples. Final compound concentration in assays typically ranged from 100 μM to 0.00056 μM for a 12-point concentration-response format. Reference compounds such as TSA (trichostatin A) and MS-275, were tested in an identical manner.

(HDAC11). The reactions were allowed to proceed at room temperature (20-23° C.). Typical incubation times for each HDAC, based on pre-determined enzyme progress curves, vary and are listed in table above.

Following incubation, the reactions were quenched by addition of 50 μL of termination buffer (100 mM HEPES, pH7.5, 0.01% Triton X-100, 0.05% SDS). Terminated plates were analyzed on a microfluidic electrophoresis instrument (Caliper LabChip® 3000, Caliper Life Sciences/Perkin Elmer) which enables electrophoretic separation of deacetylated product from acetylated substrate. A change in the relative intensity of the peptide substrate and product is the parameter measured. Activity in each test sample was determined as the product to sum ratio (PSR): P/(S+P), where P is the peak height of the product, and S is the peak height of the substrate. Percent inhibition ($P_{inh}$) is determined using the following equation:

$P_{inh}=(PSR_{0\%\ inh}-PSR_{compound})/(PSR_{0\%\ inh}-PSR_{100\%\ inh})$ *100, in which: $PSR_{compound}$ is the product/sum ratio in the presence of compound, $PSR_{0\%\ inh}$ is the product/sum ratio in the absence of compound and the $PSR_{100\%\ inh}$ is the product/sum ratio in the absence of the enzyme. To determine the $IC_{50}$ of compounds (50%-inhibition) the %-inh data ($P_{inh}$ versus compound concentration) were fitted by a 4 parameter sigmoid dose-response model using XLfit software (IDBS).

Exemplary compounds were evaluated for inhibitory activity of a panel of HDAC paralogs. The results in Tables 1-4 demonstrate that compounds of the disclosure have potent activity against HDAC6, and many compounds selectively inhibit HDAC6 over HDAC8. $IC_{50}$ ranges: A: 0.001-0.1 μM; B: >0.1-1 μM; C: >1-10 μM; D: >10-100 μM; E: >100 μM. Selectivity ranges (ratio of HDAC8 $IC_{50}$/HDAC6 $IC_{50}$): I: 0.1-1; II: >1-10; III: >10-100; IV: >100-1000; V: >1000

TABLE 1

In vitro enzymatic $IC_{50}$ values for exemplary compounds

| Compound | Selectivity (6 v 8) (fold) | HDAC6 IC50: (μM) | HDAC8 IC50: (μM) | Selectivity (6 v 8) (fold) |
|---|---|---|---|---|
| 34 | 1810.8 | A | D | V |
| 33 | 291.4 | A | C | IV |
| 32 | 351.5 | A | C | IV |
| 31 | 468.8 | A | C | IV |
| 30 | 262.4 | A | C | IV |
| 28 | 353.6 | A | C | IV |
| 27 | 229.4 | A | D | IV |
| 26 | 69.7 | A | C | III |
| 25 | 136.5 | A | D | IV |
| 24 | 153.9 | A | C | IV |
| 21 | 50.2 | B | C | III |
| 20 | 169.1 | A | D | IV |
| 19 | 164.4 | A | C | IV |
| 16 | 824.4 | A | D | IV |
| 15 | 209.2 | A | D | IV |
| 14 | 318.6 | A | D | IV |
| 13 | 168.4 | B | D | IV |
| 9 | 207.1 | A | D | IV |
| 8 | 198.5 | B | D | IV |
| 7 | 457.5 | A | C | IV |
| 4 | 229.6 | A | D | IV |
| 3 | 146 | A | C | IV |
| 2 | 43.7 | A | C | III |
| 1 | 145.7 | A | D | IV |
| 107 | 331.7 | A | D | IV |
| 108 | 496.4 | A | D | IV |
| 109 | 739.3 | A | D | IV |
| 110 | 415 | A | C | IV |
| 112 | >12414.6 | A | E | V |
| 111 | 461.1 | A | D | IV |
| 113 | 50.7 | A | C | III |
| 114 | 10.3 | A | B | III |
| 115 | 54.7 | B | C | III |
| 116 | 11 | A | B | III |
| 117 | 7.9 | A | B | II |
| 118 | 105.1 | A | C | IV |
| 93 | 364.4 | A | C | IV |
| 94 | 66 | B | C | III |
| 119 | 46.5 | B | D | III |

TABLE 1-continued

In vitro enzymatic $IC_{50}$ values for exemplary compounds

| Compound | Selectivity (6 v 8) (fold) | HDAC6 IC50: (μM) | HDAC8 IC50: (μM) | Selectivity (6 v 8) (fold) |
|---|---|---|---|---|
| 120 | 209 | A | C | IV |
| 129 | >2.9 | D | E | V |
| 130 | >2.8 | D | E | V |
| 135 | 16.2 | B | C | III |
| 136 | 225.2 | A | C | IV |
| 139 | 66.4 | A | C | III |
| 79 | 123.9 | A | C | IV |
| 145 | 141 | A | D | IV |
| 146 | 86.8 | B | D | III |
| 140 | 7 | C | D | II |
| 80 | 12.5 | B | C | III |
| 106 | 14.6 | B | C | III |
| 121 | 80.9 | B | D | III |
| 122 | 14.5 | B | C | III |
| 131 | 18.1 | B | C | III |
| 132 | 191.4 | A | C | IV |
| 89 | 3.1 | C | C | II |
| 90 | 3.6 | C | C | II |
| 143 | 88.8 | B | C | III |
| 144 | 26.7 | B | D | III |
| 137 | 126.4 | B | D | IV |
| 138 | 45 | B | D | III |
| 123 | 32.7 | B | C | III |
| 147 | 35.4 | A | C | III |
| 124 | 124.7 | A | C | IV |
| 133 | 26 | B | C | III |
| 134 | 338.7 | A | C | IV |
| 148 | 1.9 | C | C | II |
| 149 | 6.5 | B | C | II |
| 156 | 6.1 | B | C | II |
| 158 | 90.6 | A | C | III |
| 159 | 11.4 | B | C | III |
| 157 | 220.1 | A | C | IV |
| 151 | 40.8 | A | C | III |
| 152 | 394 | A | C | IV |
| 153 | 10.4 | B | C | III |
| 154 | 18.6 | B | C | III |
| 160 | 1.8 | B | B | II |
| 161 | 2 | B | C | II |
| 155 | 6.1 | A | B | II |
| 162 | 2.8 | B | C | II |
| 164 | 2.3 | C | C | II |
| 165 | 15 | B | C | III |
| 166 | 14 | B | C | III |
| 125 | 82 | A | C | III |
| 126 | 37.4 | B | C | III |
| 127 | 197.5 | A | C | IV |
| 128 | 24.9 | B | C | III |
| 78 | 0.4 | C | B | I |
| 77 | 62.2 | A | C | III |
| 167 | 41.9 | A | C | III |
| 75 | 71 | A | C | III |
| 74 | 24.9 | B | C | III |
| 73 | 35.8 | A | C | III |
| 72 | 44.8 | A | B | III |
| 71 | 33.4 | A | C | III |
| 70 | 16 | A | C | III |
| 69 | 20.6 | A | C | III |
| 68 | 27.9 | A | C | III |
| 67 | 20 | A | C | III |
| 168 | 41.2 | B | C | III |
| 169 | 59.6 | A | C | III |
| 64 | 397.3 | A | C | IV |
| 170 | 68 | A | C | III |
| 171 | 30.2 | A | C | III |
| 63 | 42.1 | A | B | III |
| 62 | 30.6 | A | B | III |
| 61 | 9.6 | B | C | II |
| 60 | 5.8 | B | C | II |
| 59 | 33.7 | A | B | III |
| 58 | 42 | A | B | III |
| 57 | 10.7 | A | B | III |
| 56 | 19 | A | B | III |
| 54 | 38.9 | A | B | III |

TABLE 1-continued

In vitro enzymatic $IC_{50}$ values for exemplary compounds

| Compound | Selectivity (6 v 8) (fold) | HDAC6 IC50: (μM) | HDAC8 IC50: (μM) | Selectivity (6 v 8) (fold) |
|---|---|---|---|---|
| 53 | 39.6 | A | B | III |
| 52 | 35.5 | A | B | III |
| 51 | 27.6 | A | B | III |
| 50 | 45.5 | A | C | III |
| 49 | 15.4 | B | C | III |
| 48 | 15.6 | A | C | III |
| 47 | 22.3 | A | B | III |
| 46 | 51 | A | B | III |
| 45 | 150.8 | A | B | IV |
| 172 | 43 | A | C | III |
| 173 | 58.9 | A | C | III |
| TSA | 183.3 | A | B | IV |

TABLE 2

In vitro enzymatic $IC_{50}$ values for exemplary compounds

| | HDAC Paralog | | | | | | | | | | |
|---|---|---|---|---|---|---|---|---|---|---|---|
| Compound | 1 | 2 | 3 | 4 | 5 | 6 | 7 | 8 | 9 | 10 | 11 |
| 34 | D | D | C | D | D | A | D | D | D | D | C |
| 33 | | | | | | A | C | C | | D | |
| 32 | | | | | | A | C | C | | D | |
| 27 | | | | | | A | C | D | | E | |
| 24 | | | | | | A | C | C | | E | |
| 20 | | | | | | A | E | D | | D | |
| 19 | | | | | | A | D | C | | D | |
| 16 | D | D | D | D | E | A | D | D | E | D | C |
| 110 | | | | | | A | D | C | | D | |
| 112 | | | | | | A | D | E | | E | |
| 111 | | | | | | A | D | D | | D | |
| 93 | D | D | C | C | C | A | C | C | C | D | C |
| 94 | E | E | D | D | D | B | C | C | C | E | E |
| 120 | | | | | | A | C | C | | E | |
| 136 | | | | | | A | C | C | | E | |
| 139 | | | | | | A | C | C | | D | |
| 79 | C | D | C | C | C | A | B | C | B | D | E |
| 106 | D | D | C | D | E | B | D | C | D | E | D |
| 124 | E | | | | | A | C | C | E | | |
| 134 | | | | | | A | D | C | | D | |
| 158 | | | | | | A | B | C | | E | |
| 157 | | | | | | A | B | C | | D | |
| 152 | D | | | | | A | B | C | B | | |
| 127 | | | | | | A | C | C | | E | |
| 128 | | | | | | B | C | C | | E | |
| 78 | | | | | | C | D | B | | E | |
| 75 | | | | | | A | C | C | | D | |
| 74 | | | | | | B | C | C | | D | |
| 67 | | | | | | A | C | C | | D | |
| 170 | | | | | | A | C | C | | D | |
| 61 | | | | | | B | C | C | | E | |
| 60 | | | | | | B | C | C | | E | |
| 59 | | | | | | A | C | B | | D | |
| 58 | D | D | C | C | C | A | C | B | C | D | E |
| 54 | | | | | | A | C | B | | E | |
| 53 | C | D | C | C | C | A | B | B | B | C | D |
| 172 | E | E | D | D | D | A | C | C | D | E | A |
| 173 | D | D | C | C | D | A | C | C | C | D | D |
| TSA | A | A | E | C | C | A | B | B | C | A | C |

Aqueous Thermodynamic Solubility

A 10 mM stock solution (in DMSO) was prepared for the test sample. From the 10 mM stock solution, a working solution of 2 μM was prepared by diluting the test sample in mobile phase solution (typically, methanol: 2 mM ammonium acetate containing suitable internal standard—carbamazepine/diclofenac). Further, the working solution was serially diluted in mobile phase solution up to 4 to 5 linearity point to prepare standard solution for plotting the calibration curve. The area for each standard sample was analyzed using LCMS/MS. The normalized area values are plotted vs. concentration to achieve calibration equation. For ascertaining the aqueous thermodynamic (TD) solubility of test compound, 1 mg powder form of the compound was added to 1 mL of Dulbecco's Phosphate Buffered Saline (DPBS, pH @ 7.4) to achieve a theoretical concentration equivalent to 1 mg/mL. Test compound (in singlet) was dispersed in buffer solution using a vortex mixer.

The resulting solution was then kept on RotoSpin (shaker) at 50 rpm for 24 hours at room temperature (25° C.). After the incubation period, the content was filtered through a 0.45 μm PVDF hydrophilic syringe filters and filtrate was quantified by LCMS/MS. The filtrate was diluted in mobile phase and, subsequently, the AUC was ascertained for diluted sample using LCMS/MS. From the AUC of test sample the corresponding concentration was calculated using 4 to 5 point linearity/calibration curve. Results are the average of three independent experiments.

Metabolic Stability in Liver Microsomes

A 10 mM stock solution (in DMSO) was prepared for the compound. From the stock solution, a working solution of 150 μM was prepared by diluting the compound in DMSO. (Note that this concentration of working solution was prepared considering a final concentration of 1 μM).

Following this, master mix of liver microsomes from the desired species (either strain (final protein conc. 0.3 mg/mL) and 0.1 M potassium phosphate buffer was prepared for required number of reactions. To this master mix, test compound was spiked at a concentration of 1 μM (0.5% DMSO). The aforementioned sample was pre-incubated at 37° C. for 5 min. Following this, samples are aliquoted for positive and negative control reactions. Subsequently, 10 mM NADPH (as a cofactor; prepared in 0.1 M potassium phosphate buffer) per reaction was added to initiate the positive control reaction (final conc. 1 mM) and 0.1 M phosphate buffer (without NADPH) was added to initiate negative control reaction. The samples were then incubated at 37° C. for desired time points with 400 rpm shaking condition.

At each time point (0, 15, 30, 60 and 120 min), samples were withdrawn and reactions were terminated using chilled acetonitrile/methanol: 2 mM ammonium acetate (80:20) and suitable internal standard (carbamazepine—60 ng/mL). The samples were centrifuged at 4000 rpm, 4° C. for 30 min and the supernatant is analyzed in duplicate by LC-MS/MS. The percent compound remaining at each time point was calculated with respect to that of the 0 min sample. The data were then analyzed to calculate half-life and intrinsic clearance ($CL_{int}$). Note that negative control samples are run without NADPH for initial and final time point only and blank samples were prepared using DMSO (without the test compound).

TABLE 3

Solubility and liver microsome stability for exemplary compounds

| Compound | Solubility in PBS pH 7.4 (MM) | Mouse BL6 Liver Microsome Stability Half-life (min) | Mouse CD1 Liver Microsome Stability Half-life (min) | Rat Liver Microsome Stability Half-life (min) | Human Liver Microsome Stability Half-life (min) |
|---|---|---|---|---|---|
| 34 | 6.97 | 10.2 | 23.6 | 4.58 | 19.1 |
| 33 | | | 7.1 | | |
| 32 | 163.82 | 93.5 | 140 | | >120 |

TABLE 3-continued

Solubility and liver microsome stability for exemplary compounds

| Compound | Solubility in PBS pH 7.4 (MM) | Mouse BL6 Liver Microsome Stability Half-life (min) | Mouse CD1 Liver Microsome Stability Half-life (min) | Rat Liver Microsome Stability Half-life (min) | Human Liver Microsome Stability Half-life (min) |
|---|---|---|---|---|---|
| 28 | 23.45 | 33.5 | | | |
| 27 | 2049.6 | >120 | | | >120 |
| 25 | 1243.98 | 8.04 | | | |
| 24 | 2389.66 | >120 | | | >120 |
| 20 | 758.36 | 44.4 | | | |
| 19 | 498.4 | 34.5 | | | 74.4 |
| 16 | 18.95 | 5.5 | | | 35.1 |
| 14 | 418.83 | 8.9 | | | |
| 7 | 2486.18 | 120 | | | >120 |
| 4 | 939.84 | 72.6 | | | |
| 3 | 54.25 | 64.6 | | | |
| 2 | 1138.1 | 93.2 | | | |
| 107 | | | 7.6 | | |
| 108 | | | 7.9 | | |
| 109 | | | 5.7 | | |
| 110 | | | 4.5 | | |
| 113 | | | 27.5 | | |
| 115 | | | >60.0 | | |
| 118 | | | >60.0 | | |
| 93 | | | >60.0 | | |
| 120 | 2764.58 | >120 | | | |
| 136 | 157.04 | 8.91 | | | |
| 139 | 3466.67 | >120 | | | |
| 79 | 2690.86 | >120 | | | >120 |
| 145 | 1256.11 | >120 | | | |
| 106 | 2397.51 | >120 | | | |
| 132 | 301.71 | >120 | | | |
| 147 | 259.5 | 5.69 | | | |
| 124 | 1057.65 | >120 | | | |
| 134 | 3485.5 | >120 | | | >120 |
| 158 | 2949.68 | >120 | | | |
| 157 | 2764.28 | >120 | | | |
| 152 | 3049.94 | >120 | | | |
| 127 | 1746.87 | 41 | | | |
| 77 | 116.78 | 9.22 | | | |
| 75 | 750.37 | 95.8 | 137 | | 142 |
| 169 | 388.74 | 119 | | | |
| 64 | 444.75 | 18.5 | | | |
| 59 | 1640.75 | | >120 | | >120 |
| 58 | 3284.71 | >120 | >120 | | >120 |
| 53 | | 264 | 213 | >120 | >120 |
| 52 | | 290 | | | |
| 46 | 179.45 | 78.5 | | | |
| 45 | 23.77 | 54.8 | | | |
| 173 | 3083.74 | >120 | | | |

Plasma Protein Binding Assay

The plasma protein binding assay was performed using the Rapid Equilibrium Dialysis (RED) method using RED device inserts from Thermo scientific (Cat #89810).

A 10 mM stock of compound was prepared in DMSO. From the stock solution, a 2.5 mM working solution of compound was prepared in DMSO and spiked in neat plasma (from desired species) to achieve the final concentration of 10 μM in incubation mixture. Subsequently, 50 μL of sample from this mixture was added into 50 μL of DPBS and immediately vortexed with 400 μL of precipitation buffer (cold 90/10 Methanol/Acetonitrile with 0.1% formic acid) containing internal standard—Carbamazepine (60 ng/mL). This resulting sample (T=0 min) was incubated on ice for 30 minutes and then centrifuged at 4000 rpm and 4° C. for 30 minutes.

The RED device was placed onto the base plate following which 200 μL of the incubation mixture was added in the chamber of the RED device which was encircled by a red ring. In the other chamber 350 μL of buffer (DPBS, pH 7.4) was added and sealed (with a sealer) to avoid any evaporation or spilling of the samples from the chamber. The base plate was then put on an orbital shaker at 300 rpm for 5 hours at 37° C. After this incubation period, the base plate was taken out and subsequently 50 μL of post dialysis samples from both chambers were collected in separate wells of the 96 well deep well plates.

Following this, 50 μL of pertinent plasma was added to the collected buffer sample and 50 μL of buffer was added to the collected plasma sample. Precipitation buffer (400 μL; cold 90/10 Methanol/Acetonitrile with 0.1% formic acid) containing internal standard—Carbamazepine (60 ng/mL) was added in order to precipitate the protein and to release the compound. The samples were vortexed and incubated on ice for 30 minutes. Following the incubation, the samples were centrifuged at 4000 rpm and 4° C. for 30 minutes. Supernatants from all the samples were collected in LCMS vials and analyzed in duplicates using LCMS/MS. The concentration of test compound was determined in the buffer and plasma chamber from the peak areas obtained (LCMS/MS analysis).

The percentage of the test compound bound and % recovery is calculated based on the following formula:

$$\% \text{ Free}=(\text{Concentration buffer chamber}/\text{Concentration plasma chamber})\times 100\%$$

$$\% \text{ Bound}=100\%-\% \text{ Free}$$

$$\% \text{ Recovery}=\{(V_{dialysate}\times C_{free}+V_{plasma}\times C_{total})/(V_{plasma}\times C_{zero})\}\times 100\%$$

wherein, $V_{dialysate}$=Volume of buffer chamber, $C_{free}$=Concentration in the buffer chamber post dialysis, $V_{plasma}$=Volume in plasma chamber, $C_{total}$=Concentration in plasma chamber post dialysis, $C_{zero}$=Initial concentration at T=0 min.

Plasma Stability Assay

A 10 mM stock solution (in DMSO) was prepared for the test compound. From the stock solution, a working solution of 2.5 mM was prepared by diluting the compound in DMSO. Following this, neat plasma (from desired species) was aliquoted and pre-incubated at 37° C. for 5 minutes. To this plasma, the test compound was spiked at a concentration of 10 μM (0.4% DMSO) to initiate the reaction. The samples were then incubated at 37° C. for desired time points.

At each time point (0, 60, 120, 240 and 300 min), samples were withdrawn and reactions were stopped using precipitation buffer (cold 90/10 Methanol/Acetonitrile with 0.1% formic acid) containing internal standard—Carbamazepine. The samples were centrifuged at 4000 rpm; 4° C. for 30 min and the supernatant was analyzed in duplicate by LC-MS/MS. The percent compound remaining at each time point was calculated with respect to that of the 0 min sample. Note that blank sample was prepared using DMSO (without the test compound).

TABLE 4

Plasma protein binding and plasma stability for exemplary compounds

| Compound | Mouse Plasma Protein Binding (% Bound after 5 hrs) | Human Plasma Protein Binding (% Bound after 5 hrs) | Mouse Plasma Stability (% Remaining at 120 min) | Human Plasma Stability (% Remaining at 120 min) |
|---|---|---|---|---|
| 34 | 99.85 | 99.6 | 71.8 | 98.8 |
| 32 | 83.1 | | 45.5 | |
| 28 | 97.9 | | | |

TABLE 4-continued

Plasma protein binding and plasma stability for exemplary compounds

| Compound | Mouse Plasma Protein Binding (% Bound after 5 hrs) | Human Plasma Protein Binding (% Bound after 5 hrs) | Mouse Plasma Stability (% Remaining at 120 min) | Human Plasma Stability (% Remaining at 120 min) |
|---|---|---|---|---|
| 27 | 8.1 | | 70.4 | |
| 25 | 98.9 | | 56.1 | |
| 24 | 15 | | | |
| 20 | 95.8 | | | |
| 19 | 98.4 | 95.9 | 77.9 | |
| 16 | 97.3 | 94.3 | 96.6 | 103 |
| 14 | 82.7 | | | |
| 7 | 70.8 | 81 | 79.5 | |
| 4 | 46.9 | | 54.6 | |
| 3 | 90.3 | | 73.6 | |
| 2 | 53.9 | | 61.4 | |
| 107 | 99.3 | | | |
| 108 | 99.5 | | | |
| 109 | 96.9 | | | |
| 110 | 95.8 | | | |
| 113 | 99.2 | | 87.6 | |
| 115 | 34.7 | | 112 | |
| 118 | 13.1 | | | |
| 93 | 14 | | | |
| 120 | 36.8 | | 64.8 | |
| 136 | 92.8 | | 66.6 | |
| 139 | 0.3 | | | |
| 79 | 19.85 | 23.2 | 53.5 | |
| 145 | 25.3 | | 44 | |
| 106 | 29 | | 93.1 | |
| 132 | 4.19 | | 84.1 | |
| 147 | 94 | | 95.6 | |
| 124 | 55 | | 61.2 | |
| 134 | 17.1 | 27.8 | 91 | |
| 158 | 0 | | 53.1 | |
| 157 | 9.45 | | 25.4 | |
| 152 | 0 | | 20.5 | |
| 127 | 44.6 | | 65.9 | |
| 77 | 97.8 | | 47 | |
| 75 | 72.8 | | 53 | |
| 169 | 0.44 | | | |
| 64 | 89.3 | | 35.8 | |
| 58 | 15.8 | 60.4 | 69.9 | |
| 53 | 25.4 | 55.5 | 71.8 | 103 |
| 46 | 93.8 | | 43.8 | |
| 45 | 96.2 | | 35.95 | |
| 173 | 15.1 | | 59.2 | |

Compound $EC_{50}$ Determination for Tubulin- and Histone H3 Acetylation in Cells Estimation of the $EC_{50}$ for exemplary compounds to alter target protein acetylation in undifferentiated SH-SY5Y cells was performed using standard Western immunoblotting methods. A representative example is shown for compound 34 in FIG. 1. SH-SY5Y cells were grown to 90% confluency on sterile cell growth plates. 10 mM compound stocks prepared in DMSO and two-fold serial dilutions were prepared from the stock and applied to cells to achieve a 12-point concentration range in cell media from an upper limit of 10 μM to a lower limit of DMSO [zero compound].

Cells were incubated under normal growth conditions (37° C., 5% $CO_2$) in the presence of compound for 4 hours, then media was aspirated and cells were rinsed two times with 1×DPBS with calcium and magnesium warmed to 37° C. Cells were frozen directly on the plates on a bed of dry ice for 5 min, then stored at −80° C. until protein extraction.

TABLE 5

$EC_{50}$ values for tubulin and histone H3 acetylation in a cell-based assay

| Compound | acTubK40 EC50 (μM) | acH3K9 EC50 (μM) |
|---|---|---|
| 75 | 1.4 | >10 μM |
| 58 | 2.6 | 2.5 μM |
| 34 | 2.1 | >10 μM |
| 32 | 0.3 | >10 μM |
| 53 | 0.2 | >10 μM |
| 16 | 2.9 | >10 μM |
| 46 | 0.1 | >10 μM |
| 45 | 1.7 | >10 μM |
| 79 | 0.44 | >10 μM |

Protein extraction was performed in RIPA buffer (50 mM Tris-HCL pH 8.0, 150 mM NaCl, 0.5% sodium deoxycholate, 0.1% sodium dodecyl sulfate, 1% NP-40) supplemented with Pierce protease inhibitor mini tables (Thermofisher cat #A32953) exactly as described by the manufacturer. After thawing the plate on a bed of wet ice for 10 minutes, lysis buffer was added to each well (e.g. 100 μL per well of a 24-well plate) and cells scraped from the bottom of each well. Lysates were then sonicated over ice (40% power, 30 pulses of 1 second on, 2 seconds off), centrifuged at 16,000 g for 10 min at 4° C., and the clarified supernatant saved. Protein concentration was determined by BCA assay and at least 3 μg prepared per lane by combining lysate supernatant aliquot with 1/3 total volume of 3× gel loading buffer containing DTT (NEB Cat. #B7703S), heating for 5 minutes at 95° C., briefly centrifuging and then loading on an SDS-PAGE gel.

Proteins were resolved on a 4-20% Tris-Glycine gel and transferred to PVDF membrane using an iBlot2 dry transfer system. The membrane was then blocked for at least 30 minutes at room temperature in TBST containing 5% milk or 5% bovine serum albumin, then incubated overnight at 4° C. with a single primary antibody from the following table:

| Name | Host (*) | Antibody Type | Species Cross-Reactivity | Recommended Dilution | MW Detected | Supplier | Catalog # | Lot |
|---|---|---|---|---|---|---|---|---|
| Primary Antibodies | | | | | | | | |
| Alpha-Tubulin | M | Monoclonal, IgG1 | Am Hu Bv Ck Fu Ms Rt Ys | 1:50K-1:200K | 50 KDa | Sigma | T6199 | 048M4751V |
| Acetyl-alpha Tubulin (K40) | M | Monoclonal, IgG2b | Hu Hm Bv Ck Mk Ms Pg Pz | 1:50K-1:200K | 50 KDa | Sigma | T7451 | 018M4873V |
| β-Actin Antibody (AC-15) | M | Monoclonal | Hu, Ms | 1:2K-1:12K | 43 KDa | Santa Cruz | sc-69879 | J0618 |
| H3 (D1H2) XP | R | Monoclonal | H M R Mk | 1:5K | 17 KDa | Cell Signalling | 4499S | 9 |
| Acetyl-H3K9 | R | Polyclonal | Hu, Ms, Rt | 1:5K | 17 KDa | EMD Millipore | 06-942 | |

-continued

| Name | Host (*) | Antibody Type | Species Cross-Reactivity | Recommended Dilution | MW Detected | Supplier | Catalog # | Lot |
|---|---|---|---|---|---|---|---|---|
| | | | | Secondary Antibodies | | | | |
| Anti-mouse HRP | H | Polyclonal | | 1:5K | N/A | CST | 7076S | 33 |
| Anti-rabbit HRP | G | Polyclonal | | 1:5K | N/A | CST | 7074S | 27 |

*M = mouse
R = rabbit,
H = horse,
G = goat

Following primary antibody incubation, membranes were washed, incubated in secondary antibody, washed and incubated in ECL prime western blotting detection reagent (Amersham #RPN223) with membrane exposure and ECL signal capture in a LI-COR Odyssey Imaging system. Example image (right) is included for cells treated with compound 34 from an upper concentration of 10 μM across a range of dilutions as described. Subsequent densitometry of immunoreactive bands was performed using the ImageStudio software and Microsoft Excel resulting in the following ratios: acetylTubulin/Tubulin and acetyl histone H3K9/histone H3. Raw ratios were uploaded to GraphPad Prism v7.0 with $EC_{50}$ values modeled using the variable slope equation for log-transformed data [log(agonist) vs response in Prism].

Microsomal and Brain Protein Binding

The microsomal protein binding assay was performed using the Rapid Equilibrium Dialysis (RED) method using RED device inserts from Thermo scientific (Cat #89810). A 10 mM stock of compound was prepared in DMSO. From the stock solution, a working solution of 1 mM was prepared in DMSO and further to 250 μM by diluting the compound in Acetonitrile:water (50:50). Liver microsomes at 0.3 mg/ml were prepared (from desired species) in 0.1 M phosphate buffer. The compound was spiked in prepared microsomes (at protein concentrations used for the respective metabolic stability incubations) to achieve the final desired concentration of 1 μM. The microsomes-compound mixture was mixed and subsequently, 50 μL aliquot from this mixture was added in 50 μL of 0.1 M phosphate buffer for T=0 hour reaction. This reaction was terminated immediately with 600 μL of acetonitrile:water (90:10) containing internal standard (carbamazepine) and samples were stored at 4 C for 16 hours.

To initiate the reaction, the RED device was placed onto the base plate following which 200 μL of the microsomes-compound mixture was added in the chamber of the RED device which is encircled by a red ring (Red Chamber). In the other chamber (white chamber) 350 μL of buffer (0.1 M Phosphate buffer, pH 7.4) was added and sealed (with a sealer) to avoid any evaporation or spilling of the samples from the chamber. The base plate was then put on an orbital shaker at 400 rpm for 16 hours at 37° C. After this incubation period, the base plate was taken out and subsequently, 50 μL of post dialysis samples from the both chambers were collected in deepwell plate. Following this, 50 μL of pertinent mice liver microsomes solution was added to the collected buffer sample from the white chamber and 50 μL of buffer was added to the collected mice liver microsomes sample from the red chamber. The reaction were terminated with 600 μL of acetonitrile:water (90:10) containing internal standard (carbamazepine) in order to precipitate the protein and to release the compound. The resulting samples from T=0 hour as well as T=16 hour were mixed and centrifuged at 13,000 rpm for 10 minutes. Supernatants from all the samples were collected in vials and analyzed in duplicates using LCMS/MS. The concentration of test compound was determined in the buffer and microsomal chamber from the peak areas obtained (LCMS/MS analysis).

The percentage of the test compound fraction unbound is calculated based on the following formula: % Fu (Fraction unbound)=1−(Concentration of Protein containing chamber−Concentration of Buffer chamber/Concentration of Protein containing chamber)

The brain protein binding assay was performed using the Rapid Equilibrium Dialysis (RED) method using RED device inserts from Thermo scientific (Cat #89810). Brain tissue homogenate samples were prepared by diluting one volume of whole brain tissue (desired species) with three volumes of dialysis buffer (phosphate buffered saline pH 7.4-0.1 M sodium phosphate and 0.15 M sodium chloride) to yield 4 times diluted homogenate. A 1 mM stock solution of test compounds were prepared in DMSO and diluted 200-fold in brain homogenate to yield concentration of 5 μM. The final DMSO concentration was 0.5%. Rapid equilibrium dialysis was performed with a rapid equilibrium dialysis (RED) device containing dialysis membrane with a molecular weight cut-off of 8,000 Daltons. Each dialysis insert contains two chambers. The red chamber was for brain homogenate while the white chamber for buffer.

A 200 μL aliquot of test compound and positive controls in brain homogenate (triplicates) was added to the red chamber of dialysis inserts. A 350 μL aliquot of dialysis buffer was added to the buffer chamber of the inserts. After sealing the RED device with an adhesive film, dialysis was done at 370 C with shaking at 100 RPM for 4 hours. A 50 μL aliquot of test compound and positive controls were separately added to 0.5 mL microcentrifuge tubes. Two aliquots were frozen immediately (0 minute sample). Two other aliquots were incubated at 37° C. for 4 hours along with the RED device. Following dialysis, an aliquot of 50 μL was removed from each well (brain homogenate and buffer) and diluted with equal volume of opposite matrix to nullify the matrix effect. Similarly, buffer was added to recovery and stability samples. An aliquot of 100 μL was submitted for LC-MS/MS analysis. A 25 μL aliquot of the positive control and test compound were crashed with 100 μL of acetonitrile containing internal standards (glipizide) and vortexed for 5 min. The samples were centrifuged at 4000 RPM at 4° C. for 10 min and 100 μL of supernatant was submitted for LC-MS/MS analysis. Samples were monitored for parent compound in MRM mode using LC-MS/MS.

TABLE 6

Mouse brain protein and liver microsome binding for exemplary compounds

| Compound | Mouse Brain Protein Binding (BPB): % Bound at 4 hr (%) | Mouse Liver Microsome Binding: fu mic (fu mic) | Mouse Liver Microsome Binding: CLint (µl/min/mg protein) | Mouse Liver Microsome Binding: U-CLint (µl/min/mg protein) |
|---|---|---|---|---|
| 34 | 99.9 | 0.0928 | | |
| 32 | | 0.854 | 24.7 | 28.9 |
| 16 | 99.8 | 0.472 | 427 | 904 |
| 7 | | 1.06 | | |
| 134 | | 0.913 | | |
| 158 | | 1.05 | <19.0 | |
| 157 | | 0.96 | <19.0 | |
| 127 | | 0.97 | 56.3 | 57.9 |
| 173 | 79.4 | | | |

In Vivo Assessment of Brain Penetration in Mice

A preliminary evaluation of brain penetration in mice was performed for select exemplary compounds and the results are shown in Table 8. A total of 4 mice were used for each study, with all the animals administered compound intravenously with solution formulation (typically in 5% NMP, 5% Solutol HS-15 and 90% normal saline) at 1 mg/kg (at 5 mL/kg dose volume). Blood samples (approximately 60 µL) were collected under light isoflurane anesthesia from two mice at 0.25 and 1 hr. Plasma was harvested by centrifugation of blood and stored at −70±10° C. until analysis. After blood collection, brain was perfused and isolated at 0.25 and 1 hr. Brain was dipped three times in ice-cold phosphate buffer saline, blotted dry, and weighed. Brain samples were homogenized using ice-cold phosphate buffer saline with twice volume of brain weight making the total homogenate three volumes and stored below −70±10° C. until analysis.

Plasma and brain samples were quantified by fit-for-purpose LC-MS/MS method. The extraction procedure for plasma/brain samples and the spiked plasma/brain calibration standards were identical: A 25 µL of study sample or spiked plasma/brain calibration standard was added to individual pre-labeled micro-centrifuge tubes followed by 100 µL of internal standard prepared in acetonitrile (Glipizide, 500 ng/mL) was added except for blank, where 100 µL of acetonitrile was added. Samples were vortexed for 5 minutes. Samples were centrifuged for 5 minutes at a speed of 4000 rpm at 4° C. Following centrifugation, 100 µL of clear supernatant was transferred in 96 well plates and analyzed using LC-MS/MS using a standard LC-MS/MS method that entailed the following:

Column: Phenomenex, Kinetex EVO, 5 µm, C18, 100A, 100×4.6 mm

Injection Volume: 5 µl

Column Temperature: 45° C.

Flow Rate: 0.8 mL/min

Mobile Phase A: 0.1% formic acid in acetonitrile

Mobile Phase B: 0.1% formic acid in water

Gradient:

| Time (Minutes) | Flow Rate (mL/min) | PUMP A (% Conc) | PUMP B (% Conc) |
|---|---|---|---|
| Initial | 0.800 | 0 | 100 |
| 0.60 | 0.800 | 100 | 0 |
| 1.80 | 0.800 | 100 | 0 |
| 2.20 | 0.800 | 0 | 100 |
| 2.80 | 0.800 | 0 | 100 |

TABLE 7

Preliminary in vivo exposure: plasma and brain levels in BL/6 Mice after IV administration of a 1 mg/kg dose

| Compound | Mouse Brain Conc (µM) at 15 min | Mouse Brain Conc (µM) at 60 min | Mouse Plasma Conc (µM) at 15 min | Mouse Plasma Conc (µM) at 60 min | Mouse B:P at 15 min | Mouse B:P at 60 min |
|---|---|---|---|---|---|---|
| 34 | 0.85 | 0.27 | 0.43 | 0.17 | 1.96 | 1.63 |
| 32 | 0.30 | 0.00 | 0.11 | 0.00 | 2.76 | 0.00 |
| 27 | 0.15 | 0.00 | 0.56 | 0.00 | 0.27 | nc |
| 24 | 0.00 | 0.00 | 0.21 | 0.00 | 0.00 | nc |
| 19 | 0.31 | 0.05 | 0.53 | 0.09 | 0.58 | 0.60 |
| 16 | 1.25 | 0.26 | 0.31 | 0.05 | 4.05 | 4.80 |
| 14 | 0.20 | 0.00 | 0.09 | 0.01 | 2.27 | 0.00 |
| 7 | 0.09 | 0.00 | 0.20 | 0.00 | 0.45 | 0.00 |
| 116 | 0.39 | 0.00 | 0.25 | 0.02 | 1.57 | 0.00 |
| 118 | 0.09 | 0.00 | 0.11 | 0.01 | 0.81 | 0.00 |
| 93 | 0.55 | 0.00 | 0.46 | 0.01 | 1.20 | 0.00 |
| 94 | 0.06 | 0.00 | 0.13 | 0.00 | 0.48 | nc |
| 136 | 1.10 | 0.03 | 0.39 | 0.01 | 2.81 | 3.13 |
| 139 | 0.05 | 0.00 | 0.14 | 0.02 | 0.34 | 0.00 |
| 79 | 0.16 | 0.09 | 0.25 | 0.02 | 0.61 | 4.81 |
| 145 | 0.62 | 0.00 | 0.20 | 0.02 | 3.15 | 0.00 |
| 106 | 0.00 | 0.00 | 0.14 | 0.03 | 0.00 | 0.00 |
| 121 | 0.19 | 0.06 | 0.96 | 0.01 | 0.19 | 5.89 |
| 124 | 0.40 | 0.00 | 0.24 | 0.00 | 1.67 | nc |
| 134 | 0.00 | 0.00 | 0.17 | 0.00 | 0.00 | nc |
| 152 | 0.09 | 0.00 | 0.14 | 0.00 | 0.65 | nc |
| 75 | 0.61 | 0.08 | 0.19 | 0.01 | 3.20 | 6.82 |
| 64 | 0.28 | 0.02 | 0.21 | 0.02 | 1.37 | 1.42 |
| 59 | 0.20 | 0.00 | 1.18 | 0.07 | 0.17 | 0.00 |
| 58 | 0.39 | 0.06 | 0.23 | 0.01 | 1.72 | 6.04 |

TABLE 7-continued

| Preliminary in vivo exposure: plasma and brain levels in BL/6 Mice after IV administration of a 1 mg/kg dose | | | | | | |
|---|---|---|---|---|---|---|
| Compound | Mouse Brain Conc (μM) at 15 min | Mouse Brain Conc (μM) at 60 min | Mouse Plasma Conc (μM) at 15 min | Mouse Plasma Conc (μM) at 60 min | Mouse B:P at 15 min | Mouse B:P at 60 min |
| 53 | 0.00 | 0.00 | 0.10 | 0.00 | 0.00 | nc |
| 46 | 0.15 | 0.03 | 0.21 | 0.05 | 0.72 | 0.60 |
| 45 | 0.22 | 0.04 | 0.19 | 0.02 | 1.11 | 1.61 |

Formulation: 5% NMP, 5% Solutol HS-15, 90% Saline, except * = Acetate buffer 50mM (pH-4.5)

Cell Viability

Cell viability following exposure to compounds for 4-48 hours was evaluated in two human cell lines; SH-SY5Y, human neuroblastoma (ATCC #CRL-2266) and HEK293, human embryonic kidney (ATCC #CRL-1573) using the CellTiter Glo assay (Promega #G7570). To perform the viability assay, SH-SY5Y and HEK293 cells were seeded at 5000 cells/50 μl growth medium/well on 96-well white clear-bottom tissue culture plates. Cells were incubated at 37° C. and 5% CO2 overnight to allow them to recover and reattach. The next day, cells were treated with test compounds for 4 and 24 hours (SH-SY5Y) or 24 and 48 hours (HEK293). The final concentration of test compounds was 30 μM and the final concentration of DMSO was 0.3%. The cytotoxin cisplatin (100 μM final concentration) was used as a positive control for cell death. After treatment, cell viability was measured by CellTiter-Glo® Luminescent Cell Viability Assay. To perform the CellTiter-Glo assay, 100 μl of CellTiter Glo reagent was added to each well and the plate was incubated at room temperature for an additional 10-20 min. Luminescence was measured using a luminometer (BioTek Synergy™ 2 microplate reader).

Assays were performed in triplicate at each concentration. In the absence of the compound (but in the presence of DMSO 0.3%, the luminescent intensity (Lt) in each data set was defined as 100%. In the absence of cells, the luminescent intensity (Lb) in each data set was defined as 0%. The percent luminescence in the presence of each compound was calculated according to the following equation: % luminescence=(L−Lb)/(Lt−Lb), where L=the luminescent intensity in the presence of the compound, Lb=the luminescent intensity in the absence of cells, and Lt=the luminescent intensity in the absence of the compound. Percent luminescence denotes percent viability in this assay and are tabulated±standard deviation.

TABLE 8

| Cell viability in dividing cells following exposure to exemplary compounds | | | | |
|---|---|---|---|---|
| | SH-SY5Y | | HEK293 | |
| Compound | 4 hrs | 24 hrs | 24 hrs | 48 hrs |
| Tubastatin A | 105.8 ± 15 | 117.3 ± 4.1 | 88.9 ± 4.8 | 55.3 ± 0.8 |
| 34 | 120.9 ± 8 | 56.6 ± 2.8 | 80 ± 3.3 | 33.5 ± 1.4 |
| Vorinostat | 117.2 ± 7.5 | 77.1 ± 4.4 | 102.6 ± 3 | 40.3 ± 1.8 |
| ACY-775 | 117.8 ± 8.8 | 95.2 ± 3.6 | 76.9 ± 4.6 | 39.4 ± 1.6 |
| 16 | 111 ± 2.4 | 66.6 ± 2.2 | 78.8 ± 3.8 | 34.2 ± 0.5 |
| ACY-1083 | 105.8 ± 3.8 | 92.7 ± 5 | 90.7 ± 7.8 | 54.6 ± 3.5 |
| 173 | 98.1 ± 6.6 | 101.9 ± 2 | 105.3 ± 3.2 | 89.5 ± 1.1 |
| DMSO | 100 ± 6.1 | 100 ± 1.4 | 100 ± 11.1 | 100 ± 3.1 |
| Cisplatin | 94.2 ± 5.7 | 62.2 ± 3.1 | 49 ± 11.4 | 36.1 ± 0.3 |

Cell Viability in Primary Rat Dorsal Root Ganglia (DRG)

Select exemplary compounds were evaluated for cell viability in primary rat dorsal root ganglia (DRG) cells following 3 or 72 hours of treatment. Data for select compounds is shown in Table 9 below. Compounds were dissolved in 100% DMSO to make 50 millimolar (mM) stock solutions. Stock solutions were diluted in DMSO and cell media using serial dilutions to create 11 doses with the top compound concentration at 100 μM, nine half-log dilutions and a DMSO (0 μM) dose.

Rat DRG cells were cultured in appropriate culture medium (90% DMEM, 10% FBS, 1% Penicillin-Streptomycin, 1% glutamine) at 37 C degrees in CO2 atmosphere. Culture medium was removed, cells were washed gently with PBS twice, and PBS was removed from the wells. Cells were digested with 3 mL 0.25% trypsin and the digestion was ended with 10 mL culture medium. DRG cells (80 μL) were plated in opaque-walled 96-well plates in culture medium and incubated for 24 hours. Compound doses (5×, 20 μL) were applied to DRG cells in triplicate for 3 or 72 hours. Wells containing medium without cells were prepared to obtain a value for background luminescence. The plate was equilibrated at room temperature for approximately 30 minutes. Cisplatin, a chemotoxic agent, served as a positive control for cell death. Vorinostat (SAHA), is a published nonselective HDAC inhibitor and is FDA approved for cancer treatment. Ricolinostat (ACY-1215) is Acetylon/Celgene/Regenacy's clinical development candidate for peripheral indications.

Cell viability was determined using the CellTiter-Glo® Luminescent Cell Viability Assay (Promega, G7573). CellTiter-Glo® Reagent (100 μL) was added to each well. Contents were mixed for 2 minutes on an orbital shaker to induce cell lysis. The plate was incubated at room temperature for 10 minutes to stabilize luminescent signal. Luminescence was recorded. The luminescent signal reflects the level of cell viability. CC50 is the concentration of a compound when cell viability is 50% and was calculated as follows:

$$\text{Cell viability (\%)}=(\text{Lum}_{CPD}-\text{Lum}_{MC})/(\text{Lum}_{CC}-\text{Lum}_{MC})*100\%$$

Lum: Luminescent signal

CC: DMSO group

MC: Medium control

CPD: Compound group

At the 3-hour time point, CC50 values were not calculable (nc) as a loss of cell viability was not observed.

TABLE 9

| Summary of cell viability data in primary rat DRGs after 3- or 72-hours of treatment | | |
|---|---|---|
| Compound | CC50 (μM) 3 h treatment | CC50 (μM) 72 h treatment |
| Cisplatin | nc | 0.58 |
| Vorinostat | nc | 0.39 |
| Ricolinostat | nc | 5.2 |
| 16 | nc | 4.4 |
| 173 | nc | 13.9 |

nc = not calculable

Pharmacokinetics

Figure 2A:
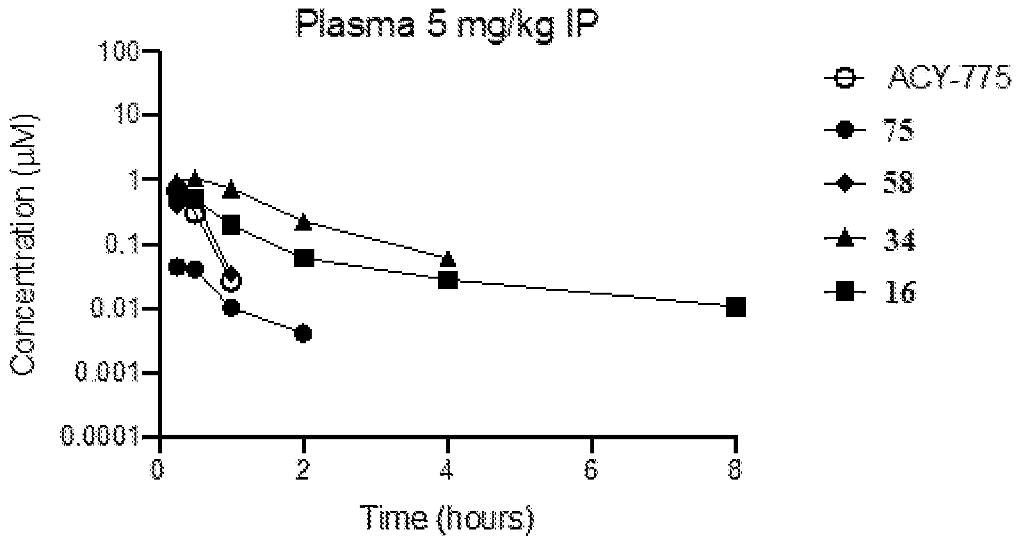
FIG. 2A is a graph showing the concentration of exemplary compounds 16, 34, 58, and 75 in plasma after intraperitoneal administration to male C57BL/6 mice.
Figure 2B:
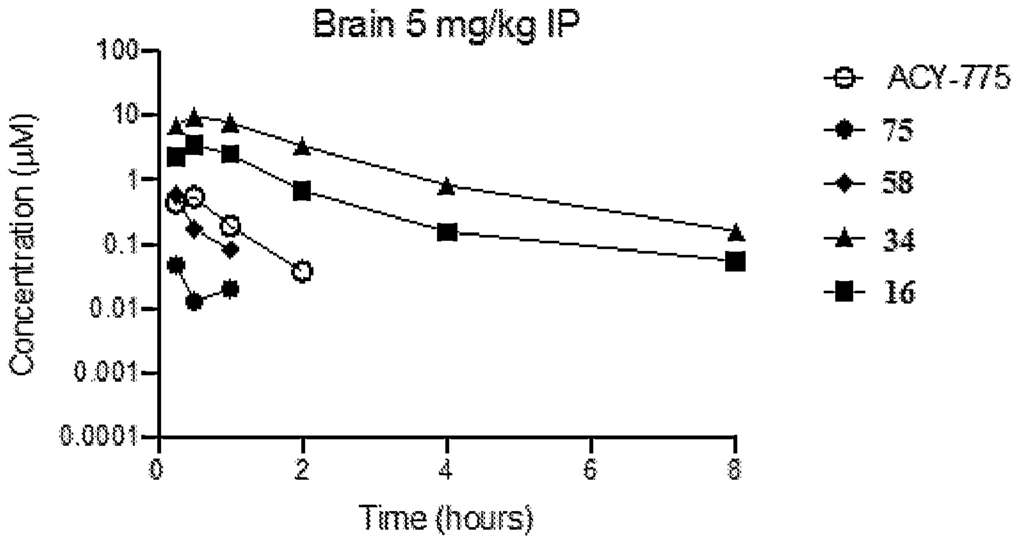
FIG. 2B is a graph showing the concentration of exemplary compounds 16, 34, 58, and 75 in brain tissue after intraperitoneal administration to male C57BL/6 mice.

Select exemplary compounds were evaluated for plasma pharmacokinetics and brain distribution in male C57BL/6 mice following a single intraperitoneal administration at 5 mg/kg. Data for select compounds is shown in FIG. 2A and FIG. 2B and summarized in Table 10 below. For each compound, a group of fourteen male mice were administered intraperitoneally with the compound formulation prepared in 5% NMP, 5% Solutol HS-15 and 90% normal saline at 5 mg/kg (or 7.5% NMP, 5% Solutol HS-15, 30% PEG-400 and 57.5% citric acid (10 mM) at 50 mg/kg dose). The blood samples were collected under light isoflurane anesthesia at 0.25, 0.5, 1, 2, 4, 8 and 24 hr (IP) in labeled micro centrifuge tubes containing $K_2EDTA$ as anticoagulant. Immediately after blood collection, plasma was harvested by centrifugation and stored at −70° C. until analysis. Following blood collection, animals were euthanized by $CO_2$ asphyxiation and brain samples were collected at each time point. Collected brain samples were dipped thrice in ice-cold phosphate buffer saline and blotted dry. Brain samples were homogenized using ice-cold phosphate buffer saline with twice volume of brain weight making the total homogenate three volumes and stored below −70±10° C. until analysis.

Table 11 below summarizes data for select exemplary compounds similarly evaluated following a single intravenous administration at 1 mg/kg or 2 mg/kg. For each compound, a group of twenty-one male mice were administered intravenously with the compound formulation prepared in compound formulation prepared in 5% NMP, 5% Solutol HS-15 and 90% normal saline at 1 mg/kg or 2 mg/kg. Blood and brain tissue samples were collected and processed as detailed above at 0.083, 0.25, 0.5, 1, 2, 4, and 8 hr or 0.25, 0.5, 1, 2, 4, 8 and 12 hr (IV).

Table 12 below summarizes data for select exemplary compounds similarly evaluated following a single peroral administration with the compound formulation prepared in 5% NMP, 5% Solutol HS-15 and 90% normal saline (10 mg/kg doses) or 7.5% NMP, 5% Solutol HS-15, 30% PEG-400 and 57.5% citric acid (10 mM) (30 mg/kg doses). Blood and brain tissue samples were collected and processed as detailed above at 0.25, 0.5, 1, 2, 4, 8 and 12 hr (PO).

All samples were processed for analysis by protein precipitation using acetonitrile and analyzed as described above with fit-for-purpose LC-MS/MS method. Pharmacokinetic parameters were calculated using the non-compartmental analysis tool of Phoenix WinNonlin® (Version 7.0).

TABLE 10

| Compound | ACY-775 | 34 | 16 | 75* | 58 | 173 | 79 |
|---|---|---|---|---|---|---|---|
| Tmax (hr)-brain | 0.5 | 0.5 | 0.5 | 0.25 | 0.25 | nc | nc |
| $T_{1/2}$ (hr)-brain | <0.5 (nc) | 1.4 | 1.7 | 0.17 | <0.25 (nc) | nc | nc |
| Cmax (μM)-brain | 0.54 | 9.8 | 3.5 | 17.3 | 0.6 | nc | nc |
| $AUC_{last}$ (μM * hr)-brain | 0.48 | 19.2 | 5.4 | 6.8 | 0.23 | nc | nc |
| B:P (AUC) | nc | 11.6 | 7.9 | 2.9 | 0.77 | nc | nc |
| B:P (Cmax) | 0.8 | 9.1 | 6.6 | 5.2 | 1.2 | nc | nc |

ACY-775, obtained from MedChem Express, is a published HDAC6-selective inhibitor and was used as a benchmark. Dose for all compounds except Compound 75 was 5 mg/kg. Compound 75 values shown are for 50 mg/kg; 5 mg/kg values were not calculable (nc) due to rapid clearance. 173 and 79 values were nc due to rapid clearance

TABLE 11

| Summary of pharmacokinetic properties in C57BL/6 mice after IV administration | | |
|---|---|---|
| Compound | 79 (2 mg/kg) | 16 (1 mg/kg) |
| $T_{1/2}$ (hr)-brain | nc | 0.68 |
| Cmax (μM)-brain | nc | 1.1 |
| $AUC_{last}$ (μM *hr)-brain | nc | 0.78 |
| CL (mL/min/kg)-brain | nc | 57.9 |
| Vss (L/kg)-brain | nc | 2.6 |
| B:P (AUC) | nc | 3.1 |
| B:P (Cmax) | nc | 1.4 |

79 values were not calculable (nc) in brain

TABLE 12

| Summary of pharmacokinetic properties in C57BL/6 mice after PO administration | | | | |
|---|---|---|---|---|
| Compound | 16 (10 mg/kg) | 16 (30 mg/kg) | 75 (10 mg/kg) | 173 (30 mg/kg) |
| Tmax (hr)-brain | 0.5 | 0.25 | nc | nc |
| $T_{1/2}$ (hr)-brain | 4.4 | 2.72 | nc | nc |
| Cmax (μM)-brain | 7.5 | 27.1 | nc | nc |
| $AUC_{last}$ (μM *hr)-brain | 10.1 | 30.8 | nc | nc |
| B:P (AUC) | 5.1 | 6.4 | nc | nc |
| B:P (Cmax) | 3.8 | 7.1 | nc | nc |

75 and 173 values were not calculable (nc) in brain

Figure 3A:
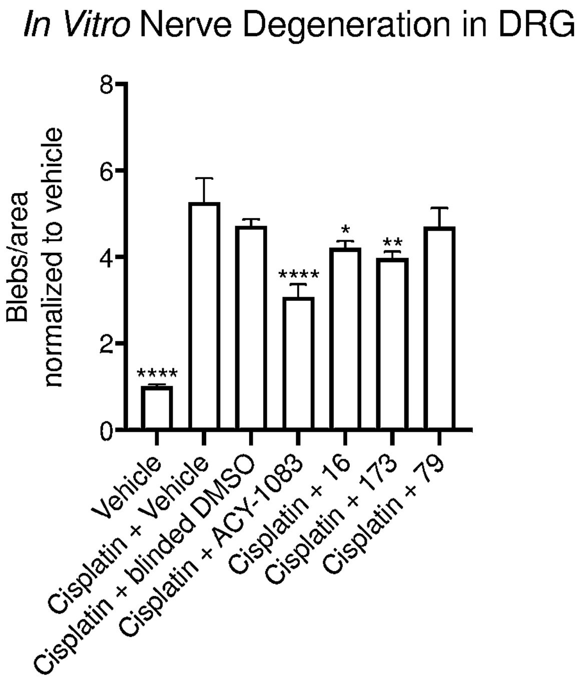
FIG. 3A is a graph showing the effect of exemplary compounds on in vitro nerve degeneration in primary rat dorsal root ganglion (DRGs) treated with cisplatin.
Figure 3B:
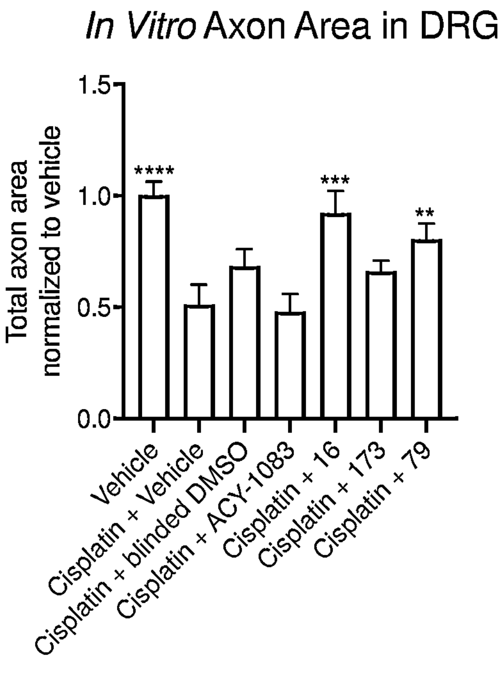
FIG. 3B is a graph showing the effect of exemplary compounds on in vitro axon area in primary rat DRGs treated with cisplatin. ACY-1083, obtained from MedChem Express, is a published HDAC6-selective inhibitor and was used as a benchmark. Blinded DMSO was used as an additional negative control. Primary adult rat dorsal root ganglia were co-treated for 4 days with 5 μM of the indicated compounds and 0.5 mM cisplatin. Nerve degeneration was evaluated by blebs per area as visualized by fluorescent imaging of beta tubulin staining. Axon area was also evaluated by fluorescent imaging of beta tubulin staining.
Figure 4A:
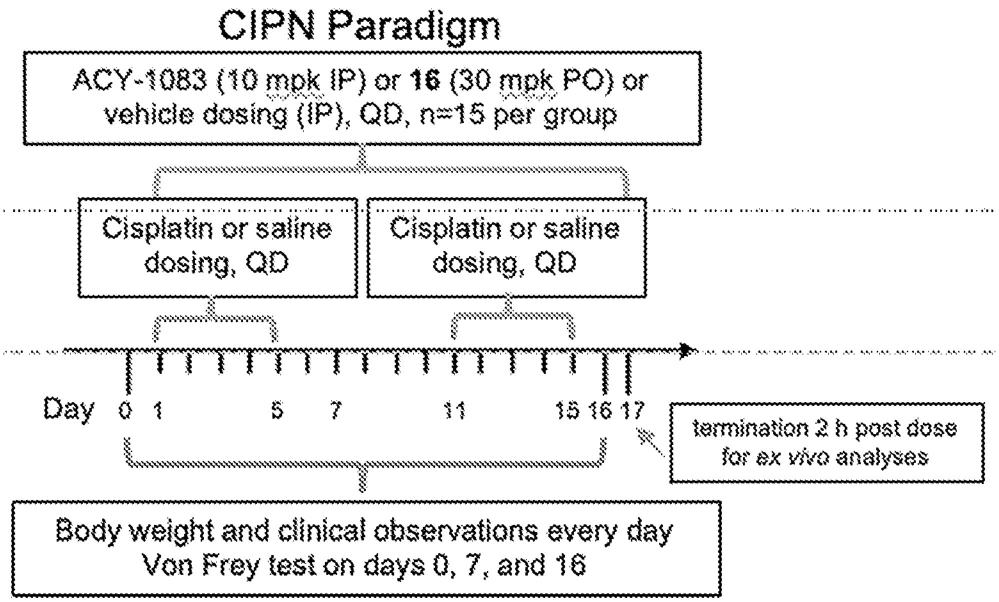
FIGS. 4A-F are a series of graphs summarizing the in vivo efficacy data of exemplary compound 16 in the chemotherapy-induced peripheral neuropathy (CIPN) mouse model. ACY-1083, obtained from MedChem Express, is a published HDAC6-selective inhibitor and was used as a benchmark. Male C57BL/6 mice were co-treated as indicated in FIG. 4A with 16 or ACY-1083 in the presence of cisplatin. Overall health was evaluated by survival and body weight. Mechanical allodynia was evaluated by the Von Frey test. Nerve integrity was evaluated by intraepidermal nerve fiber (IENF) density.
Figure 4B:
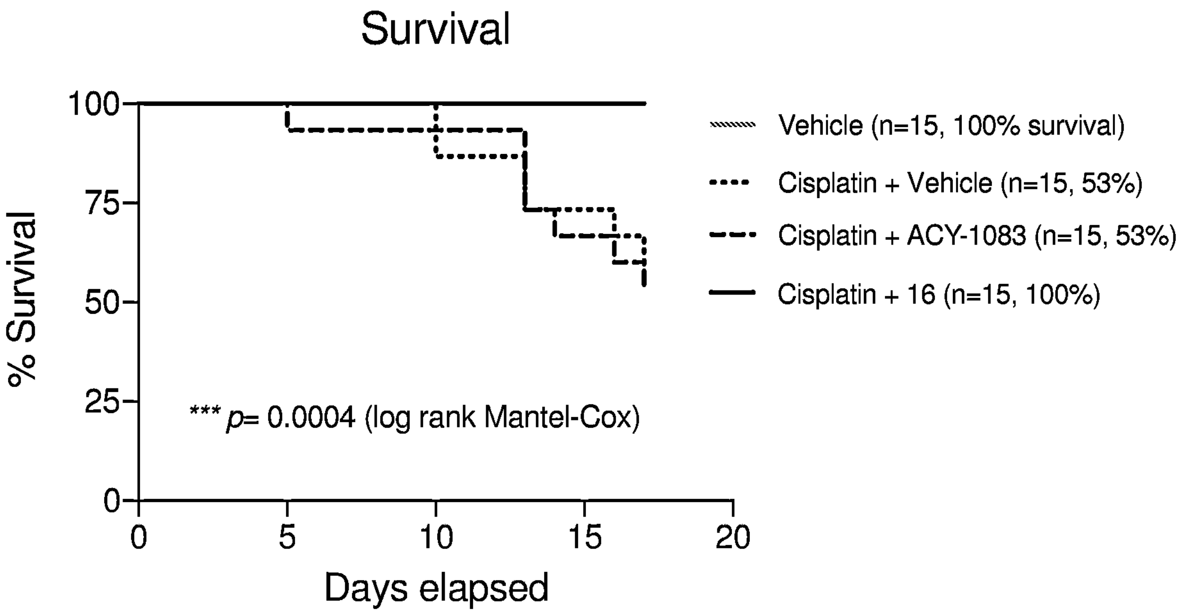
Figure 4C:
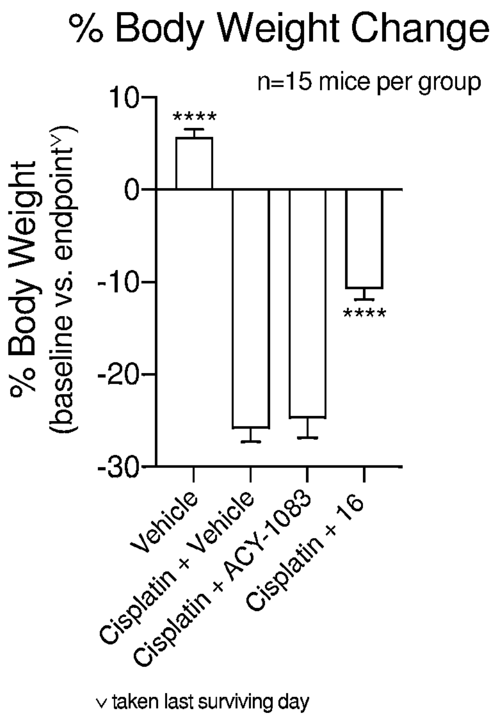
Figure 4D:
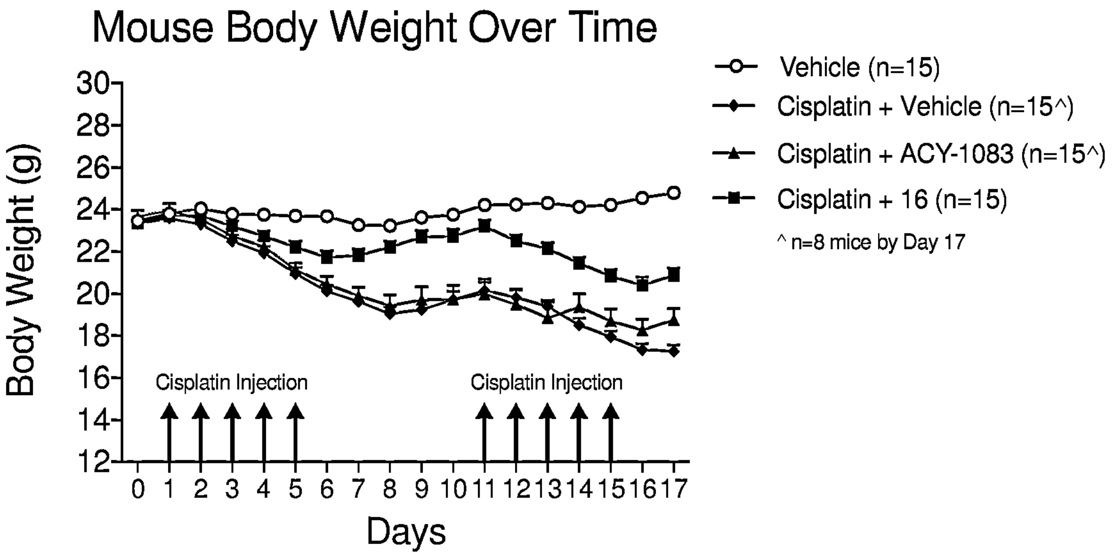
Figure 4E:
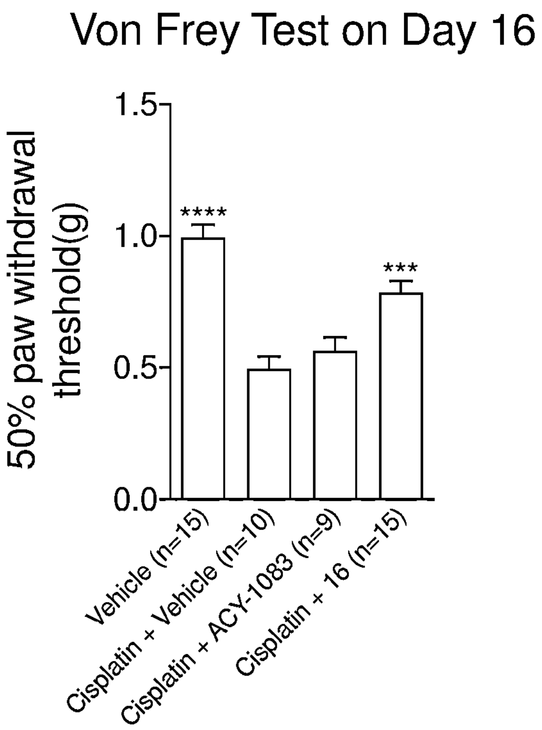
Figure 4F:
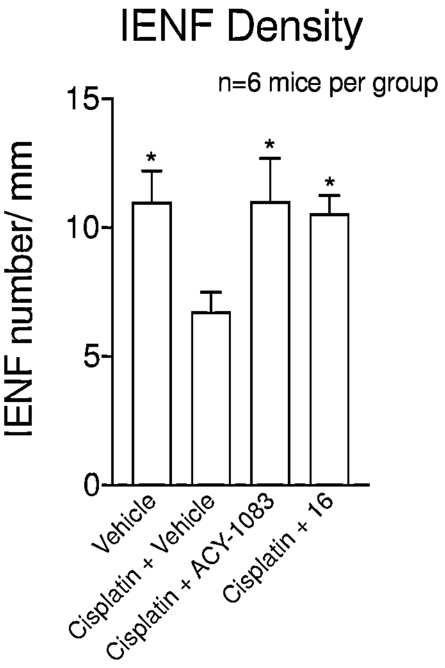

In Vitro Chemotherapy-Induced Peripheral Neuropathy in Rat DRGs Treated with Cisplatin Select exemplary compounds were evaluated for prevention of nerve degeneration in an in vitro chemotherapy induced neuropathy model using adult primary rat dorsal root ganglia (DRG). Compounds were blinded for treatment and analysis, using DMSO as a vehicle control. 16, 173, 79, ACY-1083 (benchmark) and DMSO (blinded negative control) were assessed using two coverslips per treatment. Compounds were tested after incubation on DRGs for 4 days at 5 μM in the presence of 0.5 mM cisplatin, compared to 0.5 mM cisplatin treated with vehicle. Blebs (fragments) signify the beginning of the nerve degeneration process. Total axon area is related to neuron survival and is a more general measure of neuroprotection. Data for select compounds is shown in FIGS. 3A and 3B.

Dissociation solution (100 mL of HBSS with 2 mL of HEPES (1 M, pH 7.25)) was prepared and precooled to 4° C. on study day 1. A 24 well cell culture plate was coated with ECL. Each well was coated with 0.3 mL of ECL solution (1:25 in sterile PBS) and incubated overnight at 37° C. ECL solution was aspirated and the well plate was rinsed with neurobasal medium on study day 2. Then the plate was pre-incubated with 0.5 mL per well of DRG neuronal culture medium (2 mL of B-27® Supplement 50× plus 5 mL FBS plus 3 μL gentamycin (1 ug/mL in Neurobasal®) in Neurobasal®-A medium to complete to 100 mL) and placed into the incubator.

The scissors and forceps were disinfected for 30 minutes in 70% ethanol followed by air drying. The Sprague Dawley rat (male) was terminated via cervical dislocation and the spinal cord was dissected rapidly with a pair of standard scissors. To prepare the spinal cord, the skin was incised at the ventral medial line with standard scissors. Organs were removed from the thoracic and abdominal cavity. Using standard scissors, two long cuts were made closely left and right to the spinal column. Using a stereo microscope, DRGs from all spinal levels were carefully removed and collected in 3 mL of HBSS in a 35-mm-dissecting dish placed on ice. One blade of the student spring scissors was inserted from the ventral side into the spinal canal. The other blade of the scissors was placed outside the spinal column on its ventral side. Two incisions were made along the spine, one left and one right of the midline on the ventral side. DRGs are characterized by a round shape and hyaline appearance that differs from the white color of nerve fiber bundles. The student spring scissors, Dumont #7b and #4 forceps were used to carefully isolate the exposed ganglia for each of the three pieces of the spinal cord. Isolated DRGs were collected in a 35-mm-petri dish filled with 5 mL of DRG preparation medium. The dish was kept on ice. Approximately 20 to 40 ganglia were obtained.

The thin layer of connective tissue of the epineurium surrounding the ganglion was removed with the help of a pair of spring scissors and the Dumont Forceps. Then the DRGs were transferred to a second 35-mm dish filled with DRG preparation medium on ice. Collagenase-II solution (10 mg of collagenase-II in 1 mL of dissociation solution) was prepared and preheated for 10 minutes to 37° C. Isolated DRGs were transferred into a 15-mL-centrifugation tube under a laminar flow workbench. After DRGs were settled on the tube bottom, the supernatant was removed and discarded. DRGs were rinsed with 5 mL of precooled and sterile dissociation solution. Again, the supernatant was removed. DRGs were washed three times in total, each with 5 mL of dissociation solution. After the last washing step, 2 mL of dissociation solution were left, and 1 mL of Collagenase-II solution was added. DRGs were incubated for 1 hour at 37° C. while gently shaking the Falcons every 10 minutes. An aliquot of the 2%-trypsin stock solution (100 mg of trypsin in 5 mL of HBSS) was defrosted and preheated for 20 minutes to 37° C. 150 μL of activated trypsin was added. The DRGs were incubated further for 9 minutes at 37° C. while gently shaking the falcon every 3 minutes. The supernatant was removed carefully and washed with 5 mL of dissociation solution. After the last washing step, 1.5 mL of dissociation solution was left.

To obtain single cells, DRGs were dissociated with the glass Pasteur pipettes. Two glass Pasteur pipettes were fire-polished to obtain smaller openings. Using the glass pipette with an original opening diameter of 1.1-1.3 mm, DRGs were pipetted approximately 10 times up and down until the solution appeared homogenous. Then the (fire-polished) Pasteur pipette with the smaller diameter was used and the solution triturated 8 times. Finally, the very small diameter (fire-polished) Pasteur pipette was used 3 times. The single cell suspension was centrifuged for 5 minutes at 160×g. The supernatant was removed from the cell pellet. DRG neuronal culture medium was added to the cell pellet; cells were re-suspended and centrifuged for 5 minutes at 200 RPM. The supernatant was carefully removed, and cells were re-suspended in DRG neuronal culture medium with a 1,000 μL pipette. Cells were plated in 14 wells and placed at 37 C under a 5% $CO_2$ atmosphere.

The compounds were added to the culturing medium along with chemotherapy. The cells were fixed on cover slips using methanol and stained with antibody against beta-tubulin III for neurite imaging 4 days later. For immunocytochemistry, cover slips were fixed with 100% ice-cold methanol and permeabilized with 0.02% Triton X-100. Neurons were then incubated in BSA for 1 hour at room temperature followed by incubation with respective antibodies: Beta-tubulin III (Merck, cat #T2200) and later on, secondary Alexa Fluor 594-conjugated anti Rabbit Ab. Cover slips were mounted on slides using fluorescent mounting medium (Gbi, cat #E19-s). Areas of two cover-slips per treatment group were taken. Imaging was done using BX43 Olympus microscope driven by the standard "CellSens" software by Olympus. Images were taken under 60× water-dipping objective using a DP74 camera (Olympus). To estimate axon degeneration, an ImageJ plugin—"Neurophysiology" was used. After applying the threshold settings, the "analyze particle" function was used with the pixel size (pixel 2) set from 0-∞ and circularity set from 0-1.0 to include all particles. The data output included total area of detected objects (total pixels 2), and number of blebs detected with the "find maxima" function. The neurite area and the number of blebs per image were calculated and their ratio values were compared to the cisplatin+vehicle group. Readouts were blebs per area and total axon area.

In Vivo Chemotherapy-Induced Peripheral Neuropathy in Mice Treated with Cisplatin Select exemplary compounds were evaluated for efficacy in an in vivo chemotherapy induced peripheral neuropathy (CIPN) mouse model using cisplatin. 16 (30 mg/kg PO), ACY-1083 (benchmark, 10 mg/kg IP) and vehicle (IP) were assessed in the presence of cisplatin (2.3 mg/kg IP) using a co-treatment paradigm with n=15 animals per group as outlined below. Overall health was monitored by body weight and survival. Mechanical allodynia was assessed by the Von Frey test. Nerve integrity was measured by intra-epidermal nerve fiber (IENF) density. Data for select compounds is shown in FIG. 4.

All formulations were prepared fresh before each dosing and administered by IP or PO route at the required time point. 2.3 mg/kg cisplatin was used to induce the CIPN model. Cisplatin was dissolved in sterile saline at a concentration of 0.46 mg/mL. ACY-1083 was given at a dose of 10 mg/kg via IP injection in a volume of 10 mL/kg. ACY-1083 powder was dissolved in 20% 2-hydroxypropyl-β-cyclodextrin+0.5% hydroxypropyl methylcellulose in water to achieve a solution strength of 1 mg/mL. 16 was given at a dose of 30 mg/kg via oral gavage in a volume 10 mL/kg. 16 was dissolved in 7.5% NMP; 5% Solutol HS-15; 30% PEG-400; 57.5% 10 mM Citric Acid at a solution strength of 3 mg/mL. The vehicle for ACY-1083 (20% 2-hydroxypropyl-β-cyclodextrin+0.5% hydroxypropyl methylcellulose in water; 10 mL/kg, IP route) was considered the vehicle control. Male C57BL/6 mice were housed in groups of four per cage for 7 days' acclimation. They weighed 18-22 g at the beginning of the experiment. Temperature and humidity were controlled (targeted at 23±2° C. and 50±5%, respectively). The vivarium was maintained on a 12-hour light/dark cycle (lights off at 07:00 hours). Food and water were available ad libitum.

Saline or cisplatin was administered QD on Day 1 thru Day 5 and Day 11 thru Day 15. Vehicle (IP), ACY-1083 (IP) or 16 (oral gavage) was administered QD on Day 1 thru Day 17. On Day 1 thru Day 5 and Day 11 thru Day 15 administration occurred 1 hour before cisplatin treatment. The body weight of all mice was monitored daily. Clinical observations occurred daily.

The Von Frey test was performed at three time points (baseline, day 7, and day 16). On Day 7 and Day 16, testing was performed approximately 2 hours after vehicle/ACY-1083/16 dosing. Mice were randomly grouped based on the baseline data of mechanical allodynic testing. The mice were habituated in the testing environment for 15 minutes before allodynia measurement for three days. The left paw of mouse was touched with 1 of a series of 8 von Frey hairs (S. R. Chaplan, F. W. Bacha. 1994) with logarithmically incremental stiffness (0.02, 0.04, 0.07, 0.16, 0.4, 0.6, 1.0, and 1.4 g). The von Frey hair was presented perpendicularly to the plantar surface with sufficient force to cause slight buckling against the paw and held for approximately 6-8 seconds. Stimulation was presented at intervals of several seconds, allowing for apparent resolution of any behavioral responses to previous stimuli. A positive response was noted if the paw was sharply withdrawn. Flinching immediately upon removal of the hair was also considered a positive response. Ambulation was considered an ambiguous response and in such cases, the stimulus was repeated. To determine the 50% withdrawal threshold, testing was initiated with the 0.16 g fiber. Fibers were presented in a consecutive fashion whether ascending (in the absence of a paw withdrawal response to the initially selected fiber, the next highest fiber was presented) or descending (in the event of a paw withdrawal, the next weaker fiber was presented). Observations (withdrawal (x)/non-withdrawal (o)) were then entered into a template which automatically calculated the threshold in grams. Mechanical allodynia was calculated and expressed using the formula:

$$50\%\ \text{response threshold (g)}=(10(Xf+k\delta))/10{,}000$$

Xf=value (in log units) of the final von Frey filament used k=tabular value for the pattern of positive/negative responses (Chaplan et al. 1994, appendix 1, page 62)

δ=mean difference (in log units) between stimuli.

All the animals were sacrificed two hours post final intervention dose on day 17 by $CO_2$ inhalation. Plasma and nerve were sent for mass-spec bioanalysis to confirm compound presence and determine fraction unbound. Skin from hind paws (6 of the 12 mice per group) was prepared for IENF measurement. Skin of the hind footpads were carefully dissected and transferred to 4% paraformaldehyde (in phosphate-buffered saline (PBS), pH 7.2) for 24 hours at room temperature (RT). The tissue was immersed in 20% sucrose (in PBS) solution for dehydration purposes for approximately 48 hours. The skin was embedded in the frozen buffer (O.C.T./20% sucrose (1:1)) followed by snap freezing on dry ice. Note that the proximal end of the skin was attached to the lateral wall of plastic embedding box, which will be sectioned first. The frozen tissue blocks were transferred to a cryotome cryostat (chamber temperature was set at −20° C., and specimen head −19° C.). The first 0.4 mm tissue was discarded. Then the skin slices were cut and collected at 10 m. Slices were washed with PBS two times for 5 minutes each time. 10% goat serum (in PBS) was added for 1-2 hours at RT. Primary antibody (anti-PGP9.5, rabbit-derived, 1:500 in antibody diluent) was incubated over night at 4° C. in sealed moist container. Slides were washed 3 times with PBS for 10 minutes each time. Secondary antibody (goat anti rabbit, fluorescent dye coupled, and 1:400 in antibody diluent) was incubated for 1 hour at RT. 120 μL of DAPI contained mounting medium was applied and mounted with coverslip. Slides dried overnight at 4° C. Imaging was performed using the Leica fluorescence scanner, so that the whole information of tissue sections was obtained.

The basement membrane (BM) of epidermis were drawn according to the cell morphology. The IENF were drawn along the BM, and the counting rules are listed below (following the published review of Mangus et al. in 2017).

(1) Count a nerve fiber as it penetrates the BM.

(2) Nerves that cross the BM and branch at the epidermis are counted as one IENF.

(3) Nerves that split at the dermis and then penetrate the BM are counted as separate units.

IENF Density (IENF/mm) equals the number of IENF divided by the length of epidermis (mm).

Axonal Transport in iPSC-Derived ALS Motor Neurons

Figure 5A:
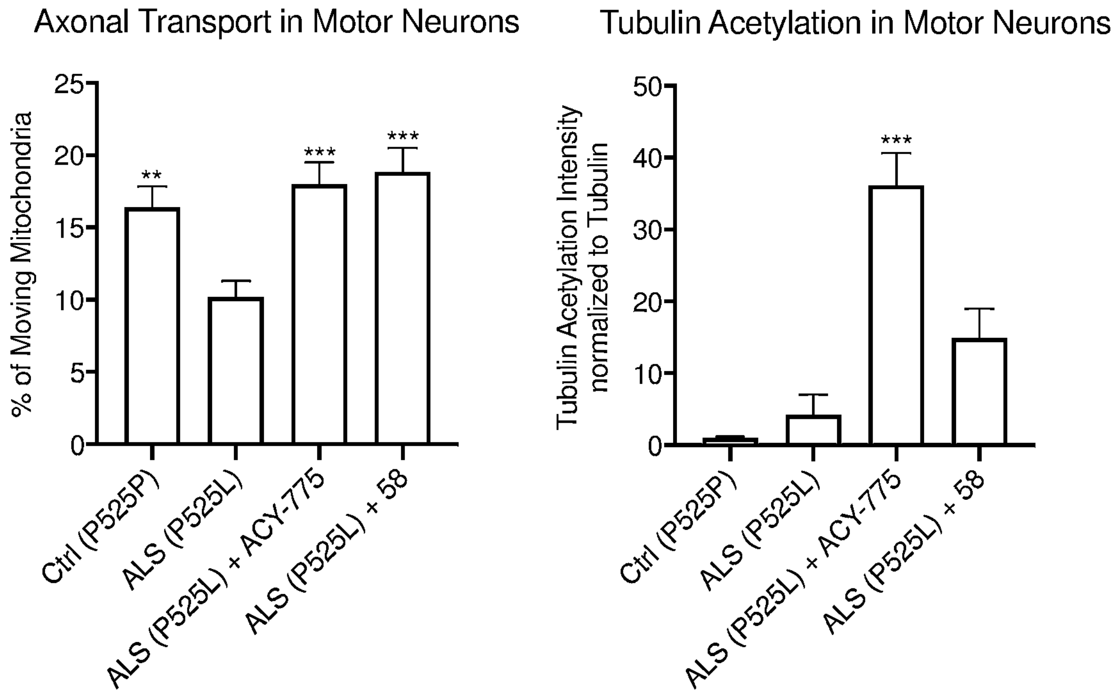
FIGS. 5A-B are a series of graphs summarizing the effect of exemplary compounds on in vitro axonal transport and tubulin acetylation in induced pluripotent stem cell (iPSC)-derived motor neurons from a patient with ALS. ACY-775, obtained from MedChem Express, is a published HDAC6-selective inhibitor and was used as a benchmark. Blinded DMSO was used as an additional negative control. iPSCs from a patient with the FUSP525L mutation and an isogenic control line were differentiated into motor neurons. Motor neurons were treated for 24 hours with 5 μM of the indicated compounds. Axonal transport was evaluated using live-cell imaging of mitochondrial trafficking as visualized by MitoTracker Red. Tubulin acetylation was measured using western blotting.
Figure 5B:
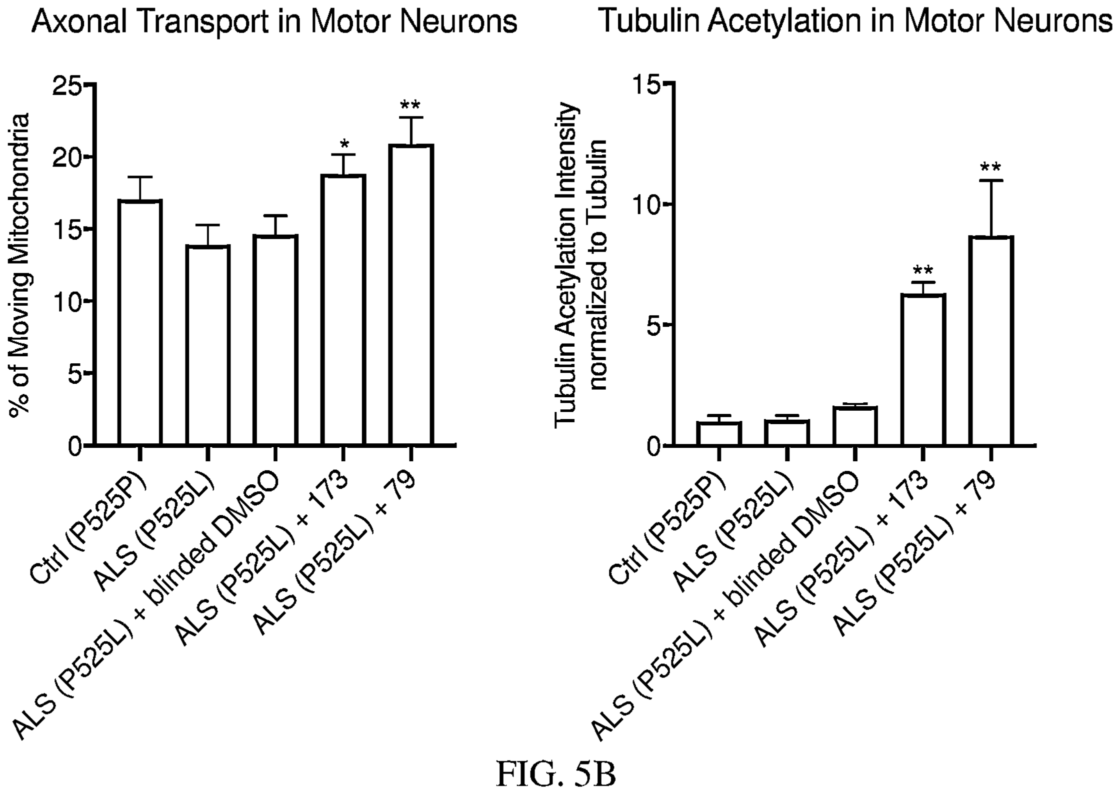

Select exemplary compounds were evaluated for rescue of axonal transport and response of tubulin acetylation in human induced pluripotent stem cell (iPSC)-derived motor neurons (MN) from a patient with amyotrophic lateral sclerosis (ALS). Data for select compounds is shown in FIG. 5. All compounds were tested in iPSC-derived MN of the FUS patient line P525L, using DMSO as a vehicle control. MN from the isogenic P525P iPSC control line were also treated with DMSO to confirm axonal transport deficits in the P525L line and the potential rescue effect of the tested compounds. Compounds were blinded for treatment and analysis, with 58 and ACY-775 (benchmark) assessed in one differentiation and 173, 79 and DMSO (blinded negative control) assessed in a separate differentiation. Compounds were tested after overnight incubation at 5 μM for axonal transport of mitochondria at differentiation days 30 and 31 and samples for Western Blot (WB) analysis of tubulin acetylation were collected at day 32.

Human iPSCs were maintained on GeltrexR (A1413302, Gibco) in Essential 8 medium (A1517001, Gibco) supplemented with penicillin-streptomycin. Colonies were routinely passaged with 0.5 mM EDTA (15575-020, Invitrogen) in Dulbecco's phosphate-buffered saline (DPBS). Cultures were routinely analysed for mycoplasma contamination by PCR. MNs were differentiated from iPSCs as described before (Guo et al. *Nat Commun* 2017). Briefly, iPSC clones were suspended and transferred from a 6-well plate into a T-25 low attachment flask with neuronal basic medium (a 1:1 mixture of Neurobasal medium and DMEM/F12 medium, with $N_2$ and B27 without vitamin A), using collagenase type IV digestion to form embryoid bodies. After 2 days incubation with 5 μM ROCK Inhibitor (Y-27632, Merck Millipore), 40 μM TGF-β inhibitor (SB 431524, SB, Tocris Bioscience), 0.2 M bone morphogenetic protein inhibitor (LDN-193189, LDN, Stemgent), and 3 μM GSK-3 inhibitor (CHIR99021, CHIR, Tocris Bioscience), suspended embryoid bodies were incubated with neuronal basic medium containing 0.1 μM retinoic acid (RA, Sigma) and 500 nM Smoothened Agonist (SAG, Merck Millipore) for 4 days. Cells were subsequently incubated for 2 days in a neuronal basic medium containing RA, SAG, 10 ng/mL brain derived neurotrophic factor (BDNF, Peprotech), and 10 ng/mL glial cell derived neurotrophic factor (GDNF, Peprotech). At day 9 of differentiation, cell spheres were dissociated into single cells using 0.05% trypsin (Gibco) for 20 minutes at 37° C. After cell counting, a defined number of cells were seeded in poly-L-ornithine (100 μg/mL) and laminin (20 g/mL)-coated plates and incubated for 5 days in a neuronal basic medium containing RA, SAG, BDNF, GDNF, and 10 μM inhibitor of γ-secretase (DAPT, from Tocris Bioscience), and then incubated for 2 days in a neuronal basic medium containing BDNF, GDNF, and 20 M DAPT. For MN maturation, cells were kept in neuronal medium supplemented with BDNF, GDNF, and ciliary neurotrophic factor (CNTF; 10 ng/ml each, Peprotech). Media were changed every other day by replacing half of the medium. All experiments were performed during the fifth week of differentiation. MN differentiation efficiency was checked in the second differentiation, showing that more than 80% of cells stained positive for the MN specific markers Chat, Isl, SMT32 without differences between any of the lines.

Motor neurons seeded in clear bottom 24-well plates (PerkinElmer, 1450-602) were loaded with 50 nM MitoTracker-Green (ThermoFisher, M7514) in a HEPES buffered salt solution (pH 7.4, 150 mM NaCl, 5 mM KCl, 1 mM MgCl2, 2 mM CaCl2, 10 mM glucose, 10 mM HEPES) for 20 minutes. Then excess MitoTracker-Green was washed with HEPES buffered salt solution and imaged using a 60× objective on an InCell Analyzer 2000 microscope in MN maintained at 37° C. (GE Healthcare Life Sciences). Each field was manually selected and 1 second timelapse images were taken for 200 seconds. All image analysis was performed using FiJi. Each neurite was manually selected to generate a kymogram using the Reslice tool, where axonal length was obtained and moving mitochondria were manually counted. In order to get the total number of mitochondria per neurite, the segmentation tool of the TrackMate PlugIn was used in the first image of each time-lapse series. The Linear Stack Alignment with SIFT PlugIn was used in some cases to align image stacks.

MN were collected and lysed in commercial RIPA buffer (Sigma, R0278) containing PhosStop (Roche, 4906845001) and cOmplete (Roche, 05892970001) for 30 minutes on ice, centrifuged for 10 minutes at 16.000 g at 4° C. and supernatant was collected. Protein concentration was determined using a standard BCA kit (ThermoFisher, 23225) and 0.5 ug per well of protein was loaded in commercial acrylamide gels (Bio-Rad, 456-8096) for protein electrophoresis. Then protein was transferred to a nitrocellulose membrane (GE Healthcare, 10600001), blocked for 1 hour with 5% BSA and blotted with the following primary antibodies: Anti-Acetylated Tubulin (Sigma, T673; 1:5000 dilution, 2 hours at room temperature), Anti-α-Tubulin (Sigma, T6199, 1:5000 dilution, overnight at 4° C.) and Anti-Calnexin (Enzo Life Sciences, ADISPA-860; 1:5000 dilution, overnight at 4° C.). After washing with TBST, membranes were incubated with secondary antibodies (Dako, P0447 and P0448, 1:500 dilution) for 1 hour at room temperature, washed with TBST and TBS and imaged using ECL and SuperSignal (ThermoFisher, 32106) and an ImageQuant LAS 4000 imager (GE Healthcare).

In Vivo Target Occupancy Measurement in Rhesus Macaque Brain

Select exemplary compounds were evaluated for in vivo target occupancy in the brain of male rhesus monkeys (*Macaca mulatta*). Data for select compounds is shown in Table 13 below. Experiments were conducted according to the Belgian code of practice for the care and use of animals, after approval from the local University Ethics Committee for Animals. Target occupancy in brain was established via baseline and heterologous-blocking positron emission tomography (PET) neuroimaging studies. Occupancies were determined in one monkey after IV pre-treatment with 0.1 and 2 mg/kg of 16 and ACY-775. IV pre-treatment studies were performed at 5 minutes prior to [$^{18}$F]Bavarostat injection in a volume of 0.4 mL/kg. Occupancies were determined in a different monkey after IV pre-treatment with 2 mg/kg of 173 and PO pre-treatment with 2 mg/kg of 16. The IV pre-treatment study was performed at 5 minutes prior to [$^{18}$F]Bavarostat injection in a volume of 0.4 mL/kg and the PO pre-treatment study was performed 2 hours prior to [$^{18}$F]Bavarostat injection in a drinking solution of ~45 mL. For the IV blocking scans with 16, 173, and ACY-775, formulation was performed using 7.5% NMP, 5% Solutol HS-15, 30% PEG-400 and 57.5% 10 mM citric acid. For the PO blocking scan with 16, formulation was performed using a suspension of 2 mg/kg compound in a 1:1 (v/v) mixture of honey and water.

The monkeys were sedated (~75 minutes before tracer injection) by an intramuscular injection of a combination of 0.3 mL Rompun (xylazine 2% solution) and 0.35 mL Nimatek (ketamine 100 mg/mL). About 60 minutes after the first injection, the monkey received an additional dose of 0.15 mL Rompun and 0.175 mL Nimatek via IV injection. 02 and $CO_2$ saturation in the blood and heart rate were constantly monitored during scanning, and body temperature was maintained via an electronically controlled heating pad.

A venous line was inserted for administration of radiotracer and blocking compounds (except for PO dose) in one limb. A catheter was placed in the femoral artery in the other limb for arterial blood sampling. Prior to pre-treatment/vehicle injection, an arterial blood sample was taken for plasma free fraction determination.

Scans of the brain were acquired using the Focus™ 220 microPET scanner (Concorde Microsystems, Knoxville, TN, USA). Before radiotracer injection, a 10-minute transmission scan using a $^{57}$Co source was obtained to assess positioning and for subsequent attenuation correction. A 120-minute dynamic PET scan was acquired in list mode concurrently with the injection of [$^{18}$F]Bavarostat (185 MBq, manual bolus over 30 seconds, vena saphena). Data were histogrammed into 4×15 s, 4×60 s, 5×180 s, 8×300 s and 6×600 s timeframes and reconstructed using the MAP algorithm (18 iterations, resolution 1.5 mm) with attenuation correction into 256×256×95 pixels. No scatter correction was applied.

A three-dimensional T1-weighted MR brain scan of each animal was obtained for co-registration purposes on a 3.0 Tesla full-body scanner (Tim Trio Scanner, Siemens) using a magnetization prepared rapid gradient echo (MPRAGE) sequence (*tfl3d1_16) with the following parameters: repetition time 2700 ms, echo time 3.8 ms, inversion time 850 ms, Flip angle 9°, 256×208×144 matrix, 0.6 mm voxel size.

Arterial blood was measured for the first four minutes post [$^{18}$F]Bavarostat injection using the Twilite in-line blood monitor (Swisstrace, Switzerland). After the initial scan period, the Swisstrace pump was switched off, the arterial blood in the Twilite radiodetector was recovered in EDTA tubes and arterial blood sampling was continued manually (via a 3-way valve) at preselected time points (5, 10, 20, 40, 60, 100 minutes post tracer injection). All collected blood samples were immediately stored on ice to stop metabolism. After centrifugation (2330×g, 5 minutes), a whole blood sample (50 μL) and plasma sample (50 μL) were separated and weighed. The remainder of plasma of the six collected samples was processed and analysed using HPLC to quantify the fraction of intact tracer at the different time points. To about 0.3 mL of plasma, an equal amount of $CH_3CN$ was added and the resulting suspension was centrifuged (2330×g, 5 minutes) to separate the precipitated proteins from the supernatant. Next, 0.5 mL of supernatant was filtered through a syringe filter (0.22 μm; Millipore), diluted with water (½ of the volume) and spiked with 10 μg of authentic Bavarostat. A volume of 0.5 mL of extract was injected onto an HPLC system consisting of an analytical XTerra column (C18; 5 μm, 4.6 mm×250 mm, Waters) eluted with a mixture of 0.05 M sodium acetate (pH 5.5+0.005M EDTA) and $CH_3CN$ (55:45 v/v) at a flow rate of 1 mL/min. For the initial studies, after passing through a radiodetector and UV detector (280 nm), the HPLC eluate was collected as 1-mL fractions using an automated fraction collector. Later on, when the radiometabolite profile was known, the HPLC eluate was collected in two fractions (fraction no 1 containing the polar radiometabolite(s) and fraction no 2 consisting of the intact tracer). Radioactivity in the filtered plasma (prior to HPLC), filter, and HPLC eluent fractions was all counted in a cross-calibrated well-type gamma counter equipped with a 3-in NaI(Tl) well crystal coupled to a multichannel analyzer (Wallac 1480 Wizard, Wallac, Turku, Finland). The results were corrected for background radiation, detector dead-time and physical decay during counting. The dose calibrator, PET camera, gamma counter and Twilite devices were cross-calibrated with a solution of [$^{18}$F]FDG on the day of the experiment.

MRI data from each animal were normalized to a macaque brain atlas using PFUSIT 4.0 (PMOD, Switzerland). Dynamic PET data were averaged and coregistered to the individual MRI scan, before volumes of interest from a publicly available brain atlas were transformed to PET space to generate time activity curves for kinetic analysis. Kinetic analysis was done in PKIN (PMOD, Switzerland), with the metabolite corrected plasma activity curve was used as an input function for 2-tissue compartmental modelling and Logan graphical analysis. For the latter, time was set to 40 minutes as data were visibly linear at this point. Compound occupancy levels were calculated via the Lassen plot using regional brain volume of distribution ($V_T$) values. $V_T$ estimates derived from 2-tissue compartmental modelling and Logan graphical analysis produced very similar results, and target occupancy is reported in the table below using $V_T$ estimates generated from Logan graphical analysis. A subset of this data is published; see Celen et al. *ACS Chemical Neuroscience* 2020.

TABLE 13

Summary of in vivo target occupancy data in rhesus macaque brain after IV or PO treatment followed by [$^{18}$F]Bavarostat PET, as determined by Lassen plots using regional distribution volume ($V_T$) estimates generated from Logan graphical analysis

| Compound | Target Occ. IV, 0.1 mg/kg | Target Occ. IV, 2.0 mg/kg | Target Occ. PO, 2.0 mg/kg |
|---|---|---|---|
| ACY-775 | 51% | 87% | Not tested |
| 16 | 87% | >99% | 73% |
| 173 | Not tested | 91% | Not tested |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

(I)

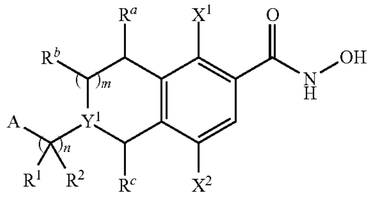

or a pharmaceutically acceptable salt thereof, wherein:

$X^1$ is hydrogen or fluoro;

$X^2$ is hydrogen or fluoro; provided that at least one of $X^1$ and $X^2$ is fluoro;

A is substituted or unsubstituted alkyl, substituted or unsubstituted carbocyclyl, substituted or unsubstituted heterocyclyl, substituted or unsubstituted heteroaryl, or substituted or unsubstituted aryl;

$R^1$ is hydrogen or substituted or unsubstituted alkyl;

$R^2$ is hydrogen or substituted or unsubstituted alkyl; or $R^1$ and $R^2$ together form a substituted or unsubstituted heterocyclyl, or a substituted or unsubstituted cycloalkyl;

$R^a$ is hydrogen or is joined with $R^c$ to form a substituted or unsubstituted bridged ring;

$R^b$ is hydrogen or is joined with $R^c$ to form a substituted or unsubstituted bridged ring;

$R^c$ is hydrogen or substituted or unsubstituted alkyl or is joined with at least one of $R^a$ and $R^b$ to form a substituted or unsubstituted bridged ring;

m is 0 or 1; and n is 0 or 1.

2. The compound of claim 1, or a pharmaceutically acceptable salt thereof, wherein:

$X^1$ is hydrogen; and $X^2$ is fluoro.

3. The compound of claim 2, or a pharmaceutically acceptable salt thereof, wherein:

A is unsubstituted $C_{1-4}$ alkyl, $C_{1-4}$ haloalkyl, substituted or unsubstituted $C_{3-14}$ carbocyclyl, substituted or unsubstituted 3-14-membered heterocyclyl, substituted or unsubstituted 5-14 membered monocyclic or polycyclic heteroaryl, or substituted or unsubstituted $C_{6-14}$ aryl.

4. The compound of claim 2, or a pharmaceutically acceptable salt thereof, wherein:

A is $—CF_3$, $—C(CH_3)_3$, phenyl, 2,6-dimethylphenyl, tetrahydrofuranyl, oxetanyl, cyclopropyl, cyclobutyl, cyclopentyl, cyclohexyl, adamantyl,

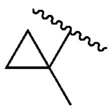
,
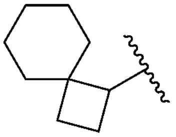
,
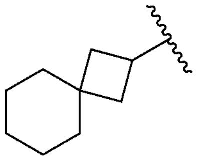
,
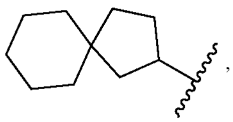
,
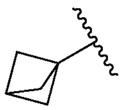
,
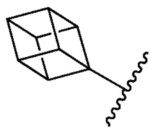
, or
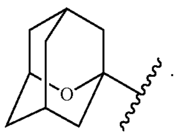
.

5. The compound of claim 3, or a pharmaceutically acceptable salt thereof, wherein:

$R^1$ is hydrogen; and $R^2$ is hydrogen.

6. The compound of claim 5, or a pharmaceutically acceptable salt thereof, wherein:

$R^a$, $R^b$, and Re are each hydrogen.

7. The compound of claim 6, or a pharmaceutically acceptable salt thereof, wherein:

n is 1.

8. The compound of claim 1, wherein the compound is of Formula (I-c) or Formula (I-d):

(I-c)

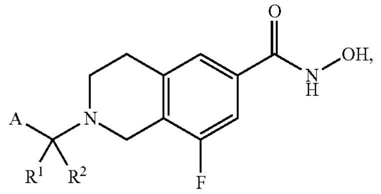

or a pharmaceutically acceptable salt thereof, wherein

A is $C_{3-14}$ carbocyclyl or 3-14 membered heterocyclyl;

$R^1$ is hydrogen, methyl or ethyl; and $R^2$ is hydrogen, methyl or ethyl; or $R^1$ and $R^2$ together form a substituted or unsubstituted $C_{3-6}$ cycloalkyl.

9. A compound of formula:

1

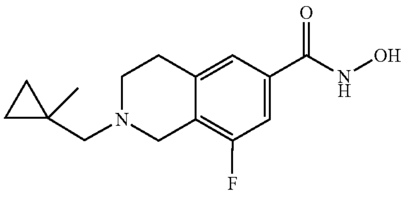

2

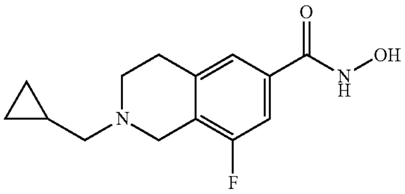

3

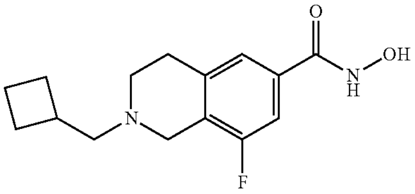

4

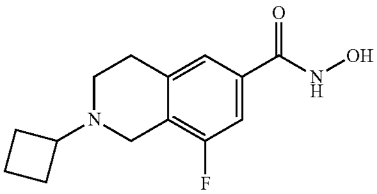

-continued
5
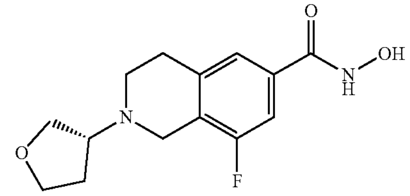
6
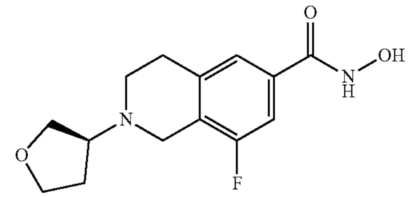
7
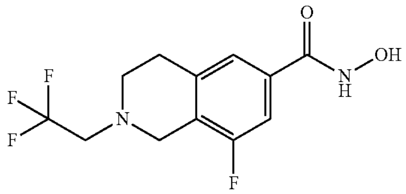
8
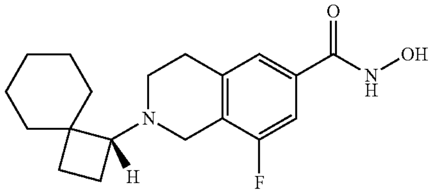
9
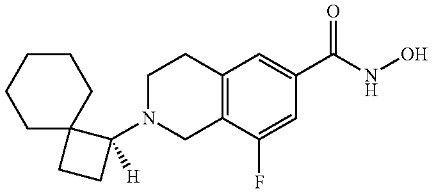
10
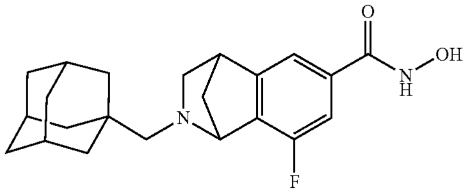
11
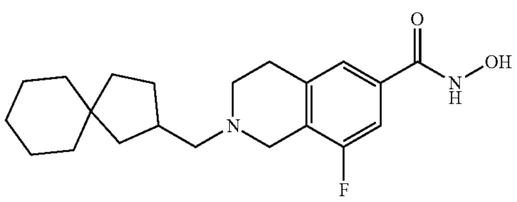
-continued
12
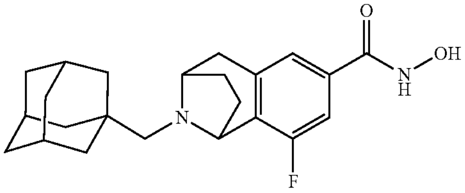
13
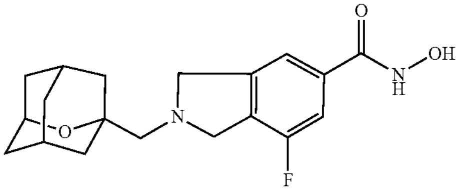
14
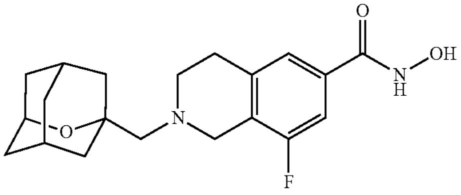
15
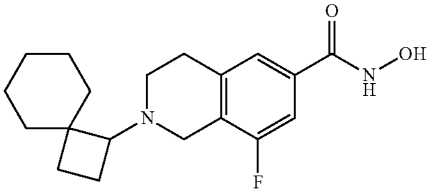
16
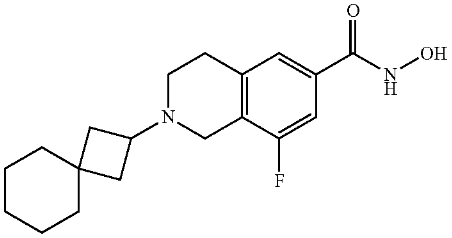
17
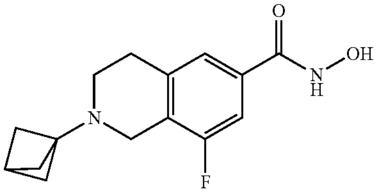
18
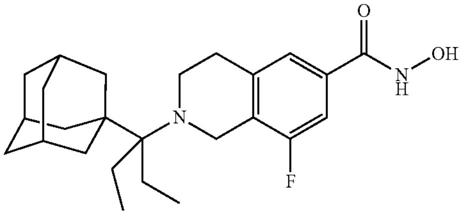

-continued
19
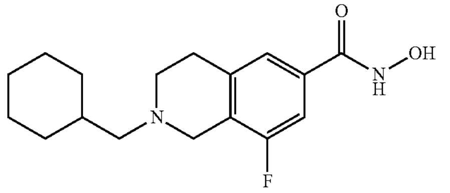
20
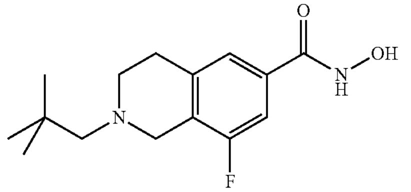
21
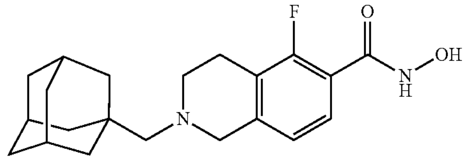
22
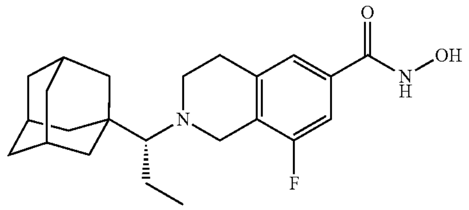
23
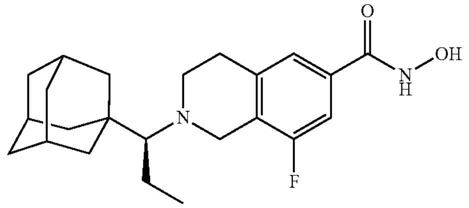
24
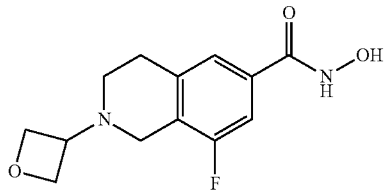
25
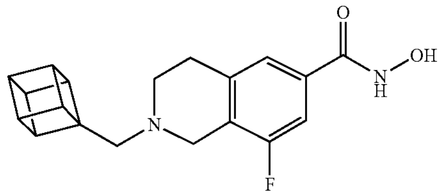
26
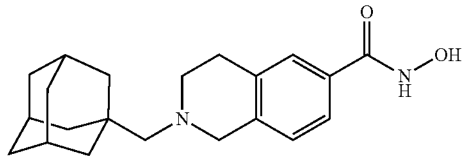
-continued
27
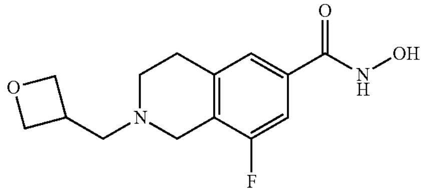
28
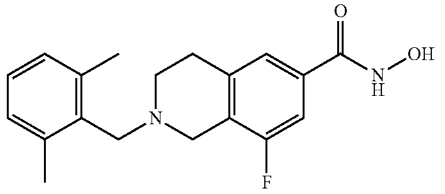
29
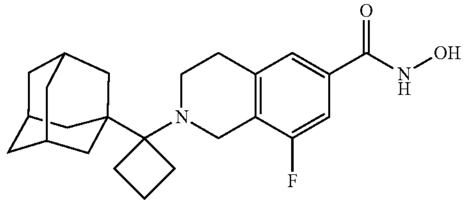
30
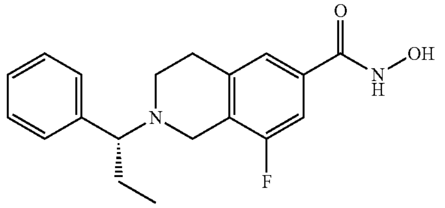
31
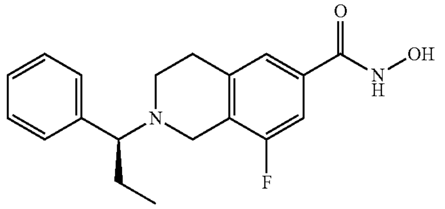
32
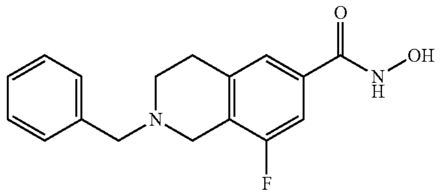
33
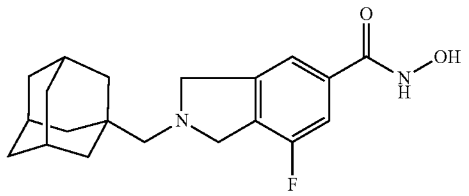

-continued

34

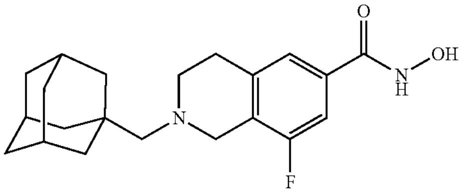

35

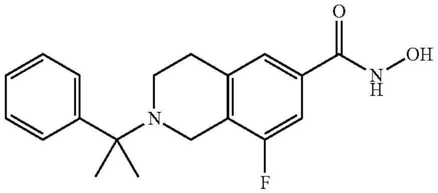

107

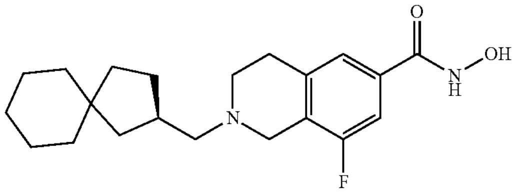

108

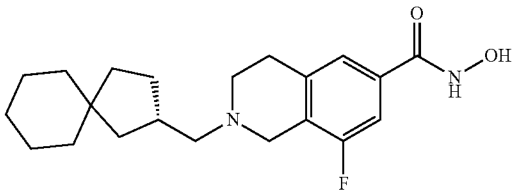

109

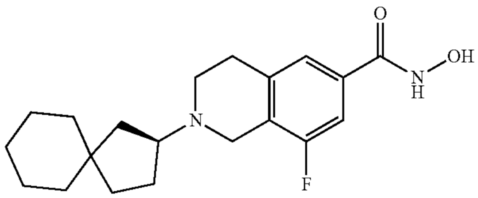

110

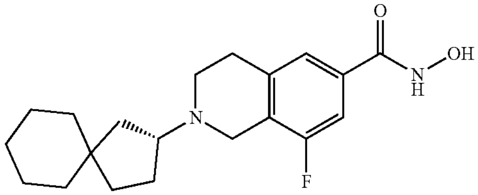

111

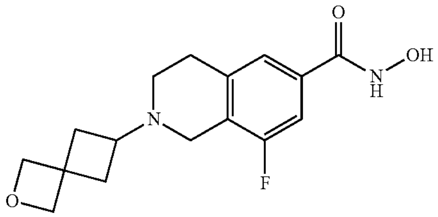

-continued

112

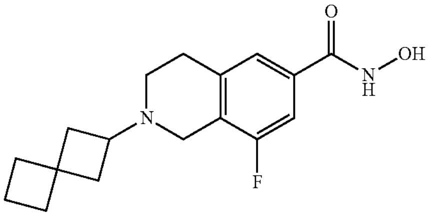

or a pharmaceutically acceptable salt thereof.

10. The compound of claim 3, or a pharmaceutically acceptable salt thereof, wherein:

$R^a$, $R^b$, and Re are each hydrogen;

$R^1$ is hydrogen, methyl, or ethyl; and $R^2$ is hydrogen, methyl, or ethyl; or $R^1$ and $R^2$ together form a $C_{3-6}$ cycloalkyl.

11. The compound of claim 10, or a pharmaceutically acceptable salt thereof, wherein A is substituted or unsubstituted $C_6$ aryl or substituted or unsubstituted 5-6 membered heteroaryl.

12. The compound of claim 10, or a pharmaceutically acceptable salt thereof, wherein A is substituted or unsubstituted $C_{3-6}$ monocyclic cycloalkyl.

13. The compound of claim 10, or a pharmaceutically acceptable salt thereof, wherein A is substituted or unsubstituted monocyclic 4-7 membered heterocyclyl.

14. The compound of claim 10, or a pharmaceutically acceptable salt thereof, wherein A is substituted or unsubstituted 8-10 membered bridged heterocyclyl.

15. The compound of claim 10, or a pharmaceutically acceptable salt thereof, wherein A is substituted or unsubstituted $C_{3-14}$ polycyclic carbocyclyl or substituted or unsubstituted 3-14 membered heterocyclyl.

16. The compound of claim 15, or a pharmaceutically acceptable salt thereof, wherein A is a substituted or unsubstituted bicyclic spirocyclic $C_{3-14}$ carbocyclyl or a substituted or unsubstituted bicyclic spirocyclic 3-14 membered heterocyclyl.

17. The compound of claim 16, or a pharmaceutically acceptable salt thereof, wherein A is a substituted or unsubstituted $C_{5-10}$ spirocyclic cycloalkyl.

18. The compound of claim 10, or a pharmaceutically acceptable salt thereof, wherein A is a substituted or unsubstituted oxetanyl, or a substituted or unsubstituted adamantyl.

19. The compound of claim 10, or a pharmaceutically acceptable salt thereof, wherein A is unsubstituted $C_{1-4}$ alkyl or $C_{1-4}$ haloalkyl.

* * * * *